United States Patent
Lauer et al.

(10) Patent No.: US 9,795,643 B2
(45) Date of Patent: *Oct. 24, 2017

(54) ONCOLYTIC MEASLES VIRUS

(71) Applicants: Ulrich M. Lauer, Tuebingen (DE);
Michael Bitzer, Rottenburg (DE);
Johanna Lampe, Helsinki (FI);
Martina Schell, Tuebingen (DE);
Susanne Berchtold, Tuebingen (DE);
Sebastian Lange, Tuebingen (DE);
Wolfgang J. Neubert, Greifenberg (DE); Sascha Bossow, Heidelberg (DE)

(72) Inventors: Ulrich M. Lauer, Tuebingen (DE);
Michael Bitzer, Rottenburg (DE);
Johanna Lampe, Helsinki (FI);
Martina Schell, Tuebingen (DE);
Susanne Berchtold, Tuebingen (DE);
Sebastian Lange, Tuebingen (DE);
Wolfgang J. Neubert, Greifenberg (DE); Sascha Bossow, Heidelberg (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/719,906

(22) Filed: May 22, 2015

(65) Prior Publication Data
US 2015/0250838 A1 Sep. 10, 2015

Related U.S. Application Data

(62) Division of application No. 13/818,053, filed as application No. PCT/EP2011/004200 on Aug. 19, 2011, now Pat. No. 9,272,008.

(30) Foreign Application Priority Data

Aug. 20, 2010 (EP) .................... 10008726

(51) Int. Cl.
A61K 35/768 (2015.01)
C12N 9/10 (2006.01)
C12N 9/78 (2006.01)
A61K 31/7088 (2006.01)
C12N 7/00 (2006.01)

(52) U.S. Cl.
CPC ........ A61K 35/768 (2013.01); A61K 31/7088 (2013.01); C12N 7/00 (2013.01); C12N 9/1077 (2013.01); C12N 9/78 (2013.01); C07K 2319/00 (2013.01); C12N 2760/18421 (2013.01); C12N 2760/18432 (2013.01); C12N 2760/18443 (2013.01); C12N 2760/18471 (2013.01); C12N 2830/60 (2013.01); C12Y 305/04001 (2013.01)

(58) Field of Classification Search
None
See application file for complete search history.

(56) References Cited

U.S. PATENT DOCUMENTS 5,654,136 A    8/1997   Sasaki et al.

FOREIGN PATENT DOCUMENTS

| EP | 1 375 512 B1 | 7/2009 |
| WO | WO 97/06270 A1 | 2/1997 |
| WO | WO 98/13501 A2 | 4/1998 |
| WO | WO 99/49017 A2 | 9/1999 |
| WO | WO 04000876 A1 | 12/2003 |

OTHER PUBLICATIONS

Bossow, et al., "Engineered Measles Viruses for Oncolytic Therapy of Pancreatic Cancer," Molecular Therapy, May 2010, vol. 18, Supplement 1, p. S321.
Fielding, Adele K., "Measles as a potential oncolytic virus," Rev. Med. Virol. 2005; vol. 15: pp. 135-142.
Blechacz, et al: "Engineered Measles Virus as a Novel Oncolytic Viral Therapy System for Heptacellular Carcinoma," Hepatology, 2006, pp. 1465-1477.
Cathomen, et al., "Measles Viruses with Altered Envelope Protein Cytoplasmic Tails Gain Cell Fusion Competence," J. Virol., Feb. 1998, vol. 72, No. 2, pp. 1224-1234.
Cattaneo, et al: "Reprogrammed viruses as cancer therapeutics: targeted, armed and shielded" Nature Reviews. Microbiology, Jul. 1, 2008, vol. 6, No. 7, pp. 529-540.
Duprex, et al., "Observation of Measles Virus Cell-to-Cell Spread in Astrocytoma Cells by Using a Green Fluorescent Protein-Expressing Recombinant Virus," J. Virol., Nov. 1999, vol. 73, No. 11, pp. 9568-9575.
Erbs, et al: "In Vivo Cancer Gene Therapy by Adenovirus-mediated Transfer of a Bifunctional Yeast Cytosine Deaminase/Uracil Phosphoribosyltransferase Fusion Gene," Cancer Research, 2000, vol. 60, pp. 3813-3822.
Galanis, et al: "Phase I Trial of Interperitoneal Administration of an Oncolytic Measels Virus Strain Engineered to Express Carcinoembryonic Antigen for Recurrent Ovarian Cancer," Cancer Research, 2010, vol. 70, pp. 875-882.
Gassen, et al., "Establishment of a Rescue System for Canine Distemper Virus," J. Virol., Nov. 2000, vol. 74, No. 22, pp. 10737-10744.
Inoue, et al: "An Improved Method for Recovering Rabies Virus from Cloned cDNA" J. Virol, 2003, vol. 107, pp. 229-236.

(Continued)

Primary Examiner — Doug Schultz
(74) Attorney, Agent, or Firm — Todd A. Lorenz

(57) ABSTRACT

The present invention pertains to a pharmaceutical composition comprising a recombinant measles virus encoding a suicide gene for use in the treatment of malignant cells with primary or secondary resistances against an oncolytic measles virus without suicide gene activity. Further, the present invention pertains to a recombinant measles virus based on measles vaccine strain Schwarz encoding a suicide gene, which comprises a fusion of a cytosine deaminase, particularly yeast cytosine deaminase, and a uracil phosphoribosyltransferase, particularly yeast uracil phosphoribosyltransferase, to a method and a kit for preparing the recombinant measles virus as claimed herein.

27 Claims, 79 Drawing Sheets

(56) References Cited

OTHER PUBLICATIONS

Kievit, et al.: "Yeast Cytosine Deaminase Improves Radiosensitization and Bystander Effect by 5-Fluorocytosine of Human Colorectal Cancer Xenografts" Cancer Research, 2000, vol. 60, pp. 6649-6655.
Laassri, et al: "Microarray Assay for Evaluation of the Genetic Stability of Modified Vaccinia Virus Ankara B5R Gene," J. Medical Virology, 2007, vol. 79, pp. 791-802.
Martin, et al.: "RNA Polymerase II-Controlled Expression of Antigenomic RNA Enhances the Rescue Efficacies of Two Different Members of the Monogavirales Independently of the Site of Genome Replication", J. Virol., Jun. 20, 2006, vol. 80, pp. 5708-5715.
Maisner, et al., "Recombinant measles virus requiring an exogenous protease for activation of infectivity," J. Gen. Virol., 2000, vol. 81, pp. 441-449.
Moeller, et al., "Recombinant Measles Viruses Expressing Altered Hemagglutinin (H) Genes: Functional Separation of Mutations Determining H Antibody Escape from Neurovirulence," J. Virol, Aug. 2001, vol. 75, No. 16, pp. 7612-7620.
Msaouel, et al: "Clinical Testing of Engineered Oncolytic Measles Vius Strains in the Treatmet of Cancer: An Overview," Curr. Opin. Mol. Ther., 2009, vol. 11 No. 1, pp. 43-53.
Nakayama, et al, "Leucine at position 278 of the AIK-C measles virus vaccine strain fusion protein is responsible for reduced syncytium formation," J. Gen. Virol., 2001, vol. 82, pp. 2143-2150.
NCBI Blast:bg-AF266286.1 Measles virus strain Edmonston (AIK-C vaccine), complete genome(15894bp), (http://blast.ncbi.nlm.nih.gov/Blast.cgi).
Neumann, et al., "A decade after the generation of a negative-sense RNA virus from cloned cDNA—what have we learned?," J. Gen. Virol., 2002, vol. 83, pp. 2635-2662.
Parks, et al., "Enhanced Measles Virus cDNA Rescue and Gene Expression after Heat Shock," J. Virol., May 1999, Vo. 73, No. 5, pp. 3560-3566.
Parks, et al: "Comparison of Predicted Amindo Acid Sequences of Measles Virus Strains in the Edmonston Vaccine Lineage," J. Virol., 2001, vol. 75, No. 2, pp. 910-920.
Parks, et al: "Analysis of the Noncoding Regions of Measles Virus Strains in the Edmonston Vaccine Lineage," J. Virol., 2001, vol. 75, No. 2, pp. 921-933.
Peng, et al: "Non-invasive in vivo Monitoring of Trackable Viruses Expressing Soluble Marker Peptides," Nature Medicine, 2002, vol. 8, No. 5, pp. 527-531.
Radecke, et al.: "Rescue of measles viruses from cloned DNA," EMBO Journal, vol. 14, Nov. 19, 2007, vol. 14, No. 23, pp. 5773-5784.
Römer-Oberdörfer, et al., "Generation of recombinant lentogenic Newcastle disease virus from cDNA," J. Gen. Virol., 1999, vol. 80, pp. 2987-2995.
Singh, et al., "A Recombinant Measles Virus Expressing Hepatitis B Virus Surface Antigen Induces Humoral Immune Response in Genetically Modified Mice," J. Virol., Jun. 1999, vol. 73, No. 6, pp. 4823-4828.
Singh, et al., "A recombinant measles virus expressing biologically active human interleukin-12," J. Gen. Virol., 1999, vol. 80, pp. 101-106.
Springfield, et al.: "Recombinant Measles viruses encoding suicide genes for oncolytic therapy," Molecular Therapy, May 2004, vol. 9, No. Supplement 1, 593, p. S224.
Stritzker, et al: "Prodrug converting enzyme gene delivery by L. monocytogenes," BMC CANCER, 2008, vol. 8, No. 94, pp. 1-10.
Takeda, et al., "Recovery of Pathogenic Measles Virus from Cloned cDNA," J. Virol., Jul. 2000, vol. 74, No. 14, pp. 6643-6647.
Takeuchi, et al, "Recombinant Wild-Type and Edmonston Strain Measles Viruses Bearing Heterologous H Proteins: Role of H Protein in Cell Fusion and Host Cell Specificity," J. Virol., May 2002, vol. 76, No. 10, pp. 4891-4900.
Tillieux, et al.: "Comparative analysis of the complete nucleotide sequences of measles, mumps, and rubella strain genomes contained in Priorix-TetraT," and ProQuadTM live attenuated combined vaccines, Vaccine, Apr. 2009, vol. 27, pp. 2265-2273.
Tiraby, et al: "Concomitant Expression of *E. coli* Cytosine Deaminase and Uracil Phosphoribosyltransferase Improves the Cytotoxicity of 5-fluorocytosine," FEMS Microbiologyy Letters, 1998, vol. 167, pp. 41-49.
Ungerechts, et al: "Next General Measles Virus Vetorfor Oncolytic Therapy: Targeted, Armed and Stealth," Molecular Therapy, May 2006, vol. 13, supplement1, p. S373.
Ungerechts, et al: "An Immunocompetent Murine Model for Oncolysis with an Armed and Targeted Measles Virus," Molecular Therapy, Nov. 2007, vol. 15, No. 11, pp. 1991-1997.
Ungerechts, et al: "Lymphoma chemoviortherapy: CD20-targeted and convertase-armed measles virus can synergize with fludarabine," Cancer Research, Nov. 15, 2007, vol. 67, No. 22, pp. 10939-10947.
Wybranietz, et al: "Enhanced Suicide Gene Effect by Adenviral Transduction of a VP22-cytosine Deaminase (CD) Fusion Gene," Gene Therapy, Nov. 1, 2001, vol. 8, No. 21, pp. 1654-1664.

FIG. 1A

```
   1 accaaacaaa gttgggtaag gatagttcaa tcaatgatca tcttctagtg cacttaggat
  61 tcaagatcct attatcaggg acaagagcag gattagggat atccgagatg gccacacttt
 121 taaggagctt agcattgttc aaaagaaaca aggacaaacc acccattaca tcaggatccg
 181 gtggagccat cagaggaatc aaacacatta ttatagtacc aatccctgga gattcctcaa
 241 ttaccactcg atccagactt ctggaccggt tggtgaggtt aattggaaac ccggatgtga
 301 gcgggcccaa actaacaggg gcactaatag gtatattatc cttatttgtg gagtctccag
 361 gtcaattgat tcagaggatc accgatgacc ctgacgttag cataaggctg ttagaggttg
 421 tccagagtga ccagtcacaa tctggcctta ccttcgcatc aagaggtacc aacatggagg
 481 atgaggcgga ccaatacttt tcacatgatg atccaattag tagtgatcaa tccaggttcg
 541 gatggttcgg gaacaaggaa atctcagata ttgaagtgca agaccctgag ggattcaaca
 601 tgattctggg taccatccta gcccaaattt gggtcttgct cgcaaaggcg ttacggccc
 661 cagacacggc agctgattcg gagctaagaa ggtggataaa gtacacccaa caaagaaggg
 721 tagttggtga atttagattg gagagaaaat ggttggatgt ggtgaggaac aggattgccg
 781 aggacctctc cttacgccga ttcatggtcg ctctaatcct ggatatcaag agaacacccg
 841 gaaacaaacc caggattgct gaaatgatat gtgacattga tacatatatc gtagaggcag
 901 gattagccag ttttatcctg actattaagt ttgggataga aactatgtat cctgctcttg
 961 gactgcatga atttgctggt gagttatcca cacttgagtc cttgatgaac ctttaccagc
1021 aaatggggga aactgcaccc tacatggtaa tcctggagaa ctcaattcag aacaagttca
1081 gtgcaggatc ataccctctg ctctggagct atgccatggg agtaggagtg aacttgaaa
1141 actccatggg aggtttgaac tttggccgat cttactttga tccagcatat tttagattag
1201 ggcaagagat ggtaaggagg tcagctggaa aggtcagttc cacattggca tctgaactcg
1261 gtatcactgc cgaggatgca aggcttgttt cagagattgc aatgcatact actgaggaca
1321 agatcagtag agcggttgga cccagacaag cccaagtatc atttctacac ggtgatcaaa
1381 gtgagaatga gctaccgaga ttgggggca aggaagatag gagggtcaaa cagagtcgag
1441 gagaagccag ggagagctac agagaaaccg ggcccagcag agcaagtgat gcgagagctg
1501 cccatcttcc aaccggcaca ccctagaca ttgacactgc aacggagtcc agccaagatc
1561 cgcaggacag tcgaaggtca gctgacgccc tgcttaggct gcaagccatg caggaatct
1621 cggaagaaca aggctcagac acggacaccc ctatagtgta caatgacaga aatcttctag
1681 actaggtgcg agaggccgag ggccagaaca acatccgcct accatccatc attgttataa
1741 aaaacttagg aaccaggtcc acacagccgc cagcccatca accatccact cccacgattg
1801 gagccaatgg cagaagagca ggcacgccat gtcaaaaacg gactggaatg catccgggct
1861 ctcaaggccg agcccatcgg ctcactggcc atcgaggaag ctatggcagc atggtcagaa
1921 atatcagaca acccagacag ggagcgagcc acctgcaggg aagagaaggc aggcagttcg
1981 ggtctcagca aaccatgcct ctcagcaatt ggatcaactg aaggcggtgc acctcgcatc
2041 cgcggtcagg gacctggaga gagcgatgac gacgctgaaa ctttgggaat cccccaaga
2101 aatctccagg catcaagcac tgggttacag tgttattacg tttatgatca cagcggtgaa
2161 gcggttaagg gaatccaaga tgctgactct atcatggttc aatcaggcct tgatggtgat
2221 agcaccctct caggaggaga caatgaatct gaaaacagcg atgtggatat tggcgaacct
2281 gataccgagg gatatgctat cactgaccgg ggatctgctc ccatctctat ggggttcagg
2341 gcttctgatg ttgaaactgc agaaggaggg gagatccacg agctcctgag actccaatcc
2401 agaggcaaca actttccgaa gcttgggaaa actctcaatg ttcctccgcc cccggacccc
2461 ggtagggcca gcacttccgg gacacccatt aaaagggca cagacgcgag attagcctca
2521 tttgaacgg agatcgcgtc tttattgaca ggtggtgcaa cccaatgtgc tcgaaagtca
2581 ccctcggaac catcagggcc aggtgcacct gcgggaatg tccccgagtg tgtgagcaat
2641 gccgcactga tacaggagtg gacacccgaa tctggtacca aatctcccc gagatcccag
2701 aataatgaag aagggggaga ctattatgat gatgagctgt tctctgatgt ccaagatatt
2761 aaaacagcct tggccaaaat acacgaggat aatcagaaga taatctccaa gctagaatca
2821 ctgctgttat tgaagggaga agttgagtca attaagaagc agatcaacag gcaaaatatc
2881 agcatatcca ccctgaaggg acacctctca agcatcatga tcgccattcc tggacttggg
2941 aaggatccca acgaccccac tgcagatgtc gaaatcaatc ccgacttgaa acccatcata
3001 ggcagagatt caggccgagc actggccgaa gttctcaaga acccgttgc cagccgacaa
3061 ctccaaggaa tgacaaatgg acggaccagt tccagaggac agctgctgaa ggaatttcag
3121 ctaaagccga tcgggaaaaa gatgagctca gccgtcgggt ttgttcctga caccggccct
3181 gcatcacgca gtgtaatccg ctccatcata aaatccagcc ggctagagga ggatcggaag
3241 cgttacctga tgactctcct tgatgatatc aaaggagcca atgatcttgc caagttccac
3301 cagatgctga tgaagataat aatgaagtag ctacagctca acttacctgc caacccatg
```

FIG. 1B

```
3361 ccagtcgacc caactagtac aacctaaatc cattataaaa aacttaggag caaagtgatt
3421 gcctcccaag gtccacaatg acagagacct acgacttcga caagtcggca tgggacatca
3481 aagggtcgat cgctccgata caacccacca cctacagtga tggcaggctg gtgccccagg
3541 tcagagtcat agatcctggt ctaggcgaca ggaaggatga atgctttatg tacatgtttc
3601 tgctggggt tgttgaggac agcgattccc tagggcctcc aatcgggcga gcatttgggt
3661 tcctgcccct aggtgttggc agatccacag caaagcccga aaaactcctc aaagaggcca
3721 ctgagcttga catagttgtt agacgtacag cagggctcaa tgaaaaactg gtgttctaca
3781 acaacacccc actaactctc ctcacacctt ggagaaaggt cctaacaaca gggagtgtct
3841 tcaacgcaaa ccaagtgtgc aatgcggtta atctgatacc gctcgatacc ccgcagaggt
3901 tccgtgttgt ttatatgagc atcacccgtc tttcggataa cgggtattac accgttccta
3961 gaagaatgct ggaattcaga tcggtcaatg cagtggcctt caacctgctg gtgaccctta
4021 ggattgacaa ggcgataggc cctgggaaga tcatcgacaa tacagagcaa cttcctgagg
4081 caacatttat ggtccacatc gggaacttca ggagaaagaa gagtgaagtc tactctgccg
4141 attattgcaa aatgaaaatc gaaaagatgg gcctggtttt tgcacttggt gggataggg
4201 gcaccagtct tcacattaga agcacaggca aaatgagcaa gactctccat gcacaactcg
4261 ggttcaagaa gaccttatgt tacccgctga tggatatcaa tgaagacctt aatcgattac
4321 tctggaggag cagatgcaag atagtaagaa tccaggcagt tttgcagcca tcagttcctc
4381 aagaattccg catttacgac gacgtgatca taaatgatga ccaaggacta ttcaaagttc
4441 tgtagaccgt agtgcccagc aatgcccgaa aacgaccccc ctcacaatga cagccagaag
4501 gcccggacaa aaaagccccc tccgaaagac tccacggacc aagcgagagg ccagccagca
4561 gccgacggca agcgcgaaca ccaggcggcc ccagcacaga acagccctga cacaaggcca
4621 ccaccagcca ccccaatctg catcctcctc gtgggacccc cgaggaccaa cccccaaggc
4681 tgccccgat ccaaaccacc aaccgcatcc ccaccaccc cgggaaagaa accccagca
4741 attggaaggc ccctcccct cttcctcaac acaagaactc cacaaccgaa ccgcacaagc
4801 gaccgaggtg acccaaccgc aggcatccga ctccctagac agatcctctc tccccggcaa
4861 actaaacaaa acttagggcc aaggaacata cacacccaac agaacccaga ccccggccca
4921 cggcgccgcg cccccaaccc ccgacaacca gagggagccc ccaaccaatc ccgccggctc
4981 ccccggtgcc cacaggcagg gacaccaacc cccgaacaga cccagcaccc aaccatcgac
5041 aatccaagac ggggggggccc ccccaaaaaa aggccccccag gggccgacag ccagcaccgc
5101 gaggaagccc acccaccccca cacacgacca cggcaaccaa accagaaccc agaccaccct
5161 gggccaccag ctcccagact cggccatcac cccgcagaaa ggaaaggcca caacccgcgc
5221 accccagccc cgatccggcg gggagccacc caacccgaac cagcacccaa gagcgatccc
5281 cgaaggaccc ccgaaccgca aaggacatca gtatcccaca gcctctccaa gtccccggt
5341 ctcctcctct tctcgaaggg accaaaagat caatccacca caccgacga cactcaactc
5401 cccaccccta aaggagacac cgggaatccc agaatcaaga ctcatccaat gtccatcatg
5461 ggtctcaagg tgaacgtctc tgccatattc atggcagtac tgttaactct ccaaacaccc
5521 accggtcaaa tccattgggg caatctctct aagatagggg tggtaggaat aggaagtgca
5581 agctacaaag ttatgactcg ttccagccat caatcattag tcataaaatt aatgcccaat
5641 ataactctcc tcaataactg cacgagggta gagattgcag aatacaggag actactgaga
5701 acagttttgg aaccaattag agatgcactt aatgcaatga cccagaatat aagaccggtt
5761 cagagtgtag cttcaagtag gagacacaag agatttgcgg gagtagtcct ggcaggtgcg
5821 gccctaggcg ttgccacagc tgctcagata acagccggca ttgcacttca ccagtccatg
5881 ctgaactctc aagccatcga caatctgaga gcgagcctgg aaactactaa tcaggcaatt
5941 gagacaatca gacaagcagg gcaggaaatg atattggctg ttcagggtgt ccaagactac
6001 atcaataatg agctgatacc gtctatgaac caactatctt gtgatttaat cggccagaag
6061 ctcgggctca aattgctcag atactataca gaaatcctgt cattatttgg ccccagttta
6121 cgggacccca tatctgcgga gatatctatc caggctttga gctatgcgct tggaggagac
6181 atcaataagg tgttagaaaa gctcggatac agtggaggtg atttactggg catcttagag
6241 agcggaggaa taaaggcccg gataactcac gtcgacacag agtcctactt cattgtcctc
6301 agtatagcct atccgacgct gtccgagatt aaggggtga ttgtccaccg gctagagggg
6361 gtctcgtaca acataggctc tcaagagtgg tataccactg tgcccaagta tgttgcaacc
6421 caagggtacc ttatctcgaa ttttgatgag tcatcgtgta ctttcatgcc agaggggact
6481 gtgtgcagcc aaaatgcctt gtacccgatg agtcctctgc tccaagaatg cctccggggg
6541 tacaccaagt cctgtgctcg tacactcgta tccgggtctt ttgggaaccg gttcattta
6601 tcacaaggga acctaatagc caattgtgca tcaatccttt gcaagtgtta cacaacagga
6661 acgatcatta atcaagaccc tgacaagatc ctaacataca ttgctgccga tcactgcccg
6721 gtagtcgagg tgaacggcgt gaccatccaa gtcggagca ggaggtatcc agacgctgtg
6781 tacttgcaca gaattgacct cggtcctccc atatcattgg agaggttgga cgtagggaca
6841 aatctgggga atgcaattgc taagttggag gatgccaagg aattgttgga gtcatcggac
6901 cagatattga ggagtatgaa aggtttatcg agcactagca tagtctacat cctgattgca
```

FIG. 1C

```
 6961 gtgtgtcttg gagggttgat agggatcccc gctttaatat gttgctgcag ggggcgttgt
 7021 aacaaaaagg gagaacaagt tggtatgtca agaccaggcc taaagcctga tcttacggga
 7081 acatcaaaat cctatgtaag gtcgctctga tcctctacaa ctcttgaaac acaaatgtcc
 7141 cacaagtctc ctcttcgtca tcaagcaacc accgcaccca gcatcaagcc cacctgaaat
 7201 tatctccggc ttccctctgg ccgaacaata tcggtagtta atcaaaactt agggtgcaag
 7261 atcatccaca atgtcaccac aacgagaccg gataaatgcc ttctacaaag ataacccca
 7321 tcccaaggga agtaggatag tcattaacag agaacatctt atgattgata gaccttatgt
 7381 tttgctggct gttctgtttg tcatgtttct gagcttgatc gggttgctag ccattgcagg
 7441 cattagactt catcgggcag ccatctacac cgcagagatc cataaaagcc tcagcaccaa
 7501 tctagatgta actaactcaa tcgagcatca ggtcaaggac gtgctgacac cactcttcaa
 7561 aatcatcggt gatgaagtgg gcctgaggac acctcagaga ttcactgacc tagtgaaatt
 7621 aatctctgac aagattaaat tccttaatcc ggatagggag tacgacttca gagatctcac
 7681 ttggtgtatc aacccgccag agagaatcaa attggattat gatcaatact gtgcagatgt
 7741 ggctgctgaa gagctcatga atgcattggt gaactcaact ctactggaga ccagaacaac
 7801 caatcagttc ctagctgtct caaagggaaa ctgctcaggg cccactacaa tcagaggtca
 7861 attctcaaac atgtcgctgt ccctgttaga cttgtattta ggtcgaggtt acaatgtgtc
 7921 atctatagtc actatgacat cccagggaat gtatggggga acttacctag tggaaaagcc
 7981 taatctgagc agcaaaaggt cagagttgtc acaactgagc atgtaccgag tgtttgaagt
 8041 aggtgttatc agaaatccgg gtttgggggc tccggtgttc catatgacaa actatcttga
 8101 gcaaccagtc agtaatgatc tcagcaactg tatggtggct ttgggggagc tcaaactcgc
 8161 agccctttgt cacggggaag attctatcac aattccctat cagggatcag ggaaaggtgt
 8221 cagcttccag ctcgtcaagc taggtgtctg gaaatcccca accgacatgc aatcctgggt
 8281 ccccttatca acggatgatc cagtgataga caggctttac ctctcatctc acagaggtgt
 8341 tatcgctgac aatcaagcaa aatgggctgt cccgacaaca cgaacagatg acaagttgcg
 8401 aatggagaca tgcttccaac aggcgtgtaa gggtaaaatc caagcactct gcgagaatcc
 8461 cgagtgggca ccattgaagg ataacaggat tccttcatac ggggtcttgt ctgttgatct
 8521 gagtctgaca gttgagctta aaatcaaaat tgcttcggga ttcgggccat tgatcacaca
 8581 cggttcaggg atggacctat acaaatccaa ccacaacaat gtgtattggc tgactatccc
 8641 gccaatgaag aacctagcct taggtgtaat caacacattg gagtggatac cgagattcaa
 8701 ggttagtccc tacctcttca ctgtcccaat taaggaagca ggcgaagact gccatgcccc
 8761 aacatacctq cctqcqqaqq tqqatqqtqa tqtcaaactc agttccaatc tggtgattct
 8821 acctggtcaa gatctccaat atgttttggc aacctacgat acttccaggg ttgaacatgc
 8881 tgtggtttat tacgtttaca gcccaagccg ctcatttttct tactttatc cttttaggtt
 8941 gcctataaag ggggtcccca tcgaattaca agtggaatgc ttcacatggg accaaaaact
 9001 ctggtgccgt cacttctgtg tgcttgcgga ctcagaatct ggtggacata tcactcactc
 9061 tgggatggtg ggcatgggag tcagctgcac agtcacccgg gaagatggaa ccaatcgcag
 9121 atagggctgc tagtgaacca atcacatgat gtcacccaga catcaggcat acccactagt
 9181 gtgaaataga catcagaatt aagaaaaacg tagggtccaa gtggttcccc gttatggact
 9241 cgctatctgt caaccagatc ttatacccctg aagttcacct agatagcccg atagttacca
 9301 ataagatagt agccatcctg gagtatgctc gagtccctca cgcttacagc ctggaggacc
 9361 ctacactgtg tcagaacatc aagcaccgcc taaaaaacgg attttccaac caatgatta
 9421 taaacaatgt ggaagttggg aatgtcatca agtccaagct taggagttat ccggcccact
 9481 ctcatattcc atatccaaat tgtaatcagg atttatttaa catagaagac aaagagtcaa
 9541 cgaggaagat ccgtgaactc ctcaaaaagg ggaattcgct gtactccaaa gtcagtgata
 9601 aggttttcca atgcttaagg gacactaact cacggcttgg cctaggctcc gaattgaggg
 9661 aggacatcaa ggagaaagtt attaacttgg gagtttacat gcacagctcc cagtggtttg
 9721 agccctttct gttttggttt acagtcaaga ctgagatgag gtcagtgatt aaatcacaaa
 9781 cccatacttg ccataggagg agacacacac ctgtattctt cactggtagt tcagttgagt
 9841 tgctaatctc tcgtgacctt gttgctataa tcagtaaaga gtctcaacat gtatattacc
 9901 tgacatttga actggttttg atgtattgtg atgtcataga ggggaggtta atgacagaga
 9961 ccgctatgac tattgatgct aggtatacag agcttctagg aagagtcaga tacatgtgga
10021 aactgataga tggtttcttc cctgcactcg ggaatccaac ttatcaaatt gtagccatgc
10081 tggagcctct ttcacttgct tacctgcagc tgagggatat aacagtagaa ctcagaggtg
10141 ctttccttaa ccactgcttt actgaaatac atgatgttct tgaccaaaac gggttttctg
10201 atgaaggtac ttatcatgag ttaactgaag ctctagatta cattttcata actgatgaca
10261 tacatctgac aggggagatt ttctcatttt tcagaagttt cggccacccc agacttgaag
10321 cagtaacggc tgctgaaaat gttaggaaat acatgaatca gcctaaagtc attgtgtatg
10381 agactctgat gaaaggtcat gccatatttt gtggaatcat aatcaacggc tatcgtgaca
10441 ggcacggagg cagttggcca ccgctgaccc tcccctgca tgctgcagac acaatccgga
10501 atgctcaagc ttcaggtgaa gggttaacac atgagcagtg cgttgataac tggaaatctt
```

FIG. 1D

```
10561  ttgctggagt gaaatttggc tgctttatgc ctcttagcct ggatagtgat ctgacaatgt
10621  acctaaagga caaggcactt gctgctctcc aaagggaatg ggattcagtt tacccgaaag
10681  agttcctgcg ttacgaccct cccaagggaa ccgggtcacg gaggcttgta gatgttttcc
10741  ttaatgattc gagctttgac ccatatgatg tgataatgta tgttgtaagt ggagcttacc
10801  tccatgaccc tgagttcaac ctgtcttaca gcctgaaaga aaaggagatc aaggaaacag
10861  gtagactttt tgctaaaatg acttacaaaa tgagggcatg ccaagtgatt gctgaaaatc
10921  taatctcaaa cgggattggc aaatatttta aggacaatgg gatggccaag gatgagcacg
10981  atttgactaa ggcactccac actctagctg tctcaggagt ccccaaagat ctcaaagaaa
11041  gtcacagggg ggggccagtc ttaaaaacct actcccgaag cccagtccac acaagtacca
11101  ggaacgtgag agcagcaaaa gggtttatag ggttccctca agtaattcgg caggaccaag
11161  acactgatca tccgagaat atggaagctt acgagacagt cagtgcattt atcacgactg
11221  atctcaagaa gtactgcctt aattggagat atgagaccat cagcttgttt gcacagaggc
11281  taaatgagat ttacggattg ccctcatttt tccagtggct gcataagagg cttgagacct
11341  ctgtcctgta tgtaagtgac cctcattgcc ccccgacct tgacgcccat atcccgttat
11401  ataaagtccc caatgatcaa atcttcatta agtaccctat gggaggtata aagggtatt
11461  gtcagaagct gtggaccatc agcaccattc cctatctata cctggctgct tatgagagcg
11521  gagtaaggat tgcttcgtta gtgcaagggg acaatcagac catagccgta acaaaaaggg
11581  tacccagcac atggccctac aaccttaaga acgggaagc tgctagagta actagagatt
11641  actttgtaat tcttaggcaa aggctacatg atattggcca tcacctcaag gcaaatgaga
11701  caattgtttc atcacatttt tttgtctatt caaaaggaat atattatgat gggctacttg
11761  tgtcccaatc actcaagagc atcgcaagat gtgtattctg tcagagact atagttgatg
11821  aaacaaggc agcatgcagt aatattgcta caacaatggc taaaagcatc gagagaggtt
11881  atgaccgtta ccttgcatat tccctgaacg tcctaaaagt gatacagcaa attctgatct
11941  ctcttggctt cacaatcaat tcaaccatga cccggatgt agtcataccc ctcctcacaa
12001  acaacgacct cttaataagg atggcactgt tgcccgctcc tattgggggg atgaattatc
12061  tgaatatgag caggctgttt gtcagaaaca tcggtgatcc agtaacatca tcaattgctg
12121  atctcaagag aatgattctc gcctcactaa tgcctgaaga gaccctccat caagtaatga
12181  cacaacaacc gggggactct tcattcctag actgggctag cgacccttac tcagcaaatc
12241  ttgtatgtgt ccagagcatc actagactcc tcaagaacat aactgcaagg tttgtcctga
12301  tccatagtcc aaacccaatg ttaaaaggat tattccatga tgacagtaaa gaagaggacg
12361  agggactggc ggcattcctc atggacaggc atattatagt acctagggca gctcatgaaa
12421  tcctggatca tagtgtcaca ggggcaagag agtctattgc aggcatgctg gataccacaa
12481  aaggcttgat tcgagccagc atgaggaagg ggggttaac ctctcgagtg ataaccagat
12541  tgtccaatta tgactatgaa caattcagag cagggatggt gctattgaca ggaagaaaga
12601  gaaatgtcct cattgacaaa gagtcatgtt cagtgcagct ggcgagagct ctaagaagcc
12661  atatgtgggc gaggctagct cgaggacggc ctatttacgg ccttgaggtc cctgatgtac
12721  tagaatctat gcgaggccac cttattcggc gtcatgagac atgtgtcatc tgcgagtgtg
12781  gatcagtcaa ctacggatgg tttttgtcc cctcgggttg ccaactggat gatattgaca
12841  aggaaacatc atccttgaga gtcccatata ttggttctac cactgatgag agaacagaca
12901  tgaagcttgc cttcgtaaga gccccaagtc gatccttgcg atctgctgtt agaatagcaa
12961  cagtgtactc atgggcttac ggtgatgatg atagctcttg gaacgaagcc tggttgttgg
13021  ctaggcaaag ggccaatgtg agcctggagg agctaagggt gatcactccc atctcaactt
13081  cgactaattt agcgcatagg ttgagggatc gtagcactca agtgaaatac tcaggtacat
13141  cccttgtccg agtggcgagg tataccacaa tctccaacga caatctctca tttgtcatat
13201  cagataagaa ggttgatact aactttatat accaacaagg aatgcttcta gggttgggtg
13261  ttttagaaac attgtttcga ctcgagaaag ataccggatc atctaacacg gtattacatc
13321  ttcacgtcga aacagattgt tgcgtgatcc cgatgataga tcatcccagg atacccagct
13381  cccgcaagct agagctgagg gcagacgtat gtaccaaccc attgatatat gataatgcac
13441  ctttaattga cagagatgca acaaggctat acacccgag ccataggagg caccttgtgg
13501  aatttgttac atggtccaca ccccaactat atcacatttt agctaagtcc acagcactat
13561  ctatgattga cctggtaaca aaatttgaga aggaccatat gaatgaaatt tcagctctca
13621  tagggatga cgatatcaat agtttcataa ctgagtttct gctcatagag ccaagattat
13681  tcactatcta cttgggccag tgtgcggcca tcaattgggc atttgatgta cattatcata
13741  gaccatcagg gaaatatcag atgggtgagc tgttgtcatc gttcctttct agaatgagca
13801  aaggagtgtt taaggtgctt gtcaatgctc taagccaccc aaagatctac aagaaattct
13861  ggcattgtgg tattatagag cctatccatg gtccttcact tgatgctcaa aacttgcaca
13921  caactgtgtg caacatggtt tacacatgct atatgaccta cctcgacctg ttgttgaatg
13981  aagagttaga agagttcaca tttctcttgt gtgaaagcga cgaggatgta gtaccggaca
14041  gattcgacaa catccaggca aaacacttat gtgttctggc agatttgtac tgtcaaccag
14101  ggacctgccc accaattcga ggtctaagac cggtagagaa atgtgcagtt ctaaccgacc
```

FIG. 1E

```
14161 atatcaaggc agaggctatg ttatctccag caggatcttc gtggaacata aatccaatta
14221 ttgtagacca ttactcatgc tctctgactt atctccggcg aggatcgatc aaacagataa
14281 gattgagagt tgatccagga ttcattttcg acgccctcgc tgaggtaaat gtcagtcagc
14341 caaagatcgg cagcaacaac atctcaaata tgagcatcaa ggctttcaga cccccacacg
14401 atgatgttgc aaaattgctc aaagatatca acacaagcaa gcacaatctt cccatttcag
14461 ggggcaatct cgccaattat gaaatccatg ctttccgcag aatcgggttg aactcatctg
14521 cttgctacaa agctgttgag atatcaacat taattaggag atgccttgag ccaggggagg
14581 acggcttgtt cttgggtgag ggatcgggtt ctatgttgat cacttataaa gagatactta
14641 aactaaacaa gtgcttctat aatagtgggg tttccgccaa ttctagatct ggtcaaaggg
14701 aattagcacc ctatccctcc gaagttggcc ttgtcgaaca cagaatggga gtaggtaata
14761 ttgtcaaagt gctctttaac gggaggcccg aagtcacgtg ggtaggcagt gtagattgct
14821 tcaatttcat agttagtaat atccctacct ctagtgtggg gtttatccat tcagatatag
14881 agaccttgcc tgacaaagat actatagaga agctagagga attggcagcc atcttatcga
14941 tggctctgct cctgggcaaa ataggatcaa tactggtgat taagcttatg cctttcagcg
15001 gggattttgt tcagggattt ataagttatg tagggtctca ttatagagaa gtgaaccttg
15061 tatacccctag atacagcaac ttcatctcta ctgaatctta tttggttatg acagatctca
15121 aggctaaccg gctaatgaat cctgaaaaga ttaagcagca gataattgaa tcatctgtga
15181 ggacttcacc tggacttata ggtcacatcc tatccattaa gcaactaagc tgcatacaag
15241 caattgtggg agacgcagtt agtagaggtg atatcaatcc tactctgaaa aaacttacac
15301 ctatagagca ggtgctgatc aattgcgggt tggcaattaa cggacctaag ctgtgcaaag
15361 aattgatcca ccatgatgtt gcctcaggc aagatggatt gcttaattct atactcatcc
15421 tctacaggga gttggcaaga ttcaaagaca accaaagaag tcaacaaggg atgttccacg
15481 cttacccgt attggtaagt agcaggcaac gagaacttat atctaggatc acccgcaaat
15541 tctgggggca cattcttctt tactccggga acaaaaagtt gataaataag tttatccaga
15601 atctcaagtc cggctatctg atactagact tacaccagaa tatcttcgtt aagaatctat
15661 ccaagtcaga gaaacagatt attatgacgg ggggtttgaa acgtgagtgg gttttaagg
15721 taacagtcaa ggagaccaaa gaatggtata agttagtcgg atacagtgcc ctgattaagg
15781 actaattggt tgaactccgg aaccctaatc ctgccctagg tggttaggca ttatttgcaa
15841 tatattaaag aaaactttga aaatacgaag tttctattcc cagctttgtc tggt
```

FIG. 2

```
atggtgacagggggaatggcaagcaagtgggatcagaagggtatggacattgcctatgagga
ggcggccttaggttacaaagagggtggtgttcctattggcggatgtcttatcaataacaaag
acggaagtgttctcggtcgtggtcacaacatgagatttcaaaagggatccgccacactacat
ggtgagatctccactttggaaaactgtgggagattagagggcaaagtgtacaaagataccac
tttgtatacgacgctgtctccatgcgacatgtgtacaggtgccatcatcatgtatggtattc
cacgctgtgttgtcggtgagaacgttaatttcaaaagtaagggcgagaaatatttacaaact
agaggtcacgaggttgttgttgttgacgatgagaggtgtaaaaagatcatgaaacaatttat
cgatgaaagacctcaggattggtttgaagatattggtgaggcttcggaaccatttaagaacg
tctacttgctacctcaaacaaaccaattgctgggtttgtacaccatcatcagaaataagaat
acaactagacctgatttcattttctactccgatagaatcatcagattgttggttgaagaagg
tttgaaccatctacctgtgcaaaagcaaattgtggaaactgacaccaacgaaaacttcgaag
gtgtctcattcatgggtaaaatctgtggtgtttccattgtcagagctggtgaatcgatggag
caaggattaagagactgttgtaggtctgtgcgtatcggtaaaatttttaattcaaagggacga
ggagactgctttaccaaagttattctacgaaaaattaccagaggatatatctgaaaggtatg
tcttcctattagacccaatgctggccaccggtggtagtgctatcatggctacagaagtcttg
attaagagaggtgttaagccagagagaatttacttcttaaacctaatctgtagtaaggaagg
gattgaaaaataccatgccgccttcccagaggtcagaattgttactggtgccctcgacagag
gtctagatgaaaacaagtatctagttccagggttgggtgactttggtgacagatactactgt
gtttaa
``` cytosine deaminase (CD)
gct - linker (alanin)
<u>uracil phosphoribosyltransferase(UPRT)</u>

Figure 3A:
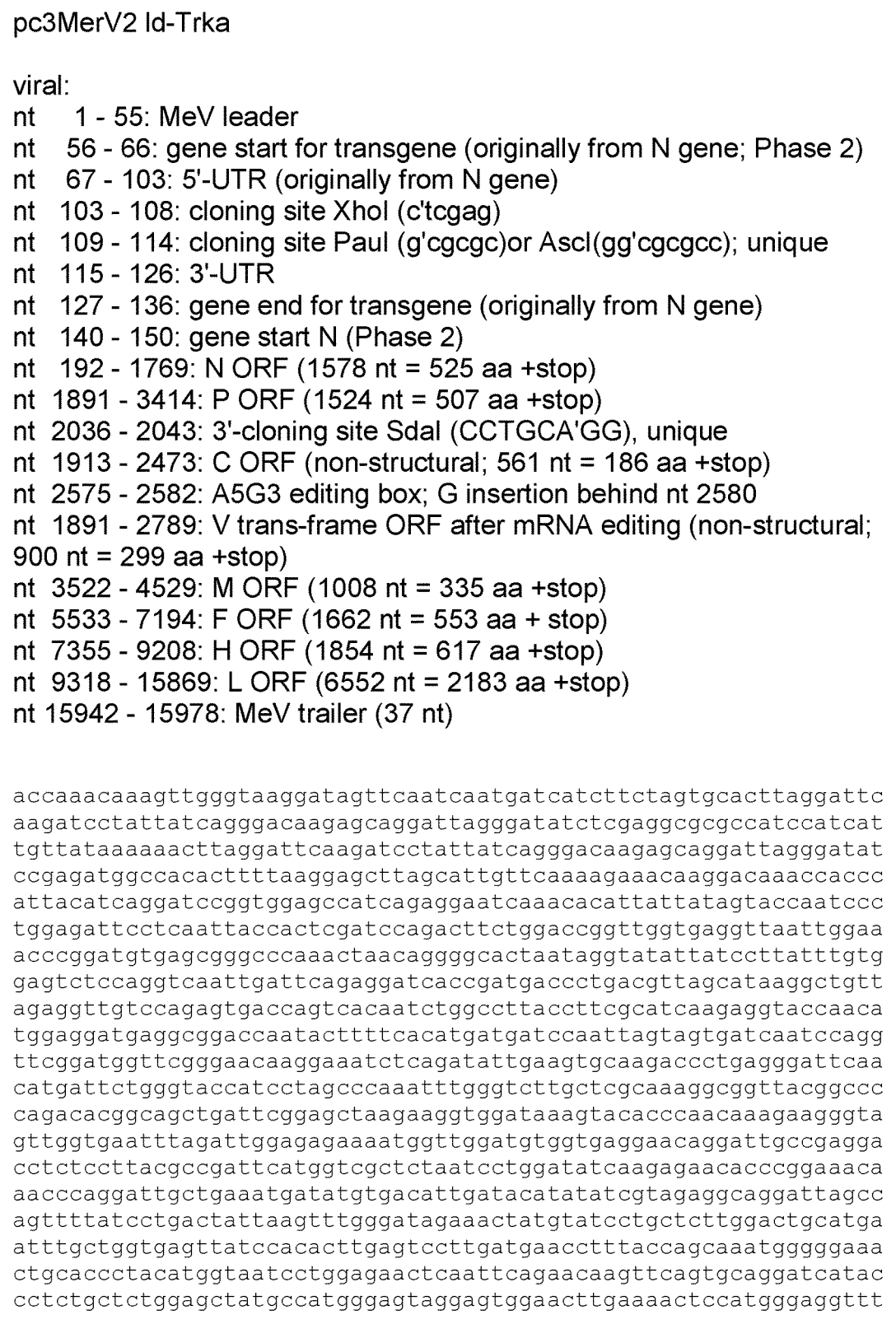

FIG. 3A pc3MerV2 ld-Trka viral:
nt   1 - 55: MeV leader
nt   56 - 66: gene start for transgene (originally from N gene; Phase 2)
nt   67 - 103: 5'-UTR (originally from N gene)
nt   103 - 108: cloning site XhoI (c'tcgag)
nt   109 - 114: cloning site PauI (g'cgcgc)or AscI(gg'cgcgcc); unique
nt   115 - 126: 3'-UTR
nt   127 - 136: gene end for transgene (originally from N gene)
nt

FIG. 3B gaactttggccgatcttactttgatccagcatattttagattagggcaagagatggtaagga
ggtcagctggaaaggtcagttccacattggcatctgaactcggtatcactgccgaggatgca
aggcttgtttcagagattgcaatgcatactactgaggacaagatcagtagagcggttggacc
cagacaagcccaagtatcatttctacacggtgatcaaagtgagaatgagctaccgagattgg
ggggcaaggaagataggagggtcaaacagagtcgaggagaagccagggagagctacagagaa
accgggcccagcagagcaagtgatgcgagagctgcccatcttccaaccggcacacccctaga
cattgacactgcaacggagtccagccaagatccgcaggacagtcgaaggtcagctgacgccc
tgcttaggctgcaagccatggcaggaatctcggaagaacaaggctcagacacggacacccct
atagtgtacaatgacagaaatcttctagactaggtgcgagaggccgagggccagaacaacat
ccgcctaccatccatcattgttataaaaacttaggaaccaggtccacacagccgccagccc
atcaaccatccactcccacgattggagccaatggcagaagagcaggcacgccatgtcaaaaa
cggactggaatgcatccgggctctcaaggccgagcccatcggctcactggccatcgaggaag
ctatggcagcatggtcagaaatatcagacaacccaggacaggagcgagccacctgcagggaa
gagaaggcaggcagttcgggtctcagcaaccatgcctctcagcaattggatcaactgaagg
cggtgcacctcgcatccgcggtcagggacctggagagagcgatgacgacgctgaaactttgg
gaatcccccaagaaatctccaggcatcaagcactgggttacagtgttattacgtttatgat
cacagcggtgaagcggttaagggaatccaagatgctgactctatcatggttcaatcaggcct
tgatggtgatagcaccctctcaggaggagacaatgaatctgaaaacagcgatgtggatattg
gcgaacctgataccgagggatatgctatcactgaccggggatctgctcccatctctatgggg
ttcagggcttctgatgttgaaactgcagaaggaggggagatccacgagctcctgagactcca
atccagaggcaacaactttccgaagcttgggaaaactctcaatgttcctccgcccccggacc
ccggtagggccagcacttccgggacacccattaaaaagggcacagacgcgagattagcctca
tttggaacggagatcgcgtctttattgacaggtggtgcaacccaatgtgctcgaaagtcacc
ctcggaaccatcagggccaggtgcacctgcggggaatgtccccgagtgtgtgagcaatgccg
cactgatacaggagtggacacccgaatctggtaccacaatctccccgagatcccagaataat
gaagaaggggggagactattatgatgatgagctgttctctgatgtccaagatattaaaacagc
cttggccaaaatacacgaggataatcagaagataatctccaagctagaatcactgctgttat
tgaagggagaagttgagtcaattaagaagcagatcaacaggcaaaatatcagcatatccacc
ctggaaggacacctctcaagcatcatgatcgccattcctggacttgggaaggatcccaacga
ccccactgcagatgtcgaaatcaatcccgacttgaaacccatcataggcagagattcaggcc
gagcactggccgaagttctcaagaaacccgttgccagccgacaactccaaggaatgacaaat
ggacggaccagttccagaggacagctgctgaaggaatttcagctaaagccgatcgggaaaaa
gatgagctcagccgtcgggtttgttcctgacaccggccctgcatcacgcagtgtaatccgct
ccattataaaatccagccggctagaggaggatcggaagcgttacctgatgactctccttgat
gatatcaaaggagccaatgatcttgccaagttccaccagatgctgatgaagataataatgaa
gtagctacagctcaacttacctgccaaccccatgccagtcgacccaactagtacaacctaaa
tccattataaaaaacttaggagcaaagtgattgcctcccaaggtccacaatgacagagacct
acgacttcgacaagtcggcatgggacatcaaagggtcgatcgctccgatacaacccaccacc
tacagtgatggcaggctggtgccccaggtcagagtcatagatcctggtctaggcgacaggaa
ggatgaatgctttatgtacatgtttctgctgggggttgttgaggacagcgattccctagggc
ctccaatcgggcgagcatttgggttcctgcccttaggtgttggcagatccacagcaaagccc
gaaaaactcctcaaagaggccactgagcttgacatagttgtagacgtacagcagggctcaa
tgaaaaactggtgttctacaacaacaccccactaactctcctcacaccttggagaaaggtcc
taacaacagggagtgtcttcaacgcaaaccaagtgtgcaatgcggttaatctgataccgctc
gataccccgcagaggttccgtgttgtttatatgagcatcacccgtctttcggataacgggta
ttacaccgttcctagaagaatgctggaattcagatcggtcaatgcagtggccttcaacctgc
tggtgacccttaggattgacaaggcgataggccctgggaagatcatcgacaatacagagcaa
cttcctgaggcaacatttatggtccacatcgggaacttcaggagaaagaagagtgaagtcta
ctctgccgattattgcaaaatgaaaatcgaaaagatgggcctggttttgcacttggtggga
taggggggcaccagtcttcacattagaagcacaggcaaaatgagcaagactctccatgcacaa

FIG. 3C ctcgggttcaagaagaccttatgttacccgctgatggatatcaatgaagaccttaatcgatt
actctggaggagcagatgcaagatagtaagaatccaggcagttttgcagccatcagttcctc
aagaattccgcatttacgacgacgtgatcataaatgatgaccaaggactattcaaagttctg
tagaccgtagtgcccagcaatgcccgaaaacgacccccctcacaatgacagccagaaggccc
ggacaaaaaagcccctccgaaagactccacggaccaagcgagaggccagccagcagccgac
ggcaagcgcgaacaccaggcggccccagcacagaacagccctgacacaaggccaccaccagc
cacccaatctgcatcctcctcgtgggaccccgaggaccaaccccaaggctgccccgat
ccaaaccaccaaccgcatcccaccaccccgggaaagaaaccccagcaattggaaggccc
ctcccctcttcctcaacacaagaactccacaaccgaaccgcacaagcgaccgaggtgaccc
aaccgcaggcatccgactccctagacagatcctctctcccggcaaactaaacaaaacttag
ggccaaggaacatacacacccaacagaacccagaccccggcccacggcgccgcgcccccaac
ccccgacaaccagagggagcccccaaccaatcccgccggctcccccggtgcccacaggcagg
gacaccaaccccgaacagacccagcacccaaccatcgacaatccaagacgggggggccccc
caaaaaaggcccccaggggccgacagccagcaccgcgaggaagcccacccaccccacaca
cgaccacggcaaccaaaccagaacccagaccaccctgggccaccagctcccagactcggcca
tcaccccgcagaaaggaaaggccacaacccgcgcaccccagccccgatccggcggggagcca
cccaacccgaaccagcacccaagagcgatccccgaaggaccccgaaccgcaaaggacatca
gtatcccacagcctctccaagtcccccggtctcctcctcttctcgaagggaccaaaagatca
atccaccacacccgacgacactcaactccccacccctaaaggagacaccgggaatcccagaa
tcaagactcatccaatgtccatcatgggtctcaaggtgaacgtctctgccatattcatggca
gtactgttaactctccaaacacccaccggtcaaatccattggggcaatctctctaagatagg
ggtggtaggaataggaagtgcaagctacaaagttatgactcgttccagccatcaatcattag
tcataaaattaatgcccaatataactctcctcaataactgcacgagggtagagattgcagaa
tacaggagactactgagaacagttttggaaccaattagagatgcacttaatgcaatgaccca
gaatataagaccggttcagagtgtagcttcaagtaggagacacaagagatttgcgggagtag
tcctggcaggtgcggccctaggcgttgccacagctgctcagataacagccggcattgcactt
caccagtccatgctgaactctcaagccatcgacaatctgagagcgagcctggaaactactaa
tcaggcaattgagacaatcagacaagcagggcaggagatgatattggctgttcagggtgtcc
aagactacatcaataatgagctgataccgtctatgaaccaactatcttgtgatttaatcggc
cagaagctcgggctcaaattgctcagatactatacagaaatcctgtcattatttggccccag
tttacgggaccccatatctgcggagatatctatccaggctttgagctatgcgcttggaggag
acatcaataaggtgttagaaaagctcggatacagtggaggtgatttactgggcatcttagag
agcggaggaataaaggcccggataactcacgtcgacacagagtcctacttcattgtcctcag
tatagcctatccgacgctgtccgagattaaggggtgattgtccaccggctagagggggtct
cgtacaacataggctctcaagagtggtataccactgtgcccaagtatgttgcaacccaaggg
taccttatctcgaattttgatgagtcatcgtgtactttcatgccagaggggactgtgtgcag
ccaaaatgccttgtacccgatgagtcctctgctccaagaatgcctccggggggtacaccaagt
cctgtgctcgtacactcgtatccgggtcttttgggaaccggttcattttatcacaagggaac
ctaatagccaattgtgcatcaatcctttgcaagtgttacacaacaggaacgatcattaatca
agaccctgacaagatcctaacatacattgctgccgatcactgcccggtagtcgaggtgaacg
gcgtgaccatccaagtcgggagcaggaggtatccagacgctgtgtacttgcacagaattgac
ctcggtcctcccatatcattggagaggttggacgtagggacaaatctggggaatgcaattgc
taagttggaggatgccaaggaattgttggagtcatcggaccagatattgaggagtatgaaag
gtttatcgagcactagcatagtctacatcctgattgcagtgtgtcttggagggttgataggg
atccccgctttaatatgttgctgcaggggcgttgtaacaaaagggagaacaagttggtat
gtcaagaccaggcctaaagcctgatcttacgggaacatcaaaatcctatgtaaggtcgctct
gatcctctacaactcttgaaacacaaatgtcccacaagtctcctcttcgtcatcaagcaacc
accgcacccagcatcaagcccacctgaaattatctccggcttccctctggccgaacaatatc
ggtagttaatcaaaacttagggtgcaagatcatccacaatgtcaccacaacgagaccggata
aatgccttctacaaagataaccccatcccaagggaagtaggatagtcattaacagagaaca

FIG. 3D

```
tcttatgattgatagaccttatgttttgctggctgttctgtttgtcatgtttctgagcttga
tcgggttgctagccattgcaggcattagacttcatcgggcagccatctacaccgcagagatc
cataaaagcctcagcaccaatctagatgtaactaactcaatcgagcatcaggtcaaggacgt
gctgacaccactcttcaaaatcatcggtgatgaagtgggcctgaggacacctcagagattca
ctgacctagtgaaattaatctctgacaagattaaattccttaatccggatagggagtacgac
ttcagagatctcacttggtgtatcaacccgccagagagaatcaaattggattatgatcaata
ctgtgcagatgtggctgctgaagagctcatgaatgcattggtgaactcaactctactggaga
ccagaacaaccaatcagttcctagctgtctcaaagggaaactgctcagggcccactacaatc
agaggtcaattctcaaacatgtcgctgtccctgttagacttgtatttaggtcgaggttacaa
tgtgtcatctatagtcactatgacatcccagggaatgtatggggaacttacctagtggaaa
agcctaatctgagcagcaaaaggtcagagttgtcacaactgagcatgtaccgagtgtttgaa
gtaggtgttatcagaaatccgggtttgggggctccggtgttccatatgacaaactatcttga
gcaaccagtcagtaatgatctcagcaactgtatggtggctttgggggagctcaaactcgcag
ccctttgtcacggggaagattctatcacaattccctatcagggatcagggaaaggtgtcagc
ttccagctcgtcaagctaggtgtctggaaatccccaaccgacatgcaatcctgggtcccctt
atcaacggatgatccagtgatagacaggctttacctctcatctcacagaggtgttatcgctg
acaatcaagcaaaatgggctgtcccgacaacacgaacagatgacaagttgcgaatggagaca
tgcttccaacaggcgtgtaagggtaaaatccaagcactctgcgagaatcccgagtgggcacc
attgaaggataacaggattccttcatacggggtcttgtctgttgatctgagtctgacagttg
agcttaaaatcaaaattgcttcgggattcgggccattgatcacacacggttcagggatggac
ctatacaaatccaaccacaacaatgtgtattggctgactatcccgccaatgaagaacctagc
cttaggtgtaatcaacacattggagtggataccgagattcaaggttagtccctacctcttca
ctgtcccaattaaggaagcaggcgaagactgccatgccccaacatacctacctgcggaggtg
gatggtgatgtcaaactcagttccaatctggtgattctacctggtcaagatctccaatatgt
tttggcaacctacgatacttccagggttgaacatgctgtggtttattacgtttacagcccaa
gccgctcattttcttacttttatccttttaggttgcctataaagggggtccccatcgaatta
caagtggaatgcttcacatgggaccaaaaactctggtgccgtcacttctgtgtgcttgcgga
ctcagaatctggtggacatatcactcactctgggatggtgggcatgggagtcagctgcacag
tcacccgggaagatggaaccaatcgcagatagggctgctagtgaaccaatcacatgatgtca
cccagacatcaggcatacccactagtgtgaaatagacatcagaattaagaaaaacgtagggt
ccaagtggttccccgttatggactcgctatctgtcaaccagatcttataccctgaagttcac
ctagatagcccgatagttaccaataagatagtagccatcctggagtatgctcgagtccctca
cgcttacagcctggaggaccctacactgtgtcagaacatcaagcaccgcctaaaaaacggat
tttccaaccaaatgattataaacaatgtggaagttgggaatgtcatcaagtccaagcttagg
agttatccggcccactctcatattccatatccaaattgtaatcaggatttatttaacataga
agacaaagagtcaacgaggaagatccgtgaactcctcaaaaagggaattcgctgtactcca
aagtcagtgataaggttttccaatgcttaagggacactaactcacggcttggcctaggctcc
gaattgagggaggacatcaaggagaaagttattaacttgggagtttacatgcacagctccca
gtggtttgagccctttctgttttggtttacagtcaagactgagatgaggtcagtgattaaat
cacaaacccatacttgccataggaggagacacacacctgtattcttcactggtagttcagtt
gagttgctaatctctcgtgaccttgttgctataatcagtaaagagtctcaacatgtatatta
cctgacatttgaactggttttgatgtattgtgatgtcatagaggggaggttaatgacagaga
ccgctatgactattgatgctaggtatacagagcttctaggaagagtcagatacatgtggaaa
ctgatagatggtttcttccctgcactcgggaatccaacttatcaaattgtagccatgctgga
gcctctttcacttgcttacctgcagctgagggatataacagtagaactcagaggtgctttcc
ttaaccactgctttactgaaatacatgatgttcttgaccaaaacgggttttctgatgaaggt
acttatcatgagttaactgaagctctagattacattttcataactgatgacatacatctgac
agggagattttctcattttcagaagtttcggccacccagacttgaagcagtaacggctg
ctgaaaatgttaggaaatacatgaatcagcctaaagtcattgtgtatgagactctgatgaaa
ggtcatgccatattttgtggaatcataatcaacggctatcgtgacaggcacggaggcagttg
```

FIG. 3E

```
gccaccgctgaccctcccctgcatgctgcagacacaatccggaatgctcaagcttcaggtg
aagggttaacacatgagcagtgcgttgataactggaaatcttttgctggagtgaaatttggc
tgctttatgcctcttagcctggatagtgatctgacaatgtacctaaaggacaaggcacttgc
tgctctccaaagggaatgggattcagtttacccgaaagagttcctgcgttacgaccctccca
agggaaccgggtcacggaggcttgtagatgttttccttaatgattcgagctttgacccatat
gatgtgataatgtatgttgtaagtggagcttacctccatgaccctgagttcaacctgtctta
cagcctgaaagaaaggagatcaaggaaacaggtagacttttttgctaaaatgacttacaaaa
tgagggcatgccaagtgattgctgaaaatctaatctcaaacgggattggcaaatattttaag
gacaatgggatggccaaggatgagcacgatttgactaaggcactccacactctagctgtctc
aggagtccccaaagatctcaaagaaagtcacagggggggccagtcttaaaaacctactccc
gaagcccagtccacacaagtaccaggaacgtgagagcagcaaaagggtttatagggttccct
caagtaattcggcaggaccaagacactgatcatccggagaatatggaagcttacgagacagt
cagtgcatttatcacgactgatctcaagaagtactgccttaattggagatatgagaccatca
gcttgtttgcacagaggctaaatgagatttacggattgccctcattttttccagtggctgcat
aagaggcttgagacctctgtcctgtatgtaagtgaccctcattgccccccgaccttgacgc
ccatatcccgttatataaagtccccaatgatcaaatcttcattaagtaccctatgggaggta
tagaagggtattgtcagaagctgtggaccatcagcaccattccctatctatacctggctgct
tatgagagcggagtaaggattgcttcgttagtgcaaggggacaatcagaccatagccgtaac
aaaaagggtacccagcacatggccctacaaccttaagaaacgggaagctgctagagtaacta
gagattactttgtaattcttaggcaaaggctacatgatattggccatcacctcaaggcaaat
gagacaattgtttcatcacattttttgtctattcaaaaggaatatattatgatgggctact
tgtgtcccaatcactcaagagcatcgcaagatgtgtattctggtcagagactatagttgatg
aaacaagggcagcatgcagtaatattgctacaacaatggctaaaagcatcgagagaggttat
gaccgttaccttgcatattccctgaacgtcctaaaagtgatacagcaaattctgatctctct
tggcttcacaatcaattcaaccatgacccgggatgtagtcatacccctcctcacaaacaacg
acctcttaataaggatggcactgttgcccgctccattgggggggatgaattatctgaatatg
agcaggctgtttgtcagaaacatcggtgatccagtaacatcatcaattgctgatctcaagag
aatgattctcgcctcactaatgcctgaagagaccctccatcaagtaatgacacaacaaccgg
gggactcttcattcctagactgggctagcgacccttactcagcaaatcttgtatgtgtccag
agcatcactagactcctcaagaacataactgcaaggtttgtcctgatccatagtccaaaccc
aatgttaaaaggattattccatgatgacagtaaagaagaggacgagggactggcggcattcc
tcatggacaggcatattatagtacctagggcagctcatgaaatcctggatcatagtgtcaca
ggggcaagagagtctattgcaggcatgctggataccacaaaaggcttgattcgagccagcat
gaggaagggggggttaacctctcgagtgataaccagattgtccaattatgactatgaacaat
tcagagcagggatggtgctattgacaggaagaaagagaaatgtcctcattgacaaagagtca
tgttcagtgcagctggcgagagctctaagaagccatatgtgggcgaggctagctcgaggacg
gcctatttacggccttgaggtccctgatgtactagaatctatgcgaggccaccttattcggc
gtcatgagacatgtgtcatctgcgagtgtggatcagtcaactacggatggttttttgtcccc
tcgggttgccaactggatgatattgacaaggaaacatcatccttgagagtcccatatattgg
ttctaccactgatgagagaacagacatgaagcttgccttcgtaagagccccaagtcgatcct
tgcgatctgctgttagaatagcaacagtgtactcatgggcttacggtgatgatgatagctct
tggaacgaagcctggttgttggctaggcaaagggccaatgtgagcctggaggagctaagggt
gatcactcccatctcaacttcgactaatttagcgcataggttgagggatcgtagcactcaag
tgaaatactcaggtacatcccttgtccgagtggcgaggtataccacaatctccaacgacaat
ctctcatttgtcatatcagataagaaggttgatactaactttatataccaacaaggaatgct
tctaggggttgggtgttttagaaacattgtttcgactcgagaaagataccggatcatctaaca
cggtattacatcttcacgtcgaaacagattgttgcgtgatcccgatgatagatcatcccagg
atacccagctcccgcaagctagagctgagggcagagctatgtaccaacccattgatatatga
taatgcacctttaattgacagagatgcaacaaggctatacacccagagccataggaggcacc
ttgtggaatttgttacatggtccacaccccaactatatcacattttagctaagtccacagca
```

FIG. 3F

```
ctatctatgattgacctggtaacaaaatttgagaaggaccatatgaatgaaatttcagctct
cataggggatgacgatatcaatagtttcataactgagtttctgctcatagagccaagattat
tcactatctacttgggccagtgtgcggccatcaattgggcatttgatgtacattatcataga
ccatcagggaaatatcagatgggtgagctgttgtcatcgttcctttctagaatgagcaaagg
agtgtttaaggtgcttgtcaatgctctaagccacccaaagatctacaagaaattctggcatt
gtggtattatagagcctatccatggtccttcacttgatgctcaaaacttgcacacaactgtg
tgcaacatggtttacacatgctatatgacctacctcgacctgttgttgaatgaagagttaga
agagttcacatttctcttgtgtgaaagcgacgaggatgtagtaccggacagattcgacaaca
tccaggcaaaacacttatgtgttctggcagatttgtactgtcaaccagggacctgcccacca
attcgaggtctaagaccggtagagaaatgtgcagttctaaccgaccatatcaaggcagaggc
tatgttatctccagcaggatcttcgtggaacataaatccaattattgtagaccattactcat
gctctctgacttatctccggcgaggatcgatcaaacagataagattgagagttgatccagga
ttcattttcgacgccctcgctgaggtaaatgtcagtcagccaaagatcggcagcaacaacat
ctcaaatatgagcatcaaggctttcagaccccacacgatgatgttgcaaaattgctcaaag
atatcaacacaagcaagcacaatcttcccatttcagggggcaatctcgccaattatgaaatc
catgctttccgcagaatcgggttgaactcatctgcttgctacaaagctgttgagatatcaac
attaattaggagatgccttgagccaggggaggacggcttgttcttgggtgagggatcgggtt
ctatgttgatcacttataagagatacttaaactaaacaagtgcttctataatagtggggtt
tccgccaattctagatctggtcaaagggaattagcaccctatccctccgaagttggccttgt
cgaacacagaatgggagtaggtaatattgtcaaagtgctctttaacgggaggcccgaagtca
cgtgggtaggcagtgtagattgcttcaatttcatagttagtaatatccctacctctagtgtg
gggtttatccattcagatatagagaccttgcctgacaaagatactatagagaagctagagga
attggcagccatcttatcgatggctctgctcctgggcaaaataggatcaatactggtgatta
agcttatgcctttcagcggggattttgttcagggatttataagttatgtagggtctcattat
agagaagtgaaccttgtataccctagatacagcaacttcatctctactgaatcttatttggt
tatgacagatctcaaggctaaccggctaatgaatcctgaaaagattaagcagcagataattg
aatcatctgtgaggacttcacctggacttataggtcacatcctatccattaagcaactaagc
tgcatacaagcaattgtgggagacgcagttagtagaggtgatatcaatcctactctgaaaaa
acttacacctatagagcaggtgctgatcaattgcgggttggcaattaacggacctaagctgt
gcaaagaattgatccaccatgatgttgcctcagggcaagatggattgcttaattctatactc
atcctctacagggagttggcaagattcaaagacaaccaaagaagtcaacaagggatgttcca
cgcttaccccgtattggtaagtagcaggcaacgagaacttatatctaggatcacccgcaaat
tctgggggcacattcttctttactccgggaacaaaaagttgataaataagtttatccagaat
ctcaagtccggctatctgatactagacttacaccagaatatcttcgttaagaatctatccaa
gtcagagaaacagattattatgacggggggtttgaaacgtgagtgggttttaaggtaacag
tcaaggagaccaaagaatggtataagttagtcggatacagtgccctgattaaggactaattg
gttgaactccggaaccctaatcctgccctaggtggttaggcattatttgcaatatattaaag
aaactttgaaaatacgaagtttctattcccagctttgtctggtggccggcatggtcccagc
ctcctcgctggcgccggctgggcaacattccgaggggaccgtcccctcggtaatggcgaatg
ggacgcggccggtcgatcgacgatccggctgctaacaaagcccgaaggaagctgagttggc
tgctgccaccgctgagcaataactagcataaccccttggggcctctaaacgggtcttgaggg
gttttttgctgaaaggaggaactatatccggatcgagatcaattctgtgagcgtatggcaaa
cgaaggaaaaatagttatagtagccgcactcgatgggacatttcaacgtaaaccgtttaata
atattttgaatcttattccattatctgaaatggtggtaaaactaactgctgtgtgtatgaaa
tgctttaaggaggcttccttttctaaacgattgggtgaggaaaccgagatagaaataatagg
aggtaatgatatgtatcaatcggtgtgtagaaagtgttacatcgactcataatattatattt
tttatctaaaaaactaaaaataaacattgattaaattttaatataatacttaaaaatggatg
ttgtgtcgttagataaaccgtttatgtattttgaggaaattgataatgagttagattacgaa
ccagaaagtgcaaatgaggtcgcaaaaaaactgccgtatcaaggacagttaaaactattact
aggagaattattttttcttagtaagttacagcgacacggtatattagatggtgccaccgtag
```

FIG. 3G

```
tgtatataggatctgctcccggtacacatatacgttatttgagagatcatttctataattta
ggagtgatcccgaaaggaagctgagttggctgctgccaccgctgagcaataactagcataac
cccttggggcctctaaacgggtcttgagggggttttttgctgaaaggaggaacgcgcctgatg
cggtattttctccttacgcatctgtgcggtatttcacaccgcatatatggtgcactctcagt
acaatctgctctgatgccgcatagttaagccagccccgacacccgccaacacccgctgacgc
gccctgacgggcttgtctgctcccggcatccgcttacagacaagctgtgaccgtctccggga
gctgcatgtgtcagaggttttcaccgtcatcaccgaaacgcgcgagacgaaagggcctcgtg
atacgcctattttataggttaatgtcatgataataatggtttcttagacgtcaggtggcac
ttttcggggaaatgtgcgcggaacccctatttgtttattttttctaaatacattcaaatatgt
atccgctcatgagacaataaccctgataaatgcttcaataatattgaaaaggaagagtatg
agtattcaactttcgtgtcgcccttattccttttttgcggcattttgccttcctgtttt
tgctcacccagaaacgctggtgaaagtaaaagatgctgaagatcagttgggtgcacgagtgg
gttacatcgaactggatctcaacagcggtaagatccttgagagttttcgccccgaagaacgt
tttccaatgatgagcacttttaaagttctgctatgtggcgcggtattatcccgtattgacgc
cgggcaagagcaactcggtcgccgcatacactattctcagaatgacttggttgagtactcac
cagtcacagaaaagcatcttacggatggcatgacagtaagagaattatgcagtgctgccata
accatgagtgataacactgcggccaacttacttctgacaacgatcggaggaccgaaggagct
aaccgcttttttgcacaacatgggggatcatgtaactcgccttgatcgttgggaaccggagc
tgaatgaagccataccaaacgacgagcgtgacaccacgatgcctgtagcaatggcaacaacg
ttgcgcaaactattaactggcgaactacttactctagcttcccggcaacaattaatagactg
gatggaggcggataaagttgcaggaccacttctgcgctcggcccttccggctggctggttta
ttgctgataaatctggagccggtgagcgtgggtctcgcggtatcattgcagcactggggcca
gatggtaagccctcccgtatcgtagttatctacacgacggggagtcaggcaactatggatga
acgaaatagacagatcgctgagataggtgcctcactgattaagcattggtaactgtcagacc
aagtttactcatatactttagattgatttaaaacttcatttttaatttaaaaggatctag
gtgaagatcctttttgataatctcatgaccaaaatcccttaacgtgagttttcgttccactg
agcgtcagaccccgtagaaaagatcaaaggatcttcttgagatcctttttttctgcgcgtaa
tctgctgcttgcaaacaaaaaaaccaccgctaccagcggtggtttgtttgccggatcaagag
ctaccaactcttttttccgaaggtaactggcttcagcagagcgcagataccaaatactgtcct
tctagtgtagccgtagttaggccaccacttcaagaactctgtagcaccgcctacatacctcg
ctctgctaatcctgttaccagtggctgctgccagtggcgataagtcgtgtcttaccgggttg
gactcaagacgatagttaccggataaggcgcagcggtcgggctgaacggggggttcgtgcac
acagcccagcttggagcgaacgacctacaccgaactgagatacctacagcgtgagcattgag
aaagcgccacgcttcccgaagggagaaaggcggacaggtatccggtaagcggcagggtcgga
acaggagagcgcacgagggagcttccaggggaaacgcctggtatctttatagtcctgtcgg
gtttcgccacctctgacttgagcgtcgatttttgtgatgctcgtcaggggggcggagcctat
ggaaaaacgccagcaacgcggcctttttacggttcctggccttttgctggccttttgctcac
atgttctttcctgcgttatccctgattctgtggataaccgtattaccgcctttgagtgagc
tgataccgctcgccgcagccgaacgaccgagcgcagcgagtcagtgagcgaggaagcggaag
agcgcccaatacgcaaaccgcctctccccgcgcgttggccgattcattaatgcagctggcac
gacaggtttcccgactggaaagcgggcagtgagcgcaacgcaattaatgtgagttagctcac
tcattaggcaccccaggctttacactttatgcttccggctcgtatgttgtgtggaattgtga
gcggataacaatttcacacaggaaacagctatgaccatgattacgccaagcttacgcgtcct
ggcattatgcccagtacatgaccttatgggactttcctacttggcagtacatctacgtatta
gtcatcgctattaccatggtgatgcggttttggcagtacatcaatgggcgtggatagcggtt
tgactcacggggatttccaagtctccacccattgacgtcaatgggagtttgttttggcacc
aaaatcaacgggactttccaaaatgtcgtaacaactccgccccattgacgcaaatgggcggt
aggcgtgtacggtgggaggtctatataagcagagctcgtttagtgaaccgtgg
```

FIG. 4A pc3MerV2 Id-SCD viral:
nt    1 - 55: MeV leader
nt   56 - 66: gene start of transgene (originally from N gene; Phase 2)
nt   67 - 103: 5'-UTR (originally from N gene)
nt  103 - 108: XhoI (c'tcgag); not singular in this context
nt  109 - 114: 5'-cloning site PauI+MluI (g'CGCGT)
nt  121 - 1242: SuperCD ORF (1122 nt = 373 aa +Stop)
nt 1243 - 1248: 3'-cloning site MluI+PauI (A'cgcgc)
nt 1249 - 1260: 3'-UTR
nt 1262 - 1270: gene end of transgene (originally from N gene)
nt 1274 - 1284: gene start N (Phase 2)
nt 1326 - 2903: N ORF (1578 nt = 525 aa +stop)
nt 3025 - 4548: P ORF (1524 nt = 507 aa +stop)
nt 3047 - 3607: C ORF (non-structural; 561 nt = 186 aa +stop)
nt 3709 - 3716: A5G3 editing box; G insertion behind nt 3714
nt 3025 - 3923: V trans-frame ORF after mRNA editing (non-structural; 900 nt = 299 aa +stop)
nt 4656 - 5663: M ORF (1008 nt = 335 aa +stop)
nt 6667 - 8328: F ORF (1662 nt = 553 aa + stop)
nt 8489 - 10342: H ORF (1854

FIG. 4B

```
agatgaaaacaagtatctagttccagggttgggtgactttggtgacagatactactgtgttt
aaacgcgccatccatcattgttataaaaaacttaggattcaagatcctattatcagggacaa
gagcaggattagggatatccgagatggccacacttttaaggagcttagcattgttcaaaaga
aacaaggacaaaccacccattacatcaggatccggtggagccatcagaggaatcaaacacat
tattatagtaccaatccctggagattcctcaattaccactcgatccagacttctggaccggt
tggtgaggttaattggaaacccggatgtgagcgggcccaaactaacaggggcactaataggt
atattatccttatttgtggagtctccaggtcaattgattcagaggatcaccgatgaccctga
cgttagcataaggctgttagaggttgtccagagtgaccagtcacaatctggccttaccttcg
catcaagaggtaccaacatggaggatgaggcggaccaatacttttcacatgatgatccaatt
agtagtgatcaatccaggttcggatggttcgggaacaaggaaatctcagatattgaagtgca
agaccctgagggattcaacatgattctgggtaccatcctagcccaaatttgggtcttgctcg
caaaggcggttacggccccagacacggcagctgattcggagctaagaaggtggataaagtac
acccaacaaagaagggtagttggtgaatttagattggagagaaaatggttggatgtggtgag
gaacaggattgccgaggacctctccttacgccgattcatggtcgctctaatcctggatatca
agagaacacccggaaacaaacccaggattgctgaaatgatatgtgacattgatacatatatc
gtagaggcaggattagccagttttatcctgactattaagtttgggatagaaactatgtatcc
tgctcttggactgcatgaatttgctggtgagttatccacacttgagtccttgatgaacccttt
accagcaaatgggggaaactgcaccctacatggtaatcctggagaactcaattcagaacaag
ttcagtgcaggatcatacccctctgctctggagctatgccatgggagtaggagtggaacttga
aaactccatgggaggtttgaactttggccgatcttactttgatccagcatattttagattag
ggcaagagatggtaaggaggtcagctggaaaggtcagttccacattggcatctgaactcggt
atcactgccgaggatgcaaggcttgtttcagagattgcaatgcatactactgaggacaagat
cagtagagcggttggacccagacaagcccaagtatcatttctacacggtgatcaaagtgaga
atgagctaccgagattgggggggcaaggaagataggagggtcaaacagagtcgaggagaagcc
agggagagctacagagaaaccgggcccagcagagcaagtgatgcgagagctgcccatcttcc
aaccggcacacccctagacattgacactgcaacggagtccagccaagatccgcaggacagtc
gaaggtcagctgacgccctgcttaggctgcaagccatggcaggaatctcggaagaacaaggc
tcagacacggacacccctatagtgtacaatgacagaaatcttctagactaggtgcgagaggc
cgagggccagaacaacatccgcctaccatccatcattgttataaaaaacttaggaaccaggt
ccacacagccgccagcccatcaaccatccactcccacgattggagccaatggcagaagagca
ggcacgccatgtcaaaaacggactggaatgcatccgggctctcaaggccgagcccatcggct
cactggccatcgaggaagctatggcagcatggtcagaaatatcagacaacccaggacaggag
cgagccacctgcagggaagagaaggcaggcagttcgggtctcagcaaaccatgcctctcagc
aattggatcaactgaaggcggtgcacctcgcatccgcggtcagggacctggagagagcgatg
acgacgctgaaactttgggaatcccccaagaaatctccaggcatcaagcactgggttacag
tgttattacgtttatgatcacagcggtgaagcggttaagggaatccaagatgctgactctat
catggttcaatcaggccttgatggtgatagcaccctctcaggaggagacaatgaatctgaaa
acagcgatgtggatattggcgaacctgataccgagggatatgctatcactgaccggggatct
gctcccatctctatggggttcagggcttctgatgttgaaactgcagaaggaggggagatcca
cgagctcctgagactccaatccagaggcaacaactttccgaagcttgggaaaactctcaatg
ttcctccgccccggaccccggtagggccagcacttccgggacacccattaaaagggcaca
gacgcgagattagcctcatttggaacggagatcgcgtctttattgacaggtggtgcaaccca
atgtgctcgaaagtcaccctcggaaccatcagggccaggtgcacctgcggggaatgtccccg
agtgtgtgagcaatgccgcactgatacaggagtggacacccgaatctggtaccacaatctcc
ccgagatcccagaataatgaagaagggggagactattatgatgatgagctgttctctgatgt
ccaagatattaaaacagccttggccaaaatacacgaggataatcagaagataatctccaagc
tagaatcactgctgttattgaagggagaagttgagtcaattaagaagcagatcaacaggcaa
aatatcagcatatccaccctggaaggacacctctcaagcatcatgatcgccattcctggact
tgggaaggatcccaacgaccccactgcagatgtcgaaatcaatcccgacttgaaacccatca
taggcagagattcaggccgagcactggccgaagttctcaagaaacccgttgccagccgacaa
```

FIG. 4C ctccaaggaatgacaaatggacggaccagttccagaggacagctgctgaaggaatttcagct
aaagccgatcgggaaaaagatgagctcagccgtcgggtttgttcctgacaccggccctgcat
cacgcagtgtaatccgctccattataaaatccagccggctagaggaggatcggaagcgttac
ctgatgactctccttgatgatatcaaaggagccaatgatcttgccaagttccaccagatgct
gatgaagataataatgaagtagctacagctcaacttacctgccaaccccatgccagtcgacc
caactagtacaacctaaatccattataaaaacttaggagcaaagtgattgcctcccaaggt
ccacaatgacagagacctacgacttcgacaagtcggcatgggacatcaaagggtcgatcgct
ccgatacaacccaccacctacagtgatggcaggctggtgccccaggtcagagtcatagatcc
tggtctaggcgacaggaaggatgaatgctttatgtacatgtttctgctgggggttgttgagg
acagcgattccctagggcctccaatcgggcgagcatttgggttcctgcccttaggtgttggc
agatccacagcaaagcccgaaaaactcctcaaagaggccactgagcttgacatagttgttag
acgtacagcagggctcaatgaaaaactggtgttctacaacaacaccccactaactctcctca
caccttggagaaaggtcctaacaacagggagtgtcttcaacgcaaaccaagtgtgcaatgcg
gttaatctgataccgctcgatacccgcagaggttccgtgttgtttatatgagcatcacccg
tctttcggataacgggtattacaccgttcctagaagaatgctggaattcagatcggtcaatg
cagtggccttcaacctgctggtgacccttaggattgacaaggcgataggccctgggaagatc
atcgacaatacagagcaacttcctgaggcaacatttatggtccacatcgggaacttcaggag
aaagaagagtgaagtctactctgccgattattgcaaaatgaaaatcgaaaagatgggcctgg
tttttgcacttggtgggatagggggcaccagtcttcacattagaagcacaggcaaaatgagc
aagactctccatgcacaactcgggttcaagaagaccttatgttacccgctgatggatatcaa
tgaagaccttaatcgattactctggaggagcagatgcaagatagtaagaatccaggcagttt
tgcagccatcagttcctcaagaattccgcatttacgacgacgtgatcataaatgatgaccaa
ggactattcaaagttctgtagaccgtagtgcccagcaatgcccgaaaacgacccccctcaca
atgacagccagaaggcccggacaaaaaagcccctccgaaagactccacggaccaagcgaga
ggccagccagcagccgacggcaagcgcgaacaccaggcggccccagcacagaacagccctga
cacaaggccaccaccagccaccccaatctgcatcctcctcgtgggaccccgaggaccaacc
cccaaggctgccccgatccaaaccaccaaccgcatcccaccaccccgggaaagaaaccc
ccagcaattggaaggcccctcccctcttcctcaacacaagaactccacaaccgaaccgcac
aagcgaccgaggtgacccaaccgcaggcatccgactccctagacagatcctctctccccggc
aaactaaacaaaacttagggccaaggaacatacacacccaacagaacccagaccccggccca
cggcgccgcgccccaaccccgacaaccagagggagccccaaccaatcccgccggctccc
ccggtgcccacaggcagggacaccaaccccgaacagacccagcacccaaccatcgacaatc
caagacggggggcccccaaaaaaggcccccaggggccgacagccagcaccgcgaggaa
gcccacccaccccacacacgaccacggcaaccaaaccagaacccagaccaccctgggccacc
agctcccagactcggccatcaccccgcagaaaggaaaggccacaacccgcgcaccccagccc
cgatccggcggggagccacccaacccgaaccagcacccaagagcgatccccgaaggacccccc
gaaccgcaaaggacatcagtatcccacagcctctccaagtcccccggtctcctcctcttctc
gaagggaccaaaagatcaatccaccacacccgacgacactcaactccccaccccctaaaggag
acaccgggaatcccagaatcaagactcatccaatgtccatcatgggtctcaaggtgaacgtc
tctgccatattcatggcagtactgttaactctccaaacacccaccggtcaaatccattgggg
caatctctctaagatagggtggtaggaataggaagtgcaagctacaaagttatgactcgtt
ccagccatcaatcattagtcataaaattaatgcccaatataactctcctcaataactgcacg
agggtagagattgcagaatacaggagactactgagaacagttttggaaccaattagagatgc
acttaatgcaatgacccagaatataagaccggttcagagtgtagcttcaagtaggagacaca
agagatttgcgggagtagtcctggcaggtgcggccctaggcgttgccacagctgctcagata
acagccggcattgcacttcaccagtccatgctgaactctcaagccatcgacaatctgagagc
gagcctggaaactactaatcaggcaattgagacaatcagacaagcagggcaggagatgatat
tggctgttcagggtgtccaagactacatcaataatgagctgataccgtctatgaaccaacta
tcttgtgatttaatcggccagaagctcgggctcaaattgctcagatactatacagaaatcct
gtcattatttggccccagtttacgggaccccatatctgcggagatatctatccaggctttga

FIG. 4D

```
gctatgcgcttggaggagacatcaataaggtgttagaaaagctcggatacagtggaggtgat
ttactgggcatcttagagagcggaggaataaaggcccggataactcacgtcgacacagagtc
ctacttcattgtcctcagtatagcctatccgacgctgtccgagattaaggggtgattgtcc
accggctagaggggtctcgtacaacataggctctcaagagtggtataccactgtgcccaag
tatgttgcaacccaagggtaccttatctcgaattttgatgagtcatcgtgtactttcatgcc
agaggggactgtgtgcagccaaaatgccttgtacccgatgagtcctctgctccaagaatgcc
tccgggggtacaccaagtcctgtgctcgtacactcgtatccgggtcttttgggaaccggttc
attttatcacaagggaacctaatagccaattgtgcatcaatcctttgcaagtgttacacaac
aggaacgatcattaatcaagaccctgacaagatcctaacatacattgctgccgatcactgcc
cggtagtcgaggtgaacggcgtgaccatccaagtcgggagcaggaggtatccagacgctgtg
tacttgcacagaattgacctcggtcctcccatatcattggagaggttggacgtagggacaaa
tctggggaatgcaattgctaagttggaggatgccaaggaattgttggagtcatcggaccaga
tattgaggagtatgaaaggtttatcgagcactagcatagtctacatcctgattgcagtgtgt
cttggagggttgatagggatccccgctttaatatgttgctgcaggggcgttgtaacaaaaa
gggagaacaagttggtatgtcaagaccaggcctaaagcctgatcttacgggaacatcaaaat
cctatgtaaggtcgctctgatcctctacaactcttgaaacacaaatgtcccacaagtctcct
cttcgtcatcaagcaaccaccgcacccagcatcaagcccacctgaaattatctccggcttcc
ctctggccgaacaatatcggtagttaatcaaaacttagggtgcaagatcatccacaatgtca
ccacaacgagaccggataaatgccttctacaaagataaccccatcccaagggaagtaggat
agtcattaacagagaacatcttatgattgatagaccttatgttttgctggctgttctgtttg
tcatgtttctgagcttgatcgggttgctagccattgcaggcattagacttcatcgggcagcc
atctacaccgcagagatccataaaagcctcagcaccaatctagatgtaactaactcaatcga
gcatcaggtcaaggacgtgctgacaccactcttcaaaatcatcggtgatgaagtgggcctga
ggacacctcagagattcactgacctagtgaaattaatctctgacaagattaaattccttaat
ccggataggagtacgacttcagagatctcacttggtgtatcaacccgccagagagaatcaa
attggattatgatcaatactgtgcagatgtggctgctgaagagctcatgaatgcattggtga
actcaactctactggagaccagaacaaccaatcagttcctagctgtctcaaagggaaactgc
tcagggcccactacaatcagaggtcaattctcaaacatgtcgctgtccctgttagacttgta
tttaggtcgaggttacaatgtgtcatctatagtcactatgacatcccagggaatgtatgggg
gaacttacctagtggaaaagcctaatctgagcagcaaaaggtcagagttgtcacaactgagc
atgtaccgagtgtttgaagtaggtgttatcagaaatccgggtttggggctccggtgttcca
tatgacaaactatcttgagcaaccagtcagtaatgatctcagcaactgtatggtggctttgg
gggagctcaaactcgcagccctttgtcacggggaagattctatcacaattccctatcaggga
tcagggaaaggtgtcagcttccagctcgtcaagctaggtgtctggaaatccccaaccgacat
gcaatcctgggtccccttatcaacggatgatccagtgatagacaggctttacctctcatctc
acagaggtgttatcgctgacaatcaagcaaaatgggctgtcccgacaacacgaacagatgac
aagttgcgaatggagacatgcttccaacaggcgtgtaagggtaaaatccaagcactctgcga
gaatcccgagtgggcaccattgaaggataacaggattccttcatacggggtcttgtctgttg
atctgagtctgacagttgagcttaaaatcaaaattgcttcgggattcgggccattgatcaca
cacggttcagggatggacctatacaaatccaaccacaacaatgtgtattggctgactatccc
gccaatgaagaacctagccttaggtgtaatcaacacattggagtggataccgagattcaagg
ttagtccctacctcttcactgtcccaattaaggaagcaggcgaagactgccatgccccaaca
tacctacctgcggaggtggatggtgatgtcaaactcagttccaatctggtgattctacctgg
tcaagatctccaatatgttttggcaacctacgatacttccagggttgaacatgctgtggttt
attacgtttacagcccaagccgctcattttcttacttttatccttttaggttgcctataaag
ggggtccccatcgaattacaagtggaatgcttcacatgggaccaaaaactctggtgccgtca
cttctgtgtgcttgcggactcagaatctggtggacatatcactcactctgggatggtgggca
tgggagtcagctgcacagtcacccgggaagatggaaccaatcgcagatagggctgctagtga
accaatcacatgatgtcacccagacatcaggcatacccactagtgtgaaatagacatcagaa
ttaagaaaaacgtagggtccaagtggttcccgttatggactcgctatctgtcaaccagatc
```

FIG. 4E

```
ttatacccctgaagttcacctagatagcccgatagttaccaataagatagtagccatcctgga
gtatgctcgagtccctcacgcttacagcctggaggaccctacactgtgtcagaacatcaagc
accgcctaaaaaacggattttccaaccaaatgattataaacaatgtggaagttgggaatgtc
atcaagtccaagcttaggagttatccggcccactctcatattccatatccaaattgtaatca
ggatttatttaacatagaagacaaagagtcaacgaggaagatccgtgaactcctcaaaaagg
ggaattcgctgtactccaaagtcagtgataaggttttccaatgcttaagggacactaactca
cggcttggcctaggctccgaattgagggaggacatcaaggagaaagttattaacttgggagt
ttacatgcacagctcccagtggtttgagccctttctgttttggtttacagtcaagactgaga
tgaggtcagtgattaaatcacaaacccatacttgccataggaggagacacacacctgtattc
ttcactggtagttcagttgagttgctaatctctcgtgaccttgttgctataatcagtaaaga
gtctcaacatgtatattacctgacatttgaactggttttgatgtattgtgatgtcatagagg
ggaggttaatgacagagaccgctatgactattgatgctaggtatacagagcttctaggaaga
gtcagatacatgtggaaactgatagatggtttcttccctgcactcgggaatccaacttatca
aattgtagccatgctggagcctcttt cacttgcttacctgcagctgagggatataacagtag
aactcagaggtgctttccttaaccactgctttactgaaatacatgatgttcttgaccaaaac
gggttttctgatgaaggtacttatcatgagttaactgaagctctagattacattttcataac
tgatgacatacatctgacaggggagattttctcattttt cagaagtttcggccacccccagac
ttgaagcagtaacggctgctgaaaatgttaggaaatacatgaatcagcctaaagtcattgtg
tatgagactctgatgaaaggtcatgccatattttgtggaatcataatcaacggctatcgtga
caggcacggaggcagttggccaccgctgaccctcccccctgcatgctgcagacacaatccgga
atgctcaagcttcaggtgaagggttaacacatgagcagtgcgttgataactggaaatctttt
gctggagtgaaatttggctgctttatgcctcttagcctggatagtgatctgacaatgtacct
aaaggacaaggcacttgctgctctccaaagggaatgggattcagtttacccgaaagagttcc
tgcgttacgaccctcccaagggaaccgggtcacggaggcttgtagatgttttccttaatgat
tcgagctttgacccatatgatgtgataatgtatgttgtaagtggagcttacctccatgaccc
tgagttcaacctgtcttacagcctgaaagaaaaggagatcaaggaaacaggtagacttttg
ctaaaatgacttacaaaatgagggcatgccaagtgattgctgaaaatctaatctcaaacggg
attggcaaatattttaaggacaatgggatggccaaggatgagcacgatttgactaaggcact
ccacactctagctgtctcaggagtccccaaagatctcaaagaaagtcacaggggggggccag
tcttaaaaacctactcccgaagcccagtccacacaagtaccaggaacgtgagagcagcaaaa
gggtttatagggttccctcaagtaattcggcaggaccaagacactgatcatccggagaatat
ggaagcttacgagacagtcagtgcatttatcacgactgatctcaagaagtactgccttaatt
ggagatatgagaccatcagcttgtttgcacagaggctaaatgagatttacggattgccctca
tttttccagtggctgcataagaggcttgagacctctgtcctgtatgtaagtgaccctcattg
ccccccccgaccttgacgcccatatcccgttatataaagtccccaatgatcaaatcttcatta
agtacctatgggaggtatagaagggtattgtcagaagctgtggaccatcagcaccattccc
tatctatacctggctgcttatgagagcggagtaaggattgcttcgttagtgcaaggggacaa
tcagaccatagccgtaacaaaagggtacccagcacatggccctacaaccttaagaaacggg
aagctgctagagtaactagagattactttgtaattcttaggcaaaggctacatgatattggc
catcacctcaaggcaaatgagacaattgtttcatcacatttttttgtctattcaaaaggaat
atattatgatgggctacttgtgtcccaatcactcaagagcatcgcaagatgtgtattctggt
cagagactatagttgatgaaacaagggcagcatgcagtaatattgctacaacaatggctaaa
agcatcgagagaggttatgaccgttaccttgcatattccctgaacgtcctaaaagtgataca
gcaaattctgatctctcttggcttcacaatcaattcaaccatgacccgggatgtagtcatac
ccctcctcacaaacaacgacctcttaataaggatggcactgttgcccgctcctattgggggg
atgaattatctgaatatgagcaggctgtttgtcagaaacatcggtgatccagtaacatcatc
aattgctgatctcaagagaatgattctcgcctcactaatgcctgaagagaccctccatcaag
taatgacacaacaaccgggggactcttcattcctagactgggctagcgacccttactcagca
aatcttgtatgtgtccagagcatcactagactcctcaagaacataactgcaaggttttgtcct
gatccatagtccaaacccaatgttaaaaggattattccatgatgacagtaaagaagaggacg
```

FIG. 4F agggactggcggcattcctcatggacaggcatattatagtacctagggcagctcatgaaatc
ctggatcatagtgtcacaggggcaagagagtctattgcaggcatgctggataccacaaaagg
cttgattcgagccagcatgaggaagggggggttaacctctcgagtgataaccagattgtcca
attatgactatgaacaattcagagcagggatggtgctattgacaggaagaaagagaaatgtc
ctcattgacaaagagtcatgttcagtgcagctggcgagagctctaagaagccatatgtgggc
gaggctagctcgaggacggcctatttacggccttgaggtccctgatgtactagaatctatgc
gaggccaccttattcggcgtcatgagacatgtgtcatctgcgagtgtggatcagtcaactac
ggatggttttttgtcccctcgggttgccaactggatgatattgacaaggaaacatcatcctt
gagagtcccatatattggttctaccactgatgagagaacagacatgaagcttgccttcgtaa
gagccccaagtcgatccttgcgatctgctgttagaatagcaacagtgtactcatgggcttac
ggtgatgatgatagctcttggaacgaagcctggttgttggctaggcaaagggccaatgtgag
cctggaggagctaagggtgatcactcccatctcaacttcgactaatttagcgcataggttga
gggatcgtagcactcaagtgaaatactcaggtacatccttgtccgagtggcgaggtatacc
acaatctccaacgacaatctctcatttgtcatatcagataagaaggttgatactaactttat
ataccaacaaggaatgcttctagggttgggtgttttagaaacattgtttcgactcgagaaag
ataccggatcatctaacacggtattacatcttcacgtcgaaacagattgttgcgtgatcccg
atgatagatcatcccaggatacccagctccgcaagctagagctgagggcagagctatgtac
caacccattgatatatgataatgcacctttaattgacagagatgcaacaaggctatacaccc
agagccataggaggcaccttgtggaatttgttacatggtccacaccccaactatatcacatt
ttagctaagtccacagcactatctatgattgacctggtaacaaaatttgagaaggaccatat
gaatgaaatttcagctctcataggggatgacgatatcaatagtttcataactgagtttctgc
tcatagagccaagattattcactatctacttgggccagtgtgcggccatcaattgggcattt
gatgtacattatcatagaccatcagggaaatatcagatgggtgagctgttgtcatcgttcct
ttctagaatgagcaaaggagtgtttaaggtgcttgtcaatgctctaagccacccaaagatct
acaagaaattctggcattgtggtattatagagcctatccatggtccttcacttgatgctcaa
aacttgcacacaactgtgtgcaacatggtttacacatgctatatgacctacctcgacctgtt
gttgaatgaagagttagaagagttcacatttctcttgtgtgaaagcgacgaggatgtagtac
cggacagattcgacaacatccaggcaaaacacttatgtgttctggcagatttgtactgtcaa
ccagggacctgcccaccaattcgaggtctaagaccggtagagaaatgtgcagttctaaccga
ccatatcaaggcagaggctatgttatctccagcaggatcttcgtggaacataaatccaatta
ttgtagaccattactcatgctctctgacttatctccggcgaggatcgatcaaacagataaga
ttgagagttgatccaggattcattttcgacgccctcgctgaggtaaatgtcagtcagccaaa
gatcggcagcaacaacatctcaaatatgagcatcaaggctttcagaccccacacgatgatg
ttgcaaaattgctcaaagatatcaacacaagcaagcacaatcttcccatttcaggggcaat
ctcgccaattatgaaatccatgctttccgcagaatcgggttgaactcatctgcttgctacaa
agctgttgagatatcaacattaattaggagatgccttgagccaggggaggacggcttgttct
tgggtgagggatcgggttctatgttgatcacttataaagagatacttaaactaaacaagtgc
ttctataatagtgggtttccgccaattctagatctggtcaaagggaattagcaccctatcc
ctccgaagttggccttgtcgaacacagaatgggagtaggtaatattgtcaaagtgctcttta
acgggaggcccgaagtcacgtgggtaggcagtgtagattgcttcaatttcatagttagtaat
atccctacctctagtgtggggtttatccattcagatatagagaccttgcctgacaaagatac
tatagagaagctagaggaattggcagccatcttatcgatggctctgctcctgggcaaaatag
gatcaatactggtgattaagcttatgcctttcagcggggattttgttcagggatttataagt
tatgtagggtctcattatagagaagtgaaccttgtatacctagatacagcaacttcatctc
tactgaatcttatttggttatgacagatctcaaggctaaccggctaatgaatcctgaaaaga
ttaagcagcagataattgaatcatctgtgaggacttcacctggacttataggtcacatccta
tccattaagcaactaagctgcatacaagcaattgtgggagacgcagttagtagaggtgatat
caatcctactctgaaaaaacttacacctatagagcaggtgctgatcaattgcgggttggcaa
ttaacggacctaagctgtgcaaagaattgatccaccatgatgttgcctcagggcaagatgga
ttgcttaattctatactcatcctctacagggagttggcaagattcaaagacaaccaaagaag

FIG. 4G

```
tcaacaagggatgttccacgcttaccccgtattggtaagtagcaggcaacgagaacttatat
ctaggatcacccgcaaattctgggggcacattcttctttactccgggaacaaaaagttgata
aataagtttatccagaatctcaagtccggctatctgatactagacttacaccagaatatctt
cgttaagaatctatccaagtcagagaaacagattattatgacgggggggtttgaaacgtgagt
gggttttttaaggtaacagtcaaggagaccaaagaatggtataagttagtcggatacagtgcc
ctgattaaggactaattggttgaactccggaacccctaatcctgccctaggtggttaggcatt
atttgcaatatattaaagaaaactttgaaaatacgaagtttctattcccagctttgtctggt
ggccggcatggtcccagcctcctcgctggcgccggctgggcaacattccgaggggaccgtcc
cctcggtaatggcgaatgggacgcggccggtcgatcgacgatccggctgctaacaaagcccg
aaaggaagctgagttggctgctgccaccgctgagcaataactagcataaccccttggggcct
ctaaacgggtcttgagggggttttttgctgaaaggaggaactatatccggatcgagatcaatt
ctgtgagcgtatggcaaacgaaggaaaaatagttatagtagccgcactcgatgggacatttc
aacgtaaaccgtttaataatattttgaatcttattccattatctgaaatggtggtaaaacta
actgctgtgtgtatgaaatgctttaaggaggcttccttttctaaacgattgggtgaggaaac
cgagatagaaataataggaggtaatgatatgtatcaatcggtgtgtagaaagtgttacatcg
actcataatattatattttttatctaaaaaactaaaaataaacattgattaaattttaatat
aatacttaaaaatggatgttgtgtcgttagataaaccgtttatgtattttgaggaaattgat
aatgagttagattacgaaccagaaagtgcaaatgaggtcgcaaaaaaactgccgtatcaagg
acagttaaaactattactaggagaattattttttcttagtaagttacagcgacacggtatat
tagatggtgccaccgtagtgtatataggatctgctcccggtacacatatacgttatttgaga
gatcatttctataatttaggagtgatcccgaaaggaagctgagttggctgctgccaccgctg
agcaataactagcataaccccttggggcctctaaacgggtcttgagggggttttttgctgaaa
ggaggaacgcgcctgatgcggtattttctccttacgcatctgtgcggtatttcaccgcat
atatggtgcactctcagtacaatctgctctgatgccgcatagttaagccagccccgacaccc
gccaacacccgctgacgcgccctgacgggcttgtctgctcccggcatccgcttacagacaag
ctgtgaccgtctccgggagctgcatgtgtcagaggttttcaccgtcatcaccgaaacgcgcg
agacgaaagggcctcgtgatacgcctatttttataggttaatgtcatgataataatggtttc
ttagacgtcaggtggcacttttcggggaaatgtgcgcggaacccctatttgtttattttct
aaatacattcaaatatgtatccgctcatgagacaataaccctgataaatgcttcaataatat
tgaaaaaggaagagtatgagtattcaacatttccgtgtcgcccttattcccttttttgcggc
attttgccttcctgttttgctcacccagaaacgctggtgaaagtaaaagatgctgaagatc
agttgggtgcacgagtgggttacatcgaactggatctcaacagcggtaagatccttgagagt
tttcgccccgaagaacgttttccaatgatgagcacttttaaagttctgctatgtggcgcggt
attatcccgtattgacgccgggcaagagcaactcggtcgccgcatacactattctcagaatg
acttggttgagtactcaccagtcacagaaaagcatcttacggatggcatgacagtaagagaa
ttatgcagtgctgccataaccatgagtgataacactgcggccaacttacttctgacaacgat
cggaggaccgaaggagctaaccgcttttttgcacaacatggggatcatgtaactcgccttg
atcgttgggaaccggagctgaatgaagccataccaaacgacgagcgtgacaccacgatgcct
gtagcaatggcaacaacgttgcgcaaactattaactggcgaactacttactctagcttccg
gcaacaattaatagactggatggaggcggataaagttgcaggaccacttctgcgctcggccc
ttccggctggctggtttattgctgataaatctggagccggtgagcgtgggtctcgcggtatc
attgcagcactggggccagatggtaagccctcccgtatcgtagttatctacacgacggggag
tcaggcaactatggatgaacgaaatagacagatcgctgagataggtgcctcactgattaagc
attggtaactgtcagaccaagtttactcatatatactttagattgatttaaaacttcatttt
taatttaaaaggatctaggtgaagatcctttttgataatctcatgaccaaaatcccttaacg
tgagttttcgttccactgagcgtcagaccccgtagaaaagatcaaaggatcttcttgagatc
ctttttttctgcgcgtaatctgctgcttgcaaacaaaaaaaccaccgctaccagcggtggtt
tgtttgccggatcaagagctaccaactctttttccgaaggtaactggcttcagcagagcgca
gataccaaatactgtccttctagtgtagccgtagttaggccaccacttcaagaactctgtag
caccgcctacatacctcgctctgctaatcctgttaccagtggctgctgccagtggcgataag
```

FIG. 4H

```
tcgtgtcttaccgggttggactcaagacgatagttaccggataaggcgcagcggtcgggctg
aacgggggttcgtgcacacagcccagcttggagcgaacgacctacaccgaactgagatacc
tacagcgtgagcattgagaaagcgccacgcttcccgaagggagaaaggcggacaggtatccg
gtaagcggcagggtcggaacaggagagcgcacgagggagcttccaggggggaaacgcctggta
tctttatagtcctgtcgggtttcgccacctctgacttgagcgtcgattttttgtgatgctcgt
caggggggcggagcctatggaaaaacgccagcaacgcggccttttttacggttcctggccttt
tgctggccttttgctcacatgttcttttcctgcgttatcccctgattctgtggataaccgtat
taccgcctttgagtgagctgataccgctcgccgcagccgaacgaccgagcgcagcgagtcag
tgagcgaggaagcggaagagcgcccaatacgcaaaccgcctctccccgcgcgttggccgatt
cattaatgcagctggcacgacaggtttcccgactggaaagcgggcagtgagcgcaacgcaat
taatgtgagttagctcactcattaggcacccaggctttacactttatgcttccggctcgta
tgttgtgtggaattgtgagcggataacaatttcacacaggaaacagctatgaccatgattac
gccaagcttacgcgtcctggcattatgcccagtacatgaccttatgggactttcctacttgg
cagtacatctacgtattagtcatcgctattaccatggtgatgcggttttggcagtacatcaa
tgggcgtggatagcggtttgactcacggggatttccaagtctccaccccattgacgtcaatg
ggagtttgttttggcaccaaaatcaacgggactttccaaaatgtcgtaacaactccgcccca
ttgacgcaaatgggcggtaggcgtgtacggtgggaggtctatataagcagagctcgtttagt
gaaccgtgg
```

FIG. 5A pcDIMer-N nt 1358 - 2935: N ORF MeV Schwarz (1578 nt = 525 aa + stop codon)

```
agcttgcatgcctgcaggtcaattccctggcattatgcccagtacatgaccttatgggactt
tcctacttggcagtacatctacgtattagtcatcgctattaccatggtgatgcggttttggc
agtacatcaatgcgcgtggataccggtttgactcacggggatttccaagtctccaccccatt
cacgtcaatgggagtttgttttggcaccaaaatcaacgggactttccaaaatgtcgtaacaa
ctccgccccattgacgcaaatgggcggtaggcgtgtacggtgggaggtctatataagcagag
ctcgtttagtgaaccgtcagatcgcctggagacgccatccacgctgttttgacctccataga
agacaccgggaccgatccagcctggggatctagcctccgcggccgggaacggtgcattggaa
cgcggattccccgtgccaagagtgacgtaagtaccgcctatagagtctataggcccaccccc
ttggcttcttatgcatgctatactgtttttggcttggggtctatacacccccgcttcctcat
gttataggtgatggtatagcttagcctataggtgtgggttattgaccattattgaccactcc
cctattggtgacgatactttccattactaatccataacatggctctttgccacaactctctt
tattggctatatgccaatacactgtccttcagagactgacacggactctgtatttttacagg
atggggtctcatttattatttacaaattcacatatacaacaccaccgtccccagtgcccgca
gtttttattaaacataacgtgggatctccacgcgaatctcgggtacgtgttccggacatggg
ctcttctccggtagcggcggagctcctacatccgagccctgctcccatgcctccagcgactc
atggtcgctcggcagctccttgctcctaacagtggaggccagacttaggcacagcacgatgc
ccaccaccaccagtgtgccgcacaaggccgtggcggtagggtatgtgtctgaaaatgagctc
ggggagcgggcttgcaccgctgacgcatttggaagacttaaggcagcggcagaagaagatgc
aggcagctgagttgttgtgttctgataagagtcagaggtaactcccgttgcggtgctgttaa
cggtggagggcagtgtagtctgagcagtactcgttgctgccgcgcgcgccaccagacataat
agctgacagactaacagactgttcctttccatgggtcttttctgcagtcaccgtccttgaca
cgatcggatcccgggtacctctagaagatctgatatcgtcgacctcgaggccaccatggcca
cacttttaaggagcttagcattgttcaaaagaaacaaggacaaaccacccattacatcagga
tccggtggagccatcagaggaatcaaacacattattatagtaccaatccctggagattcctc
aattaccactcgatccagacttctggaccggttggtgaggttaattggaaacccggatgtga
gcgggcccaaactaacaggggcactaataggtatattatccttatttgtggagtctccaggt
caattgattcagaggatcaccgatgaccctgacgttagcataaggctgttagaggttgtcca
gagtgaccagtcacaatctggccttaccttcgcatcaagaggtaccaacatggaggatgagg
cggaccaatacttttcacatgatgatccaattagtagtgatcaatccaggttcggatggttc
gggaacaaggaaatctcagatattgaagtgcaagaccctgagggattcaacatgattctggg
taccatcctagcccaaatttgggtcttgctcgcaaaggcggttacggccccagacacggcag
ctgattcggagctaagaaggtggataaagtacacccaacaaagaagggtagttggtgaattt
agattggagagaaaatggttggatgtggtgaggaacaggattgccgaggacctctccttacg
ccgattcatggtcgctctaatcctggatatcaagagaacacccggaaacaaacccaggattg
ctgaaatgatatgtgacattgatacatatatcgtagaggcaggattagccagttttatcctg
actattaagtttgggatagaaactatgtatcctgctcttggactgcatgaatttgctggtga
gttatccacacttgagtccttgatgaacctttaccagcaaatgggggaaactgcaccctaca
tggtaatcctggagaactcaattcagaacaagttcagtgcaggatcataccctctgctctgg
agctatgccatgggagtaggagtggaacttgaaaactccatgggaggtttgaactttggccg
atcttactttgatccagcatattttagattagggcaagagatggtaaggaggtcagctggaa
aggtcagttccacattggcatctgaactcggtatcactgccgaggatgcaaggcttgtttca
gagattgcaatgcatactactgaggacaagatcagtagagcggttggacccagacaagccca
agtatcatttctacacggtgatcaaagtgagaatgagctaccgagattgggggcaaggaag
ataggagggtcaaacagagtcgaggagaagccagggagagctacagagaaaccgggcccagc
```

FIG. 5B

```
agagcaagtgatgcgagagctgcccatcttccaaccggcacaccccctagacattgacactgc
aacggagtccagccaagatccgcaggacagtcgaaggtcagctgacgccctgcttaggctgc
aagccatggcaggaatctcggaagaacaaggctcagacacggacacccctatagtgtacaat
gacagaaatcttctagactaggtgcgagaggccgagggccagaacaacatccgcctaccatc
catcattctcgaggaattctagatcccacgtcactattgtatactctatattatactctatg
ttatactctgtaatcctactcaataaacgtgtcacgcctgtgaaaccgtactaagtctcccg
tgtcttcttataccatcaggtgacatcctcgcccaggctgtcaatcatgccggtatcgatt
ccagtagcaccggccccacgctgacaacccactcttgcagcgttagcagcgcccctcttaac
aagccgaccccaccagcgtcgcggttactaacactcctctccccgacctgcagcccaagct
ctagagggccctattctatagtgtcacctaaatgctagagctcgctgatcagcctcgactgt
gccttctagttgccagccatctgttgtttgcccctccccgtgccttccttgacctggaag
gtgccactcccactgtcctttcctaataaaatgaggaaattgcatcgcattgtctgagtagg
tgtcattctattctgggggggtggggtggggcaggacagcaaggggggaggattgggaagacaa
tagcaggcatgctggggatgcggtggctctatggcttctgaggcggaaagaaccagctggg
gctctagggggtatccccacgcgccctgtagcggcgcattaagcgcggcgggtgtggtggtt
acgcgcagcgtgaccgctacacttgccagcgccctagcgccgctcctttcgctttcttccc
ttccttctcgccacgttcgccggctttccccgtcaagctctaaatcggggcatcccttag
ggttccgatttagtgctttacggcacctcgaccccaaaaaacttgattagggtgatggttca
cgtagtgggccatcgccctgatagacggttttttcgcccttttgacgttggagtccacgttctt
taatagtggactcttgttccaaactggaacaacactcaaccctatctcggtctattcttttg
atttataagggattttggggatttcggcctattggttaaaaaatgagctgatttaacaaaaa
tttaacgcgaattaattctgtggaatgtgtgtcagttagggtgtggaaagtccccaggctcc
ccaggcaggcagaagtatgcaaagcatgcatctcaattagtcagcaaccaggtgtggaaagt
ccccaggctccccagcaggcagaagtatgcaaagcatgcatctcaattagtcagcaaccata
gtcccgcccctaactccgcccatcccgccctaactccgcccagttccgcccattctccgcc
ccatggctgactaattttttttatttatgcagaggccgaggccgcctctgcctctgagctat
tccagaagtagtgaggaggcttttttggaggcctaggcttttgcaaaaagctcccgggagct
tgtatatccattttcggatctgatcaagagacaggatgaggatcgtttcgcatgattgaaca
agatggattgcacgcaggttctccggccgcttgggtggagaggctattcggctatgactggg
cacaacagacaatcggctgctctgatgccgccgtgttccggctgtcagcgcaggggcgcccg
gttcttttgtcaagaccgacctgtccggtgccctgaatgaactgcaggacgaggcagcgcg
gctatcgtggctggccacgacgggcgttccttgcgcagctgtgctcgacgttgtcactgaag
cgggaagggactggctgctattgggcgaagtgccggggcaggatctcctgtcatctcaccttgctcctgccgagaaagtatccatcatggctgatgcaatgcggcggctgcatacgcttgatcc
ggctacctgcccattcgaccaccaagcgaaacatcgcatcgagcgagcacgtactcggatgg
aagccggtcttgtcgatcaggatgatctggacgaagagcatcaggggctcgcgccagccgaa
ctgttcgccaggctcaaggcgcgcatgcccgacggcgaggatctcgtcgtgacccatggcga
tgcctgcttgccgaatatcatggtggaaaatggccgcttttctggattcatcgactgtggcc
ggctgggtgtggcggaccgctatcaggacatagcgttggctacccgtgatattgctgaagag
cttggcggcgaatgggctgaccgcttcctcgtgctttacggtatcgccgctcccgattcgca
gcgcatcgccttctatcgccttcttgacgagttcttctgagcgggactctggggttcgaaat
gaccgaccaagcgacgcccaacctgccatcacgagatttcgattccaccgccgccttctatg
aaaggttgggcttcggaatcgttttccgggacgccggctggatgatcctccagcgcggggat
ctcatgctggagttcttcgcccaccccaacttgtttattgcagcttataatggttacaaata
aagcaatagcatcacaaatttcacaaataaagcattttttttcactgcattctagttgtggtt
tgtccaaactcatcaatgtatcttatcatgtctgtataccgtcgacctctagctagagcttg
gcgtaatcatggtcatagctgtttcctgtgtgaaattgttatccgctcacaattccacacaa
catacgagccggaagcataaagtgtaaagcctggggtgcctaatgagtgagctaactcacat
taattgcgttgcgctcactgcccgctttccagtcgggaaacctgtcgtgccagctgcattaa
tgaatcggccaacgcgcggggagaggcggtttgcgtattgggcgctcttccgcttcctcgct
```

FIG. 5C

```
cactgactcgctgcgctcggtcgttcggctgcggcgagcggtatcagctcactcaaaggcgg
taatacggttatccacagaatcaggggataacgcaggaaagaacatgtgagcaaaaggccag
caaaaggccaggaaccgtaaaaaggccgcgttgctggcgttttccataggctccgccccc
tgacgagcatcacaaaaatcgacgctcaagtcagaggtggcgaaacccgacaggactataaa
gataccaggcgtttccccctggaagctccctcgtgcgctctcctgttccgaccctgccgctt
accggatacctgtccgcctttctcccttcgggaagcgtggcgctttctcaatgctcacgctg
taggtatctcagttcggtgtaggtcgttcgctccaagctgggctgtgtgcacgaaccccccg
ttcagcccgaccgctgcgccttatccggtaactatcgtcttgagtccaacccggtaagacac
gacttatcgccactggcagcagccactggtaacaggattagcagagcgaggtatgtaggcgg
tgctacagagttcttgaagtggtggcctaactacggctacactagaaggacagtatttggta
tctgcgctctgctgaagccagttaccttcggaaaaagagttggtagctcttgatccggcaaa
caaccaccgctggtagcggtggtttttttgtttgcaagcagcagattacgcgcagaaaaaa
aggatctcaagaagatcctttgatcttttctacggggtctgacgctcagtggaacgaaaact
cacgttaagggattttggtcatgagattatcaaaaaggatcttcacctagatccttttaaat
taaaaatgaagttttaaatcaatctaaagtatatatgagtaaacttggtctgacagttacca
atgcttaatcagtgaggcacctatctcagcgatctgtctatttcgttcatccatagttgcct
gactccccgtcgtgtagataactacgatacgggagggcttaccatctggccccagtgctgca
atgataccgcgagacccacgctcaccggctccagatttatcagcaataaaccagccagccgg
aagggccgagcgcagaagtggtcctgcaactttatccgcctccatccagtctattaattgtt
gccgggaagctagagtaagtagttcgccagttaatagtttgcgcaacgttgttgccattgct
acaggcatcgtggtgtcacgctcgtcgtttggtatggcttcattcagctccggttcccaacg
atcaaggcgagttacatgatccccatgttgtgcaaaaaagcggttagctccttcggtcctc
cgatcgttgtcagaagtaagttggccgcagtgttatcactcatggttatggcagcactgcat
aattctcttactgtcatgccatccgtaagatgcttttctgtgactggtgagtactcaaccaa
gtcattctgagaatagtgtatgcggcgaccgagttgctcttgcccggcgtcaatacgggata
ataccgcgccacatagcagaactttaaaagtgctcatcattggaaaacgttcttcggggcga
aaactctcaaggatcttaccgctgttgagatccagttcgatgtaacccactcgtgcacccaa
ctgatcttcagcatcttttactttcaccagcgtttctgggtgagcaaaaacaggaaggcaaa
atgccgcaaaaagggaataagggcgacacggaaatgttgaatactcatactcttcctttt
caatattattgaagcatttatcagggttattgtctcatgagcggatacatatttgaatgtat
ttagaaaaataaacaatagggttccgcgcacatttccccgaaaagtgccacctgacgtcg
acggatcgggagatc
```

FIG. 6A pcDIMer-P nt 1358 - 2881: P ORF MeV Schwarz (1524 nt = 507 aa + stop codon)

agcttgcatgcctgcaggtcaattccctggcattatgcccagtacatgaccttatgggactt
tcctacttggcagtacatctacgtattagtcatcgctattaccatggtgatgcggttttggc
agtacatcaatgcgcgtggataccggtttgactcacggggatttccaagtctccaccccatt
cacgtcaatgggagtttgttttggcaccaaaatcaacgggacttttccaaaatgtcgtaacaa
ctccgccccattgacgcaaatgggcggtaggcgtgtacggtgggaggtctatataagcagag
ctcgtttagtgaaccgtcagatcgcctggagacgccatccacgctgttttgacctccataga
agacaccgggaccgatccagcctggggatctagcctccgcggccgggaacggtgcattggaa
cgcggattccccgtgccaagagtgacgtaagtaccgcctatagtctataggcccaccccc
ttggcttcttatgcatgctatactgttttggcttggggtctatacaccccgcttcctcat
gttataggtgatggtatagcttagcctataggtgtgggttattgaccattattgaccactcc
cctattggtgacgatacttttccattactaatccataacatggctctttgccacaactctctt
tattggctatatgccaatacactgtccttcagagactgacacggactctgtattttacagg
atggggtctcatttattatttacaaattcacatatacaacaccaccgtccccagtgcccgca
gttttattaaacataacgtgggatctccacgcgaatctcgggtacgtgttccggacatggg
ctcttctccggtagcggcggagctcctacatccgagccctgctccatgcctccagcgactc
atggtcgctcggcagctccttgctcctaacagtggaggccagacttaggcacagcacgatgc
ccaccaccaccagtgtgccgcacaaggccgtggcggtagggtatgtgtctgaaaatgagctc
ggggagcgggcttgcaccgctgacgcatttggaagacttaaggcagcggcagaagaagatgc
aggcagctgagttgttgtgttctgataagagtcagaggtaactcccgttgcggtgctgttaa
cggtggagggcagtgtagtctgagcagtactcgttgctgccgcgcgccaccagacataat
agctgacagactaacagactgttccttccatgggtcttttctgcagtcaccgtccttgaca
cgatcggatcccgggtacctctagaagatctgatatcgtcgacctcgaggccaccatggcag
aagagcaggcacgccatgtcaaaaacggactggaatgcatccgggctctcaaggccgagccc
atcggctcactggccatcgaggaagctatggcagcatggtcagaaatatcagacaacccagg
acaggagcgagccacctgcagggaagagaaggcaggcagttcgggtctcagcaaaccatgcc
tctcagcaattggatcaactgaaggcggtgcacctcgcatccgcggtcagggacctggagag
agcgatgacgacgctgaaactttgggaatcccccaagaaatctccaggcatcaagcactgg
gttacagtgttattacgtttatgatcacagcggtgaagcggttaagggaatccaagatgctg
actctatcatggttcaatcaggccttgatggtgatagcaccctctcaggaggagacaatgaa
tctgaaaacagcgatgtggatattggcgaacctgataccgagggatatgctatcactgaccg
gggatctgctccatctctatggggttcagggcttctgatgttgaaactgcagaaggagggg
agatccacgagctcctgagactccaatccagaggcaacaactttccgaagcttgggaaaact
ctcaatgttcctccgcccccggaccccggtagggccagcacttccgggacacccattaaaaa
gggcacagacgcgagattagcctcatttggaacggagatcgcgtctttattgacaggtggtg
caacccaatgtgctcgaaagtcaccctcggaaccatcagggccaggtgcacctgcggggaat
gtccccgagtgtgtgagcaatgccgcactgatacaggagtggacacccgaatctggtaccac
aatctccccgagatcccagaataatgaagaaggggggagactattatgatgatgagctgttct
ctgatgtccaagatattaaaacagccttggccaaaatacacgaggataatcagaagataatc
tccaagctagaatcactgctgttattgaagggagaagttgagtcaattaagaagcagatcaa
caggcaaaatatcagcatatccaccctggaaggacacctctcaagcatcatgatcgccattc
ctggacttgggaaggatcccaacgaccccactgcagatgtcgaaatcaatcccgacttgaaa
cccatcataggcagagattcaggccgagcactggccgaagttctcaagaaacccgttgccag
ccgacaactccaaggaatgacaaatggacggaccagttccagaggacagctgctgaaggaat
ttcagctaaagccgatcgggaaaaagatgagctcagccgtcgggttgttcctgacaccggc
cctgcatcacgcagtgtaatccgctccattataaaatccagccggctagaggaggatcggaa

FIG. 6B

```
gcgttacctgatgactctccttgatgatatcaaaggagccaatgatcttgccaagttccacc
agatgctgatgaagataataatgaagtagctacagctcaacttacctgccaacccatgcca
gtcgacccaactagtacaacctaaatcctcgaggaattctagatcccacgtcactattgtat
actctatattatactctatgttatactctgtaatcctactcaataaacgtgtcacgcctgtg
aaaccgtactaagtctcccgtgtcttcttatcaccatcaggtgacatcctcgcccaggctgt
caatcatgccggtatcgattccagtagcaccggccccacgctgacaacccactcttgcagcg
ttagcagcgcccctcttaacaagccgaccccaccagcgtcgcggttactaacactcctctc
cccgacctgcagcccaagctctagagggccctattctatagtgtcacctaaatgctagagct
cgctgatcagcctcgactgtgccttctagttgccagccatctgttgtttgcccctccccgt
gccttccttgacctggaaggtgccactcccactgtcctttcctaataaaatgaggaaattg
catcgcattgtctgagtaggtgtcattctattctgggggtgggtggggcaggacagcaag
ggggaggattgggaagacaatagcaggcatgctggggatgcggtgggctctatggcttctga
ggcggaaagaaccagctggggctctaggggtatccccacgcgcctgtagcggcgcattaa
gcgcggcggtgtggtggttacgcgcagcgtgaccgctacacttgccagcgccctagcgccc
gctcctttcgctttcttccttcctttctcgccacgttcgccggctttccccgtcaagctct
aaatcggggcatccctttagggttccgatttagtgctttacggcacctcgaccccaaaaac
ttgattagggtgatggttcacgtagtgggccatcgccctgatagacggttttttcgccttg
acgttggagtccacgttctttaatagtggactcttgttccaaactggaacaacactcaaccc
tatctcggtctattcttttgatttataagggattttggggatttcggcctattggttaaaaa
atgagctgatttaacaaaaatttaacgcgaattaattctgtggaatgtgtgtcagttaggt
gtggaaagtccccaggctccccaggcaggcagaagtatgcaaagcatgcatctcaattagtc
agcaaccaggtgtggaaagtccccaggctccccagcaggcagaagtatgcaaagcatgcatc
tcaattagtcagcaaccatagtcccgcccctaactccgcccatcccgcccctaactccgccc
agttccgcccattctccgcccatggctgactaattttttttatttatgcagaggccgaggc
cgcctctgcctctgagctattccagaagtagtgaggaggcttttttggaggcctaggctttt
gcaaaaagctcccgggagcttgtatatccattttcggatctgatcaagagacaggatgagga
tcgtttcgcatgattgaacaagatggattgcacgcaggttctccggccgcttgggtggagag
gctattcggctatgactgggcacaacagacaatcggctgctctgatgccgccgtgttccggc
tgtcagcgcaggggcgcccggttcttttttgtcaagaccgacctgtccggtgccctgaatgaa
ctgcaggacgaggcagcgcggctatcgtggctggccacgacgggcgttccttgcgcagctgt
gctcgacgttgtcactgaagcgggaagggactggctgctattgggcgaagtgccggggcagg
atctcctgtcatctcaccttgctcctgccgagaaagtatccatcatggctgatgcaatgcgg
cggctgcatacgcttgatccggctacctgcccattcgaccaccaagcgaaacatcgcatcga
gcgagcacgtactcggatggaagccggtcttgtcgatcaggatgatctggacgaagagcatc
agggctcgcgccagccgaactgttcgccaggctcaaggcgcgcatgcccgacggcgaggat
ctcgtcgtgacccatggcgatgcctgcttgccgaatatcatggtggaaaatggccgctttc
tggattcatcgactgtggccggctgggtgtggcggaccgctatcaggacatagcgttggcta
cccgtgatattgctgaagagcttggcggcgaatgggctgaccgcttcctcgtgctttacggt
atcgccgctcccgattcgcagcgcatcgccttctatcgccttcttgacgagttcttctgagc
gggactctggggttcgaaatgaccgaccaagcgacgcccaacctgccatcacgagatttcga
ttccaccgccgccttctatgaaaggttgggcttcggaatcgttttccgggacgccggctgga
tgatcctccagcgcggggatctcatgctggagttcttcgcccaccccaacttgtttattgca
gcttataatggttacaaataaagcaatagcatcacaaatttcacaaataaagcatttttttc
actgcattctagttgtggtttgtccaaactcatcaatgtatcttatcatgtctgtataccgt
cgacctctagctagagcttggcgtaatcatggtcatagctgtttcctgtgtgaaattgttat
ccgctcacaattccacacaacatacgagccggaagcataaagtgtaaagcctggggtgccta
atgagtgagctaactcacattaattgcgttgcgctcactgcccgctttccagtcgggaaacc
tgtcgtgccagctgcattaatgaatcggccaacgcgcggggagaggcggtttgcgtattggg
cgctcttccgcttcctcgctcactgactcgctgcgctcggtcgttcggctgcggcgagcggt
atcagctcactcaaaggcggtaatacggttatccacagaatcaggggataacgcaggaaaga
```

FIG. 6C

```
acatgtgagcaaaaggccagcaaaaggccaggaaccgtaaaaaggccgcgttgctggcgttt
ttccataggctccgcccccctgacgagcatcacaaaaatcgacgctcaagtcagaggtggcg
aaacccgacaggactataaagataccaggcgtttccccctggaagctccctcgtgcgctctc
ctgttccgaccctgccgcttaccggatacctgtccgcctttctcccttcgggaagcgtggcg
ctttctcaatgctcacgctgtaggtatctcagttcggtgtaggtcgttcgctccaagctggg
ctgtgtgcacgaaccccccgttcagcccgaccgctgcgccttatccggtaactatcgtcttg
agtccaacccggtaagacacgacttatcgccactggcagcagccactggtaacaggattagc
agagcgaggtatgtaggcggtgctacagagttcttgaagtggtggcctaactacggctacac
tagaaggacagtatttggtatctgcgctctgctgaagccagttaccttcggaaaaagagttg
gtagctcttgatccggcaaacaaaccaccgctggtagcggtggttttttgtttgcaagcag
cagattacgcgcagaaaaaaaggatctcaagaagatcctttgatcttttctacggggtctga
cgctcagtggaacgaaaactcacgttaagggattttggtcatgagattatcaaaaaggatct
tcacctagatccttttaaattaaaaatgaagttttaaatcaatctaaagtatatatgagtaa
acttggtctgacagttaccaatgcttaatcagtgaggcacctatctcagcgatctgtctatt
tcgttcatccatagttgcctgactccccgtcgtgtagataactacgatacgggagggcttac
catctggccccagtgctgcaatgataccgcgagacccacgctcaccggctccagatttatca
gcaataaaccagccagccggaagggccgagcgcagaagtggtcctgcaactttatccgcctc
catccagtctattaattgttgccgggaagctagagtaagtagttcgccagttaatagtttgc
gcaacgttgttgccattgctacaggcatcgtggtgtcacgctcgtcgtttggtatggcttca
ttcagctccggttcccaacgatcaaggcgagttacatgatccccatgttgtgcaaaaaagc
ggttagctccttcggtcctccgatcgttgtcagaagtaagttggccgcagtgttatcactca
tggttatggcagcactgcataattctcttactgtcatgccatccgtaagatgcttttctgtg
actggtgagtactcaaccaagtcattctgagaatagtgtatgcggcgaccgagttgctcttg
cccggcgtcaatacgggataataccgcgccacatagcagaactttaaaagtgctcatcattg
gaaaacgttcttcgggcgaaaactctcaaggatcttaccgctgttgagatccagttcgatg
taacccactcgtgcacccaactgatcttcagcatcttttactttcaccagcgtttctgggtg
agcaaaaacaggaaggcaaaatgccgcaaaaaagggaataagggcgacacggaaatgttgaa
tactcatactcttccttttcaatattattgaagcatttatcagggttattgtctcatgagc
ggatacatatttgaatgtatttagaaaaataaacaataggggttccgcgcacatttccccg
aaaagtgccacctgacgtcgacggatcgggagatc
```

FIG. 7A pcDIMer-L nt 1358 - 7909: L ORF MeV Schwarz (6552 nt = 2183 aa + stop codon)

agcttgcatgcctgcaggtcaattccctggcattatgcccagtacatgaccttatgggactt
tcctacttggcagtacatctacgtattagtcatcgctattaccatggtgatgcggttttggc
agtacatcaatgcgcgtggataccggtttgactcacggggatttccaagtctccaccccatt
cacgtcaatgggagtttgttttggcaccaaaatcaacgggactttccaaaatgtcgtaacaa
ctccgccccattgacgcaaatgggcggtaggcgtgtacggtgggaggtctatataagcagag
ctcgtttagtgaaccgtcagatcgcctggagacgccatccacgctgttttgacctccataga
agacaccgggaccgatccagcctggggatctagcctccgcggccgggaacggtgcattggaa
cgcggattccccgtgccaagagtgacgtaagtaccgcctatagagtctataggcccaccccc
ttggcttcttatgcatgctatactgtttttggcttggggtctatacacccccgcttcctcat
gttataggtgatggtatagcttagcctataggtgtgggttattgaccattattgaccactcc
cctattggtgacgatactttccattactaatccataacatggctctttgccacaactctctt
tattggctatatgccaatacactgtccttcagagactgacacggactctgtatttttacagg
atggggtctcatttattatttacaaattcacatatacaacaccaccgtccccagtgcccgca
gtttttattaaacataacgtgggatctccacgcgaatctcgggtacgtgttccggacatggg
ctcttctccggtagcggcggagctcctacatccgagccctgctcccatgcctccagcgactc
atggtcgctcggcagctccttgctcctaacagtggaggccagacttaggcacagcacgatgc
ccaccaccaccagtgtgccgcacaaggccgtggcggtagggtatgtgtctgaaaatgagctc
ggggagcgggcttgcaccgctgacgcatttggaagacttaaggcagcggcagaagaagatgc
aggcagctgagttgttgtgttctgataagagtcagaggtaactcccgttgcggtgctgttaa
cggtggagggcagtgtagtctgagcagtactcgttgctgccgcgcgcgccaccagacataat
agctgacagactaacagactgttcctttccatgggtcttttctgcagtcaccgtccttgaca
cgatcggatcccgggtacctctagaagatctgatatcgtcgacctcgacgccaccatggact
cgctatctgtcaaccagatcttataccctgaagttcacctagatagcccgatagttaccaat
aagatagtagccatcctggagtatgctcgagtccctcacgcttacagcctggaggaccctac
actgtgtcagaacatcaagcaccgcctaaaaaacggattttccaaccaaatgattataaaca
atgtggaagttgggaatgtcatcaagtccaagcttaggagttatccggcccactctcatatt
ccatatccaaattgtaatcaggatttatttaacatagaagacaaagagtcaacgaggaagat
ccgtgaactcctcaaaaaggggaattcgctgtactccaaagtcagtgataaggttttccaat
gcttaagggacactaactcacggcttggcctaggctccgaattgagggaggacatcaaggag
aaagttattaacttgggagtttacatgcacagctcccagtggtttgagccctttctgttttg
gtttacagtcaagactgagatgaggtcagtgattaaatcacaaacccatacttgccatagga
ggagacacacacctgtattcttcactggtagttcagttgagttgctaatctctcgtgacctt
gttgctataatcagtaaagagtctcaacatgtatattacctgacatttgaactggttttgat
gtattgtgatgtcatagaggggaggttaatgacagagaccgctatgactattgatgctaggt
atacagagcttctaggaagagtcagatacatgtggaaactgatagatggtttcttccctgca
ctcgggaatccaacttatcaaattgtagccatgctggagcctctttcacttgcttacctgca
gctgagggatataacagtagaactcagaggtgctttccttaaccactgctttactgaaatac
atgatgttcttgaccaaaacgggttttctgatgaaggtacttatcatgagttaactgaagct
ctagattacattttcataactgatgacatacatctgacaggggagattttctcatttttcag
aagtttcggccaccccagacttgaagcagtaacggctgctgaaaatgttaggaaatacatga
atcagcctaaagtcattgtgtatgagactctgatgaaaggtcatgccatattttgtggaatc
ataatcaacggctatcgtgacaggcacggaggcagttggccaccgctgaccctcccccctgca
tgctgcagacacaatccggaatgctcaagcttcaggtgaagggttaacacatgagcagtgcg
ttgataactggaaatcttttgctggagtgaaatttggctgctttatgcctcttagcctggat
agtgatctgacaatgtacctaaaggacaaggcacttgctgctctccaaagggaatgggattc

FIG. 7B

```
agtttacccgaaagagttcctgcgttacgaccctcccaagggaaccgggtcacggaggcttg
tagatgttttccttaatgattcgagctttgacccatatgatgtgataatgtatgttgtaagt
ggagcttacctccatgaccctgagttcaacctgtcttacagcctgaaagaaaaggagatcaa
ggaaacaggtagacttttttgctaaaatgacttacaaaatgagggcatgccaagtgattgctg
aaaatctaatctcaaacgggattggcaaatattttaaggacaatgggatggccaaggatgag
cacgatttgactaaggcactccacactctagctgtctcaggagtccccaaagatctcaaaga
agtcacagggggggccagtcttaaaaacctactcccgaagcccagtccacacaagtacca
ggaacgtgagagcagcaaaagggtttatagggttccctcaagtaattcggcaggaccaagac
actgatcatccggagaatatggaagcttacgagacagtcagtgcatttatcacgactgatct
caagaagtactgccttaattggagatatgagaccatcagcttgtttgcacagaggctaaatg
agatttacggattgccctcattttccagtggctgcataagaggcttgagacctctgtcctg
tatgtaagtgaccctcattgccccccgaccttgacgcccatatcccgttatataaagtccc
caatgatcaaatcttcattaagtacccatgggaggtatagaagggtattgtcagaagctgt
ggaccatcagcaccattccctatctatacctggctgcttatgagagcggagtaaggattgct
tcgttagtgcaaggggacaatcagaccatagccgtaacaaaaagggtacccagcacatggcc
ctacaaccttaagaaacgggaagctgctagagtaactagagattactttgtaattcttaggc
aaaggctacatgatattggccatcacctcaaggcaaatgagacaattgtttcatcacatttt
tttgtctattcaaaaggaatatattatgatgggctacttgtgtcccaatcactcaagagcat
cgcaagatgtgtattctggtcagagactatagttgatgaaacaagggcagcatgcagtaata
ttgctacaacaatggctaaaagcatcgagagaggttatgaccgttaccttgcatattccctg
aacgtcctaaaagtgatacagcaaattctgatctctcttggcttcacaatcaattcaaccat
gacccgggatgtagtcatacccctcctcacaaacaacgacctcttaataaggatggcactgt
tgcccgctcctattgggggatgaattatctgaatatgagcaggctgtttgtcagaaacatc
ggtgatccagtaacatcatcaattgctgatctcaagagaatgattctcgcctcactaatgcc
tgaagagaccctccatcaagtaatgacacaacaaccggggggactcttcattcctagactggg
ctagcgaccttactcagcaaatcttgtatgtgtccagagcatcactagactcctcaagaac
ataactgcaaggtttgtcctgatccatagtccaaacccaatgttaaaaggattattccatga
tgacagtaaagaagaggacgagggactggcggcattcctcatggacaggcatattatagtac
ctagggcagctcatgaaatcctggatcatagtgtcacaggggcaagagagtctattgcaggc
atgctggataccacaaaaggcttgattcgagccagcatgaggaagggggggttaacctctcg
agtgataaccagattgtccaattatgactatgaacaattcagagcagggatggtgctattga
caggaagaaagagaaatgtcctcattgacaaagagtcatgttcagtgcagctggcgagagct
ctaagaagccatatgtgggcgaggctagctcgaggacggcctatttacggccttgaggtccc
tgatgtactagaatctatgcgaggccaccttattcggcgtcatgagacatgtgtcatctgcg
agtgtggatcagtcaactacggatggttttttgtccctcgggttgccaactggatgatatt
gacaaggaaacatcatccttgagagtcccatatattggttctaccactgatgagagaacaga
catgaagcttgccttcgtaagagccccaagtcgatccttgcgatctgctgttagaatagcaa
cagtgtactcatgggcttacggtgatgatgatagctcttggaacgaagcctggttgttggct
aggcaaagggccaatgtgagcctggaggagctaagggtgatcactcccatctcaacttcgac
taatttagcgcataggttgagggatcgtagcactcaagtgaaatactcaggtacatcccttg
tccgagtggcgaggtataccacaatctccaacgacaatctctctttgtcatatcagataag
aaggttgatactaactttatataccaacaaggaatgcttctaggggttgggtgttttagaaac
attgtttcgactcgagaaagataccggatcatctaacacggtattacatcttcacgtcgaaa
cagattgttgcgtgatcccgatgatagatcatcccaggatacccagctcccgcaagctagag
ctgagggcagagctatgtaccaacccattgatatgataatgcacctttaattgacagaga
tgcaacaaggctatacacccagagccataggaggcaccttgtggaatttgttacatggtcca
caccccaactatatcacattttagctaagtccacagcactatctatgattgacctggtaaca
aaatttgagaaggaccatatgaatgaaatttcagctctcataggggatgacgatatcaatag
tttcataactgagtttctgctcatagagccaagattattcactatctacttgggccagtgtg
cggccatcaattgggcatttgatgtacattatcatagaccatcagggaaatatcagatgggt
```

FIG. 7C

```
gagctgttgtcatcgttcctttctagaatgagcaaaggagtgtttaaggtgcttgtcaatgc
tctaagccacccaaagatctacaagaaattctggcattgtggtattatagagcctatccatg
gtccttcacttgatgctcaaaacttgcacacaactgtgtgcaacatggtttacacatgctat
atgacctacctcgacctgttgttgaatgaagagttagaagagttcacatttctcttgtgtga
aagcgacgaggatgtagtaccggacagattcgacaacatccaggcaaaacacttatgtgttc
tggcagatttgtactgtcaaccagggacctgcccaccaattcgaggtctaagaccggtagag
aaatgtgcagttctaaccgaccatatcaaggcagaggctatgttatctccagcaggatcttc
gtggaacataaatccaattattgtagaccattactcatgctctctgacttatctccggcgag
gatcgatcaaacagataagattgagagttgatccaggattcattttcgacgccctcgctgag
gtaaatgtcagtcagccaaagatcggcagcaacaacatctcaaatatgagcatcaaggcttt
cagaccccacacgatgatgttgcaaaattgctcaaagatatcaacacaagcaagcacaatc
ttcccatttcagggggcaatctcgccaattatgaaatccatgctttccgcagaatcggttg
aactcatctgcttgctacaaagctgttgagatatcaacattaattaggagatgccttgagcc
aggggaggacggcttgttcttgggtgagggatcgggttctatgttgatcacttataaagaga
tacttaaactaaacaagtgcttctataatagtgggtttccgccaattctagatctggtcaa
agggaattagcaccctatccctccgaagttggccttgtcgaacacagaatgggagtaggtaa
tattgtcaaagtgctctttaacgggaggcccgaagtcacgtgggtaggcagtgtagattgct
tcaatttcatagttagtaatatccctacctcagtgtggggtttatccattcagatatagag
accttgcctgacaaagatactatagagaagctagaggaattggcagccatcttatcgatggc
tctgctcctgggcaaaataggatcaatactggtgattaagcttatgcctttcagcggggatt
ttgttcagggatttataagttatgtagggtctcattatagagaagtgaaccttgtataccct
agatacagcaacttcatctctactgaatcttatttggttatgacagatctcaaggctaaccg
gctaatgaatcctgaaaagattaagcagcagataattgaatcatctgtgaggacttcacctg
gacttataggtcacatcctatccattaagcaactaagctgcatacaagcaattgtgggagac
gcagttagtagaggtgatatcaatcctactctgaaaaaacttacacctatagagcaggtgct
gatcaattgcgggttggcaattaacggacctaagctgtgcaaagaattgatccaccatgatg
ttgcctcagggcaagatggattgcttaattctatactcatcctctacagggagttggcaaga
ttcaaagacaaccaaagaagtcaacaagggatgttccacgcttacccgtattggtaagtag
caggcaacgagaacttatatctaggatcacccgcaaattctgggggcacattcttctttact
ccgggaacaaaaagttgataaataagtttatccagaatctcaagtccggctatctgatacta
gacttacaccagaatatcttcgttaagaatctatccaagtcagagaaacagattattatgac
gggggggtttgaaacgtgagtgggttttttaaggtaacagtcaaggagaccaaagaatggtata
agttagtcggatacagtgccctgattaaggactaattggttgaactccggaaccctaatcct
gccctaggtggttaggcattatttgcagaattctagatcccacgtcactattgtatactcta
tattatactctatgttatactctgtaatcctactcaataaacgtgtcacgcctgtgaaaccg
tactaagtctcccgtgtcttcttatcaccatcaggtgacatcctcgcccaggctgtcaatca
tgccggtatcgattccagtagcaccggccccacgctgacaacccactcttgcagcgttagca
gcgcccctcttaacaagccgaccccaccagcgtcgcggttactaacactcctctccccgac
ctgcagcccaagctctagagggccctattctatagtgtcacctaaatgctagagctcgctga
tcagcctcgactgtgccttctagttgccagccatctgttgtttgcccctccccgtgccttc
cttgaccctggaaggtgccactcccactgtcctttcctaataaaatgaggaaattgcatcgc
attgtctgagtaggtgtcattctattctggggggtggggtggggcaggacagcaaggggag
gattgggaagacaatagcaggcatgctgggatgcggtgggctctatggcttctgaggcgga
aagaaccagctggggctctaggggtatccccacgcgccctgtagcggcgcattaagcgcgg
cgggtgtggtggttacgcgcagcgtgaccgctacacttgccagcgccctagcgcccgctcct
ttcgctttcttcccttcctttctcgccacgttcgccggctttccccgtcaagctctaaatcg
gggcatccctttagggttccgatttagtgctttacggcacctcgaccccaaaaaacttgatt
agggtgatggttcacgtagtgggccatcgccctgatagacggttttttcgccctttgacgttg
gagtccacgttctttaatagtggactcttgttccaaactggaacaacactcaaccctatctc
ggtctattcttttgatttataagggattttggggatttcggcctattggttaaaaaatgagc
```

FIG. 7D

```
tgatttaacaaaaatttaacgcgaattaattctgtggaatgtgtgtcagttagggtgtggaa
agtccccaggctcccaggcaggcagaagtatgcaaagcatgcatctcaattagtcagcaac
caggtgtggaaagtccccaggctcccagcaggcagaagtatgcaaagcatgcatctcaatt
agtcagcaaccatagtcccgcccctaactccgcccatcccgcccctaactccgcccagttcc
gcccattctccgcccatggctgactaattttttttatttatgcagaggccgaggccgcctc
tgcctctgagctattccagaagtagtgaggaggctttttggaggcctaggcttttgcaaaa
agctcccgggagcttgtatatccattttcggatctgatcaagagacaggatgaggatcgttt
cgcatgattgaacaagatggattgcacgcaggttctccggccgcttgggtggagaggctatt
cggctatgactgggcacaacagacaatcggctgctctgatgccgccgtgttccggctgtcag
cgcaggggcgcccggttcttttttgtcaagaccgacctgtccggtgccctgaatgaactgcag
gacgaggcagcgcggctatcgtggctggccacgacgggcgttccttgcgcagctgtgctcga
cgttgtcactgaagcgggaagggactggctgctattgggcgaagtgccggggcaggatctcc
tgtcatctcaccttgctcctgccgagaaagtatccatcatggctgatgcaatgcggcggctg
catacgcttgatccggctacctgcccattcgaccaccaagcgaaacatcgcatcgagcgagc
acgtactcggatggaagccggtcttgtcgatcaggatgatctggacgaagagcatcaggggc
tcgcgccagccgaactgttcgccaggctcaaggcgcgcatgcccgacggcgaggatctcgtc
gtgacccatggcgatgcctgcttgccgaatatcatggtggaaaatggccgcttttctggatt
catcgactgtggccggctgggtgtggcggaccgctatcaggacatagcgttggctacccgtg
atattgctgaagagcttggcggcgaatgggctgaccgcttcctcgtgctttacggtatcgcc
gctcccgattcgcagcgcatcgccttctatcgccttcttgacgagttcttctgagcgggact
ctggggttcgaaatgaccgaccaagcgacgcccaacctgccatcacgagatttcgattccac
cgccgccttctatgaaaggttgggcttcggaatcgttttccgggacgccggctggatgatcc
tccagcgcggggatctcatgctggagttcttcgcccacccccaacttgtttattgcagcttat
aatggttacaaataaagcaatagcatcacaaatttcacaaataaagcattttttttcactgca
ttctagttgtggtttgtccaaactcatcaatgtatcttatcatgtctgtataccgtcgacct
ctagctagagcttggcgtaatcatggtcatagctgtttcctgtgtgaaattgttatccgctc
acaattccacacaacatacgagccggaagcataaagtgtaaagcctggggtgcctaatgagt
gagctaactcacattaattgcgttgcgctcactgcccgctttccagtcgggaaacctgtcgt
gccagctgcattaatgaatcggccaacgcgcggggagaggcggtttgcgtattgggcgctct
tccgcttcctcgctcactgactcgctgcgctcggtcgttcggctgcggcgagcggtatcagc
tcactcaaaggcggtaatacggttatccacagaatcaggggataacgcaggaaagaacatgt
gagcaaaaggccagcaaaaggccaggaaccgtaaaaaggccgcgttgctggcgttttttccat
aggctccgcccccctgacgagcatcacaaaaatcgacgctcaagtcagaggtggcgaaaccc
gacaggactataaagataccaggcgtttccccctggaagctccctcgtgcgctctcctgttc
cgaccctgccgcttaccggatacctgtccgcctttctcccttcgggaagcgtggcgctttct
caatgctcacgctgtaggtatctcagttcggtgtaggtcgttcgctccaagctgggctgtgt
gcacgaaccccccgttcagcccgaccgctgcgccttatccggtaactatcgtcttgagtcca
acccggtaagacacgacttatcgccactggcagcagccactggtaacaggattagcagagcg
aggtatgtaggcggtgctacagagttcttgaagtggtggcctaactacggctacactagaag
gacagtatttggtatctgcgctctgctgaagccagttaccttcggaaaaagagttggtagct
cttgatccggcaaacaaaccaccgctggtagcggtggtttttttgtttgcaagcagcagatt
acgcgcagaaaaaaaggatctcaagaagatcctttgatcttttctacggggtctgacgctca
gtggaacgaaaactcacgttaagggattttggtcatgagattatcaaaaaggatcttcacct
agatccttttaaattaaaaatgaagttttaaatcaatctaaagtatatatgagtaaacttgg
tctgacagttaccaatgcttaatcagtgaggcacctatctcagcgatctgtctatttcgttc
atccatagttgcctgactccccgtcgtgtagataactacgatacgggagggcttaccatctg
gccccagtgctgcaatgataccgcgagacccacgctcaccggctccagatttatcagcaata
aaccagccagccggaagggccgagcgcagaagtggtcctgcaactttatccgcctccatcca
gtctattaattgttgccgggaagctagagtaagtagttcgccagttaatagtttgcgcaacg
ttgttgccattgctacaggcatcgtggtgtcacgctcgtcgtttggtatggcttcattcagc
```

FIG. 7E tccggttcccaacgatcaaggcgagttacatgatcccccatgttgtgcaaaaaagcggttag
ctccttcggtcctccgatcgttgtcagaagtaagttggccgcagtgttatcactcatggtta
tggcagcactgcataattctcttactgtcatgccatccgtaagatgcttttctgtgactggt
gagtactcaaccaagtcattctgagaatagtgtatgcggcgaccgagttgctcttgcccggc
gtcaatacgggataataccgcgccacatagcagaactttaaaagtgctcatcattggaaaac
gttcttcggggcgaaaactctcaaggatcttaccgctgttgagatccagttcgatgtaaccc
actcgtgcacccaactgatcttcagcatcttttactttcaccagcgtttctgggtgagcaaa
aacaggaaggcaaaatgccgcaaaaagggaataagggcgacacggaaatgttgaatactca
tactcttccttttcaatattattgaagcatttatcagggttattgtctcatgagcggatac
atatttgaatgtatttagaaaaataaacaatagggttccgcgcatttccccgaaaagt
gccacctgacgtcgacggatcgggagatc

FIG. 8B

RBE

| 5-FC | control | MOI 0.01 | MOI 0.1 | MOI 1 |
|---|---|---|---|---|
| 0 | 100.00 | 112.35 | 85.27 | 41.90 |
| 0.0001 | 109.83 | 118.46 | 73.62 | 37.70 |
| 0.001 | 110.54 | 108.68 | 45.03 | 27.18 |
| 0.01 | 107.05 | 91.61 | 25.56 | 10.36 |
| 0.1 | 101.41 | 69.78 | 11.91 | 1.51 |
| 1 | 92.62 | 56.72 | 9.08 | 1.94 |

TFK-1

| 5-FC | control | MOI 0.01 | MOI 0.1 | MOI 1 |
|---|---|---|---|---|
| 0 | 100.00 | 83.05 | 47.97 | 13.61 |
| 0.0001 | 100.03 | 77.25 | 32.41 | 8.74 |
| 0.001 | 101.18 | 69.85 | 21.43 | 6.42 |
| 0.01 | 100.83 | 51.79 | 13.35 | 5.24 |
| 0.1 | 95.16 | 33.38 | 6.76 | 3.92 |
| 1 | 94.60 | 15.83 | 2.75 | 2.70 |

HuCCT1

| 5-FC | control | MOI 0.01 | MOI 0.1 | MOI 1 |
|---|---|---|---|---|
| 0 | 100.00 | 89.26 | 71.27 | 47.98 |
| 0.0001 | 98.55 | 95.65 | 76.40 | 44.87 |
| 0.001 | 97.64 | 93.53 | 64.04 | 27.78 |
| 0.01 | 96.01 | 80.94 | 39.96 | 21.98 |
| 0.1 | 96.95 | 51.17 | 17.00 | 5.21 |
| 1 | 90.08 | 33.41 | 2.68 | 1.43 |

FIG. 10B

SAS

| 5-FC | control | MOI 0.01 | MOI 0.1 | MOI 1 |
|---|---|---|---|---|
| 0 | 100.00 | 122.22 | 112.75 | 101.55 |
| 0.0001 | 124.51 | 147.54 | 127.69 | 84.64 |
| 0.001 | 130.56 | 147.65 | 114.36 | 45.82 |
| 0.01 | 129.65 | 140.91 | 79.77 | 35.27 |
| 0.1 | 130.95 | 104.41 | 52.75 | 23.72 |
| 1 | 105.35 | 84.26 | 40.10 | 17.44 |

HTB-43 FaDu

| 5-FC | control | MOI 0.01 | MOI 0.1 | MOI 1 |
|---|---|---|---|---|
| 0 | 100.00 | 84.96 | 76.55 | 33.43 |
| 0.0001 | 116.65 | 94.74 | 83.10 | 39.22 |
| 0.001 | 115.59 | 86.81 | 74.80 | 29.12 |
| 0.01 | 115.42 | 91.38 | 52.71 | 16.48 |
| 0.1 | 114.71 | 68.53 | 29.39 | 9.25 |
| 1 | 102.32 | 36.96 | 18.29 | 5.71 |

FIG. 11B

| 5-FC | HTB-43 FaDu | | | | 5-FC | SAS | | | |
| --- | --- | --- | --- | --- | --- | --- | --- | --- | --- |
| | control | MOI 0.01 | MOI 0.1 | MOI 1 | | control | MOI 0.01 | MOI 0.1 | MOI 1 |
| 0 | 5.21 | 4.99 | 7.72 | 16.40 | 0 | 4.97 | 4.31 | 6.30 | 17.65 |
| 0.0001 | 3.06 | 2.85 | 5.44 | 10.29 | 0.0001 | 2.86 | 3.28 | 2.87 | 15.63 |
| 0.001 | 2.82 | 2.55 | 5.77 | 9.33 | 0.001 | 2.35 | 2.83 | 2.84 | 20.98 |
| 0.01 | 2.32 | 2.86 | 6.33 | 15.28 | 0.01 | 2.21 | 2.57 | 4.62 | 27.94 |
| 0.1 | 3.69 | 5.01 | 9.28 | 23.26 | 0.1 | 2.34 | 3.52 | 6.81 | 36.13 |
| 1 | 4.19 | 12.06 | 15.02 | 36.48 | 1 | 3.22 | 6.19 | 10.26 | 37.72 |

| 5-FC | control | MOI 0.01 | MOI 0.1 | MOI 1 |
|---|---|---|---|---|
| 0 | 100.00 | 62.90 | 30.46 | 3.88 |
| 0.0001 | 124.63 | 69.80 | 28.06 | 3.73 |
| 0.001 | 118.90 | 70.17 | 13.83 | 2.41 |
| 0.01 | 120.45 | 45.01 | 8.12 | 3.14 |
| 0.1 | 118.41 | 25.78 | 3.52 | 1.78 |
| 1 | 108.66 | 17.93 | 2.64 | 2.39 |

BRZ

| 5-FC | control | MOI 0.01 | MOI 0.1 | MOI 1 |
|---|---|---|---|---|
| 0 | 100.00 | 94.02 | 85.64 | 24.64 |
| 0.0001 | 97.08 | 95.68 | 83.49 | 28.30 |
| 0.001 | 96.60 | 97.67 | 80.17 | 22.26 |
| 0.01 | 99.55 | 92.16 | 63.81 | 17.90 |
| 0.1 | 98.34 | 90.63 | 35.95 | 12.91 |
| 1 | 94.72 | 75.29 | 25.75 | 9.00 |

SRH

| 5-FC | control | MOI 0.01 | MOI 0.1 | MOI 1 |
|---|---|---|---|---|
| 0 | 100.00 | 108.37 | 100.90 | 89.80 |
| 0.0001 | 108.46 | 123.06 | 116.04 | 96.24 |
| 0.001 | 109.91 | 123.13 | 108.19 | 83.86 |
| 0.01 | 114.29 | 116.24 | 110.56 | 62.09 |
| 0.1 | 117.06 | 121.99 | 73.92 | 52.01 |
| 1 | 106.57 | 90.65 | 53.43 | 44.59 |

| 5-FC | control | MOI 0.01 | MOI 0.1 | MOI 1 |
|---|---|---|---|---|
| 0 | 11.52 | 9.12 | 20.72 | 53.89 |
| 0.0001 | 4.39 | 6.73 | 12.28 | 40.86 |
| 0.001 | 4.42 | 6.37 | 10.72 | 44.62 |
| 0.01 | 3.33 | 4.93 | 18.52 | 53.52 |
| 0.1 | 3.69 | 10.22 | 21.94 | 74.71 |
| 1 | 5.12 | 16.01 | 37.49 | 80.47 |

SRH

| 5-FC | control | MOI 0.01 | MOI 0.1 | MOI 1 |
|---|---|---|---|---|
| 0 | 14.64 | 10.98 | 19.49 | 22.90 |
| 0.0001 | 8.59 | 10.07 | 11.21 | 18.43 |
| 0.001 | 6.55 | 8.62 | 10.65 | 21.91 |
| 0.01 | 6.34 | 7.38 | 10.78 | 22.64 |
| 0.1 | 13.65 | 9.42 | 17.34 | 27.86 |
| 1 | 8.05 | 16.84 | 25.07 | 31.23 |

FIG. 15B

| 5-FC | LM | | | | CCS | | | |
|---|---|---|---|---|---|---|---|---|
| | control | MOI 0.1 | MOI 1 | MOI 10 | 5-FC | control | MOI 0.1 | MOI 1 | MOI 10 |
| 0 | 100.00 | 99.75 | 75.41 | 26.68 | 0 | 100.00 | 105.29 | 94.73 | 50.04 |
| 0.0001 | 110.92 | 109.42 | 75.58 | 19.10 | 0.0001 | 110.26 | 115.57 | 103.50 | 56.67 |
| 0.001 | 118.08 | 106.01 | 51.44 | 7.93 | 0.001 | 119.40 | 118.08 | 99.57 | 41.23 |
| 0.01 | 118.36 | 81.25 | 22.82 | 5.79 | 0.01 | 120.31 | 107.84 | 64.13 | 26.07 |
| 0.1 | 115.34 | 37.63 | 16.96 | 4.71 | 0.1 | 117.63 | 72.38 | 43.60 | 17.27 |
| 1 | 103.00 | 20.20 | 5.59 | 2.09 | 1 | 115.72 | 45.22 | 21.35 | 8.07 |

FIG. 16B

ZAF

| 5-FC | control | MOI 0.01 | MOI 0.1 | MOI 1 |
|---|---|---|---|---|
| 0 | 99.92 | 102.19 | 51.36 | 12.64 |
| 0.0001 | 106.79 | 98.75 | 54.55 | 6.01 |
| 0.001 | 111.00 | 103.62 | 47.79 | 5.39 |
| 0.01 | 108.04 | 71.75 | 15.92 | 1.97 |
| 0.1 | 114.76 | 38.10 | 5.71 | 1.08 |
| 1 | 105.84 | 26.66 | 3.38 | 1.24 |

STO

| 5-FC | control | MOI 0.01 | MOI 0.1 | MOI 1 |
|---|---|---|---|---|
| 0 | 100.00 | 89.47 | 66.29 | 23.53 |
| 0.0001 | 118.38 | 104.52 | 70.59 | 24.92 |
| 0.001 | 107.95 | 100.76 | 61.99 | 18.46 |
| 0.01 | 115.28 | 92.52 | 41.69 | 10.93 |
| 0.1 | 115.60 | 56.72 | 20.27 | 6.34 |
| 1 | 110.65 | 33.31 | 13.69 | 5.88 |

KD

| 5-FC | control | MOI 0.01 | MOI 0.1 | MOI 1 |
|---|---|---|---|---|
| 0 | 100.00 | 93.33 | 43.65 | 5.89 |
| 0.0001 | 107.06 | 96.33 | 43.66 | 4.77 |
| 0.001 | 105.86 | 90.88 | 27.11 | 3.20 |
| 0.01 | 108.86 | 71.89 | 20.16 | 3.15 |
| 0.1 | 107.89 | 44.46 | 14.72 | 2.99 |
| 1 | 104.54 | 25.59 | 10.26 | 2.20 |

FIG. 17B

| 5-FC | LNT 229 | | | | 5-FC | LNT 229 CTS-1 | | | |
|---|---|---|---|---|---|---|---|---|---|
| | control | MOI 0.1 | MOI 1 | MOI 10 | | control | MOI 0.1 | MOI 1 | MOI 10 |
| 0 | 100.00 | 89.35 | 43.51 | 6.79 | 0 | 100.00 | 93.55 | 73.07 | 36.29 |
| 0.0001 | 103.18 | 90.30 | 41.21 | 5.84 | 0.0001 | 105.58 | 98.10 | 73.09 | 36.00 |
| 0.001 | 102.32 | 89.94 | 29.37 | 3.49 | 0.001 | 103.02 | 96.18 | 58.57 | 20.31 |
| 0.01 | 103.93 | 78.49 | 18.76 | 3.19 | 0.01 | 106.34 | 87.12 | 31.76 | 7.90 |
| 0.1 | 105.24 | 48.50 | 4.35 | 4.29 | 0.1 | 107.32 | 56.77 | 7.78 | 3.76 |
| 1 | 104.76 | 22.70 | 2.59 | 4.17 | 1 | 108.52 | 15.21 | 4.23 | 5.01 |

FIG. 18B

| 5-FC | LN 18 | | | | 5-FC | LN 18 Apoptosis resistant | | | |
|---|---|---|---|---|---|---|---|---|---|
| | control | MOI 0.1 | MOI 1 | MOI 10 | | control | MOI 0.1 | MOI 1 | MOI 10 |
| 0 | 100.00 | 100.61 | 66.89 | 7.78 | 0 | 100.00 | 106.54 | 78.31 | 21.79 |
| 0.0001 | 101.78 | 100.29 | 66.99 | 8.87 | 0.0001 | 104.10 | 107.26 | 82.75 | 22.26 |
| 0.001 | 105.74 | 97.77 | 40.18 | 5.07 | 0.001 | 106.21 | 101.39 | 67.85 | 15.34 |
| 0.01 | 104.95 | 71.13 | 12.20 | 3.41 | 0.01 | 109.17 | 95.91 | 42.64 | 10.47 |
| 0.1 | 103.62 | 32.49 | 3.69 | 4.17 | 0.1 | 109.98 | 69.32 | 23.56 | 11.25 |
| 1 | 104.71 | 13.19 | 3.45 | 4.00 | 1 | 101.87 | 52.57 | 17.38 | 8.95 |

FIG. 19B

ACHN

| 5-FC | control | MOI 0.1 | MOI 1 | MOI 10 |
|---|---|---|---|---|
| 0 | 100.00 | 93.63 | 79.79 | 42.91 |
| 1 | 96.38 | 41.95 | 14.62 | 1.89 |

HOP-62

| 5-FC | control | MOI 0.1 | MOI 1 | MOI 10 |
|---|---|---|---|---|
| 0 | 100.00 | 95.50 | 83.74 | 50.50 |
| 1 | 103.08 | 32.71 | 13.50 | 9.55 |

M14

| 5-FC | control | MOI 0.1 | MOI 1 | MOI 10 |
|---|---|---|---|---|
| 0 | 100.00 | 96.22 | 84.30 | 41.96 |
| 1 | 106.23 | 40.71 | 24.12 | 15.06 |

| 5-FC | control | MOI 0.1 | MOI 1 | MOI 10 |
|---|---|---|---|---|
| 0 | 100.00 | 100.65 | 86.91 | 29.73 |
| 1 | 99.34 | 45.75 | 5.98 | 1.76 |

HCT-15

| 5-FC | control | MOI 0.1 | MOI 1 | MOI 10 |
|---|---|---|---|---|
| 0 | 100.00 | 110.12 | 98.41 | 85.13 |
| 1 | 94.77 | 68.66 | 34.54 | 1.71 |

FIG. 28A pMerV2 P-SCD (coding for MeV P-SCD)

```
accaaacaaagttgggtaaggatagttcaatcaatgatcatcttctagtgcacttaggatt
caagatcctattatcagggacaagagcaggattagggatatccgagatggccacactttta
aggagcttagcattgttcaaaagaaacaaggacaaaccacccattacatcaggatccggtg
gagccatcagaggaatcaaacacattattatagtaccaatccctggagattcctcaattac
cactcgatccagacttctggaccggttggtgaggttaattggaaacccggatgtgagcggg
cccaaactaacaggggcactaataggtatattatccttatttgtggagtctccaggtcaat
tgattcagaggatcaccgatgaccctgacgttagcataaggctgttagaggttgtccagag
tgaccagtcacaatctggccttaccttcgcatcaagaggtaccaacatggaggatgaggcg
gaccaatacttttcacatgatgatccaattagtagtgatcaatccaggttcggatggttcg
ggaacaaggaaatctcagatattgaagtgcaagaccctgagggattcaacatgattctggg
taccatcctagcccaaatttgggtcttgctcgcaaaggcggttacggccccagacacggca
gctgattcggagctaagaaggtggataaagtacacccaacaaagaagggtagttggtgaat
ttagattggagagaaaatggttggatgtggtgaggaacaggattgccgaggacctctcctt
acgccgattcatggtcgctctaatcctggatatcaagagaacacccggaaacaaacccagg
attgctgaaatgatatgtgacattgatacatatcgtagaggcaggattagccagttttta
tcctgactattaagtttgggatagaaactatgtatcctgctcttggactgcatgaatttgc
tggtgagttatccacacttgagtccttgatgaaccttaccagcaaatgggggaaactgca
ccctacatggtaatcctggagaactcaattcagaacaagttcagtgcaggatcataccctc
tgctctggagctatgccatgggagtaggagtggaacttgaaaactccatgggaggtttgaa
ctttggccgatcttactttgatccagcatattttagattagggcaagagatggtaaggagg
tcagctggaaaggtcagttccacattggcatctgaactcggtatcactgccgaggatgcaa
ggcttgtttcagagattgcaatgcatactactgaggacaagatcagtagagcggttggacc
cagacaagcccaagtatcatttctacacggtgatcaaagtgagaatgagctaccgagattg
ggggcaaggaagataggagggtcaaacagagtcgaggagaagccagggagagctacagag
aaaccgggcccagcagagcaagtgatgcgagagctgcccatcttccaaccggcacacccct
agacattgacactgcaacggagtccagccaagatccgcaggacagtcgaaggtcagctgac
gccctgcttaggctgcaagccatggcaggaatctcggaagaacaaggctcagacacggaca
cccctatagtgtacaatgacagaaatcttctagactaggtgcgagaggccgagggccagaa
caacatccgcctaccatccatcattgttataaaaacttaggaaccaggtccacacagccg
ccagcccatcaaccatccactcccacgattggagccaatggcagaagagcaggcacgccat
gtcaaaaacggactggaatgcatccgggctctcaaggccgagcccatcggctcactggcca
tcgaggaagctatggcagcatggtcagaaatatcagacaacccaggacaggagcgagccac
ctgcagggaagagaaggcaggcagttcgggtctcagcaaaccatgcctctcagcaattgga
tcaactgaaggcggtgcacctcgcatccgcggtcagggacctggagagagcgatgacgacg
ctgaaactttgggaatcccccaagaaatctccaggcatcaagcactgggttacagtgtta
ttacgtttatgatcacagcggtgaagcggttaagggaatccaagatgctgactctatcatg
gttcaatcaggccttgatggtgatagcaccctctcaggaggagacaatgaatctgaaaaca
gcgatgtggatattggcgaacctgataccgagggatatgctatcactgaccggggatctgc
```

FIG. 28B

```
tcccatctctatggggttcagggcttctgatgttgaaactgcagaaggaggggagatccac
gagctcctgagactccaatccagaggcaacaactttccgaagcttgggaaaactctcaatg
ttcctccgcccccggaccccggtagggccagcacttccgggacacccattaaaaagggcac
agacgcgagattagcctcatttggaacggagatcgcgtctttattgacaggtggtgcaacc
caatgtgctcgaaagtcaccctcggaaccatcagggccaggtgcacctgcggggaatgtcc
ccgagtgtgtgagcaatgccgcactgatacaggagtggacacccgaatctggtaccacaat
ctccccgagatcccagaataatgaagaaggggggagactattatgatgatgagctgttctct
gatgtccaagatattaaaacagccttggccaaaatacacgaggataatcagaagataatct
ccaagctagaatcactgctgttattgaagggagaagttgagtcaattaagaagcagatcaa
caggcaaaatatcagcatatccaccctggaaggacacctctcaagcatcatgatcgccatt
cctggacttgggaaggatcccaacgaccccactgcagatgtcgaaatcaatcccgacttga
aacccatcataggcagagattcaggccgagcactggccgaagttctcaagaaacccgttgc
cagccgacaactccaaggaatgacaaatggacggaccagttccagaggacagctgctgaag
gaatttcagctaaagccgatcgggaaaaagatgagctcagccgtcgggtttgttcctgaca
ccggccctgcatcacgcagtgtaatccgctccattataaaatccagccggctagaggagga
tcggaagcgttacctgatgactctccttgatgatatcaaaggagccaatgatcttgccaag
ttccaccagatgctgatgaagataataatgaagtagctacagctcaacttacctgccaacc
ccatgccagtcgacccaactagtcctccatcattgttataaaaacttaggaaccaggtcc
atacaccgtacgctcgaggcgcgtgccaccatggtgacaggggggaatggcaagcaagtggg
atcagaagggtatggacattgcctatgaggaggcggccttaggttacaaagagggtggtgt
tcctattggcggatgtcttatcaataacaaagacggaagtgttctcggtcgtggtcacaac
atgagatttcaaaagggatccgccacactacatggtgagatctccactttggaaaactgtg
ggagattagagggcaaagtgtacaaagataccactttgtatacgacgctgtctccatgcga
catgtgtacaggtgccatcatcatgtatggtattccacgctgtgttgtcggtgagaacgtt
aatttcaaaagtaagggcgagaaatatttacaaactagaggtcacgaggttgttgttgttg
acgatgagaggtgtaaaaagatcatgaaacaatttatcgatgaaagacctcaggattggtt
tgaagatattggtgaggcttcggaaccatttaagaacgtctacttgctacctcaaacaaac
caattgctgggtttgtacaccatcatcagaataagaatacaactagacctgatttcattt
tctactccgatagaatcatcagattgttggttgaagaaggtttgaaccatctacctgtgca
aaagcaaattgtggaaactgacaccaacgaaaacttcgaaggtgtctcattcatgggtaaa
atctgtggtgtttccattgtcagagctggtgaatcgatggagcaaggattaagagactgtt
gtaggtctgtgcgtatcggtaaaattttaattcaaagggacgaggagactgcttaccaaa
gttattctacgaaaaattaccagaggatatatctgaaaggtatgtcttcctattagaccca
atgctggccaccggtggtagtgctatcatggctacagaagtcttgattaagagaggtgtta
agccagagagaatttacttcttaaacctaatctgtagtaaggaagggattgaaaaatacca
tgccgccttcccagaggtcagaattgttactggtgccctcgacagaggtctagatgaaaac
aagtatctagttccagggttgggtgactttggtgacagatactactgtgtttaaacgcgcg
acgtctagtacaacctaaatccattataaaaaacttaggagcaaagtgattgcctcccaag
gtccacaatgacagagacctacgacttcgacaagtcggcatgggacatcaaagggtcgatc
gctccgatacaacccaccacctacagtgatggcaggctggtgccccaggtcagagtcatag
atcctggtctaggcgacaggaaggatgaatgctttatgtacatgtttctgctggggttgt
tgaggacagcgattccctagggcctccaatcgggcgagcatttgggttcctgcccttaggt
gttggcagatccacagcaaagcccgaaaaactcctcaaagaggccactgagcttgacatag
ttgttagacgtacagcagggctcaatgaaaaactggtgttctacaacaacaccccactaac
tctcctcacaccttggagaaaggtcctaacaacagggagtgtcttcaacgcaaaccaagtg
```

FIG. 28C

```
tgcaatgcggttaatctgataccgctcgataccccgcagaggttccgtgttgtttatatga
gcatcacccgtctttcggataacgggtattacaccgttcctagaagaatgctggaattcag
atcggtcaatgcagtggccttcaacctgctggtgacccttaggattgacaaggcgataggc
cctgggaagatcatcgacaatacagagcaacttcctgaggcaacatttatggtccacatcg
ggaacttcaggagaaagaagagtgaagtctactctgccgattattgcaaatgaaaatcga
aaagatgggcctggttttttgcacttggtgggatagggggcaccagtcttcacattagaagc
acaggcaaaatgagcaagactctccatgcacaactcgggttcaagaagaccttatgttacc
cgctgatggatatcaatgaagaccttaatcgattactctggaggagcagatgcaagatagt
aagaatccaggcagttttgcagccatcagttcctcaagaattccgcatttacgacgacgtg
atcataaatgatgaccaaggactattcaaagttctgtagaccgtagtgcccagcaatgccc
gaaaacgacccccctcacaatgacagccagaaggcccggacaaaaaagccccctccgaaag
actccacggaccaagcgagaggccagccagcagccgacggcaagcgcgaacaccaggcggc
cccagcacagaacagccctgacacaaggccaccaccagccaccccaatctgcatcctcctc
gtgggaccccgaggaccaaccccccaaggctgcccccgatccaaaccaccaaccgcatccc
caccaccccgggaaagaaaccccccagcaattggaaggcccctcccccctcttcctcaacac
aagaactccacaaccgaaccgcacaagcgaccgaggtgacccaaccgcaggcatccgactc
cctagacagatcctctctccccggcaaactaaacaaaacttagggccaaggaacatacaca
cccaacagaacccagaccccggcccacggcgccgcgccccaaccccgacaaccagaggg
agcccccaaccaatcccgccggctccccggtgcccacaggcagggacaccaaccccgaa
cagacccagcacccaaccatcgacaatccaagacggggggggccccccaaaaaaaggcccc
caggggccgacagccagcaccgcgaggaagcccaccaccccacacacgaccacggcaacc
aaaccagaacccagaccacccctgggccaccagctcccagactcggccatcaccccgcagaa
aggaaaggccacaacccgcgcaccccagccccgatccggcggggagccacccaacccgaac
cagcacccaagagcgatccccgaaggaccccgaaccgcaaggacatcagtatcccacag
cctctccaagtccccggtctcctcctcttctcgaagggaccaaaagatcaatccaccaca
cccgacgacactcaactccccacccctaaaggagacaccgggaatcccagaatcaagactc
atccaatgtccatcatgggtctcaaggtgaacgtctctgccatattcatggcagtactgtt
aactctccaaacacccaccggtcaaatccattggggcaatctctctaagatagggtggta
ggaataggaagtgcaagctacaaagttatgactcgttccagccatcaatcattagtcataa
aattaatgcccaatataactctcctcaataactgcacgagggtagagattgcagaatacag
gagactactgagaacagttttggaaccaattagagatgcacttaatgcaatgacccagaat
ataagaccggttcagagtgtagcttcaagtaggagacacaagagatttgcgggagtagtcc
tggcaggtgcggccctaggcgttgccacagctgctcagataacagccggcattgcacttca
ccagtccatgctgaactctcaagccatcgacaatctgagagcgagcctggaaactactaat
caggcaattgagacaatcagacaagcagggcaggagatgatattggctgttcagggtgtcc
aagactacatcaataatgagctgataccgtctatgaaccaactatcttgtgatttaatcgg
ccagaagctcgggctcaaattgctcagatactatacagaaatcctgtcattatttggcccc
agtttacgggaccccatatctgcggagatatctatccaggctttgagctatgcgcttggag
gagacatcaataaggtgttagaaaagctcggatacagtggaggtgatttactgggcatctt
agagagcggaggaataaaggcccggataactcacgtcgacacagagtcctacttcattgtc
ctcagtatagcctatccgacgctgtccgagattaaggggggtgattgtccaccggctagagg
gggtctcgtacaacataggctctcaagagtggtataccactgtgcccaagtatgttgcaac
ccaagggtaccttatctcgaattttgatgagtcatcgtgtactttcatgccagaggggact
gtgtgcagccaaaatgccttgtacccgatgagtcctctgctccaagaatgcctccgggggt
acaccaagtcctgtgctcgtacactcgtatccgggtcttttgggaaccggttcattttatc
```

FIG. 28D

```
acaagggaacctaatagccaattgtgcatcaatcctttgcaagtgttacacaacaggaacg
atcattaatcaagaccctgacaagatcctaacatacattgctgccgatcactgcccggtag
tcgaggtgaacggcgtgaccatccaagtcgggagcaggaggtatccagacgctgtgtactt
gcacagaattgacctcggtcctcccatatcattggagaggttggacgtagggacaaatctg
gggaatgcaattgctaagttggaggatgccaaggaattgttggagtcatcggaccagatat
tgaggagtatgaaaggtttatcgagcactagcatagtctacatcctgattgcagtgtgtct
tggagggttgatagggatccccgctttaatatgttgctgcaggggcgttgtaacaaaaag
ggagaacaagttggtatgtcaagaccaggcctaaagcctgatcttacgggaacatcaaaat
cctatgtaaggtcgctctgatcctctacaactcttgaaacacaaatgtcccacaagtctcc
tcttcgtcatcaagcaaccaccgcacccagcatcaagcccacctgaaattatctccggctt
ccctctggccgaacaatatcggtagttaatcaaaacttagggtgcaagatcatccacaatg
tcaccacaacgagaccggataaatgccttctacaaagataaccccccatcccaagggaagta
ggatagtcattaacagagaacatcttatgattgatagaccttatgttttgctggctgttct
gtttgtcatgtttctgagcttgatcgggttgctagccattgcaggcattagacttcatcgg
gcagccatctacaccgcagagatccataaaagcctcagcaccaatctagatgtaactaact
caatcgagcatcaggtcaaggacgtgctgacaccactcttcaaaatcatcggtgatgaagt
gggcctgaggacacctcagagattcactgacctagtgaaattaatctctgacaagattaaa
ttccttaatccggatagggagtacgacttcagagatctcacttggtgtatcaacccgccag
agagaatcaaattggattatgatcaatactgtgcagatgtggctgctgaagagctcatgaa
tgcattggtgaactcaactctactggagaccagaacaaccaatcagttcctagctgtctca
aagggaaactgctcagggcccactacaatcagaggtcaattctcaaacatgtcgctgtccc
tgttagacttgtatttaggtcgaggttacaatgtgtcatctatagtcactatgacatccca
gggaatgtatggggaacttacctagtggaaaagcctaatctgagcagcaaaaggtcagag
ttgtcacaactgagcatgtaccgagtgtttgaagtaggtgttatcagaaatccgggtttgg
gggctccggtgttccatatgacaaactatcttgagcaaccagtcagtaatgatctcagcaa
ctgtatggtggctttgggggagctcaaactcgcagccctttgtcacggggaagattctatc
acaattccctatcagggatcagggaaaggtgtcagcttccagctcgtcaagctaggtgtct
ggaaatccccaaccgacatgcaatcctgggtccccttatcaacggatgatccagtgataga
caggctttacctctcatctcacagaggtgttatcgctgacaatcaagcaaaatgggctgtc
ccgacaacacgaacagatgacaagttgcgaatggagacatgcttccaacaggcgtgtaagg
gtaaaatccaagcactctgcgagaatcccgagtgggcaccattgaaggataacaggattcc
ttcatacggggtcttgtctgttgatctgagtctgacagttgagcttaaaatcaaaattgct
tcgggattcgggccattgatcacacggttcagggatggacctatacaaatccaaccaca
acaatgtgtattggctgactatcccgccaatgaagaacctagccttaggtgtaatcaacac
attggagtggataccgagattcaaggttagtccctacctcttcactgtcccaattaaggaa
gcaggcgaagactgccatgccccaacatacctacctgcggaggtggatggtgatgtcaaac
tcagttccaatctggtgattctacctggtcaagatctccaatatgttttggcaacctacga
tacttccagggttgaacatgctgtggtttattacgtttacagcccaagccgctcatttct
tactttatccttttaggttgcctataaaggggtccccatcgaattacaagtggaatgct
tcacatgggaccaaaaactctggtgccgtcacttctgtgtgcttgcggactcagaatctgg
tggacatatcactcactctgggatggtgggcatgggagtcagctgcacagtcacccgggaa
gatggaaccaatcgcagatagggctgctagtgaaccaatcacatgatgtcacccagacatc
aggcatacccactagtgtgaaatagacatcagaattaagaaaaacgtagggtccaagtggt
tccccgttatggactcgctatctgtcaaccagatcttatacccctgaagttcacctagatag
cccgatagttaccaataagatagtagccatcctggagtatgctcgagtccctcacgcttac
```

FIG. 28E

```
agcctggaggaccctacactgtgtcagaacatcaagcaccgcctaaaaaacggattttcca
accaaatgattataaacaatgtggaagttgggaatgtcatcaagtccaagcttaggagtta
tccggcccactctcatattccatatccaaattgtaatcaggatttatttaacatagaagac
aaagagtcaacgaggaagatccgtgaactcctcaaaaaggggaattcgctgtactccaaag
tcagtgataaggttttccaatgcttaagggacactaactcacggcttggcctaggctccga
attgagggaggacatcaaggagaaagttattaacttgggagtttacatgcacagctcccag
tggtttgagccctttctgttttggtttacagtcaagactgagatgaggtcagtgattaaat
cacaaacccatacttgccataggaggagacacacacctgtattcttcactggtagttcagt
tgagttgctaatctctcgtgaccttgttgctataatcagtaaagagtctcaacatgtatat
tacctgacatttgaactggttttgatgtattgtgatgtcatagagggggaggttaatgacag
agaccgctatgactattgatgctaggtatacagagcttctaggaagagtcagatacatgtg
gaaactgatagatggtttcttccctgcactcgggaatccaacttatcaaattgtagccatg
ctggagcctctttcacttgcttacctgcagctgagggatataacagtagaactcagaggtg
ctttccttaaccactgctttactgaaatacatgatgttcttgaccaaaacgggttttctga
tgaaggtacttatcatgagttaactgaagctctagattacattttcataactgatgacata
catctgacaggggagattttctcattttttcagaagtttcggccaccccagacttgaagcag
taacggctgctgaaaatgttaggaaatacatgaatcagcctaaagtcattgtgtatgagac
tctgatgaaaggtcatgccatattttgtggaatcataatcaacggctatcgtgacaggcac
ggaggcagttggccaccgctgaccctcccccctgcatgctgcagacacaatccggaatgctc
aagcttcaggtgaagggttaacacatgagcagtgcgttgataactggaaatcttttgctgg
agtgaaatttggctgctttatgcctcttagcctggatagtgatctgacaatgtacctaaag
gacaaggcacttgctgctctccaagggaatgggattcagtttacccgaaagagttcctgc
gttacgaccctcccaagggaaccgggtcacggaggcttgtagatgttttccttaatgattc
gagctttgacccatatgatgtgataatgtatgttgtaagtggagcttacctccatgaccct
gagttcaacctgtcttacagcctgaaagaaaaggagatcaaggaaacaggtagactttttg
ctaaaatgacttacaaaatgagggcatgccaagtgattgctgaaaatctaatctcaaacgg
gattggcaaatattttaaggacaatgggatggccaaggatgagcacgatttgactaaggca
ctccacactctagctgtctcaggagtccccaaagatctcaaagaaagtcacgggggggggc
cagtcttaaaaacctactcccgaagcccagtccacacaagtaccaggaacgtgagagcagc
aaaagggtttatagggttccctcaagtaattcggcaggaccaagacactgatcatccggag
aatatggaagcttacgagacagtcagtgcatttatcacgactgatctcaagaagtactgcc
ttaattggagatatgagaccatcagcttgtttgcacagaggctaaatgagatttacggatt
gccctcattttttccagtggctgcataagaggcttgagacctctgtcctgtatgtaagtgac
cctcattgccccccccgaccttgacgcccatatcccgttatataaagtccccaatgatcaaa
tcttcattaagtaccctatgggaggtatagaagggtattgtcagaagctgtggaccatcag
caccattccctatctatacctggctgcttatgagagcggagtaaggattgcttcgttagtg
caaggggacaatcagaccatagccgtaacaaaagggtacccagcacatggccctacaacc
ttaagaaacgggaagctgctagagtaactagagattactttgtaattcttaggcaaaggct
acatgatattggccatcacctcaaggcaaatgagacaattgtttcatcacattttttgtc
tattcaaaaggaatatattatgatgggctacttgtgtcccaatcactcaagagcatcgcaa
gatgtgtattctggtcagagactatagttgatgaaacaagggcagcatgcagtaatattgc
tacaacaatggctaaaagcatcgagagaggttatgaccgttaccttgcatattccctgaac
gtcctaaaagtgatacagcaaattctgatctctcttggcttcacaatcaattcaaccatga
cccgggatgtagtcatacccctcctcacaaacaacgacctcttaataaggatggcactgtt
gcccgctcctattgggggatgaattatctgaatatgagcaggctgtttgtcagaaacatc
```

FIG. 28F

```
ggtgatccagtaacatcatcaattgctgatctcaagagaatgattctcgcctcactaatgc
ctgaagagaccctccatcaagtaatgacacaacaaccgggggactcttcattcctagactg
ggctagcgacccttactcagcaaatcttgtatgtgtccagagcatcactagactcctcaag
aacataactgcaaggtttgtcctgatccatagtccaaacccaatgttaaaaggattattcc
atgatgacagtaaagaagaggacgagggactggcggcattcctcatggacaggcatattat
agtacctagggcagctcatgaaatcctggatcatagtgtcacaggggcaagagagtctatt
gcaggcatgctggataccacaaaaggcttgattcgagccagcatgaggaagggggggttaa
cctctcgagtgataaccagattgtccaattatgactatgaacaattcagagcagggatggt
gctattgacaggaagaaagagaaatgtcctcattgacaaagagtcatgttcagtgcagctg
gcgagagctctaagaagccatatgtgggcgaggctagctcgaggacggcctatttacggcc
ttgaggtccctgatgtactagaatctatgcgaggccaccttattcggcgtcatgagacatg
tgtcatctgcgagtgtggatcagtcaactacggatggttttttgtccctcgggttgccaa
ctggatgatattgacaaggaaacatcatccttgagagtcccatatattggttctaccactg
atgagagaacagacatgaagcttgccttcgtaagagccccaagtcgatccttgcgatctgc
tgttagaatagcaacagtgtactcatgggcttacggtgatgatgatagctcttggaacgaa
gcctggttgttggctaggcaaagggccaatgtgagcctggaggagctaagggtgatcactc
ccatctcaacttcgactaatttagcgcataggttgagggatcgtagcactcaagtgaaata
ctcaggtacatcccttgtccgagtggcgaggtataccacaatctccaacgacaatctctca
tttgtcatatcagataagaaggttgatactaactttatataccaacaaggaatgcttctag
ggttgggtgttttagaaacattgtttcgactcgagaaagataccggatcatctaacacggt
attacatcttcacgtcgaaacagattgttgcgtgatcccgatgatagatcatcccaggata
cccagctcccgcaagctagagctgagggcagagctatgtaccaacccattgatatatgata
atgcacctttaattgacagagatgcaacaaggctatacacccagagccataggaggcacct
tgtggaatttgttacatggtccacaccccaactatatcacattttagctaagtccacagca
ctatctatgattgacctggtaacaaaatttgagaaggaccatatgaatgaaatttcagctc
tcatagggatgacgatatcaatagtttcataactgagtttctgctcatagagccaagatt
attcactatctacttgggccagtgtgcggccatcaattgggcatttgatgtacattatcat
agaccatcagggaaatatcagatgggtgagctgttgtcatcgttcctttctagaatgagca
aaggagtgtttaaggtgcttgtcaatgctctaagccacccaaagatctacaagaaattctg
gcattgtggtattatagagcctatccatggtccttcacttgatgctcaaaacttgcacaca
actgtgtgcaacatggttttacacatgctatatgacctacctcgacctgttgttgaatgaag
agttagaagagttcacatttctcttgtgtgaaagcgacgaggatgtagtaccggacagatt
cgacaacatccaggcaaaacacttatgtgttctggcagatttgtactgtcaaccagggacc
tgcccaccaattcgaggtctaagaccggtagagaaatgtgcagttctaaccgaccatatca
aggcagaggctatgttatctccagcaggatcttcgtggaacataaatccaattattgtaga
ccattactcatgctctctgacttatctccggcgaggatcgatcaaacagataagattgaga
gttgatccaggattcattttcgacgccctcgctgaggtaaatgtcagtcagccaaagatcg
gcagcaacaacatctcaaatatgagcatcaaggctttcagaccccacacgatgatgttgc
aaaattgctcaaagatatcaacacaagcaagcacaatcttcccatttcaggggcaatctc
gccaattatgaaatccatgctttcgcagaatcgggttgaactcatctgcttgctacaaag
ctgttgagatatcaacattaattaggagatgccttgagccaggggaggacggcttgttctt
gggtgagggatcgggttctatgttgatcacttataaagagatacttaaactaaacaagtgc
ttctataatagtggggtttccgccaattctagatctggtcaaagggaattagcaccctatc
cctccgaagttggccttgtcgaacacagaatgggagtaggtaatattgtcaaagtgctctt
taacgggaggcccgaagtcacgtgggtaggcagtgtagattgcttcaatttcatagttagt
```

FIG. 28G

```
aatatccctacctctagtgtggggtttatccattcagatatagagaccttgcctgacaaag
atactatagagaagctagaggaattggcagccatcttatcgatggctctgctcctgggcaa
aataggatcaatactggtgattaagcttatgcctttcagcggggattttgttcagggattt
ataagttatgtagggtctcattatagagaagtgaaccttgtatacccagatacagcaact
tcatctctactgaatcttatttggttatgacagatctcaaggctaaccggctaatgaatcc
tgaaaagattaagcagcagataattgaatcatctgtgaggacttcacctggacttataggt
cacatcctatccattaagcaactaagctgcatacaagcaattgtgggagacgcagttagta
gaggtgatatcaatcctactctgaaaaaacttacacctatagagcaggtgctgatcaattg
cgggttggcaattaacggacctaagctgtgcaaagaattgatccaccatgatgttgcctca
gggcaagatggattgcttaattctatactcatcctctacagggagttggcaagattcaaag
acaaccaaagaagtcaacaagggatgttccacgcttaccccgtattggtaagtagcaggca
acgagaacttatatctaggatcacccgcaaattctgggggcacattcttctttactccggg
aacaaaaagttgataaataagtttatccagaatctcaagtccggctatctgatactagact
tacaccagaatatcttcgttaagaatctatccaagtcagagaaacagattattatgacggg
gggtttgaaacgtgagtgggttttttaaggtaacagtcaaggagaccaaagaatggtataag
ttagtcggatacagtgccctgattaaggactaattggttgaactccggaaccctaatcctg
ccctaggtggttaggcattatttgcaatatattaaagaaaactttgaaaatacgaagtttc
tattcccagctttgtctggtggccggcatggtcccagcctcctcgctggcgccggctgggc
aacattccgaggggaccgtcccctcggtaatggcgaatgggacgcggccggtcgatcgacg
atccggctgctaacaaagcccgaaaggaagctgagttggctgctgccaccgctgagcaata
actagcataaccccttggggcctctaaacgggtcttgagggggttttttgctgaaaggagga
actatatccggatcgagatcaattctgtgagcgtatggcaaacgaaggaaaaatagttata
gtagccgcactcgatgggacatttcaacgtaaaccgtttaataatattttgaatcttattc
cattatctgaaatggtggtaaaactaactgctgtgtgtatgaaatgctttaaggaggcttc
cttttctaaacgattgggtgaggaaaccgagatagaaataataggaggtaatgatatgtat
caatcggtgtgtagaaagtgttacatcgactcataatattatattttttatctaaaaaact
aaaaataaacattgattaaattttaatataatacttaaaaatggatgttgtgtcgttagat
aaaccgtttatgtattttgaggaaattgataatgagttagattacgaaccagaaagtgcaa
atgaggtcgcaaaaaaactgccgtatcaaggacagttaaaactattactaggagaattatt
ttttcttagtaagttacagcgacacggtatattagatggtgccaccgtagtgtatatagga
tctgctcccggtacacatatacgttatttgagagatcatttctataatttaggagtgatcc
cgaaaggaagctgagttggctgctgccaccgctgagcaataactagcataaccccttgggg
cctctaaacgggtcttgagggggttttttgctgaaaggaggaacgcgcctgatgcggtattt
tctccttacgcatctgtgcggtatttcacaccgcatatggtgcactctcagtacaatct
gctctgatgccgcatagttaagccagccccgacacccgccaacacccgctgacgcgccctg
acgggcttgtctgctcccggcatccgcttacagacaagctgtgaccgtctccgggagctgc
atgtgtcagaggttttcaccgtcatcaccgaaacgcgcgagacgaaagggcctcgtgatac
gcctatttttataggttaatgtcatgataataatggtttcttagacgtcaggtggcacttt
tcggggaaatgtgcgcggaacccctatttgtttattttctaaatacattcaaatatgtat
ccgctcatgagacaataaccctgataaatgcttcaataatattgaaaaggaagagtatga
gtattcaacatttccgtgtcgcccttattcccttttttgcggcatttttgccttcctgtttt
tgctcacccagaaacgctggtgaaagtaaaagatgctgaagatcagttgggtgcacgagtg
ggttacatcgaactggatctcaacagcggtaagatccttgagagttttcgccccgaagaac
gttttccaatgatgagcacttttaaagttctgctatgtggcgcggtattatcccgtattga
cgccgggcaagagcaactcggtcgccgcatacactattctcagaatgacttggttgagtac
```

FIG. 28H

```
tcaccagtcacagaaaagcatcttacggatggcatgacagtaagagaattatgcagtgctg
ccataaccatgagtgataacactgcggccaacttacttctgacaacgatcggaggaccgaa
ggagctaaccgcttttttgcacaacatgggggatcatgtaactcgccttgatcgttgggaa
ccggagctgaatgaagccataccaaacgacgagcgtgacaccacgatgcctgtagcaatgg
caacaacgttgcgcaaactattaactggcgaactacttactctagcttcccggcaacaatt
aatagactggatggaggcggataaagttgcaggaccacttctgcgctcggcccttccggct
ggctggtttattgctgataaatctggagccggtgagcgtgggtctcgcggtatcattgcag
cactggggccagatggtaagccctcccgtatcgtagttatctacacgacggggagtcaggc
aactatggatgaacgaaatagacagatcgctgagataggtgcctcactgattaagcattgg
taactgtcagaccaagtttactcatatactttagattgatttaaaacttcattttaat
ttaaaaggatctaggtgaagatcctttttgataatctcatgaccaaaatcccttaacgtga
gttttcgttccactgagcgtcagaccccgtagaaaagatcaaaggatcttcttgagatcct
ttttttctgcgcgtaatctgctgcttgcaaacaaaaaaaccaccgctaccagcggtggttt
gtttgccggatcaagagctaccaactcttttccgaaggtaactggcttcagcagagcgca
gataccaaatactgtccttctagtgtagccgtagttaggccaccacttcaagaactctgta
gcaccgcctacatacctcgctctgctaatcctgttaccagtggctgctgccagtggcgata
agtcgtgtcttaccgggttggactcaagacgatagttaccggataaggcgcagcggtcggg
ctgaacggggggttcgtgcacacagcccagcttggagcgaacgacctacaccgaactgaga
tacctacagcgtgagcattgagaaagcgccacgcttcccgaagggagaaaggcggacaggt
atccggtaagcggcagggtcggaacaggagagcgcacgagggagcttccaggggaaacgc
ctggtatctttatagtcctgtcgggtttcgccacctctgacttgagcgtcgatttttgtga
tgctcgtcagggggcggagcctatggaaaaacgccagcaacgcggccttttacggttcc
tggccttttgctggccttttgctcacatgttctttcctgcgttatcccctgattctgtgga
taaccgtattaccgcctttgagtgagctgataccgctcgccgcagccgaacgaccgagcgc
agcgagtcagtgagcgaggaagcggaagagcgcccaatacgcaaaccgcctctccccgcgc
gttggccgattcattaatgcagctggcacgacaggtttcccgactggaaagcgggcagtga
gcgcaacgcaattaatgtgagttagctcactcattaggcaccccaggctttacactttatg
cttccggctcgtatgttgtgtggaattgtgagcggataacaatttcacacaggaaacagct
atgaccatgattacgccaagcttacgcgtgtaatacgactcactataggg
```

FIG. 29A pc3MerV2 ld-VP22SCD (coding for MeV ld-VP22SCD)

```
accaaacaaagttgggtaaggatagttcaatcaatgatcatcttctagtgcacttaggatt
caagatcctattatcagggacaagagcaggattagggatatctcgaggcgcgtgccaccat
gacctctcgccgctccgtgaagtcgggtccgcgggaggttccgcgcgatgagtacgaggat
ctgtactacaccccgtcttcaggtatggcgagtcccgatagtccgcctgacacctcccgcc
gtggcgccctacagacacgctcgcgccagaggggcgaggtccgtttcgtccagtacgacga
gtcggattatgccctctacggggctcgtcatccgaagacgacgaacacccggaggtcccc
cggacgcggcgtcccgtttccggggcggttttgtccggcccggggcctgcgcgggcgcctc
cgccaccgctgggtccggaggggccggacgcacacccaccaccgcccccgggcccccccg
aacccagcgggtggcgactaaggccccgcggccccggcggcggagaccacccgcggcagg
aaatcggcccagccagaatccgccgcactcccagacgcccccgcctcgacggcgccaaccc
gatccaagacacccgcgcaggggctggccagaaagctgcactttagcaccgccccccaaa
ccccgacgcgccatggaccccgggtggccggctttaacaagcgcgtcttctgcgccgcg
gtcgggcgcctggcggccatgcatgcccggatggcggcggtccagctctgggacatgtcgc
gtccgcgcacagacgaagacctcaacgaactccttggcatcaccaccatccgcgtgacggt
ctgcgagggcaaaaacctgcttcagcgcgccaacgagttggtgaatccagacgtggtgcag
gacgttgacgcggccacggcgactcgagggcgttctgcggcgtcgcgccccaccgagcgac
ctcgagccccagcccgctccgcttctcgccccagacggcccgtcgaggatatcgccaccat
ggtgacaggggggaatggcaagcaagtgggatcagaagggtatggacattgcctatgaggag
gcggccttaggttacaaagagggtggtgttcctattggcggatgtcttatcaataacaaag
acggaagtgttctcggtcgtggtcacaacatgagatttcaaaagggatccgccacactaca
tggtgagatctccactttggaaaactgtgggagattagagggcaaagtgtacaaagatacc
actttgtatacgacgctgtctccatgcgacatgtgtacaggtgccatcatcatgtatggta
ttccacgctgtgttgtcggtgagaacgttaatttcaaaagtaagggcgagaaatatttaca
aactagaggtcacgaggttgttgttgttgacgatgagaggtgtaaaagatcatgaaacaa
tttatcgatgaaagacctcaggattggtttgaagatattggtgaggcttcggaaccattta
agaacgtctacttgctacctcaaacaaaccaattgctgggtttgtacaccatcatcagaaa
taagaatacaactagacctgatttcattttctactccgatagaatcatcagattgttggtt
gaagaaggtttgaaccatctacctgtgcaaaagcaaattgtggaaactgacaccaacgaaa
acttcgaaggtgtctcattcatgggtaaaatctgtggtgtttccattgtcagagctggtga
atcgatggagcaaggattaagagactgttgtaggtctgtgcgtatcggtaaattttaatt
caaagggacgaggagactgctttaccaaagttattctacgaaaaattaccagaggatatat
ctgaaaggtatgtcttcctattagacccaatgctggccaccggtggtagtgctatcatggc
tacagaagtcttgattaagagaggtgttaagccagagagaatttacttcttaaacctaatc
tgtagtaaggaagggattgaaaaataccatgccgccttcccagaggtcagaattgttactg
gtgccctcgacagaggtctagatgaaaacaagtatctagttccagggttgggtgactttgg
tgacagatactactgtgtttaataaacgcgccatccatcattgttataaaaaacttaggat
tcaagatcctattatcagggacaagagcaggattagggatatccgagatggccacactttt
aaggagcttagcattgttcaaaagaaacaaggacaaaccacccattacatcaggatccggt
ggagccatcagaggaatcaaacacattattatagtaccaatccctggagattcctcaatta
ccactcgatccagacttctggaccggttggtgaggttaattggaaacccggatgtgagcgg
gcccaaactaacaggggcactaataggtatattccttatttgtggagtctccaggtcaa
ttgattcagaggatcaccgatgaccctgacgttagcataaggctgttagaggttgtccaga
gtgaccagtcacaatctggccttaccttcgcatcaagaggtaccaacatggaggatgaggc
```

FIG. 29B

```
ggaccaatacttttcacatgatgatccaattagtagtgatcaatccaggttcggatggttc
gggaacaaggaaatctcagatattgaagtgcaagaccctgagggattcaacatgattctgg
gtaccatcctagcccaaatttgggtcttgctcgcaaaggcggttacggccccagacacggc
agctgattcggagctaagaaggtggataaagtacacccaacaaagaagggtagttggtgaa
tttagattggagagaaaatggttggatgtggtgaggaacaggattgccgaggacctctcct
tacgccgattcatggtcgctctaatcctggatatcaagagaacacccggaaacaaacccag
gattgctgaaatgatatgtgacattgatacatatcgtagaggcaggattagccagtttt
atcctgactattaagtttgggatagaaactatgtatcctgctcttggactgcatgaatttg
ctggtgagttatccacacttgagtccttgatgaacctttaccagcaaatgggggaaactgc
accctacatggtaatcctggagaactcaattcagaacaagttcagtgcaggatcataccct
ctgctctggagctatgccatgggagtaggagtggaacttgaaaactccatgggaggtttga
actttggccgatcttactttgatccagcatatttagattagggcaagagatggtaaggag
gtcagctggaaaggtcagttccacattggcatctgaactcggtatcactgccgaggatgca
aggcttgtttcagagattgcaatgcatactactgaggacaagatcagtagagcggttggac
ccagacaagcccaagtatcatttctacacggtgatcaaagtgagaatgagctaccgagatt
gggggcaaggaagataggagggtcaaacagagtcgaggagaagccagggagagctacaga
gaaaccgggcccagcagagcaagtgatgcgagagctgcccatcttccaaccggcacacccc
tagacattgacactgcaacggagtccagccaagatccgcaggacagtcgaaggtcagctga
cgccctgcttaggctgcaagccatggcaggaatctcggaagaacaaggctcagacacggac
accccctatagtgtacaatgacagaaatcttctagactaggtgcgagaggccgagggccaga
acaacatccgcctaccatccatcattgttataaaaacttaggaaccaggtccacacagcc
gccagcccatcaaccatccactcccacgattggagccaatggcagaagagcaggcacgcca
tgtcaaaaacggactggaatgcatccgggctctcaaggccgagcccatcggctcactggcc
atcgaggaagctatggcagcatggtcagaaatatcagacaacccaggacaggagcgagcca
cctgcagggaagagaaggcaggcagttcgggtctcagcaaaccatgcctctcagcaattgg
atcaactgaaggcggtgcacctcgcatccgcggtcagggacctggagagagcgatgacgac
gctgaaactttgggaatcccccaagaaatctccaggcatcaagcactgggttacagtgtt
attacgtttatgatcacagcggtgaagcggttaagggaatccaagatgctgactctatcat
ggttcaatcaggccttgatggtgatagcaccctctcaggaggagacaatgaatctgaaaac
agcgatgtggatattggcgaacctgataccgagggatatgctatcactgaccggggatctg
ctcccatctctatggggttcagggcttctgatgttgaaactgcagaaggaggggagatcca
cgagctcctgagactccaatccagaggcaacaactttccgaagcttgggaaaactctcaat
gttcctccgcccccggaccccggtagggccagcacttccgggacacccattaaaaagggca
cagacgcgagattagcctcatttggaacggagatcgcgtctttattgacaggtggtgcaac
ccaatgtgctcgaaagtcaccctcggaaccatcagggccaggtgcacctgcggggaatgtc
cccgagtgtgtgagcaatgccgcactgatacaggagtggacacccgaatctggtaccacaa
tctccccgagatcccagaataatgaagaaggggagactattatgatgatgagctgttctc
tgatgtccaagatattaaaacagccttggccaaaatacacgaggataatcagaagataatc
tccaagctagaatcactgctgttattgaagggagaagttgagtcaattaagaagcagatca
acaggcaaaatatcagcatatccaccctggaaggacacctctcaagcatcatgatcgccat
tcctggacttgggaaggatcccaacgaccccactgcagatgtcgaaatcaatcccgacttg
aaacccatcataggcagagattcaggccgagcactggccgaagttctcaagaaacccgttg
ccagccgacaactccaaggaatgacaaatggacggaccagttccagaggacagctgctgaa
ggaatttcagctaaagccgatcgggaaaaagatgagctcagccgtcgggtttgttcctgac
accggccctgcatcacgcagtgtaatccgctccattataaaatccagccggctagaggagg
```

FIG. 29C

```
atcggaagcgttacctgatgactctccttgatgatatcaaaggagccaatgatcttgccaa
gttccaccagatgctgatgaagataataatgaagtagctacagctcaacttacctgccaac
cccatgccagtcgacccaactagtacaacctaaatccattataaaaaacttaggagcaaag
tgattgcctcccaaggtccacaatgacagagacctacgacttcgacaagtcggcatgggac
atcaaagggtcgatcgctccgatacaacccaccacctacagtgatggcaggctggtgcccc
aggtcagagtcatagatcctggtctaggcgacaggaaggatgaatgctttatgtacatgtt
tctgctgggggttgttgaggacagcgattccctagggcctccaatcgggcgagcatttggg
ttcctgcccttaggtgttggcagatccacagcaaagcccgaaaaactcctcaaagaggcca
ctgagcttgacatagttgttagacgtacagcagggctcaatgaaaaactggtgttctacaa
caacaccccactaactctcctcacaccttggagaaaggtcctaacaacagggagtgtcttc
aacgcaaaccaagtgtgcaatgcggttaatctgataccgctcgataccccgcagaggttcc
gtgttgtttatatgagcatcacccgtctttcggataacgggtattacaccgttcctagaag
aatgctggaattcagatcggtcaatgcagtggccttcaacctgctggtgacccttaggatt
gacaaggcgataggccctgggaagatcatcgacaatacagagcaacttcctgaggcaacat
ttatggtccacatcgggaacttcaggagaaagaagagtgaagtctactctgccgattattg
caaaatgaaaatcgaaaagatgggcctggttttttgcacttggtgggatagggggcaccagt
cttcacattagaagcacaggcaaaatgagcaagactctccatgcacaactcgggttcaaga
agaccttatgttacccgctgatggatatcaatgaagaccttaatcgattactctggaggag
cagatgcaagatagtaagaatccaggcagttttgcagccatcagttcctcaagaattccgc
atttacgacgacgtgatcataaatgatgaccaaggactattcaaagttctgtagaccgtag
tgcccagcaatgcccgaaaacgaccccctcacaatgacagccagaaggcccggacaaaaa
agcccctccgaaagactccacggaccaagcgagaggccagccagcagccgacggcaagcg
cgaacaccaggcggccccagcacagaacagccctgacacaaggccaccaccagccacccca
atctgcatcctcctcgtgggaccccgaggaccaaccccaaggctgcccccgatccaaac
caccaaccgcatccccaccaccccgggaaagaaaccccagcaattggaaggcccctccc
cctcttcctcaacacaagaactccacaaccgaaccgcacaagcgaccgaggtgacccaacc
gcaggcatccgactccctagacagatcctctctccccggcaaactaaacaaaacttagggc
caaggaacatacacacccaacagaacccagaccccggcccacggcgccgcgcccccaaccc
ccgacaaccagagggagcccccaaccaatcccgccggctccccggtgcccacaggcaggg
acaccaaccccgaacagacccagcacccaaccatcgacaatccaagacgggggggcccccc
ccaaaaaaaggcccccaggggccgacagccagcaccgcgaggaagcccacccaccccacac
acgaccacggcaaccaaaccagaacccagaccaccctgggccaccagctcccagactcggc
catcaccccgcagaaaggaaaggccacaacccgcgcacccagccccgatccggcggggag
ccacccaacccgaaccagcacccaagagcgatccccgaaggaccccgaaccgcaaggac
atcagtatcccacagcctctccaagtccccggtctcctcctcttctcgaagggaccaaaa
gatcaatccaccacacccgacgacactcaactccccaccccctaaaggagacaccgggaatc
ccagaatcaagactcatccaatgtccatcatgggtctcaaggtgaacgtctctgccatatt
catggcagtactgttaactctccaaacacccaccggtcaaatccattggggcaatctctct
aagatagggtggtaggaataggaagtgcaagctacaaagttatgactcgttccagccatc
aatcattagtcataaaattaatgcccaatataactctcctcaataactgcacgagggtaga
gattgcagaatacaggagactactgagaacagttttggaaccaattagagatgcacttaat
gcaatgacccagaatataagaccggttcagagtgtagcttcaagtaggagacacaagagat
ttgcgggagtagtcctggcaggtgcggccctaggcgttgccacagctgctcagataacagc
cggcattgcacttcaccagtccatgctgaactctcaagccatcgacaatctgagagcgagc
ctggaaactactaatcaggcaattgagacaatcagacaagcagggcaggagatgatattgg
```

FIG. 29D

```
ctgttcagggtgtccaagactacatcaataatgagctgataccgtctatgaaccaactatc
ttgtgatttaatcggccagaagctcgggctcaaattgctcagatactatacagaaatcctg
tcattatttggccccagtttacgggaccccatatctgcggagatatctatccaggctttga
gctatgcgcttggaggagacatcaataaggtgttagaaaagctcggatacagtggaggtga
tttactgggcatcttagagagcggaggaataaaggcccggataactcacgtcgacacagag
tcctacttcattgtcctcagtatagcctatccgacgctgtccgagattaaggggggtgattg
tccaccggctagaggggtctcgtacaacataggctctcaagagtggtataccactgtgcc
caagtatgttgcaacccaagggtaccttatctcgaattttgatgagtcatcgtgtactttc
atgccagaggggactgtgtgcagccaaaatgccttgtaccgatgagtcctctgctccaag
aatgcctccgggggtacaccaagtcctgtgctcgtacactcgtatccgggtcttttgggaa
ccggttcatttatcacaagggaacctaatagccaattgtgcatcaatcctttgcaagtgt
tacacaacaggaacgatcattaatcaagaccctgacaagatcctaacatacattgctgccg
atcactgccggtagtcgaggtgaacggcgtgaccatccaagtcgggagcaggaggtatcc
agacgctgtgtacttgcacagaattgacctcggtcctcccatatcattggagaggttggac
gtagggacaaatctggggaatgcaattgctaagttggaggatgccaaggaattgttggagt
catcggaccagatattgaggagtatgaaaggtttatcgagcactagcatagtctacatcct
gattgcagtgtgtcttggagggttgatagggatccccgctttaatatgttgctgcagggg
cgttgtaacaaaagggagaacaagttggtatgtcaagaccaggcctaaagcctgatctta
cgggaacatcaaaatcctatgtaaggtcgctctgatcctctacaactcttgaaacacaaat
gtcccacaagtctcctcttcgtcatcaagcaaccaccgcacccagcatcaagcccacctga
aattatctccggcttccctctggccgaacaatatcggtagttaatcaaaacttagggtgca
agatcatccacaatgtcaccacaacgagaccggataaatgccttctacaaagataaccccc
atcccaagggaagtaggatagtcattaacagagaacatcttatgattgatagaccttatgt
tttgctggctgttctgtttgtcatgtttctgagcttgatcgggttgctagccattgcaggc
attagacttcatcgggcagccatctacaccgcagagatccataaaagcctcagcaccaatc
tagatgtaactaactcaatcgagcatcaggtcaaggacgtgctgacaccactcttcaaaat
catcggtgatgaagtgggcctgaggacacctcagagattcactgacctagtgaaattaatc
tctgacaagattaaattccttaatccggatagggagtacgacttcagagatctcacttggt
gtatcaacccgccagagagaatcaaattggattatgatcaatactgtgcagatgtggctgc
tgaagagctcatgaatgcattggtgaactcaactctactggagaccagaacaaccaatcag
ttcctagctgtctcaaagggaaactgctcagggcccactacaatcagaggtcaattctcaa
acatgtcgctgtccctgttagacttgtatttaggtcgaggttacaatgtgtcatctatagt
cactatgacatcccagggaatgtatgggggaacttacctagtggaaaagcctaatctgagc
agcaaaaggtcagagttgtcacaactgagcatgtaccgagtgtttgaagtaggtgttatca
gaaatccgggtttgggggctccggtgttccatatgacaaactatcttgagcaaccagtcag
taatgatctcagcaactgtatggtggctttggggagctcaaactcgcagcccttgtcac
ggggaagattctatcacaattccctatcagggatcagggaaggtgtcagcttccagctcg
tcaagctaggtgtctggaaatccccaaccgacatgcaatcctgggtccccttatcaacgga
tgatccagtgatagacaggctttacctctcatctcacagaggtgttatcgctgacaatcaa
gcaaaatgggctgtcccgacaacacgaacagatgacaagttgcgaatggagacatgcttcc
aacaggcgtgtaagggtaaaatccaagcactctgcgagaatcccgagtgggcaccattgaa
ggataacaggattccttcatacggggtcttgtctgttgatctgagtctgacagttgagctt
aaaatcaaaattgcttcgggattcgggccattgatcacacacggttcagggatggacctat
acaaatccaaccacaacaatgtgtattggctgactatcccgccaatgaagaacctagcctt
aggtgtaatcaacacattggagtggataccgagattcaaggttagtccctacctcttcact
```

FIG. 29E

```
gtcccaattaaggaagcaggcgaagactgccatgccccaacatacctacctgcggaggtgg
atggtgatgtcaaactcagttccaatctggtgattctacctggtcaagatctccaatatgt
tttggcaacctacgatacttccagggttgaacatgctgtggtttattacgtttacagccca
agccgctcatttctttacttttatccttttaggttgcctataaaggggtcccatcgaat
tacaagtggaatgcttcacatgggaccaaaaactctggtgccgtcacttctgtgtgcttgc
ggactcagaatctggtggacatatcactcactctgggatggtgggcatgggagtcagctgc
acagtcacccgggaagatggaaccaatcgcagatagggctgctagtgaaccaatcacatga
tgtcacccagacatcaggcatacccactagtgtgaaatagacatcagaattaagaaaaacg
tagggtccaagtggttccccgttatggactcgctatctgtcaaccagatcttatacc ctga
agttcacctagatagcccgatagttaccaataagatagtagccatcctggagtatgctcga
gtccctcacgcttacagcctggaggaccctacactgtgtcagaacatcaagcaccgcctaa
aaaacggattttccaaccaaatgattataaacaatgtggaagttgggaatgtcatcaagtc
caagcttaggagttatccggcccactctcatattccatatccaaattgtaatcaggattta
tttaacatagaagacaaagagtcaacgaggaagatccgtgaactcctcaaaaaggggaatt
cgctgtactccaaagtcagtgataaggttttccaatgcttaagggacactaactcacggct
tggcctaggctccgaattgagggaggacatcaaggagaaagttattaacttgggagtttac
atgcacagctcccagtggtttgagccctttctgttttggtttacagtcaagactgagatga
ggtcagtgattaaatcacaaacccatacttgccataggaggagacacacacctgtattctt
cactggtagttcagttgagttgctaatctctcgtgaccttgttgctataatcagtaaagag
tctcaacatgtatattacctgacatttgaactggttttgatgtattgtgatgtcatagagg
ggaggttaatgacagagaccgctatgactattgatgctaggtatacagagcttctaggaag
agtcagatacatgtggaaactgatagatggtttcttccctgcactcgggaatccaacttat
caaattgtagccatgctggagcctctttcacttgcttacctgcagctgagggatataacag
tagaactcagaggtgctttccttaaccactgctttactgaaatacatgatgttcttgacca
aaacggttttctgatgaaggtacttatcatgagttaactgaagctctagattacattttc
ataactgatgacatacatctgacaggggagattttctcattttcagaagtttcggccacc
ccagacttgaagcagtaacggctgctgaaaatgttaggaaatacatgaatcagcctaaagt
cattgtgtatgagactctgatgaaaggtcatgccatattttgtggaatcataatcaacggc
tatcgtgacaggcacggaggcagttggccaccgctgacc ctcccc ctgcatgctgcagaca
caatccggaatgctcaagcttcaggtgaagggttaacacatgagcagtgcgttgataactg
gaaatcttttgctggagtgaaatttggctgctttatgcctcttagcctggatagtgatctg
acaatgtacctaaaggacaaggcacttgctgctctccaaagggaatgggattcagtttacc
cgaaagagttcctgcgttacgaccctcccaagggaaccgggtcacggaggcttgtagatgt
tttccttaatgattcgagctttgacccatatgatgtgataatgtatgttgtaagtggagct
tacctccatgaccctgagttcaacctgtcttacagcctgaaagaaaaggagatcaaggaaa
caggtagacttttttgctaaaatgacttacaaaatgagggcatgccaagtgattgctgaaaa
tctaatctcaaacgggattggcaaatattttaaggacaatgggatggccaaggatgagcac
gatttgactaaggcactccacactctagctgtctcaggagtccccaaagatctcaaagaaa
gtcaggggggggccagtcttaaaaacctactcccgaagcccagtccacacaagtaccag
gaacgtgagagcagcaaaagggtttataggttccctcaagtaattcggcaggaccaagac
actgatcatccggagaatatggaagcttacgagacagtcagtgcatttatcacgactgatc
tcaagaagtactgccttaattggagatatgagaccatcagcttgtttgcacagaggctaaa
tgagatttacggattgccctcattttccagtggctgcataagaggcttgagcctctgtc
ctgtatgtaagtgaccctcattgcccccccgaccttgacgcccatatcccgttatataaag
tccccaatgatcaaatcttcattaagtaccctatgggaggtatagaagggtattgtcagaa
```

FIG. 29F gctgtggaccatcagcaccattccctatctatacctggctgcttatgagagcggagtaagg
attgcttcgttagtgcaaggggacaatcagaccatagccgtaacaaaaagggtacccagca
catggccctacaaccttaagaaacgggaagctgctagagtaactagagattactttgtaat
tcttaggcaaaggctacatgatattggccatcacctcaaggcaaatgagacaattgtttca
tcacattttttgtctattcaaaaggaatatattatgatgggctacttgtgtcccaatcac
tcaagagcatcgcaagatgtgtattctggtcagagactatagttgatgaaacaagggcagc
atgcagtaatattgctacaacaatggctaaaagcatcgagagaggttatgaccgttacctt
gcatattccctgaacgtcctaaaagtgatacagcaaattctgatctctcttggcttcacaa
tcaattcaaccatgacccgggatgtagtcatacccctcctcacaaacaacgacctcttaat
aaggatggcactgttgcccgctcctattgggggatgaattatctgaatatgagcaggctg
tttgtcagaaacatcggtgatccagtaacatcatcaattgctgatctcaagagaatgattc
tcgcctcactaatgcctgaagagaccctccatcaagtaatgacacaacaaccgggggactc
ttcattcctagactgggctagcgaccttactcagcaaatcttgtatgtgtccagagcatc
actagactcctcaagaacataactgcaaggtttgtcctgatccatagtccaaacccaatgt
taaaaggattattccatgatgacagtaaagaagaggacgagggactggcggcattcctcat
ggacaggcatattatagtacctagggcagctcatgaaatcctggatcatagtgtcacaggg
gcaagagagtctattgcaggcatgctggataccacaaaaggcttgattcgagccagcatga
ggaaggggggttaacctctcgagtgataaccagattgtccaattatgactatgaacaatt
cagagcagggatggtgctattgacaggaagaaagagaaatgtcctcattgacaaagagtca
tgttcagtgcagctggcgagagctctaagaagccatatgtgggcgaggctagctcgaggac
ggcctatttacggccttgaggtccctgatgtactagaatctatgcgaggccaccttattcg
gcgtcatgagacatgtgtcatctgcgagtgtggatcagtcaactacggatggttttttgtc
ccctcgggttgccaactggatgatattgacaaggaaacatcatccttgagagtcccatata
ttggttctaccactgatgagagaacagacatgaagcttgccttcgtaagagccccaagtcg
atccttgcgatctgctgttagaatagcaacagtgtactcatgggcttacggtgatgatgat
agctcttggaacgaagcctggttgttggctaggcaaagggccaatgtgagcctggaggagc
taagggtgatcactcccatctcaacttcgactaatttagcgcataggttgagggatcgtag
cactcaagtgaaatactcaggtacatcccttgtccgagtggcgaggtataccacaatctcc
aacgacaatctctcatttgtcatatcagataagaaggttgatactaacttttatataccaac
aaggaatgcttctagggttgggtgttttagaaacattgtttcgactcgagaaagataccgg
atcatctaacacggtattacatcttcacgtcgaaacagattgttgcgtgatcccgatgata
gatcatcccaggatacccagctcccgcaagctagagctgagggcagagctatgtaccaacc
cattgatatgataatgcacctttaattgacagagatgcaacaaggctatacacccagag
ccataggaggcaccttgtggaatttgttacatggtccacaccccaactatatcacatttta
gctaagtccacagcactatctatgattgacctggtaacaaaatttgagaaggaccatatga
atgaaatttcagctctcataggggatgacgatatcaatagtttcataactgagtttctgct
catagagccaagattattcactatctactttgggccagtgtgcggccatcaattgggcattt
gatgtacattatcatagaccatcagggaaatatcagatgggtgagctgttgtcatcgttcc
tttctagaatgagcaaaggagtgtttaaggtgcttgtcaatgctctaagccacccaaagat
ctacaagaaattctggcattgtggtattatagagcctatccatggtccttcacttgatgct
caaaacttgcacacaactgtgtgcaacatggtttacacatgctatatgacctacctcgacc
tgttgttgaatgaagagttagaagagttcacatttctcttgtgtgaaagcgacgaggatgt
agtaccggacagattcgacaacatccaggcaaaacacttatgtgttctggcagatttgtac
tgtcaaccagggacctgcccaccaattcgaggtctaagaccggtagagaaatgtgcagttc
taaccgaccatatcaaggcagaggctatgttatctccagcaggatcttcgtggaacataaa

FIG. 29G

```
tccaattattgtagaccattactcatgctctctgacttatctccggcgaggatcgatcaaa
cagataagattgagagttgatccaggattcattttcgacgccctcgctgaggtaaatgtca
gtcagccaaagatcggcagcaacaacatctcaaatatgagcatcaaggctttcagaccccc
acacgatgatgttgcaaaattgctcaaagatatcaacacaagcaagcacaatcttcccatt
tcaggggcaatctcgccaattatgaaatccatgctttccgcagaatcggttgaactcat
ctgcttgctacaaagctgttgagatatcaacattaattaggagatgccttgagccagggga
ggacggcttgttcttgggtgagggatcggttctatgttgatcacttataaagagatactt
aaactaaacaagtgcttctataatagtggggtttccgccaattctagatctggtcaaaggg
aattagcaccctatccctccgaagttggccttgtcgaacacagaatgggagtaggtaatat
tgtcaaagtgctctttaacgggaggcccgaagtcacgtgggtaggcagtgtagattgcttc
aatttcatagttagtaatatccctacctctagtgtggggtttatccattcagatatagaga
ccttgcctgacaaagatactatagagaagctagaggaattggcagccatcttatcgatggc
tctgctcctgggcaaaataggatcaatactggtgattaagcttatgcctttcagcggggat
tttgttcagggatttataagttatgtagggtctcattatagagaagtgaaccttgtatacc
ctagatacagcaacttcatctctactgaatcttatttggttatgacagatctcaaggctaa
ccggctaatgaatcctgaaaagattaagcagcagataattgaatcatctgtgaggacttca
cctggacttataggtcacatcctatccattaagcaactaagctgcatacaagcaattgtgg
gagacgcagttagtagaggtgatatcaatcctactctgaaaaaacttacacctatagagca
ggtgctgatcaattgcgggttggcaattaacggacctaagctgtgcaaagaattgatccac
catgatgttgcctcagggcaagatggattgcttaattctatactcatcctctacagggagt
tggcaagattcaaagacaaccaaagaagtcaacaagggatgttccacgcttaccccgtatt
ggtaagtagcaggcaacgagaacttatatctaggatcacccgcaaattctgggggcacatt
cttctttactccgggaacaaaaagttgataaataagtttatccagaatctcaagtccggct
atctgatactagacttacaccagaatatcttcgttaagaatctatccaagtcagagaaaca
gattattatgacgggggtttgaaacgtgagtgggttttttaaggtaacagtcaaggagacc
aaagaatggtataagttagtcggatacagtgccctgattaaggactaattggttgaactcc
ggaaccctaatcctgccctaggtggttaggcattatttgcaatatattaaagaaaactttg
aaaatacgaagtttctattcccagctttgtctggtggccggcatggtcccagcctcctcgc
tggcgccggctgggcaacattccgaggggaccgtccctcggtaatggcgaatgggacgcg
gccggtcgatcgacgatccggctgctaacaaagcccgaaggaagctgagttggctgctgc
caccgctgagcaataactagcataacccctggggcctctaaacgggtcttgagggttttt
ttgctgaaaggaggaactatatccggatcgagatcaattctgtgagcgtatggcaaacgaa
ggaaaaatagttatagtagccgcactcgatgggacatttcaacgtaaaccgtttaataata
ttttgaatcttattccattatctgaaatggtggtaaaactaactgctgtgtgtatgaaatg
ctttaaggaggcttccttttctaaacgattgggtgaggaaaccgagatagaaataatagga
ggtaatgatatgtatcaatcggtgtgtagaaagtgttacatcgactcataatattatattt
tttatctaaaaaactaaaaataaacattgattaaattttaatataatacttaaaaatggat
gttgtgtcgttagataaaccgtttatgtattttgaggaaattgataatgagttagattacg
aaccagaaagtgcaaatgaggtcgcaaaaaaactgccgtatcaaggacagttaaaactatt
actaggagaattattttttcttagtaagttacagcgacacggtatattagatggtgccacc
gtagtgtatataggatctgctcccggtacacatatacgttatttgagagatcatttctata
atttaggagtgatcccgaaaggaagctgagttggctgctgccaccgctgagcaataactag
cataacccctggggcctctaaacgggtcttgagggttttttgctgaaaggaggaacgcg
cctgatgcggtattttctccttacgcatctgtgcggtatttcacaccgcatatatggtgca
ctctcagtacaatctgctctgatgccgcatagttaagccagccccgacacccgccaacacc
```

FIG. 29H

```
cgctgacgcgccctgacgggcttgtctgctcccggcatccgcttacagacaagctgtgacc
gtctccgggagctgcatgtgtcagaggttttcaccgtcatcaccgaaacgcgcgagacgaa
agggcctcgtgatacgcctattttataggttaatgtcatgataataatggtttcttagac
gtcaggtggcacttttcggggaaatgtgcgcggaacccctatttgtttattttctaaata
cattcaaatatgtatccgctcatgagacaataaccctgataaatgcttcaataatattgaa
aaaggaagagtatgagtattcaacatttccgtgtcgcccttattccctttttttgcggcatt
ttgccttcctgttttttgctcacccagaaacgctggtgaaagtaaaagatgctgaagatcag
ttgggtgcacgagtgggttacatcgaactggatctcaacagcggtaagatccttgagagtt
ttcgccccgaagaacgttttccaatgatgagcacttttaaagttctgctatgtggcgcggt
attatcccgtattgacgccgggcaagagcaactcggtcgccgcatacactattctcagaat
gacttggttgagtactcaccagtcacagaaaagcatcttacggatggcatgacagtaagag
aattatgcagtgctgccataaccatgagtgataacactgcggccaacttacttctgacaac
gatcggaggaccgaaggagctaaccgcttttttgcacaacatggggatcatgtaactcgc
cttgatcgttgggaaccggagctgaatgaagccataccaaacgacgagcgtgacaccacga
tgcctgtagcaatggcaacaacgttgcgcaaactattaactggcgaactacttactctagc
ttcccggcaacaattaatagactggatggaggcggataaagttgcaggaccacttctgcgc
tcggcccttccggctggctggtttattgctgataaatctggagccggtgagcgtgggtctc
gcggtatcattgcagcactggggccagatggtaagccctcccgtatcgtagttatctacac
gacggggagtcaggcaactatggatgaacgaaatagacagatcgctgagataggtgcctca
ctgattaagcattggtaactgtcagaccaagtttactcatatactttagattgatttaa
aacttcattttaatttaaaaggatctaggtgaagatcctttttgataatctcatgaccaa
aatcccttaacgtgagttttcgttccactgagcgtcagaccccgtagaaaagatcaaagga
tcttcttgagatccttttttttctgcgcgtaatctgctgcttgcaaacaaaaaaaccaccgc
taccagcggtggtttgtttgccggatcaagagctaccaactcttttttccgaaggtaactgg
cttcagcagagcgcagataccaaatactgtccttctagtgtagccgtagttaggccaccac
ttcaagaactctgtagcaccgcctacatacctcgctctgctaatcctgttaccagtggctg
ctgccagtggcgataagtcgtgtcttaccggtttggactcaagacgatagttaccggataa
ggcgcagcggtcgggctgaacggggggttcgtgcacacagcccagcttggagcgaacgacc
tacaccgaactgagatacctacagcgtgagcattgagaaagcgccacgcttcccgaaggga
gaaaggcggacaggtatccggtaagcggcagggtcggaacaggagagcgcacgagggagct
tccaggggaaacgcctggtatctttatagtcctgtcgggtttcgccacctctgacttgag
cgtcgattttgtgatgctcgtcaggggggcggagcctatggaaaaacgccagcaacgcgg
cctttttacggttcctggccttttgctggccttttgctcacatgttctttcctgcgttatc
ccctgattctgtggataaccgtattaccgcctttgagtgagctgataccgctcgccgcagc
cgaacgaccgagcgcagcgagtcagtgagcgaggaagcggaagagcgcccaatacgcaaac
cgcctctccccgcgcgttggccgattcattaatgcagctggcacgacaggtttcccgactg
gaaagcgggcagtgagcgcaacgcaattaatgtgagttagctcactcattaggcaccccag
gctttacactttatgcttccggctcgtatgttgtgtggaattgtgagcggataacaatttc
acacaggaaacagctatgaccatgattacgccaagcttacgcgtcctggcattatgcccag
tacatgaccttatgggactttcctacttggcagtacatctacgtattagtcatcgctatta
ccatggtgatgcggttttggcagtacatcaatgggcgtggatagcggtttgactcacgggg
atttccaagtctccaccccattgacgtcaatgggagtttgttttggcaccaaaatcaacgg
gactttccaaaatgtcgtaacaactccgccccattgacgcaaatgggcggtaggcgtgtac
ggtgggaggtctatataagcagagctcgtttagtgaaccgtgg
```

ONCOLYTIC MEASLES VIRUS

FIELD OF THE INVENTION

The present invention pertains to a pharmaceutical composition comprising a recombinant measles virus comprising a suicide gene for use in the treatment of malignant cells with primary or secondary resistances against an oncolytic measles virus without suicide gene activity. Further, the present invention pertains to a recombinant measles virus based on the genome of measles vaccine strain Schwarz comprising a suicide gene, which comprises a fusion of yeast cytosine deaminase and yeast uracil phosphoribosyltransferase, to a method and a kit for preparing the recombinant measles virus as claimed herein.

BACKGROUND OF THE INVENTION

Despite significant progress in the past, for example in the development of chemotherapeutics, antibody-based therapies, tumor vaccination, and radiation therapy, there is still an urgent and unmet need for the development of novel therapeutics and therapeutic approaches for the treatment of tumors and related malignant diseases.

While gene therapy approaches have substantial promise for such treatments, and while anti-tumoral results have been observed in different gene therapy models, certain limitations, particularly in the transfer of genes of interest to the tumor cells, have hampered the further development of such approaches.

In the past, it had occasionally been observed that natural infections or vaccinations with measles virus resulted in spontaneous tumor remissions, particularly in hematological malignancies, such as leukemias, resulting in the identification of the oncolytic potential of measles virus.

Measles virus is an enveloped, single-stranded, negative-sense paramyxo-virus of the genus *Morbillivirus* that is causing the infectious measles disease, an infection of the respiratory system. The genome of the measles virus contains six genes encoding eight proteins: the nucleocapsid (N), phospho- (P), matrix (M), fusion (F), hemagglutinin (H) and large (L) proteins, and two accessory proteins, termed C and V. The virus enters the target cells via pH-independent membrane fusion. The H and F proteins are involved in receptor binding and membrane fusion, respectively. Entry of measles virus into cells occurs via interaction of the surface H glycoprotein with the two known receptors for measles virus: CD46, which is ubiquitously present on nucleated primate cells, but is frequently over-expressed in tumors, and the signaling lymphocyte-activation molecule (SLAM) that is primarily located on B- and T-cells. CD46 is a membrane-associated complement regulatory protein that protects human cells against autologous complement lysis by acting as a cofactor in the proteolytic inactivation of C3b and C4b complement products, thus providing protection for tumor cells against complement-mediated lysis. Receptor recognition by the H protein leads to conformational changes of the F protein resulting in fusion with target cell membranes and subsequent viral entry. Infected cells, including tumor cells, express the viral F and H proteins on the cell surface. Recognition of the viral receptor in neighboring infected or uninfected cells similarly triggers cell-to-cell fusion. Therefore, the typical cytopathic effect of measles virus is the formation of giant mononuclear cell aggregates (syncytia).

Most of the measles virus preparations used for measles vaccines or for the research on oncolytic measles virus are based on an attenuated live measles virus derived from the so-called Edmonston vaccine strain, an isolate originally obtained in 1954, which was used to create the Edmonston-Enders cell line, and based on that, Edmonston A and B seed lines by serial passages on human cells and subsequent adaptation to chicken embryo fibroblastic (CEF) cells. Use of the originally developed live attenuated vaccine based on the Edmonston B lineage had to be stopped due to its high reactogenicity. By further attenuation of the Edmonston lines Edmonston-Enders and Edmonston A and B, additional measles derivatives were developed (Edmonston-Enders: AIK-C, Edmonston Zagreb; Edmonston A: Schwarz; Edmonston B: Moraten).

Despite the progress that has been made since the discovery of the oncolytic potential of measles virus, which is summarized in a recent review article (Msaouel, P., Dispenzieri, A., and Galanis, E., Clinical testing of engineered oncolytic measles virus strains in the treatment of cancer: An overview, Curr Opin Mol Ther. 2009; 11: 43-53), no therapeutic product based on oncolytic measles virus has yet reached the market, a fact that may, at least in part, be due to the potential of wild-type viruses to cause serious side effects, and particularly technical limitations in manufacturing virus preparations of high purity for clinical use. While the expanding knowledge of the biology of measles virus, as well as the development of a reverse genetics system that allows rescue of recombinant measles virus strains and viral engineering, have opened new opportunities for the development of measles virus as therapeutic in cancer treatment, there are still several limitations in the constructs that are presently in use.

For example, many of the research and development programs that are currently being pursued are based on the work of Martin Billeter and colleagues (Radecke, F., Spielhofer, P., Schneider, H., Kaelin, K., Huber, M., Dötsch, K, Christiansen, G., and Billeter, M., Rescue of measles viruses from cloned DNA. EMBO Journal 14 (1995) 5773-5784; WO 97/06270). Subsequently, it was shown that the sequence of the cloned viral genome deviated from the Edmonston B sequence, being closer to the wild-type Edmonston strain and having substitutions being related to the Edmonston subgroup (Parks et al., J. Virol. 75 (2001) 910-920; Parks et al., J. Virol. 75 (2001) 921-933).

Furthermore, measles virus preparations are currently rescued from cell lines not being approved for vaccine production like chicken embryo fibroblastic (CEF) cells or 293 human embryonic kidney cells, both complicating and thereby increasing the costs for the large-scale production of recombinant measles virus particles in conformity with GMP requirements.

Additionally, it has been shown that, for example, tumors derived from certain cell lines (eg, RPMI 8226 and HT1080) were resistant to treatment with oncolytic measles virus despite repeated virus injections (Peng K W, Facteau S, Wegman T, O'Kane D, Russell S J. Non-invasive in vivo monitoring of trackable viruses expressing soluble marker peptides. Nat Med. (2002); 8:527-31).

Therefore, there remains a continuous need for an improved pharmaceutical composition comprising a recombinant measles virus for use in the treatment of a malignant cells and improved methods for the generation of such pharmaceutical compositions and recombinant measles virus.

OBJECTS OF THE INVENTION

Accordingly, in view of the problems of the prior art, a first object of the present invention is to provide an improved pharmaceutical composition comprising a recombinant measles virus with oncolytic activity against tumors that are resistant to measles virus of the prior art.

The second object of the present invention is an improved pharmaceutical composition comprising a recombinant measles virus having a viral genome corresponding to the genome of established attenuated live measles vaccines.

The third object of the present invention is a safer and cheaper method for rescuing recombinant measles virus for use in the treatment of malignant cells.

SUMMARY OF THE INVENTION

These and other objects are solved by a pharmaceutical composition comprising a recombinant measles virus comprising a suicide gene for use in the treatment of malignant cells with primary or secondary resistances against an oncolytic measles virus without suicide gene activity.

The invention of a recombinant measles virus encoding a suicide gene for use in the treatment of malignant cells with primary or secondary resistances against an oncolytic measles virus without suicide gene activity enables a much more efficient treatment of solid tumors which concomitantly allows the employment of a reduced number of infectious measles virus particles without any loss in anti-tumor efficiency. Thereby, costs of virotherapeutic therapy can be reduced significantly.

In another aspect, the present invention relates to a recombinant measles virus based on measles vaccine strain Schwarz comprising a suicide gene, which comprises a fusion of a cytosine deaminase, particularly yeast cytosine deaminase, and a uracil phosphoribosyltransferase, particularly yeast uracil phosphoribosyltransferase, particularly wherein said suicide gene comprises a sequence according to SEQ-ID NO. 2.

In another aspect, the present invention relates to a method of treatment of malignant cells with primary or secondary resistances against an oncolytic measles virus without suicide gene activity, comprising the step of administering a recombinant measles virus comprising a suicide gene according to the present invention to a patient in need thereof.

In another aspect, the present invention relates to a method for generating the recombinant measles virus according to the present invention, comprising the step of (a) cloning (i) the genome of measles vaccine strain Schwarz, and (ii) a suicide gene, which comprises a fusion of a cytosine deaminase, particularly yeast cytosine deaminase, and a uracil phosphoribosyltransferase, particularly yeast uracil phosphoribosyltransferase, into a plasmid under the control of an RNA polymerase II promoter.

In yet another aspect, the present invention relates to a kit comprising
(a) a plasmid comprising (i) the genome of measles vaccine strain Schwarz, and (ii) a suicide gene, which comprises a fusion of a cytosine deaminase, particularly yeast cytosine deaminase, and a uracil phosphoribosyltransferase, particularly yeast uracil phosphoribosyltransferase, under the control of an RNA polymerase II promoter, particularly wherein said suicide gene comprises a sequence according to SEQ-ID No. 2, particularly wherein the plasmid has the sequence according to SEQ-ID No. 4 SEQ-ID No. 8, or SEQ-ID No. 9, more particularly SEQ-ID No. 4;
(b) at least one plasmid comprising measles virus helper genes N, P and L, in form of single genes, each under the control of an RNA polymerase II promoter.

FIGURES

FIG. 1 shows the genetic sequence of measles vaccine strain Schwarz (SEQ-ID NO. 1).

FIG. 2 shows genetic sequence of fusion of yeast cytosine deaminase and yeast uracil phosphoribosyltransferase (with linker sequence) (SEQ-ID NO. 2).

FIG. 3 shows the complete genetic sequence of the plasmid pc3MerV2 Id-Trka coding for the basic recombinant measles virus engineered from the MeV Schwarz strain without any transgenes but with additional transcription cassette (SEQ-ID NO. 3).

FIG. 4 shows the genetic sequence of vector pc3MerV2 Id-SCD (coding for MeV Id-SCD) (SEQ-ID NO. 4).

FIG. 5 shows the genetic sequence of the helper plasmid required for the expression of the N gene (SEQ-ID No. 5), which is based on the CMV promoter variant construct pc3, encompassing CMV promoter nucleotides from −301 until −1 (+1 being defined as transcription initiation site) plus three nucleotides (TGG) additionally inserted after position −1:
  nt 1358-2935: N ORF of MeV Schwarz (1578 nt=525 aa+stop codon)

FIG. 6 shows the genetic sequence of the helper plasmid required for the expression of the P gene (SEQ-ID No. 6), which is based on the CMV promoter variant construct pc3:
  nt 1358-2881: P ORF of MeV Schwarz (1524 nt=507 aa+stop codon)

FIG. 7 shows the genetic sequence of the helper plasmid required for the expression of the L gene (SEQ-ID No. 7), which is based on the CMV promoter variant construct pc3:
  nt 1358-7909: L ORF of MeV Schwarz (6552 nt=2183 aa+stop codon)

Figure 8A:
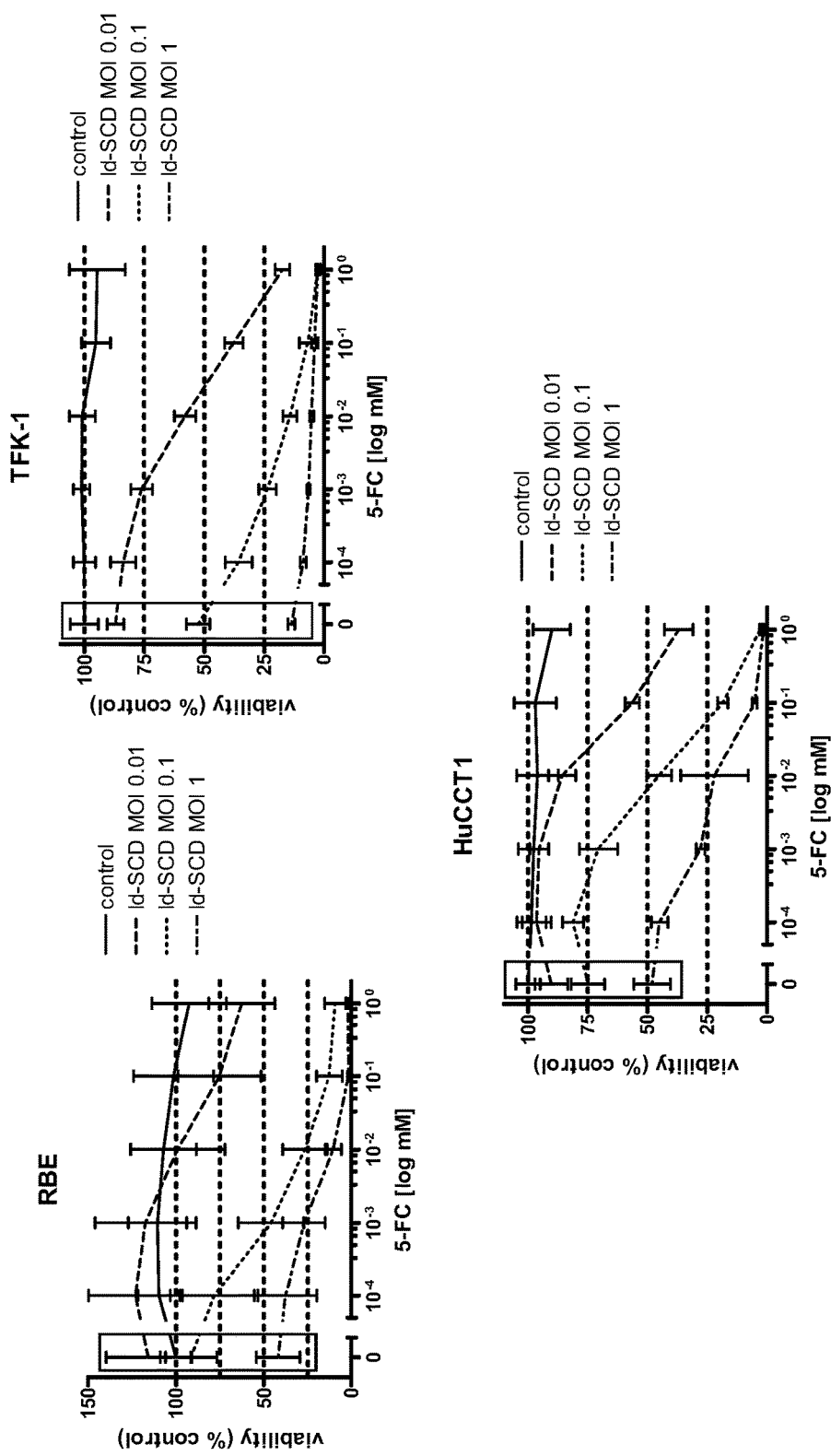

FIG. 8 shows the results of an SRB proliferation assay of HuCCT1, RBE, and TFK-1 cells (human cholangiocarcinoma cells) treated with viral particles rescued from the plasmid pc3MerV2 Id-SCD (Id-SCD) and incubated with prodrug 5-FC.

Figure 9:
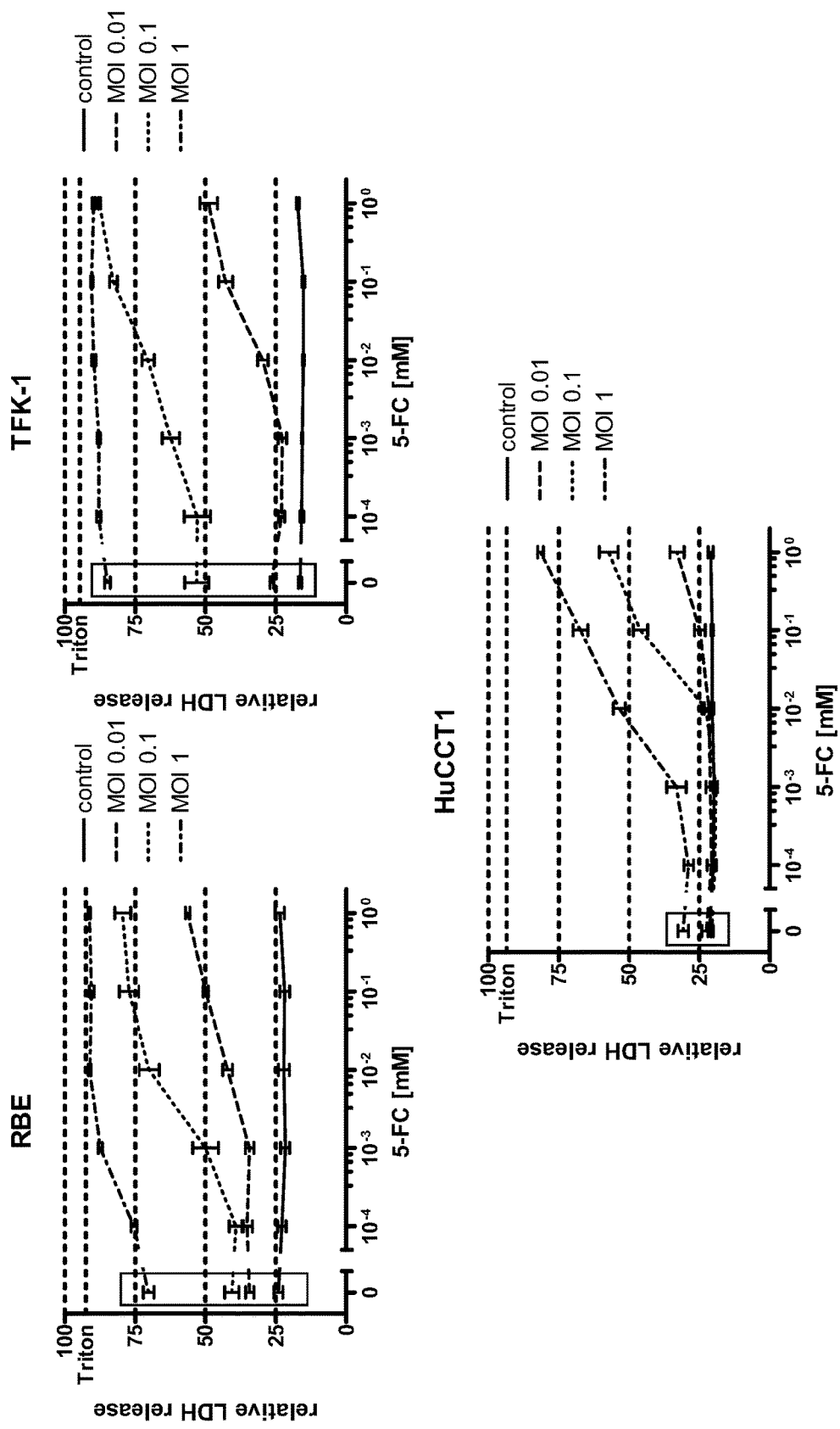

FIG. 9 shows the results of an LDH release assay of HuCCT1, RBE, and TFK-1 cells (human cholangiocarcinoma cells) treated with viral particles rescued from the plasmid pc3MerV2 Id-SCD (Id-SCD).

Figure 10A:
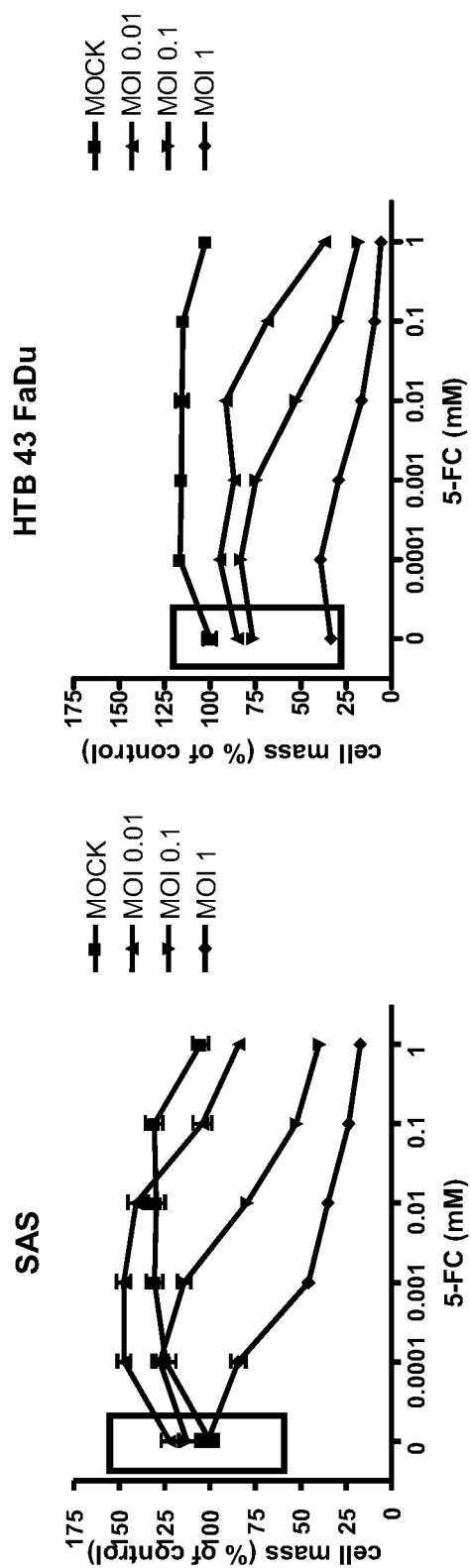

FIG. 10 shows the results of an SRB proliferation assay of SAS and HTB-43 FaDu cells (human Head & Neck (H&N) cancer cells) treated with viral particles rescued from the plasmid pc3MerV2 Id-SCD (Id-SCD).

Figure 11A:
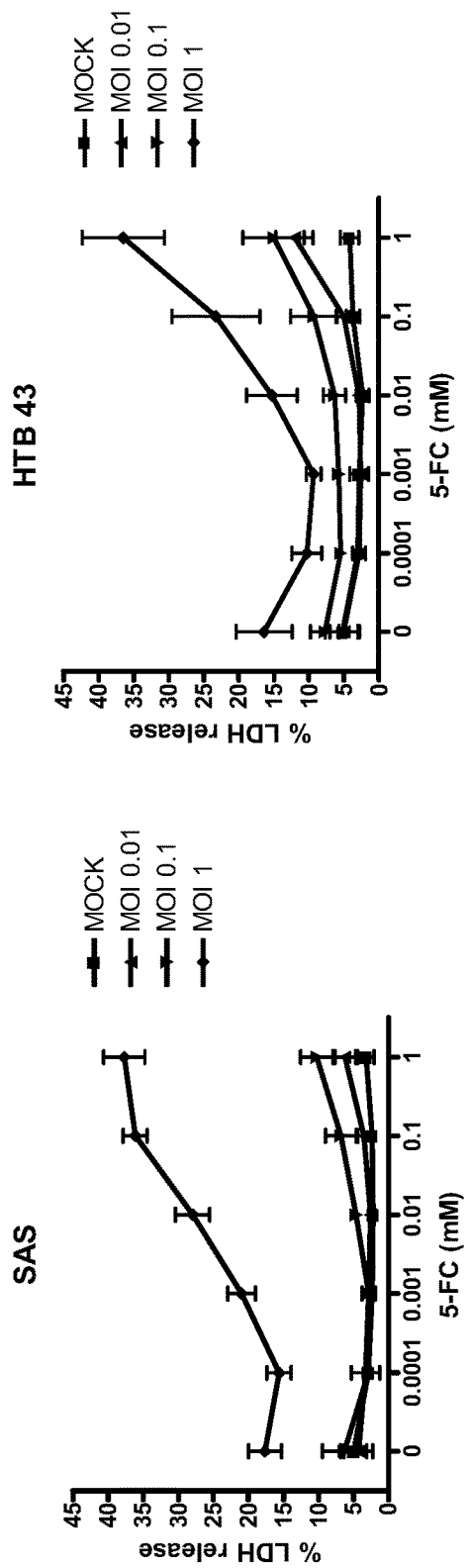

FIG. 11 shows the results of an LDH release assay of SAS and HTB-43 FaDu cells (human H&N cancer cells) treated with viral particles rescued from the plasmid pc3MerV2 Id-SCD (Id-SCD).

Figure 12A:
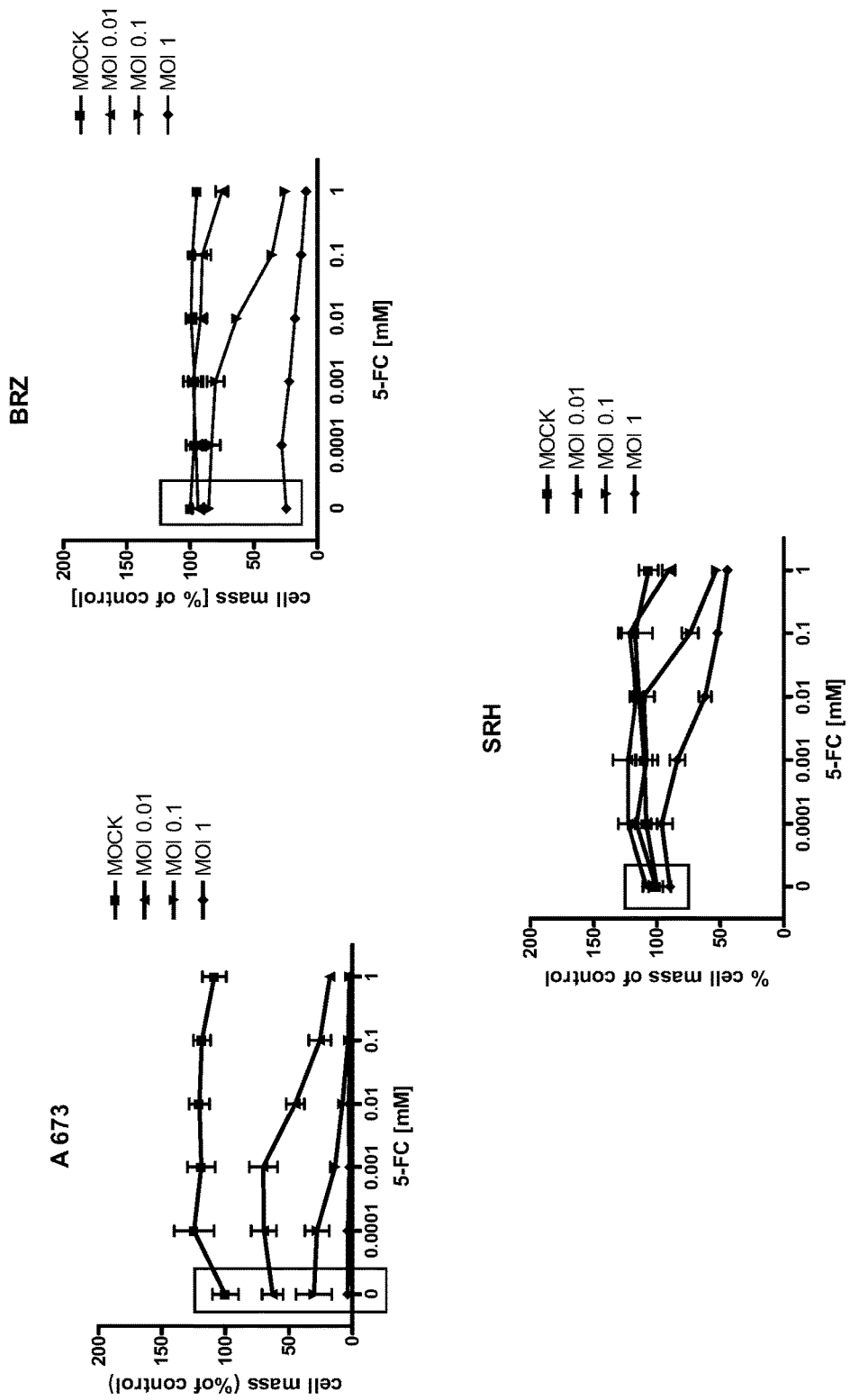

FIG. 12 shows the results of an SRB proliferation assay of A 673, BRZ, and SRH cells (human sarcoma cells) treated with viral particles rescued from the plasmid pc3MerV2 Id-SCD (Id-SCD).

Figure 13A:
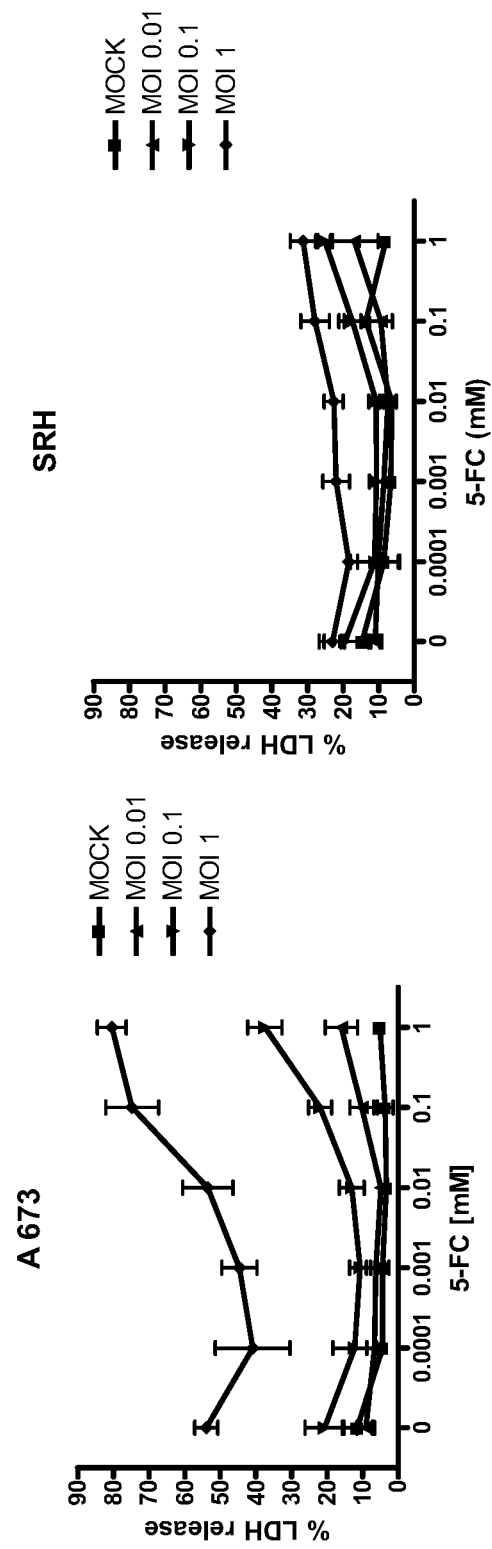

FIG. 13 shows the results of an LDH release assay of A 673 and SRH cells (human sarcoma cells) treated with viral particles rescued from pc3MerV2 Id-SCD (Id-SCD).

Figure 14:
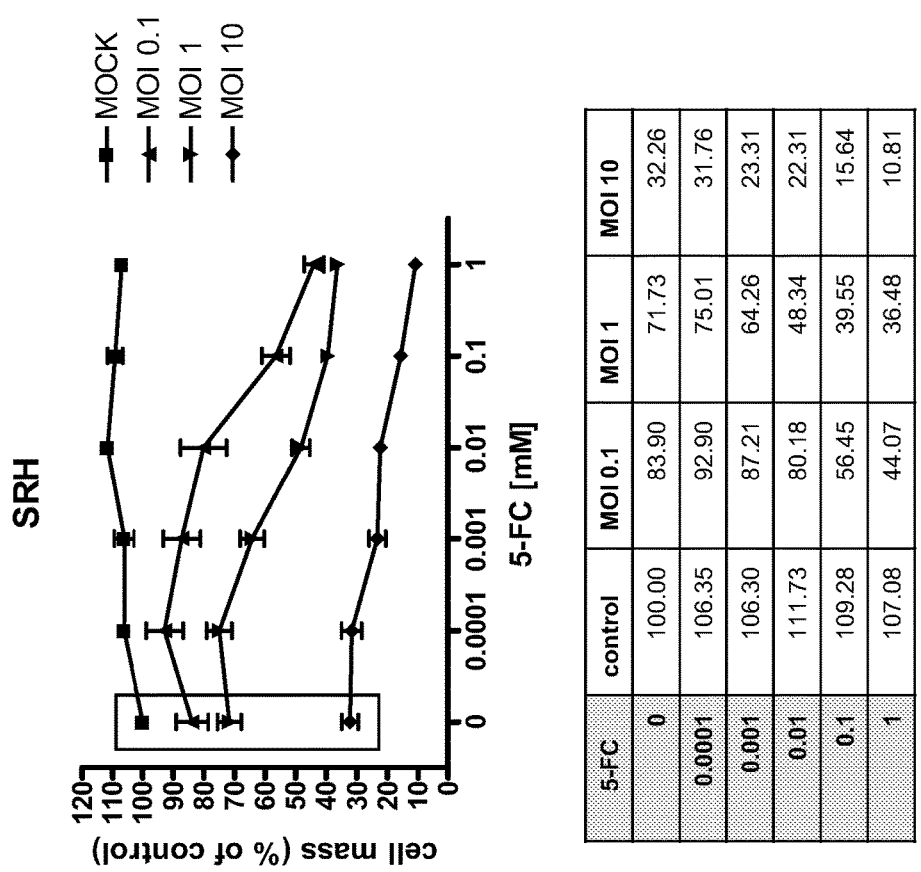

FIG. 14 shows the results of an SRB proliferation assay of SRH cells treated with viral particles rescued from the plasmid pc3MerV2 Id-SCD (Id-SCD).

Figure 15A:
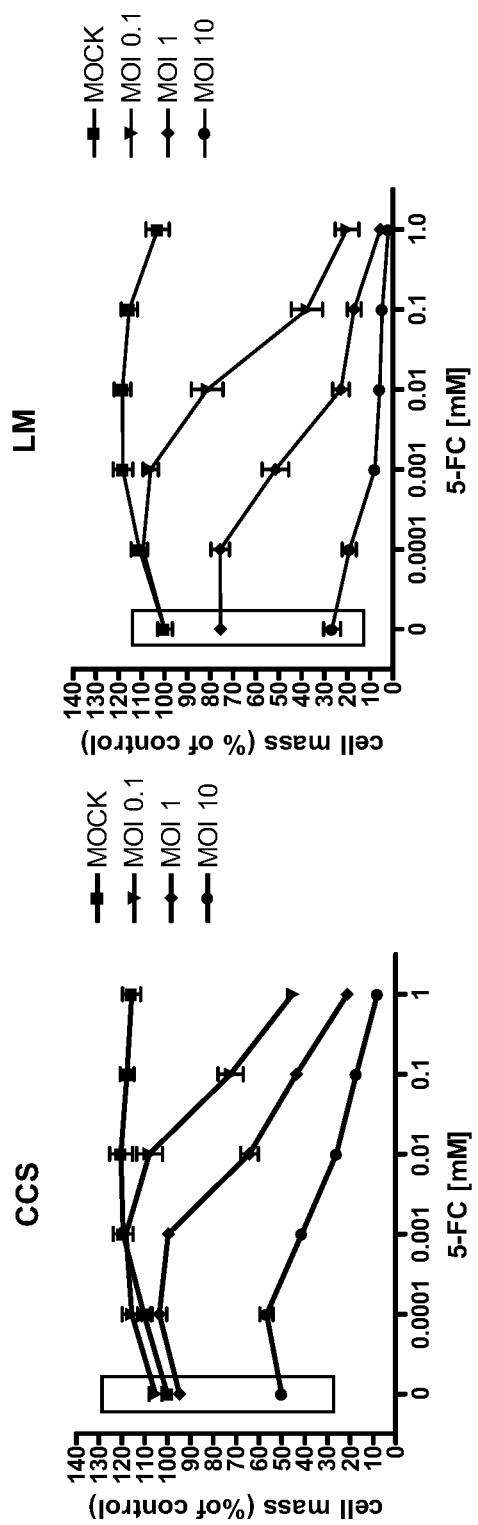

FIG. 15 shows the results of an SRB proliferation assay of sarcoma tumor cells (cell lines CCS, LM) treated with viral particles rescued from the plasmid pc3MerV2 Id-SCD (Id-SCD).

Figure 16A:
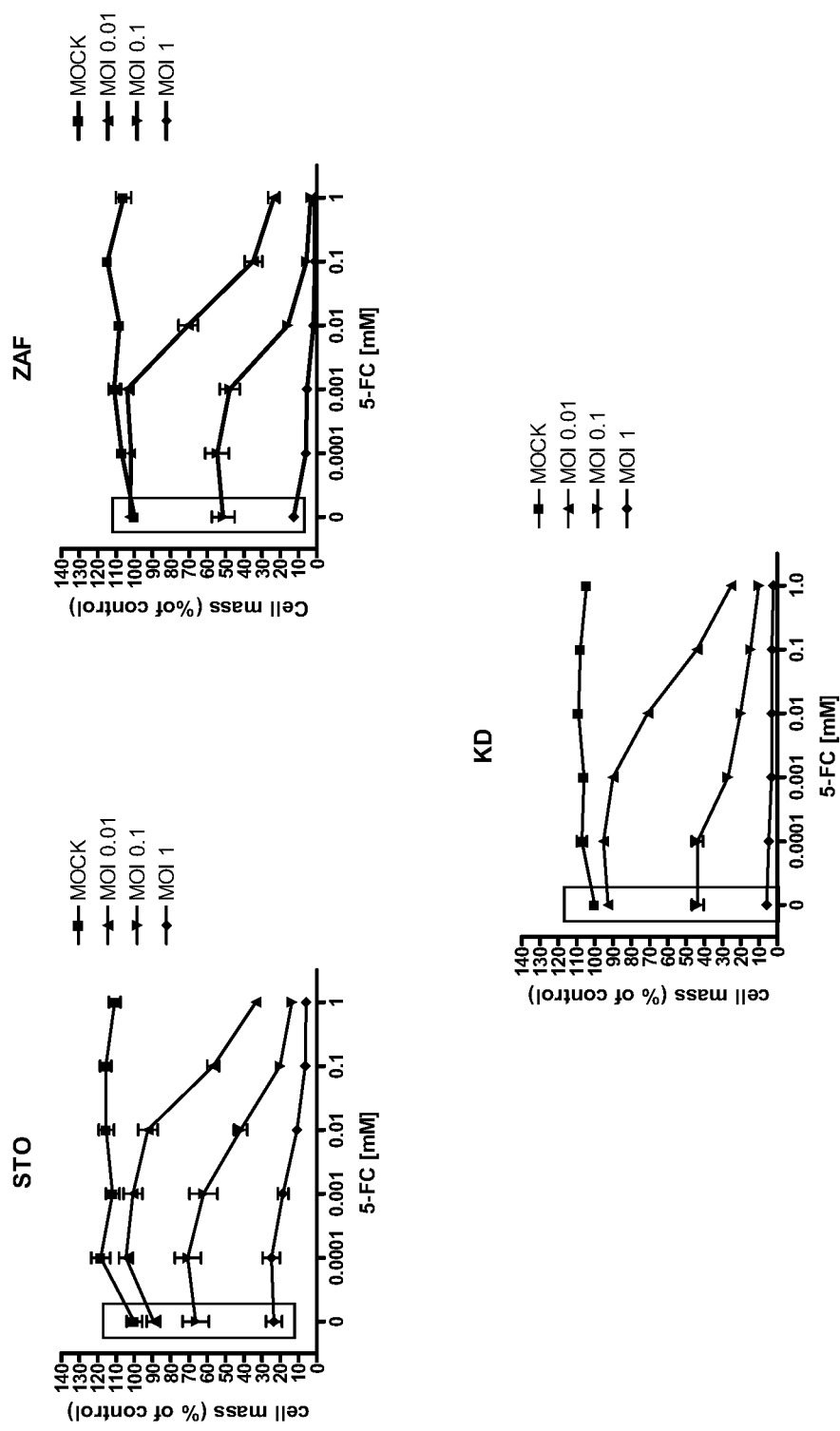

FIG. 16 shows the results of an SRB proliferation assay of sarcoma tumor cells (cell lines STO, ZAF, KD) treated with viral particles rescued from the plasmid pc3MerV2 Id-SCD (Id-SCD).

Figure 17A:
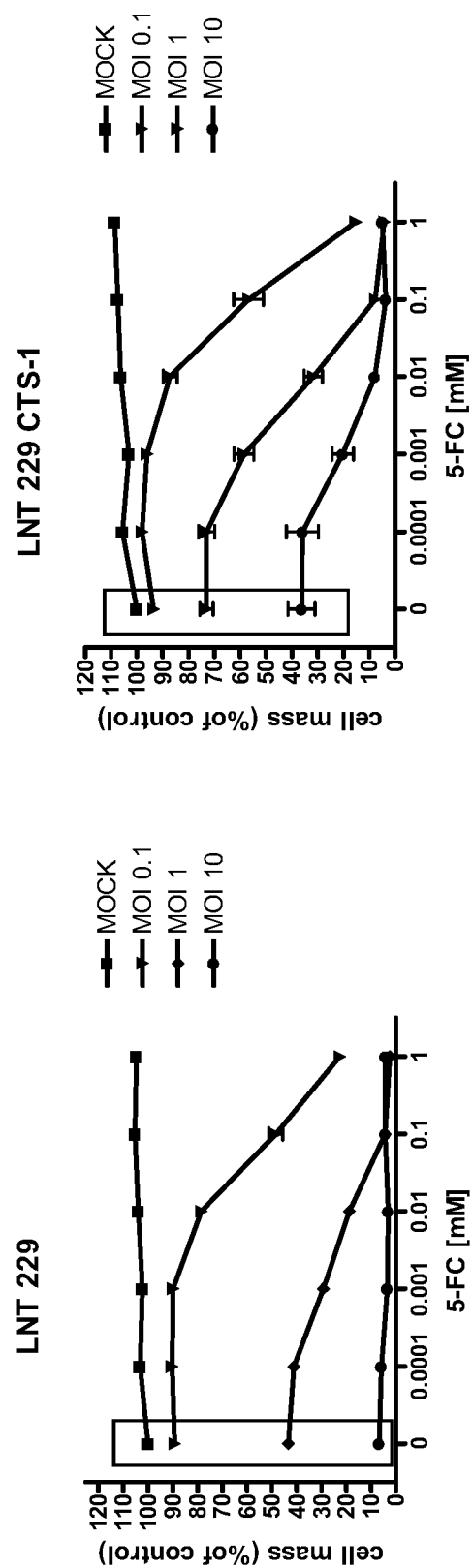

FIG. 17 shows the results of an SRB proliferation assay of glioblastoma tumor cells (cell lines LNT 229, LNT 229 CTS-1) treated with viral particles rescued from the plasmid pc3MerV2 Id-SCD (Id-SCD).

Figure 18A:
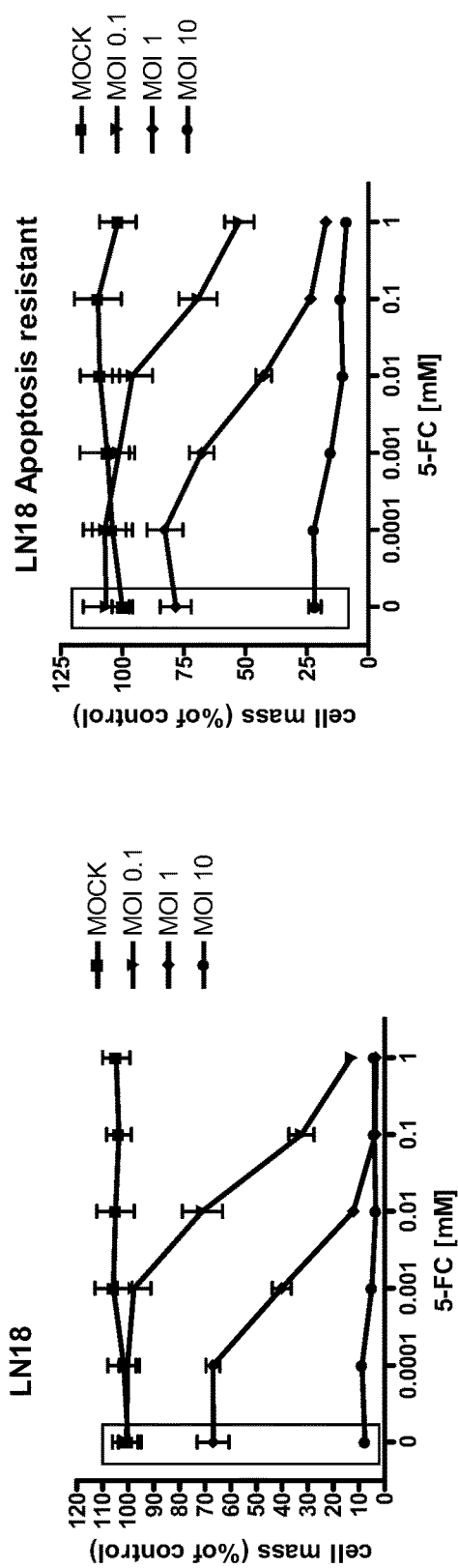

FIG. 18 shows the results of an SRB proliferation assay of glioblastoma tumor cells (cell lines LN 18, LN 18 Apoptosis resistant) treated with viral particles rescued from the plasmid pc3MerV2 Id-SCD (Id-SCD).

Figure 19A:
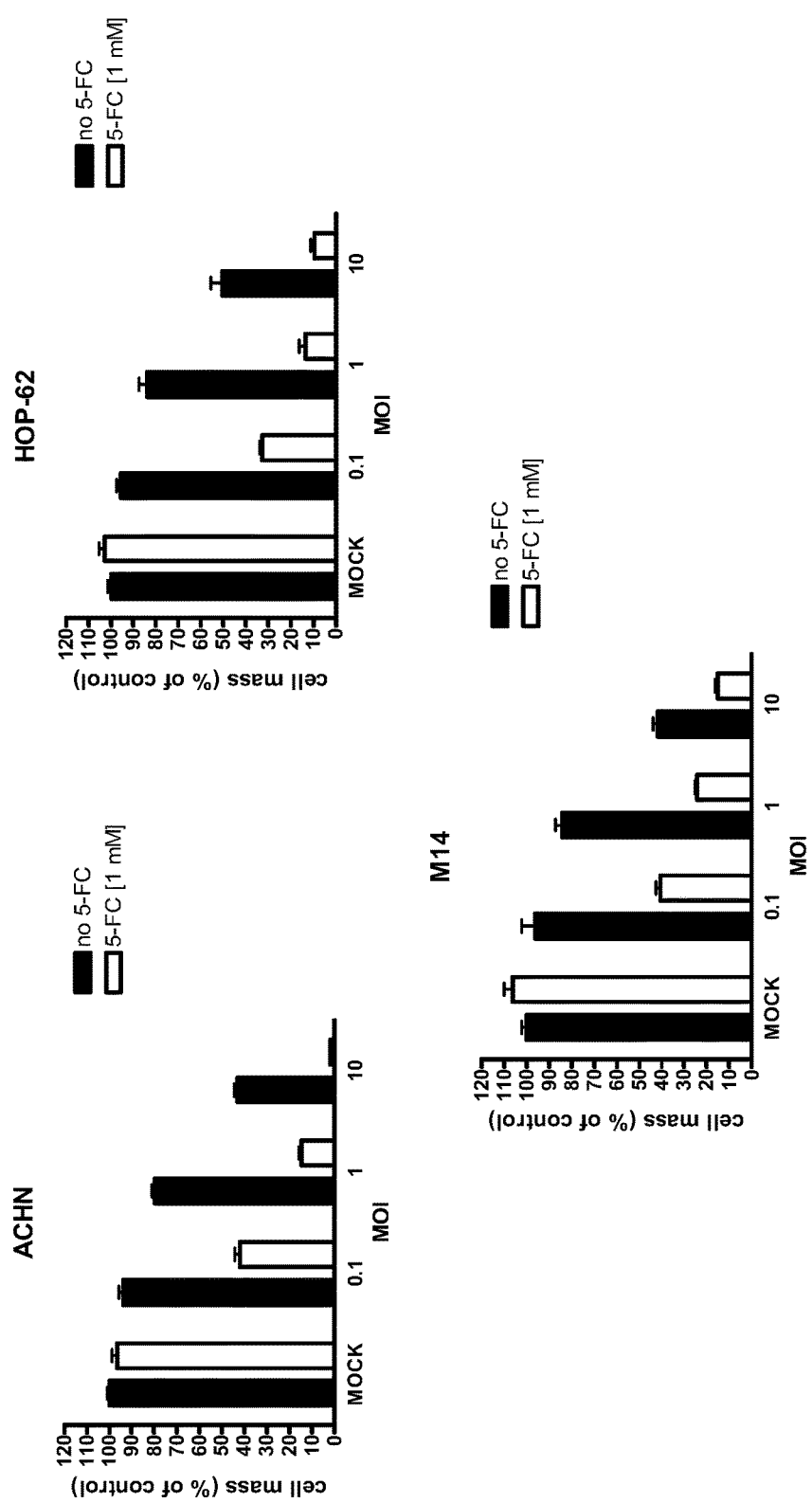

FIG. 19 shows the results of an SRB proliferation assay of renal cell carcinoma (ACHN), pulmonary adenocarcinoma (HOP-62) and melanoma (M14) tumor cells treated with viral particles rescued from the plasmid pc3MerV2 Id-SCD (Id-SCD).

Figure 20A:
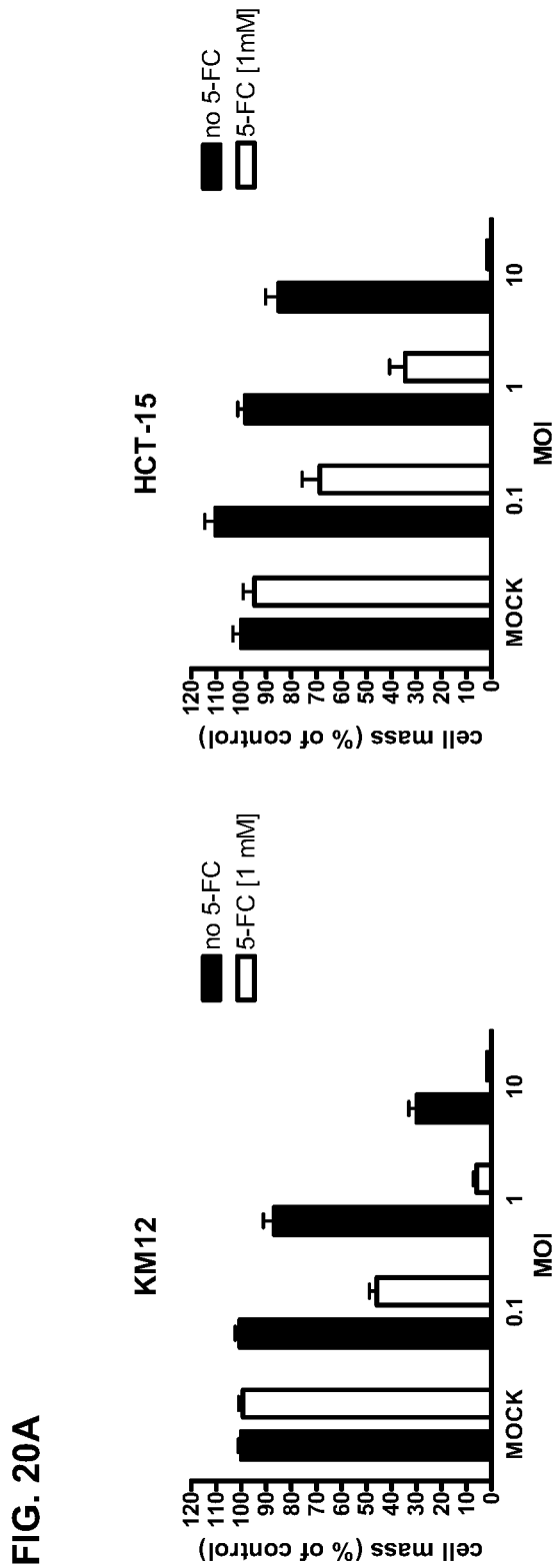

FIG. 20 shows the results of an SRB proliferation assay of colonic adenocarcinoma tumor cells (cell lines KM-12, HCT-15) treated with viral particles rescued from the plasmid pc3MerV2 Id-SCD (Id-SCD).

Figure 21:
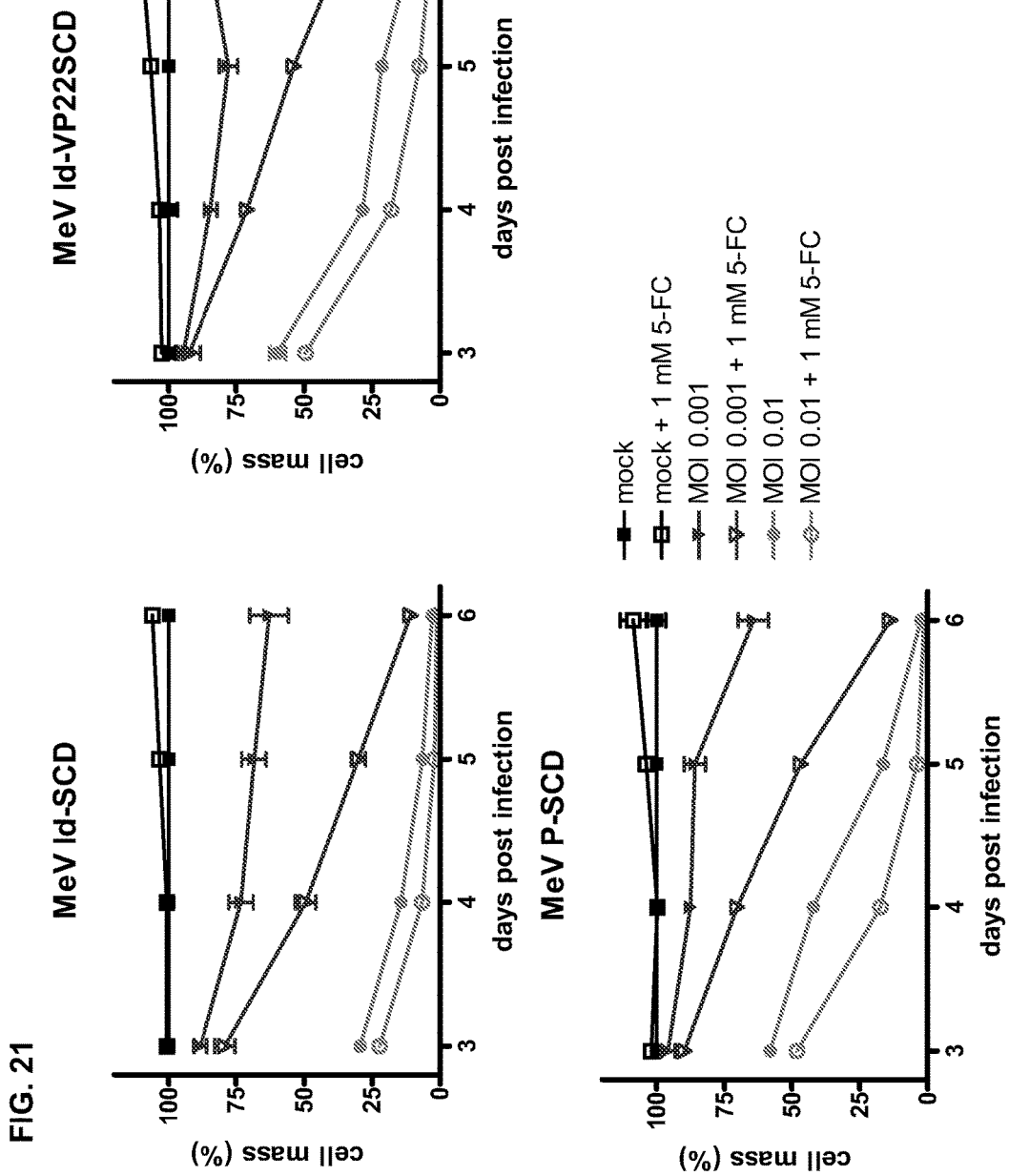

FIG. 21 shows the effect of three different armed MeV vectors on Hep3B human hepatocellular carcinoma cells (vectors pc3MerV2 Id-SCD, pc3MerV2 Id-VP22SCD, and pMerV2 P-SCD); all experiments were performed in quadruplicates; experiments were repeated three times; values: mean+SEM.

Figure 22:
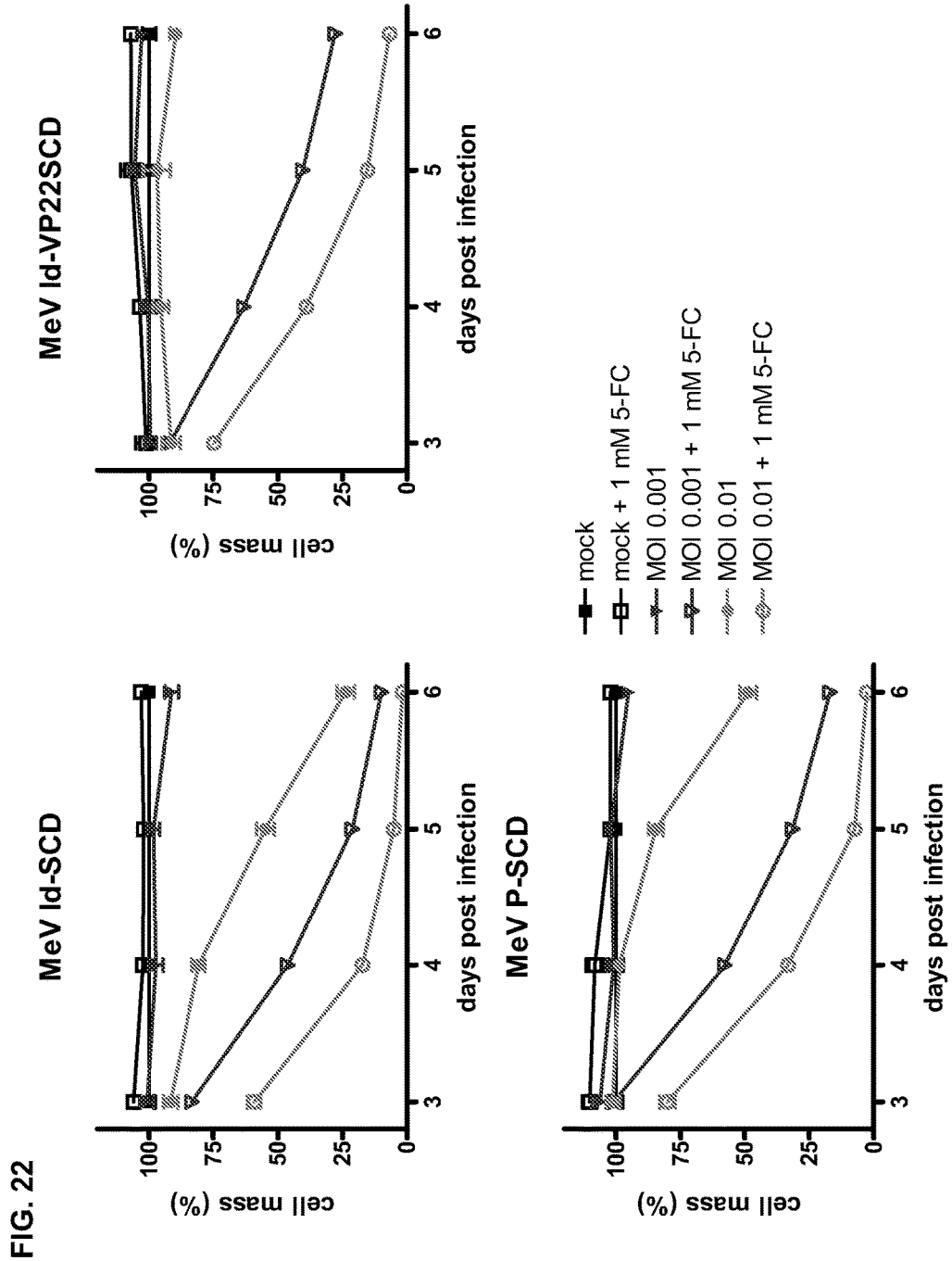

FIG. 22 shows the effect of three different armed MeV vectors on HepG2 human hepatocellular carcinoma cells (vectors pc3MerV2 Id-SCD, pc3MerV2 Id-VP22SCD, and pMerV2 P-SCD); all experiments were performed in quadruplicates; experiments were repeated three times; values: mean+SEM.

Figure 23:
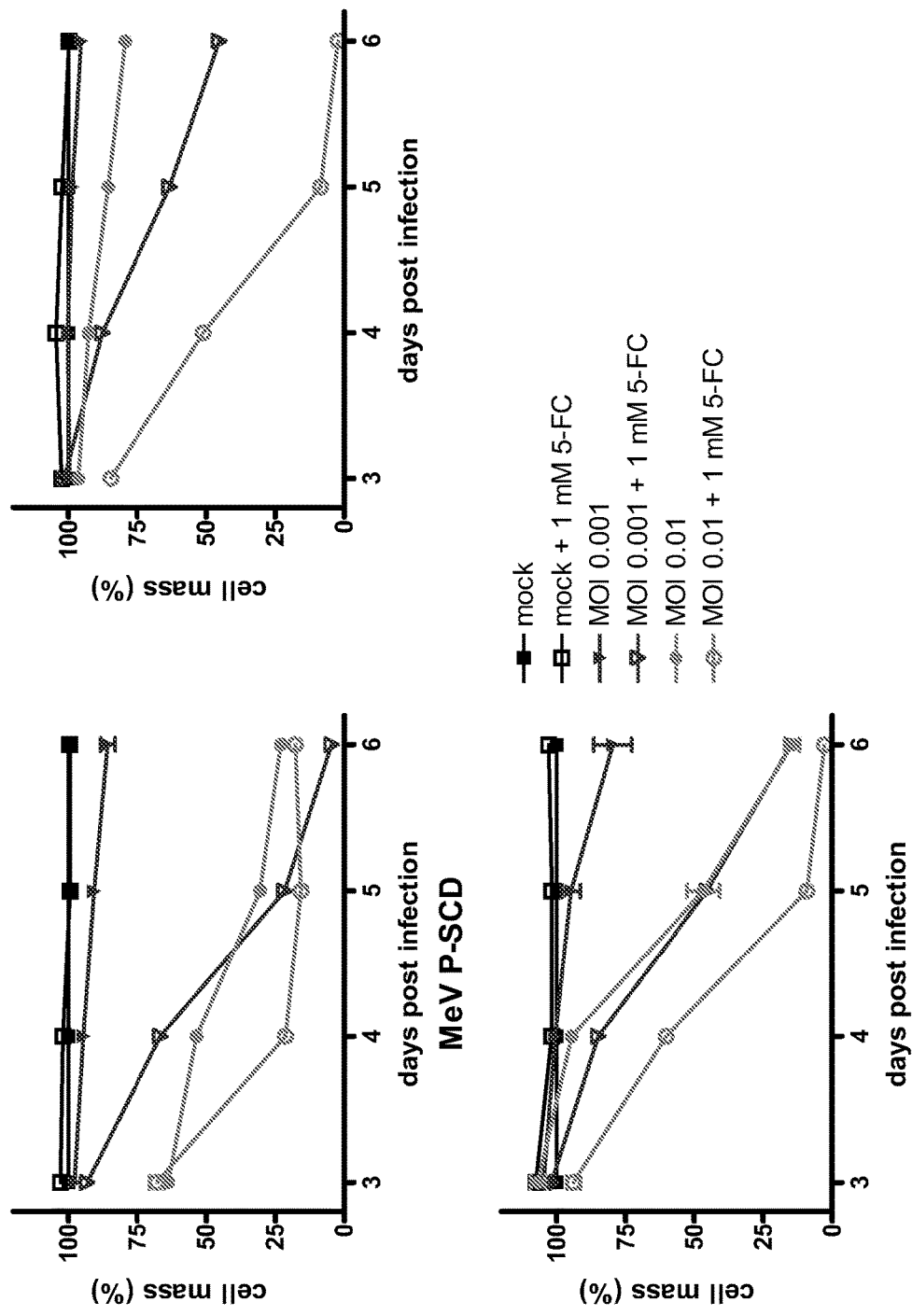

FIG. 23 shows the effect of three different armed MeV vectors on PLC/PRF/5 human hepatocellular carcinoma cells (vectors pc3MerV2 Id-SCD, pc3MerV2 Id-VP22SCD, and pMerV2 P-SCD); all experiments were performed in quadruplicates; experiments were repeated three times; values: mean+SEM.

Figure 24:
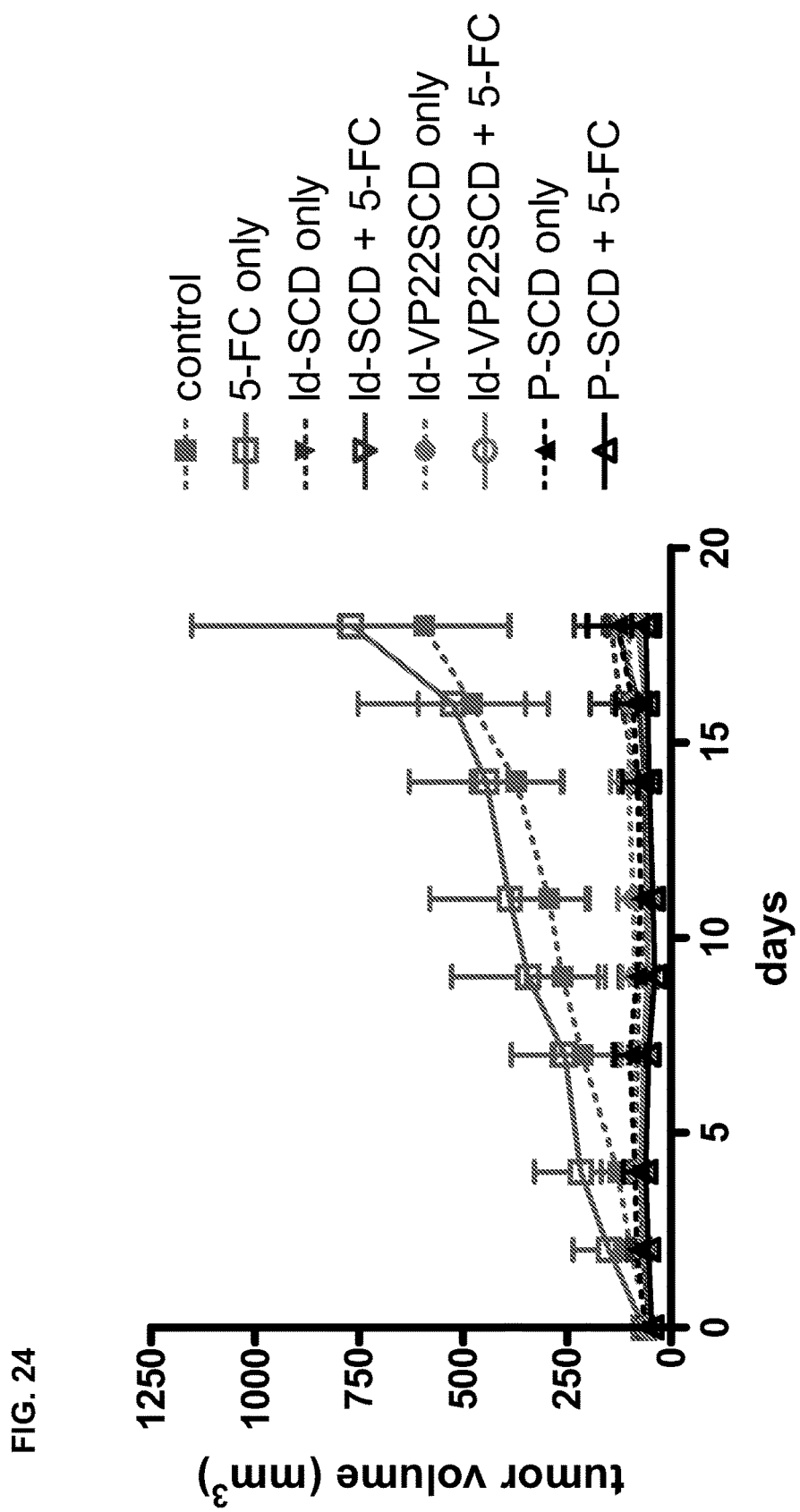

FIG. 24 shows the results of a determination of tumor volumes in a xenograft animal HCC tumor model (Hep3B model).

Figure 25:
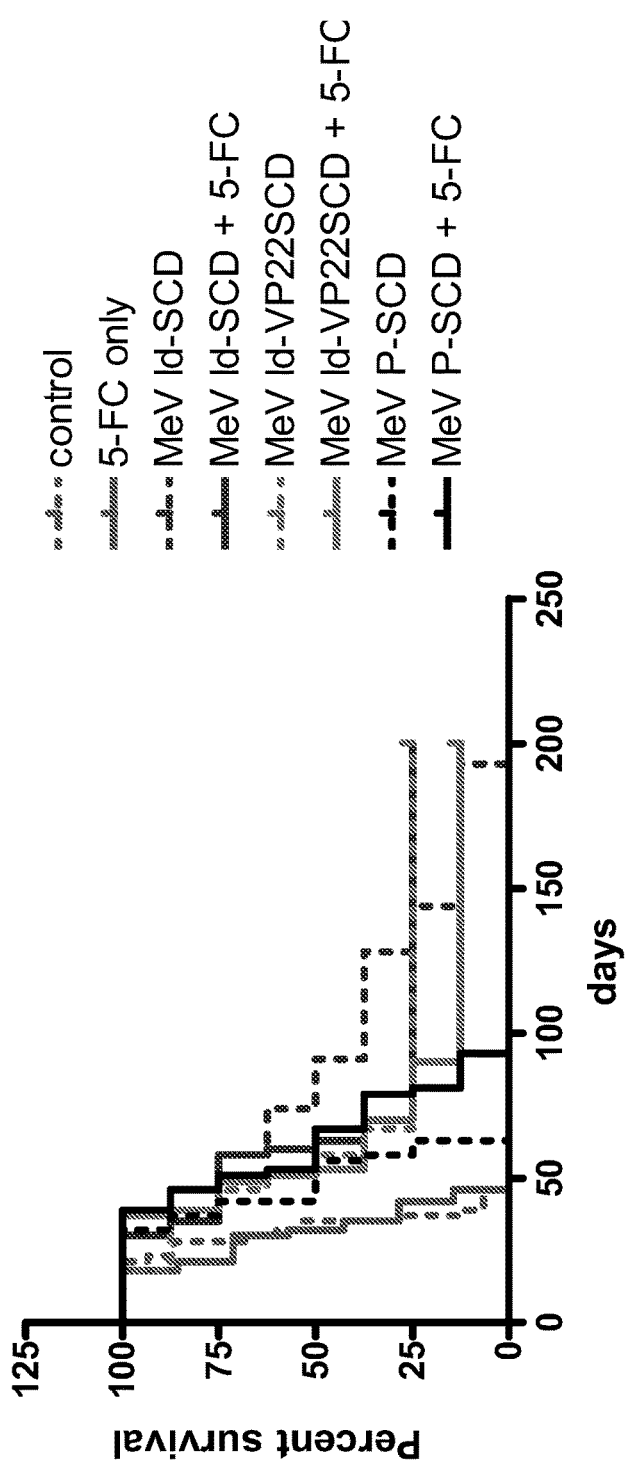

FIG. 25 shows the results of a determination of survival data in a xenograft animal HCC tumor model (Hep3B model).

Figure 26:
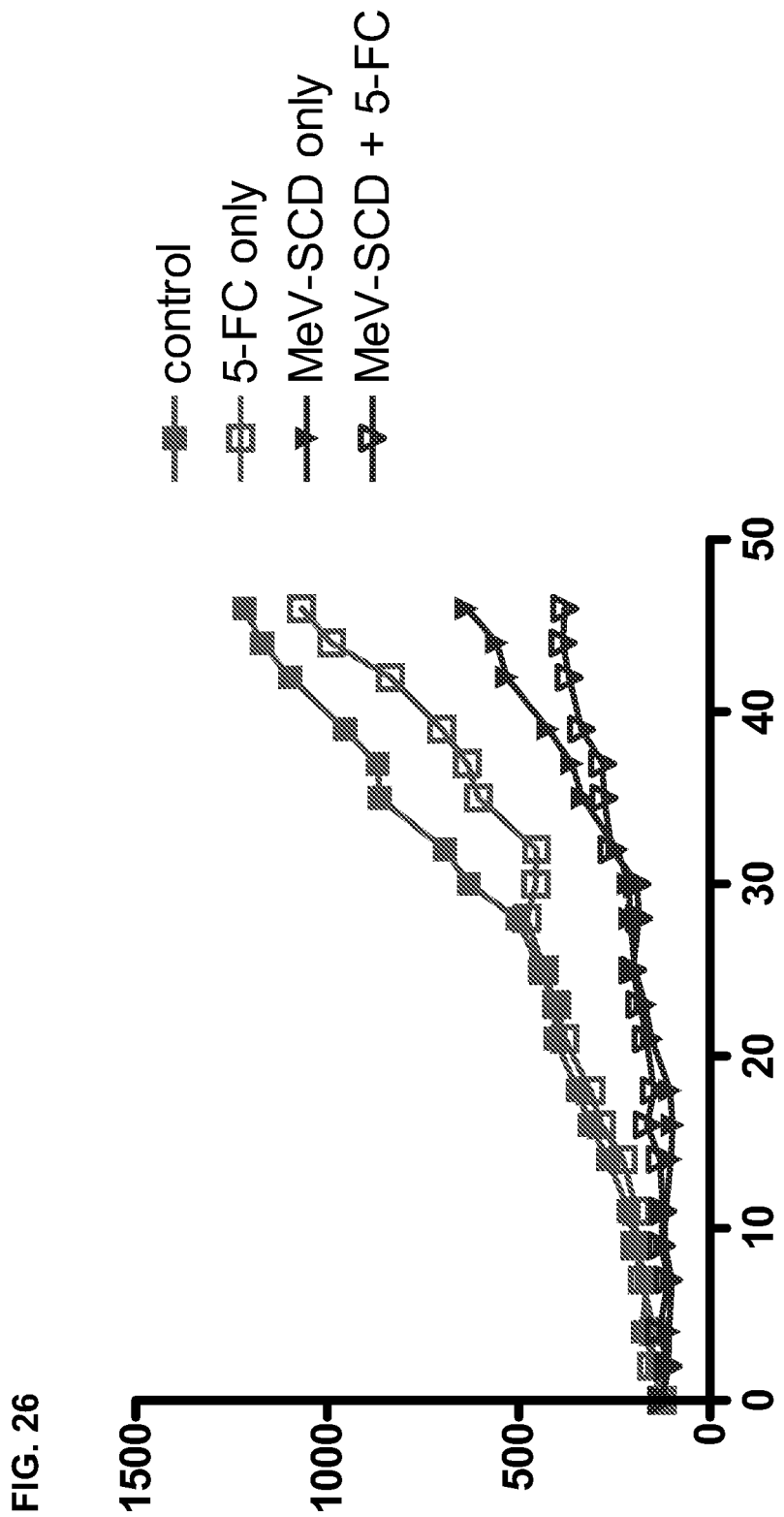

FIG. 26 shows the results of a determination of tumor volumes in a xenograft animal CC tumor model (TFK-1 model).

Figure 27:
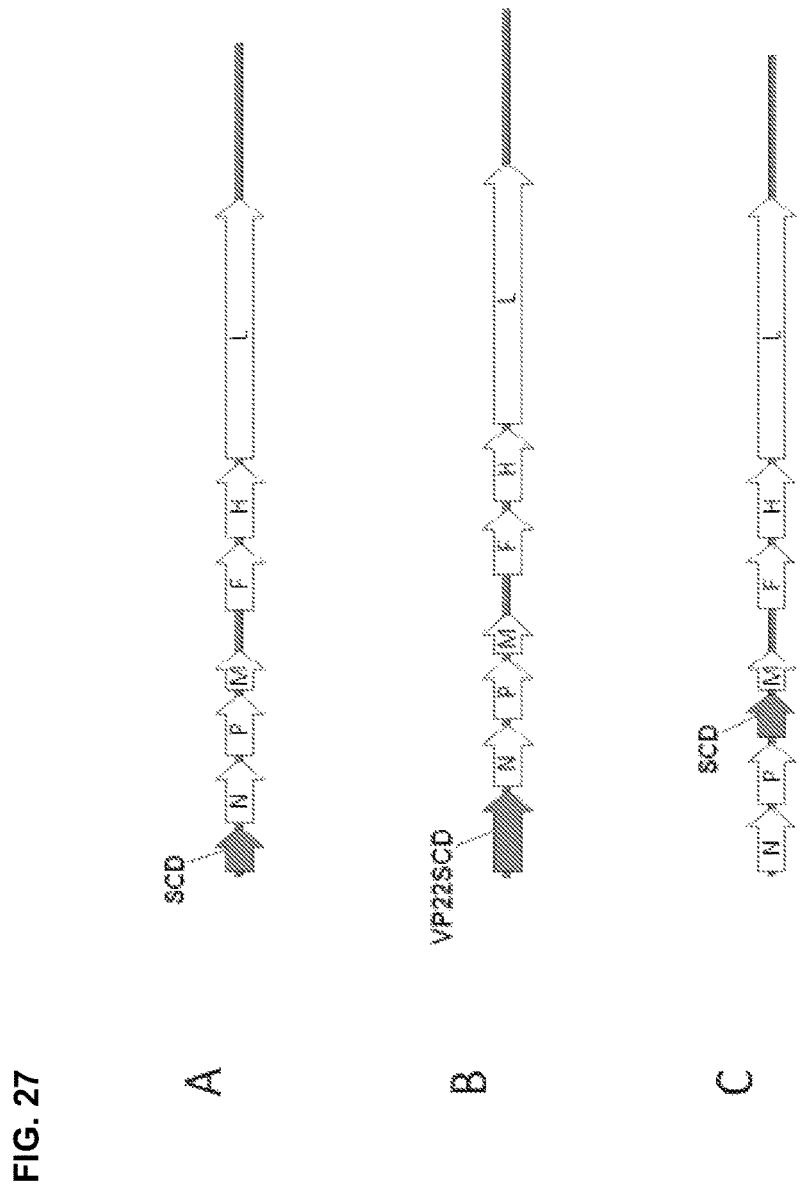

FIG. 27 shows a schematic overview of viral cDNAs and the respective viral vectors. Plasmids (A) pc3MerV2 Id-SCD (20,841 bp), (B) pc3MerV2 Id-VP22SCD (21,759 bp), and (C) pMerV2 P-SCD (20,546 bp) are shown. Open reading frames are displayed as arrows (viral genes in white, transgenes in dark). Nontranslated regions and the plasmid backbone are depicted as straight lines. N: Nucleocapsid protein, P: Phosphoprotein, M: Matrix protein, F: Fusion protein, H: Hemagluttinin, L: Large protein, SCD: Supercytosine deaminase, VP22SCD: Fusion of SCD and the herpes simplex virus protein VP22.

FIG. 28 shows the genetic sequence of vector pMerV2 P-SCD (coding for MeV P-SCD) (SEQ-ID NO. 8).

FIG. 29 shows the genetic sequence of vector pc3MerV2 Id-VP22SCD (coding for MeV Id-VP22SCD) (SEQ-ID NO. 9).

DETAILED DESCRIPTION OF THE INVENTION

The present invention relates to a pharmaceutical composition comprising a recombinant measles virus comprising a suicide gene for use in the treatment of malignant cells with primary or secondary resistances against an oncolytic measles virus without suicide gene activity.

The terms "comprise" and "contain" within the meaning of the invention introduce a non-exhaustive list of features. Likewise, the word "one" is to be understood in the sense of "at least one".

In the context of the present invention, the term "suicide gene" refers to a gene, the expression of which in a host cell causes or results in a reduced viability of such host cells. In particular settings, the suicide gene will cause a cell to kill itself through apoptosis. In certain such settings, expression of the suicide gene will result in an enzyme, which catalyzes the generation of a cytotoxic drug from a non-toxic prodrug.

In a particular embodiment of the pharmaceutical composition according to the present invention, the malignant cells are identified by performing the following step:
(a) determining the percentage of living cells in a population of cells derived from said malignant cells 72 h, or preferably 96 h, after infecting said population with the oncolytic measles virus at a multiplicity of infection of 1, wherein a percentage of 40% or more of living cells in said population, particularly 50% or more, more particularly 60% or more, is indicative for said malignant cells being primarily or secondarily resistant against an oncolytic measles virus without suicide gene activity.

In a particular embodiment, the recombinant measles virus is based on measles vaccine strain Schwarz.

A description of the measles vaccine strain Schwarz, including its full genomic sequence and its comparison with other vaccine strains, can be found in Tillieux et al. (Tillieux, S. L., Halseyb, W. S., Satheb, G. M., and Vassilev, V. Comparative analysis of the complete nucleotide sequences of measles, mumps, and rubella strain genomes contained in Priorix-Tetra™ and ProQuad™ live attenuated combined vaccines. Vaccine 27 (2009) 2265-2273).

In a particular embodiment, the oncolytic measles virus without suicide gene activity is from measles vaccine strain Schwarz. More particularly, the oncolytic measles virus without suicide gene activity has a sequence according to SEQ-ID No. 1 (see FIG. 1).

In the context of the present invention, the term "has a sequence according to SEQ-ID No. 1" depends on the context given and refers to either the DNA sequence as depicted in SEQ-ID No. 1 (cDNA of measles virus particles from the Schwarz strain), or to the corresponding RNA sequence, as found packaged in the viral particle rescued from a vector comprising such cDNA sequence.

In a particular embodiment of the pharmaceutical composition according to the present invention, the suicide gene comprises a cytosine deaminase, particularly yeast cytosine deaminase.

Cytosine deaminases, particularly yeast cytosine deaminase, and their use as prodrug-converting enzyme in cancer gene therapy has been discussed and examined in various publications (see, for example: Kievit, E., Nyati, M. K., Ng, E., Stegman, L. D., Parsels, J., Ross, B. D., Rehemtulla, A., Lawrence, T. S. Yeast cytosine deaminase improves radiosensitization and bystander effect by 5-fluorocytosine of human colorectal cancer xenografts. Cancer Res. 60 (2000) 6649-55).

In a particular embodiment, the suicide gene further comprises a uracil phosphoribosyltransferase, particularly yeast uracil phosphoribosyltransferase.

It could be shown that the concomitant expression of a cytosine deaminase and a uracil phosphoribosyltransferase improves the enzymatic conversion of 5-fluorocytosine fluorocytosine to cytotoxic metabolites (Tiraby M, Cazaux C, Baron M, Drocourt D, Reynes J P, Tiraby G. FEMS Microbiol Lett. 167 (1998) 41-9).

More particularly, the suicide gene comprises a fusion of a cytosine deaminase, particularly yeast cytosine deaminase, and a uracil phosphoribosyltransferase, particularly yeast uracil phosphoribosyltransferase, called SCD (SuperCD).

The use of a fusion gene comprising a cytosine deaminase and a uracil phosphoribosyltransferase has been described for an adenoviral system (Erbs, P., Regulier, E., Kintz, J., Leroy, P., Poitevin, Y., Exinger, F., Jund, R., and Mehtali, M. In vivo cancer gene therapy by adenovirus-mediated transfer of a bifunctional yeast cytosine deaminase/uracil phosphoribosyltransferase fusion gene. Cancer Res. 60 (2000) 3813-22).

Most particularly, the suicide gene comprises a sequence according to SEQ-ID NO. 2 (see FIG. 2).

In the context of the present invention, the term "comprises a sequence according to SEQ-ID No. . . . " depends on the context given and refers to either the DNA sequence as depicted in said SEQ-ID No., or to the corresponding RNA sequence, as found packaged in the viral particle rescued from a vector comprising such DNA sequence.

In a particular embodiment, the recombinant measles virus comprises an RNA sequence corresponding to SEQ-ID No. 3 (see FIG. 3), SEQ-ID No. 4 (see FIG. 4), SEQ-ID No. 8 (see FIG. 28), or SEQ-ID No. 9 (see FIG. 29), particularly SEQ-ID No. 4.

In a particular embodiment of the pharmaceutical composition according to said the present invention, the malignant cells are additionally non-responsive to chemotherapeutics and/or radiation therapy.

In a particular embodiment, the malignant cells are selected from the list of: malignant cells from cholangiocarcinoma, head and neck cancer, and sarcoma.

In a particular embodiment, the pharmaceutical composition is for use in a treatment, which is a repeated treatment, particularly every week, or every two weeks, or every three weeks, or every four weeks, employing such a recombinant measles virus comprising a suicide gene for use in the treatment of malignant cells with primary or secondary resistances against an oncolytic measles virus without suicide gene activity.

Recently, employment of a clinical regime of repetitive application of a recombinant measles virus without suicide gene activity (every 4 weeks for up to 6 cycles) has demonstrated that serum anti-measles antibody levels at baseline and on study completion remained stable both in blood and in peritoneal fluid as compared with baseline, indicating a lack of significant boost to the humoral immune response (Galanis E, Hartmann L C, Cliby W A, Long H J, Peethambaram P P, Barrette B A, Kaur J S, Haluska P J Jr, Aderca I, Zollman P J, Sloan J A, Keeney G, Atherton P J, Podratz K C, Dowdy S C, Stanhope C R, Wilson T O, Federspiel M J, Peng K W, Russell S J. Cancer Res. 2010; 70(3):875-82). Therefore, repetitive application of recombinant measles viruses was found to be feasible in the treatment of cancer patients.

In another aspect, the present invention relates to a recombinant measles virus based on measles vaccine strain Schwarz encoding a suicide gene, which comprises a fusion of a cytosine deaminase, particularly a yeast cytosine deaminase, and a uracil phosphoribosyltransferase, particularly a yeast uracil phosphoribosyltransferase.

In a particular embodiment of the recombinant measles virus according to the present invention, the suicide gene comprises a sequence according to SEQ-ID NO. 2 (see FIG. 2).

In a particular embodiment, the recombinant measles virus comprises an RNA sequence according to SEQ-ID No. 3 (see FIG. 3), SEQ-ID No. 4 (see FIG. 4), SEQ-ID No. 8 (see FIG. 28), or SEQ-ID No. 9 (see FIG. 29), particularly SEQ-ID No. 4.

In another aspect, the present invention relates to a method of treatment of malignant cells with primary or secondary resistances against an oncolytic measles virus without suicide gene activity, comprising the step of administering a recombinant measles virus comprising a suicide gene according to the present invention to a patient in need thereof.

In certain embodiments of that aspect of the invention, the treatment is the treatment of a cholangiocarcinoma, head and neck cancer, or sarcoma.

In certain embodiment, the method of treatment is a repeated treatment, particularly every week, or every two weeks, or every three weeks, or every four weeks.

In another aspect, the present invention relates to a method for generating the recombinant measles virus according to the present invention, comprising the step of (a) cloning (i) the genome of measles vaccine strain Schwarz, and (ii) a suicide gene, into a plasmid under the control of an RNA polymerase II promoter.

The use of the RNA polymerase II promoter system for the efficient expression of antigenomic RNA (cRNA) from cDNA of Mononegavirales has been shown for Borna disease virus (BDV) and measles virus (Martin, A., Staeheli, P., and Schneider, U. RNA Polymerase II-Controlled Expression of Antigenomic RNA Enhances the Rescue Efficacies of Two Different Members of the Mononegavirales Independently of the Site of Viral Genome Replication, J. Virol. 80 (2006) 5708-5715).

In a particular embodiment of the method according to the present invention, the suicide gene comprises a cytosine deaminase, particularly yeast cytosine deaminase.

In another particular embodiment, the suicide gene further comprises a uracil phosphoribosyltransferase, particularly yeast uracil phosphoribosyltransferase.

In another particular embodiment, the suicide gene comprises a fusion of a cytosine deaminase, particularly yeast cytosine deaminase, and a uracil phosphoribosyltransferase, particularly yeast uracil phosphoribosyltransferase.

In a particular embodiment of the method according to the present invention, the suicide gene comprises a sequence according to SEQ-ID NO. 2 (see FIG. 2).

In a particular embodiment, the method further comprises the step of (b) cloning measles virus helper genes N, P and L, each under the control of an RNA polymerase II promoter, into at least one vector.

In a particular embodiment, the viral helper genes N, P and L, are each cloned into a separate vector under the control of an RNA polymerase II promoter, particularly a plasmid vector, resulting in (i) a plasmid encoding the measles virus helper gene N, (ii) a plasmid encoding the measles virus helper gene P, and (iii) a plasmid encoding the measles virus helper gene L.

Thus, such embodiment relates to a method comprising the steps of (b) cloning measles virus helper genes N under the control of an RNA polymerase II promoter, into a first vector, particularly a plasmid vector;

(c) cloning measles virus helper gene P under the control of an RNA polymerase II promoter into a second vector, particularly a plasmid vector;
(d) cloning measles virus helper gene L under the control of an RNA polymerase II promoter into a third vector, particularly a plasmid vector.

In a particular embodiment, steps (a) and/or (b), or (a) and/or (b) to (d), further comprise the step of removing putative splicing sequences from said genome and/or said helper genes.

In a particular embodiment, step (a) results in the plasmid having the sequence according to SEQ-ID No. 4 (see FIG. 4), SEQ-ID No. 8 (see FIG. 28), or SEQ-ID No. 9 (see FIG. 29), particularly SEQ-ID No. 4.

20. In a particular embodiment, steps (b) to (d) result in plasmids having the sequences according to SEQ-ID No. 5, SEQ-ID No. 6, and SEQ-ID No. 7 (see FIGS. 5 to 7).

In a particular embodiment, the method according to the present invention further comprises the step of
(e) transfecting host cells with plasmids of steps (a) and (b), particularly host cells from a certified cell line approved for vaccine production, particularly from Vero or MRC-5 cell lines.

One of the most important factors for the production of live viral vaccines is their genetic stability. Genetic stability includes questions related to the potential reversion of the vaccine strain to more virulent forms, the recombination with other viral sequences to produce potentially pathogenic viruses, and any genetic drift that could result in decrease of immunogenicity and efficacy. In various cases it has been shown that propagation of live vaccine strains in Vero and MRC-5 cell lines maintains genetic stability of the vaccine strains (see, for example, Laassri M, Meseda C A, Williams O, Merchlinsky M, Weir J P, Chumakov K., Microarray assay for evaluation of the genetic stability of modified vaccinia virus Ankara B5R gene. J. Med. Virol. 79 (2007) 791-802).

In a particular embodiment, the method further comprises the step of
(f) rescuing recombinant measles virus from the host cell transfected in step (e).

In another aspect, the present invention relates to a kit comprising
(a) a plasmid comprising (i) the genome of measles vaccine strain Schwarz, and (ii) a suicide gene, which comprises a fusion of a cytosine deaminase, particularly yeast cytosine deaminase, and a uracil phosphoribosyltransferase, particularly yeast uracil phosphoribosyltransferase, under the control of an RNA polymerase II promoter, particularly wherein said suicide gene comprises a sequence according to SEQ-ID No. 2 (see FIG. 2), particularly wherein the plasmid has the sequence according to SEQ-ID No. 4 (see FIG. 4) SEQ-ID No. 8 (see FIG. 28), or SEQ-ID No. 9 (see FIG. 29), more particularly SEQ-ID No. 4;
(b) at least one plasmid comprising measles virus helper genes N, P, and L, each in form of a single gene under the control of an RNA polymerase II promoter.

In a particular embodiment of the kit according to the present invention, the viral helper genes N, P, and L, are each cloned into a separate plasmid, each under the control of an RNA polymerase II promoter particularly wherein the plasmids have the sequences according to SEQ-ID No. 5, SEQ-ID No. 6, and SEQ-ID No. 7 (see FIGS. 5 to 7).

The invention is now described with reference to the following examples. These examples are provided for the purpose of illustration only and the invention should not be construed as being limited to these examples, but rather should be construed to encompass any and all variations which become evident as a result of the teaching provided herein. The following materials and methods are provided with respect to the subsequent examples but do not limit a multiplicity of materials and methodologies encompassed by the present invention.

EXAMPLES

Example 1: Preparation of MeV cDNA Plasmid Vector pc3MerV2 Id-Trka (SEQ-ID NO. 3)

Preparation of the measles virus cDNA vector was performed essentially as described recently (Inoue K, Shoji Y, Kurane I, Iijima T, Sakai T, Morimoto K. J Virol Methods. 2003; 107:229-36; Martin A, Staeheli P, Schneider U. J Virol. 2006; 80:5708-15), but with the following important modifications.

initially, it was unclear (i) which sequence parts/segments of the widely used cytomegalovirus (CMV) RNA polymerase II (Pol II) promoter had to be considered as optimal when employed for the rescue and amplification of recombinant measles virus vectors and (ii) which of the different CMV virus genomes described in GenBank (M60321, M21295) should be used for the generation of a CMV-based minimal promoter; therefore, a systematic analysis on different minimal CMV-derived promoter constructs had to be undertaken first; the results of this study revealed that the promoter variant construct pc3, encompassing CMV promoter nucleotides from −301 until −1 (+1 being defined as transcription initiation site) plus three nucleotides (TGG) additionally inserted after position −1, gave an optimal yield in both viral rescue and virus amplification;

this very short version of the cytomegalovirus-derived promoter, exhibiting only 301 plus 3 nucleotides (nt), provides the further advantage of shortening the overall length of the plasmid containing the recombinant measles virus vector genome, which enhances efficiency of plasmid replication;

furthermore, lack of intron sequences in the minimal pc3 CMV promoter (301 nt+3 nt) hinders the direction of mRNAs to the splicing machinery before mRNA export from the nucleus; a thereby reduced splicing efficiency improves both measles virus rescue and amplification;

in addition, purposeful incorporation of a 3' placed hepatitis delta virus (HDV) ribozyme was used to exactly process the 3'-end of all transcripts.

The sequence of pc3MerV2 Id-Trka (see FIG. 1) can be described as follows with reference to the position of the nucleotides (nt); UTR—untranslated region; ORF—open reading frame:

| | |
|---|---|
| nt 1-55: | MeV leader sequence |
| nt 56-66: | gene start for transgene transcription (gene start sequence obtained from the MeV N gene) |
| nt 67-103: | 5'-UTR (5'-UTR sequence obtained from the MeV N gene) |
| nt 103-108: | cloning site, exhibiting recognition site for restriction endonuclease XhoI (C'TCGAG) |
| nt 109-114: | cloning site, exhibiting recognition sites for restriction endonuclease PauI (G'CGCGC) or AscI (GG'CGCGCC); both recognition site represent unique sites being present only once in the complete vector sequence |
| nt 115-126: | 3'-UTR derived from MeV N gene |
| nt 127-136: | gene end for transgene transcription (obtained from the MeV N gene) |

-continued

| | |
|---|---|
| nt 140-150: | gene start of MeV N |
| nt 192-1769: | N ORF (1578 nt = 525 aa + stop codon) |
| nt 1891-3414: | P ORF (1524 nt = 507 aa + stop codon) |
| nt 2036-2043: | 3'-cloning site, exhibiting recognition site for restriction endonuclease SdaI (CCTGCA'GG), unique site being present only once in the complete vector sequence |
| nt 1913-2473: | C ORF (non-structural gene; 561 nt = 186 aa + stop codon) |
| nt 2575-2582: | A5G3 editing box; single nucleotide (G) insertion after nt 2580 |
| nt 1891-2789: | V trans-frame ORF after mRNA editing (non-structural gene; 900 nt = 299 aa + stop codon) |
| nt 3522-4529: | M ORF (1008 nt = 335 aa + stop codon) |
| nt 5533-7194: | F ORF (1662 nt = 553 aa + stop codon) |
| nt 7355-9208: | H ORF (1854 nt = 617 aa + stop codon) |
| nt 9318-15869: | L ORF (6552 nt = 2183 aa + stop codon) |
| nt 15942-15978: | MeV trailer sequence (37 nt) |

Example 2: Preparation of MeV Id-SCD (Id-SCD) Plasmid Vector pc3MerV2 Id-SCD (SEQ-ID NO. 4)

For generation of the recombinant MeV Id-SCD (Id-SCD) measles virus vector, plasmid pUC-SCD, encoding the SCD suicide fusion gene, was digested with restriction endonuclease MluI and the fragment containing the open reading frame of the SCD suicide fusion gene was ligated into basic vector pc3MerV2 Id-Trka (derivative of parental vector pc3 encompassing the optimized (shortened and modified) CMV RNA polymerase II (Pol II) promoter) which had been linearized with restriction endonuclease AscI. The correct integration of the fragment was verified by restriction digest and sequencing. Infectious viral particles were successfully produced by the subsequent rescue procedure.

pc3MerV2 Id-SCD (SEQ-ID NO. 4). The sequence of pc3MerV2 Id-SCD (see FIG. 2) can be described as follows with reference to the position of the nt:

| | |
|---|---|
| nt 1-55: | MeV leader sequence |
| nt 56-66: | gene start for transgene transcription (gene start sequence obtained from the MeV N gene) |
| nt 67-103: | 5'-UTR (5'-UTR sequence obtained from the MeV N gene) |
| nt 103-108: | cloning site, exhibiting recognition site for restriction endonuclease XhoI (C'TCGAG) |
| nt 109-114: | cloning site, exhibiting recognition sites for restriction endonuclease PauI (G'CGCGC) or AscI (GG'CGCGCC); both recognition site represent unique sites being present only once in the complete vector sequence |
| nt 121-1242: | SCD ORF (1122 nt = 373 aa + stop codon) |
| nt 1243-1248: | cloning sites, exhibiting recognition sites for restriction endonucleases MluI (A'CGCGT) + PauI (A'CGCGC) |
| nt 1249-1260: | 3'-UTR |
| nt 1262-1270: | gene end for transgene transcription (obtained from the MeV N gene) |
| nt 1274-1284: | gene start of MeV N |
| nt 1326-2903: | N ORF (1578 nt = 525 aa + stop codon) |
| nt 3025-4548: | P ORF (1524 nt = 507 aa + stop codon) |
| nt 3047-3607: | C ORF (non-structural gene; 561 nt = 186 aa + stop codon) |
| nt 3709-3716: | A5G3 editing box; single nucleotide (G) insertion after nt 2580 |
| nt 3025-3923: | V trans-frame ORF after mRNA editing (non-structural gene; 900 nt = 299 aa + stop codon) |
| nt 4656-5663: | M ORF (1008 nt = 335 aa + stop codon) |
| nt 6667-8328: | F ORF (1662 nt = 553 aa + stop codon) |
| nt 8489-10342: | H ORF (1854 nt = 617 aa + stop codon) |
| nt 10452-17003: | L ORF (6552 nt = 2183 aa + stop codon) |
| nt 17076-17112: | MeV trailer sequence (37 nt) |

Example 3: Preparation of Helper Plasmids (SEQ-ID NOs. 5 to 7)

Preparation of helper plasmids carrying either the N, the P, or the L gene, respectively, was performed essentially as described recently (Martin A, Staeheli P, Schneider U. J Virol. 2006; 80:5708-15), but with the following important modifications:
- as a result of a systematic analysis of different minimal CMV-derived promoter constructs the promoter variant construct pc3, being found to give an optimal yield in both viral rescue and virus amplification, was employed also for the helper plasmid generation;
- lack of intron sequences in the minimal pc3 CMV promoter (301 nt+3 nt) hinders the direction of mRNAs to the splicing machinery before mRNA export from the nucleus; a thereby reduced splicing efficiency improves both measles virus rescue and amplification;
- in addition, purposeful incorporation of a 3' placed hepatitis delta virus (HDV) ribozyme was used to exactly process the 3'-end of all transcripts.
- finally, this promoter variant pc3 was found not only to enable efficient Pol II-mediated transcription of the N, the P, and the L gene of measles virus, but transcripts of the N, the P, and the L gene of measles virus are also efficiently exported from the nucleus without abundant splicing of cryptic splice sites.

Example 4: Rescue of Measles Virus Particles from MeV Id-SCD (Id-SCD) Vector

On day 0, Vero cells (ATCC CCL-81) were seeded in a 6-well plate at a density of $4 \times 10^5$ cells/well. On day 1, the Vero cells were transfected using the following transfection conditions 200 µl DMEM medium were pipetted into a 1.5 ml tube. Then, the following amounts of plasmid DNA were added:

| Plasmid | Amount [µg] |
|---|---|
| pcDI-DsRed | 0.1 |
| pcDIMER-N | 0.5 |
| pcDIMER-P | 0.1 |
| pcDIMER-L | 0.5 |
| MeV full length plasmid | 5.0 |

After mixing, the mixture was spun down and 18.6 µl FuGene HD (Roche) (i.e. 3 µl FuGene/1 µg DNA) were added directly into the liquid. After vortexing, the mixture was spun down. The reaction mixture was incubated for 25 min at room temperature.

The cells were washed two times with PBS. After addition of 1.8 ml DMEM+2% FCS+PS, the transfection mixture was added drop wise to the cells, and the plate was swirled.

The cell culture was incubated at 37° C. and 5% $CO_2$.

On days 2 and 3, the medium was changed (1 ml DMEM+2% FCS+PS).

When syncytia appeared (approx. at day 4), the Vero cells were plated in 10 cm dishes for overlay (one confluent T75 in 10 ml, seed approximately 0.5 ml per dish).

On the next day, an overlay was done by scraping rescue cells in medium, pipetting up and drop wise down on Vero cells.

When syncytia appeared (approx. 1 day post overlay), $3 \times 10^5$ Vero cells were plated in a 6-well plate for passage 0 of virus (P.0).

On the next day syncytia were picked (2-3 per construct). Medium was removed from the 10 cm dish and 5-10 µl medium were pipetted directly onto a syncytium. By pipetting up and down and by scraping, the syncytium was dislodged and pipetted on the fresh Vero cells in a 6-well plate.

When syncytia appeared, cells were scraped into medium and stored at −80° C. (=P.0).

As a result of our procedure employing these plasmids encoding
(a) the genome of measles vaccine strain Schwarz, and a suicide gene, which comprises a fusion of yeast cytosine deaminase and yeast uracil phosphoribosyltransferase,
(b) the measles virus helper gene N,
(c) the measles virus helper gene P,
(d) the measles virus helper gene L, each under the control of an RNA polymerase II promoter, a maximum of 16.000 infectious spots (syncytia) could be achieved at passage 1 (P.1), which is much higher when compared with the results expressing the same genomes and transgenes under the control of bacteriophage T7 RNA polymerase, yielding only a maximum of 8.800 infectious spots (syncytia) at P.1. Thus, it has been demonstrated that usage of the CMV-derived RNA polymerase II promoter system results in a highly efficient production of infectious recombinant measles virus particles.

Example 5: SRB Proliferation Assay of HuCCT1, RBE, and TFK-1 Cells

FIG. 8 shows the results of an SRB proliferation assay of HuCCT1, RBE, and TFK-1 cells (human cholangiocarcinoma cells) treated with MeV Id-SCD viral particles rescued from the plasmid pc3MerV2 Id-SCD (Id-SCD) and incubated with prodrug 5-FC.

In general, for the SRB proliferation assay, cells were seeded on day 0. and infected after 24 h with either 0.001, 0.01, 0.1, 1 or 10 MOI (see the individual experiments and/or accompanying Figures) of viral particles, and in the case of prodrug treatment, 5-FC was added 3 h post infection. The SRB assay was performed 96 h post infection.

When RBE or TFK-1 cells were infected with MeV Id-SCD at a multiplicity of infection of 1 (MOI 1) and then cultivated without the addition of the prodrug 5-FC, the loss in cell mass after 96 h (as measured by the SRB proliferation assay) was calculated to be in the range of 58% (RBE) or 86% (TFK-1) in comparison to non-infected control cells (set to a cell mass of 100%), respectively (values encircled by the rectangle placed on the left hand side of the graphics); in contrast.

HuCCT1 cells being infected with MeV Id-SCD (MOI 1) and then cultivated without the addition of the prodrug 5-FC demonstrated a loss in cell mass after 96 h only in the range of 42% in comparison to non-infected control cells (set to a cell mass of 100%). Thereby, HuCCT1 cells display a primary resistance to measles virus of the prior art (no employment of an additional suicide gene function). However, when MeV Id-SCD (MOI 1)-infected HuCCT1 cells were cultivated with the addition of the prodrug 5-FC (ranging from $10^{-4}$ to $10^0$ mM) a loss in cell mass after 96 h was demonstrated in a range of up to 99% in comparison to non-infected control cells (set to a cell mass of 100%). Thus it was shown, that a primary resistance to measles virus of the prior art (no employment of an additional suicide gene function) of HuCCT1 cells could be overcome through usage of the SCD suicide gene function which catalyzes the generation of a cytotoxic drug (5-FU and derivatives) from a non-toxic prodrug (5-FC).

Example 6: LDH Release Assay of HuCCT1, RBE, and TFK-1 Cells

FIG. 9 shows the results of an LDH release assay of HuCCT1, RBE, and TFK-1 cells (human cholangiocarcinoma cells) treated with MeV Id-SCD viral particles rescued from the plasmid pc3MerV2 Id-SCD (Id-SCD) and incubated with prodrug 5-FC.

When RBE or TFK-1 cells were infected with MeV Id-SCD at MOI 1 and then cultivated without the addition of the prodrug 5-FC, the release of the enzyme LDH (here used as a surrogate parameter for loss of cell integrity) after 96 h (as measured by the LDH release assay) was calculated to be in the range of 70% (RBE) or 85% (TFK-1) in comparison to non-infected control cells being completely lysed by treatment with the detergent Triton X-100 (set to a LDH release of 100%), respectively (values encircled by the rectangle placed on the left hand side of the graphics).

In contrast, HuCCT1 cells being infected with MeV Id-SCD (MOI 1) and then cultivated without the addition of the prodrug 5-FC demonstrated a release of the enzyme LDH after 96 h only in the range of 31% in comparison to non-infected control cells, respectively. Thereby, it again was demonstrated that HuCCT1 cells display a primary resistance to measles virus of the prior art (no employment of an additional suicide gene function). However, when MeV Id-SCD (MOI 1)-infected HuCCT1 cells were cultivated with the addition of the prodrug 5-FC (ranging from $10^{-4}$ to $10^0$ mM) a highly significant increase in the release of the enzyme LDH after 96 h was demonstrated in a range of up to 82% in comparison to non-infected control cells (set to a cell mass of 100%), respectively.

Thus it again was shown, that a primary resistance to measles virus of the prior art (no employment of an additional suicide gene function) of HuCCT1 cells could be overcome through usage of the SCD suicide gene function.

Example 7: SRB Proliferation Assay of SAS and HTB-43 FaDu Cells

FIG. 10 shows the results of an SRB proliferation assay of SAS and HTB-43 FaDu cells (human Head & Neck (H&N) cancer cells) treated with MeV Id-SCD viral particles rescued from the plasmid pc3MerV2 Id-SCD (Id-SCD) and incubated with prodrug 5-FC.

When HTB-43 FaDu cells were infected with MeV Id-SCD at MOI 1 and then cultivated without the addition of the prodrug 5-FC, the loss in cell mass after 96 h was calculated to be in the range of 66% in comparison to non-infected control cells (values encircled by the rectangle placed on the left hand side of the graphics).

In contrast, SAS cells infected with MeV Id-SCD (MOI 1) and then cultivated without the addition of the prodrug 5-FC demonstrated no loss in cell mass at all (0%) after 96 h in comparison to non-infected control cells. Thereby, SAS cells display a primary resistance to measles virus of the prior art (no employment of an additional suicide gene function). However, when MeV Id-SCD (MOI 1)-infected SAS cells were cultivated with the addition of the prodrug 5-FC (ranging from $10^{-4}$ to $10^0$ mM) a loss in cell mass after 96 h was demonstrated in the range of up to 83% in comparison to non-infected control cells, respectively.

Thus it was shown, that a primary resistance to measles virus of the prior art (no employment of an additional suicide gene function) of SAS cells could be overcome through usage of the SCD suicide gene function.

Example 8: LDH Release Assay of SAS and HTB-43 FaDu Cells

FIG. 11 shows the results of an LDH release assay of SAS and HTB-43 FaDu cells (human H&N cancer cells) treated with MeV Id-SCD viral particles rescued from the plasmid pc3MerV2 Id-SCD (Id-SCD) and incubated with prodrug 5-FC.

When HTB-43 FaDu cells were infected with MeV Id-SCD at MOI 1 and then cultivated without the addition of the prodrug 5-FC, the release of the enzyme LDH after 96 h was calculated to be in the range of 16% in comparison to non-infected control cells being completely lysed by treatment with the detergent Triton X-100, respectively (values encircled by the rectangle placed on the left hand side of the graphics).

SAS cells being infected with MeV Id-SCD (MOI 1) and then cultivated without the addition of the prodrug 5-FC demonstrated a release of the enzyme LDH after 96 h only in the range of 18% in comparison to non-infected control cells, respectively. However, when MeV Id-SCD (MOI 1)-infected SAS cells were cultivated with the addition of the prodrug 5-FC (ranging from 10E-4 to 10E0 mM) a strong increase in the release of the enzyme LDH after 96 h was demonstrated in a range of up to 38% in comparison to non-infected control cells (set to a cell mass of 100%).

Thus it again was shown, that a primary resistance to measles virus of the prior art (no employment of an additional suicide gene function) of SAS cells could be overcome through usage of the SCD suicide gene function.

Example 9: SRB Proliferation Assay of A 673, BRZ, and SRH Cells

FIG. 12 shows the results of an SRB proliferation assay of A 673, BRZ, and SRH cells (human sarcoma cells) treated with MeV Id-SCD viral particles rescued from the plasmid pc3MerV2 Id-SCD (Id-SCD) and incubated with prodrug 5-FC.

When A 673 or BRZ cells were infected with MeV Id-SCD at MOI 1 and then cultivated without the addition of the prodrug 5-FC, the loss in cell mass after 96 h was calculated to be in the range of 96% or 75%, respectively, in comparison to non-infected control cells (values encircled by the rectangle placed on the left hand side of the graphics).

In contrast, SRH cells being infected with MeV Id-SCD (MOI 1) and then cultivated without the addition of the prodrug 5-FC demonstrated a loss in cell mass after 96 h only in the range of 10% in comparison to non-infected control cells. Thereby, SRH cells display a primary resistance to measles virus of the prior art (no employment of an additional suicide gene function). However, when MeV Id-SCD-infected SRH cells (MOI 1) were cultivated with the addition of the prodrug 5-FC (ranging from $10^{-4}$ to $10^0$ mM) a loss in cell mass after 96 h was demonstrated in the range of up to 55% in comparison to non-infected control cells.

Thus it was shown, that a primary resistance to measles virus of the prior art (no employment of an additional suicide gene function) of SAS cells could be significantly improved, but not yet overcome under the chosen conditions (MOI 1) through usage of the SCD suicide gene function.

Example 10: LDH Release Assay of A 673 and SRH Cells

FIG. 13 shows the results of an LDH release assay of A 673 and SRH cells (human sarcoma cells) treated with MeV Id-SCD viral particles rescued from pc3MerV2 Id-SCD (Id-SCD) and incubated with prodrug 5-FC.

When A 673 cells were infected with MeV Id-SCD at MOI 1 and then cultivated without the addition of the prodrug 5-FC, the release of the enzyme LDH after 96 h was calculated to be in the range of 54% in comparison to non-infected control cells being completely lysed by treatment with the detergent Triton X-100 (values encircled by the rectangle placed on the left hand side of the graphics).

SRH cells being infected with MeV Id-SCD (MOI 1) and then cultivated without the addition of the prodrug 5-FC demonstrated a release of the enzyme LDH after 96 h only in the range of 23% in comparison to non-infected control cells. Of note, when MeV Id-SCD (MOI 1)-infected SRH cells were cultivated with the addition of the prodrug 5-FC (ranging from $10^{-4}$ to $10^0$ mM) an increase in the release of the enzyme LDH of 31% after 96 h was demonstrated in comparison to non-infected control cells (set to a cell mass of 100%).

Thus it was shown, that a primary resistance to measles virus of the prior art (no employment of an additional suicide gene function) of SRH cells could not yet be sufficiently overcome under the chosen conditions (MOI 1) through usage of the SCD suicide gene function.

Example 11: SRB Proliferation Assay of SRH Cells

FIG. 14 shows the results of an SRB proliferation assay of SRH cells treated with MeV Id-SCD viral particles rescued from the plasmid pc3MerV2 Id-SCD (Id-SCD) at an elevated MOI of 10 (usually, a MOI of 1 is used; here increase in "viral load" was employed to overcome phenomena of resistance observed at MOI 1 in the presence of the prodrug 5-FC).

SRH cells being infected with MeV Id-SCD at MOI 10 and then cultivated without the addition of the prodrug 5-FC demonstrated a loss in cell mass after 96 h in the range of now 68% in comparison to non-infected control cells, which is significantly improved in comparison to the results obtained at MOI 1, at which only 28% of loss in cell mass was obtained in comparison to non-infected control cells. Furthermore, when MeV Id-SCD (MOI 10)-infected SRH cells were cultivated with the addition of the prodrug 5-FC (ranging from 10-4 to $10^0$ mM) a loss in cell mass after 96 h was demonstrated in the range of up to 89% in comparison to non-infected control cells.

Thus it was shown, that a primary resistance to measles virus of the prior art (no employment of an additional suicide gene function) of SRH cells could be overcome under the chosen conditions (MOI 10) through additional usage of the SCD suicide gene function.

Example 12: SRB Proliferation Assay of Sarcoma Tumor Cells (Cell Lines CCS, LM)

FIG. 15 shows the results of an SRB proliferation assay of sarcoma tumor cells (cell lines CCS, LM) treated with viral particles rescued from the plasmid pc3MerV2 Id-SCD (Id-SCD) and incubated with prodrug 5-FC.

CCS or LM cells infected with vector MeV Id-SCD at MOI 1 and then cultivated without the addition of the prodrug 5-FC demonstrated a loss in cell mass after 96 h in the range of 5% or 25%, respectively, in comparison to non-infected control cells (values encircled by the rectangle placed on the left hand side of the graphics). Thus, both CCS and LM cells display a primary resistance to measles virus of the prior art (no employment of an additional suicide gene function). However, when MeV Id-SCD-infected CCS or LM cells (MOI 1) were cultivated with the addition of the prodrug 5-FC (ranging from $10^{-4}$ to $10^0$ mM) a loss in cell mass after 96 h was demonstrated in the range of up to 79% or 94%, respectively, in comparison to non-infected control cells.

Thus it was shown, that a primary resistance to measles virus of the prior art (no employment of an additional suicide gene function) of CCS and LM cells could be strongly improved, and in the case of LM cells almost fully overcome under the chosen conditions (MOI 1) through usage of the SCD suicide gene function.

Example 13: SRB Proliferation Assay of Sarcoma Tumor Cells (Cell Lines STO, ZAF, KD)

FIG. 16 shows the results of an SRB proliferation assay of sarcoma tumor cells (cell lines STO, ZAF, KD) treated with MeV Id-SCD viral particles rescued from the plasmid pc3MerV2 Id-SCD (Id-SCD) and incubated with prodrug 5-FC.

When STO, ZAF, or KD cells were infected with MeV Id-SCD at MOI 1 and then cultivated without the addition of the prodrug 5-FC, the loss in cell mass after 96 h was calculated to be in the range of 76%, 87% or 94%, respectively, in comparison to non-infected control cells (values encircled by the rectangle placed on the left hand side of the graphics).

Thus, STO, ZAF, or KD cells do not display a primary resistance to measles virus of the prior art (no employment of an additional suicide gene function). When MeV Id-SCD-infected STO, ZAF, or KD cells (MOI 1) were cultivated with the addition of the prodrug 5-FC (ranging from $10^{-4}$ to $10^0$ mM) a loss in cell mass after 96 h was demonstrated in the range of up to 94%, 99%, or 98%, respectively, in comparison to non-infected control cells.

Example 14: SRB Proliferation Assay of Sarcoma Tumor Cells (Cell Lines CCS, LM)

FIG. 17 shows the results of an SRB proliferation assay of glioblastoma tumor cells (cell lines LNT 229, LNT 229 CTS-1) treated with MeV Id-SCD viral particles rescued from the plasmid pc3MerV2 Id-SCD (Id-SCD) and incubated with prodrug 5-FC.

LNT 229 or LNT 229 CTS-1 cells infected with MeV Id-SCD at MOI 1 and then cultivated without the addition of the prodrug 5-FC demonstrated a loss in cell mass after 96 h in the range of 56% or 27%, respectively, in comparison to non-infected control cells (values encircled by the rectangle placed on the left hand side of the graphics). Thus, both LNT 229 or LNT 229 CTS-1 cells display a primary resistance to measles virus of the prior art (no employment of an additional suicide gene function). However, when MeV Id-SCD-infected LNT 229 or LNT 229 CTS-1 cells (MOI 1) were cultivated with the addition of the prodrug 5-FC (ranging from $10^{-4}$ to $10^0$ mM) a loss in cell mass after 96 h was demonstrated in the range of up to 97% or 96%, respectively, in comparison to non-infected control cells.

Thus it was shown, that a primary resistance to measles virus of the prior art (no employment of an additional suicide gene function) of LNT 229 or LNT 229 CTS-1 cells could be almost fully overcome under the chosen conditions (MOI 1) through usage of the SCD suicide gene function.

Example 15: SRB Proliferation Assay of Glioblastoma Tumor Cells (Cell Lines LN 18, LN 18 Apoptosis Resistant)

FIG. 18 shows the results of an SRB proliferation assay of glioblastoma tumor cells (cell lines LN 18, LN 18 Apoptosis resistant) treated with MeV Id-SCD viral particles rescued from the plasmid pc3MerV2 Id-SCD (Id-SCD) and incubated with prodrug 5-FC.

LN 18 or LN 18 Apoptosis resistant cells infected with MeV Id-SCD at MOI 1 and then cultivated without the addition of the prodrug 5-FC demonstrated a loss in cell mass after 96 h in the range of 33% or 22%, respectively, in comparison to non-infected control cells (values encircled by the rectangle placed on the left hand side of the graphics). Thus, both LN 18 or LN 18 Apoptosis resistant cells display a primary resistance to measles virus of the prior art (no employment of an additional suicide gene function). However, when MeV Id-SCD-infected LN 18 or LN 18 Apoptosis resistant cells (MOI 1) were cultivated with the addition of the prodrug 5-FC (ranging from $10^{-4}$ to $10^0$ mM) a loss in cell mass after 96 h was demonstrated in the range of up to 97% or 83%, respectively, in comparison to non-infected control cells.

Thus it was shown, that a primary resistance to measles virus of the prior art (no employment of an additional suicide gene function) of LN 18 or LN 18 Apoptosis resistant cells could be strongly improved, and in the case of LN 18 cells almost fully overcome under the chosen conditions (MOI 1) through usage of the SCD suicide gene function.

Example 16: SRB Proliferation Assay of Renal Cell Carcinoma (ACHN), Pulmonary Adenocarcinoma (HOP-62) and Melanoma (M14) Tumor Cells FIG. 19 shows the results of an SRB proliferation assay of renal cell carcinoma (ACHN), pulmonary adenocarcinoma (HOP-62) and melanoma (M14) tumor cells treated with MeV Id-SCD viral particles rescued from the plasmid pc3MerV2 Id-SCD (Id-SCD) and incubated with prodrug 5-FC.

ACHN, HOP-62, or M14 cells infected with MeV Id-SCD at MOI 1 and then cultivated without the addition of the prodrug 5-FC demonstrated a loss in cell mass after 96 h in the range of 20%, 16%, or 16%, respectively, in comparison to non-infected control cells. Thus, ACHN, HOP-62, and M14 cells display a primary resistance to measles virus of the prior art (no employment of an additional suicide gene function). However, when MeV Id-SCD-infected ACHN, HOP-62, or M14 cells (MOI 1) were cultivated with the addition of 1 mM prodrug 5-FC, a loss in cell mass after 96 h was demonstrated in the range of up to 85%, 86% or 76%, respectively, in comparison to non-infected control cells.

Thus it was shown, that a primary resistance to measles virus of the prior art (no employment of an additional suicide gene function) of ACHN, HOP-62, and M14 cells could be strongly improved under the chosen conditions (MOI 1) through usage of the SCD suicide gene function.

Example 17: SRB Proliferation Assay of Colonic Adenocarcinoma Tumor Cells (Cell Lines KM-12, HCT-15)

FIG. 20 shows the results of an SRB proliferation assay of colonic adenocarcinoma tumor cells (cell lines KM-12, HCT-15) treated with viral particles rescued from the plasmid pc3MerV2 Id-SCD (Id-SCD) and incubated with prodrug 5-FC.

KM-12 or HCT-15 cells infected with vector MeV Id-SCD at MOI 1 and then cultivated without the addition of the prodrug 5-FC demonstrated a loss in cell mass after 96 h in the range of 13% or 2%, respectively, in comparison to non-infected control cells (values encircled by the rectangle placed on the left hand side of the graphics). Thus, both KM-12 and HCT-15 cells display a primary resistance to measles virus of the prior art (no employment of an additional suicide gene function). However, when MeV Id-SCD-infected KM-12 or HCT-15 cells (MOI 1) were cultivated with the addition of 1 mM prodrug 5-FC, a loss in cell mass after 96 h was demonstrated in the range of up to 94% or 65%, respectively, in comparison to non-infected control cells.

Thus it was shown, that a primary resistance to measles virus of the prior art (no employment of an additional suicide gene function) of KM-12 or HCT-15 cells could be strongly improved, and in the case of KM-12 cells almost fully overcome under the chosen conditions (MOI 1) through usage of the SCD suicide gene function.

Example 18: Construction of Alternative Viral Vectors

Three vectors differing in their suicide gene array concerning the (i) positioning within the Measles virus genome as well as (ii) their context of SCD gene expression (here in the context of a fusion gene; i.e. with the Herpes simplex virus type 1 (HSV-1) tegument protein VP22 which mediates the function of protein spreading of fusion proteins) were constructed (see FIG. 27).

As the genome position at which a transgene is inserted in the Measles virus genome effects both viral replication and transgene expression, we compared two versions of positioning of the super-cytosine deaminase (SCD) transgene. Genome position one for SCD in vector pc3MerV2 Id-SCD, genome position three for SCD in vector pMerV2 P-SCD.

Additionally, a third vector, vector pc3MerV2 Id-VP22SCD, was constructed and compared with the other two vectors. At genome position one, this vector pc3MerV2 Id-VP22SCD expresses a fusion of the SCD transgene with the Herpes simplex virus type 1 (HSV-1) tegument protein VP22 gene, which mediates the function of protein spreading of fusion proteins (here: VP22SCD) from expressing cells to neighboring cells, which have not been infected hitherto with this MeV Id-VP22SCD viral particles rescued from vector pc3MerV2 Id-VP22SCD, thus making it a promising tool for compensation of inadequate primary vector transfer efficiencies.

DETAILS of the construction of pc3MerV2 Id-VP22SCD: To newly generate a third armed measles vaccine virus (MeV Id-VP22SCD) the plasmid pc3MerV2 Id-Trka was used as the starting basis. This plasmid codes for the viral cDNA with 100% identity to the vaccine strain Schwarz and contains an empty additional transcription unit (ATU, or Trka, transcription cassette) between the leader sequence and the N-gene. This additional transcription unit contains all regulatory sequences needed for expression of a transgene from the viral genome. The gene-start and the gene-end sequence and the nontranslated regions are identical to those from the N gene. Transgenes can be inserted via restriction enzyme sites XhoI or PauI.

The open reading frame (ORF) for VP22SCD was derived from the plasmid pUC29-VP22SCD. Since this ORF contains two SalI restriction sites and as further cloning steps in the MeV full length construct would be most likely carried out via SalI, these restriction sites had to be removed first by site-directed mutagenesis. As the ORF was already flanked by MluI sites which produces termini identical to those produced by PauI, and as the MluI-MluI fragment derived from this plasmid already contained the correct number of nucleotides to produce a MeV genome according to the rule of six, it was possible to insert this fragment into the MeV cDNA after removal of the SalI sites without any further modification. Thus, the cloning strategy was composed of three steps:

Removal of the SalI sites by site-directed mutagenesis
Insertion of VP22SCD into pc3MerV2 Id-Trka
Rescue of the virus Removal of the SalI sites: Two rounds of a single-site mutagenesis were applied. In the first round, the SalI site at position 802 was successfully removed, as shown by restriction analysis. The produced plasmid was then digested by DpnI and amplified in XL-1 blue supercompetent bacteria and was used as a template for the second round of mutagenesis, where the site at position 1127 was removed, as shown again by restriction analysis. Removal of both sites as well as the correct sequence of the ORF was verified by sequencing. The resulting plasmid was named pUC29-VP22SCD_w/oSalI.

Insertion of VP22SCD into pc3MerV2 Id-Trka: The recipient plasmid pc3MerV2 Id-Trka was digested with PauI. To avoid mechanical shearing of the ~20 kb plasmid, the linearized plasmid was not gel-purified. The restriction enzyme was heat-inactivated and the DNA fragment was dephosphorylated and subjected directly to ligation. pUC29-VP22SCD_w/oSalI was digested with MluI, gel-purified and subjected to ligation. Successful insertion of the transgene was shown by HindIII-digest and by sequencing. The resulting plasmid was named pc3MerV2 Id-VP22SCD.

Example 19: Comparison of Alternative Viral Vectors

The three different viral vectors synthesized as described in Example 18 were compared with the aim to identify the most effective one (see FIGS. 21 to 23).

FIG. 21 shows the effect of viral particles MeV Id-SCD, MeV Id-VP22SCD, and MeV P-SCD on Hep3B human hepatocellular carcinoma cells.

Hep3B cells were infected at an MOI of 0.001 or 0.01 with viral particles rescued from pc3MerV2 Id-SCD, pMerV2 P-SCD, and pc3MerV2 Id-VP22SCD, and tumor cell mass was determined either in the presence of 1 mM or the absence of 5-FC over time.

As can be seen, viral particles rescued from pc3MerV2 Id-SCD exhibited a drastically higher oncolytic potential even in the absence of 5-FC in the case of an MOI of 0.01, and led to an almost complete loss of tumor cell mass after 6 days even in the case of an MOI of 0.001 in the presence of 5-FC.

FIG. 22 shows the effect of viral particles rescued from vectors pc3MerV2 Id-SCD, pMerV2 P-SCD, and pc3MerV2 Id-VP22SCD on HepG2 human hepatocellular carcinoma cells.

HepG2 cells were infected at an MOI of 0.001 or 0.01 with viral particles rescued from pc3MerV2 Id-SCD, pMerV2 P-SCD, and pc3MerV2 Id-VP22SCD, and tumor cell mass was determined either in the presence of 1 mM or the absence of 5-FC over time.

As can be seen, MeV Id-SCD viral particles exhibited a substantially higher oncolytic potential even in the absence of 5-FC in the case of an MOI of 0.01, and led to a substantially higher loss of tumor cell mass after 6 days even in the case of an MOI of 0.001 in the presence of 5-FC.

FIG. 23 shows the effect of viral particles rescued from vectors pc3MerV2 Id-SCD, pMerV2 P-SCD, and pc3MerV2 Id-VP22SCD on PLC/PRF/5 human hepatocellular carcinoma cells.

PLC/PRF/5 cells were infected at an MOI of 0.001 or 0.01 with viral particles rescued from vectors pc3MerV2 Id-SCD, pMerV2 P-SCD, and pc3MerV2 Id-VP22SCD, and tumor cell mass was determined either in the presence of 1 mM or the absence of 5-FC over time.

As can be seen, viral particles rescued from vector pc3MerV2 Id-SCD exhibited a substantially higher oncolytic potential even in the absence of 5-FC in the case of an MOI of 0.01, and led to a substantially higher loss of tumor cell mass after 6 days even in the case of an MOI of 0.001 in the presence of 5-FC.

Thus, surprisingly it was found that the positioning of the SCD suicide gene within the Measles virus genome as well as the context of SCD gene expression had a strong influence of the oncolytic activity of the viral particles, with particles from vector pc3MerV2 Id-SCD being substantially better than particles rescued from vectors pMerV2 P-SCD, and pc3MerV2 Id-VP22SCD.

Example 20: In Vivo Characterization of Armed Vectors in Xenograft Animal Tumor Models To test the armed vectors pc3MerV2 Id-SCD, pMerV2 P-SCD, and pc3MerV2 Id-VP22SCD in vivo, a murine xenograft model of human HCC was applied. As measles virus does not infect murine cells, it is not possible to use a murine model with syngeneic tumors to test vectors without special modifications of the surface glycoproteins.

To compare the armed vectors, a mouse model of subcutaneously grown Hep3B tumors was chosen. This decision was based on the facts (i) that Hep3B can be efficiently infected by MeV and support MeV replication at high levels, (ii) that in Hep3B, the conversion of 5-FC into 5-FU is fast and efficient and (iii) that over an incubation of 1-4 days after addition of the prodrug to infected cells, an increasing gap between the treatment with virus alone and the combination treatment can be observed. Additionally, a mouse model of Hep3B has been described before (Blechacz B, Splinter P L, Greiner S, Myers R, Peng K W, Federspiel M J, Russell S J, LaRusso N F. Hepatology. 2006 December; 44(6):1465-77) with a high engraftment ratio (80%, personal communication with Boris Blechacz, Mayo Clinic, Rochester, Minn., USA). In contrast, this ratio is much lower in PLC/PRF/5 (60%) and in HepG2, both determined in our laboratory.

For this in vivo experiment, six week old nude mice received subcutaneous injections of 100 µl cell suspension containing $10^6$ Hep3B cells in PBS. As expected, the cells grafted in 80% of the mice, although the duration between tumor cell implantation and appearance of the tumors was found to be quite heterogeneous. The tumors were very well vascularized and appeared blue through the nude skin of the mice. After the tumors had grown to a diameter of approximately 5 mm, the mice received five intratumoral injections of the respective virus (MeV Id-SCD, MeV Id-VP22SCD or MeV P-SCD) with $2*10^6$ pfu per injection and one injection daily (total dose: 107 pfu). Control groups were treated with medium only. On the following seven days, the mice received 500 mg/kg bodyweight 5-FC in PBS intraperitoneally. Tumor volume and weight of the animals were determined three times a week.

To ensure that the above described treatment schedule does not lead to toxicities, mice were monitored daily and weight was determined three times a week. The combinatorial treatment (MeV-SCD+5-FC) did neither lead to any visible changes in the behavior of the animals, nor did they show reactions like enhanced sensitivity to touch. The skin of the mice looked healthy, no changes in their movement or feeding behaviors were observed and their weight remained stable.

Treatment of tumor-bearing mice with the suicide gene therapy both reduces tumor volume and extends survival significantly.

As a result of the in vivo testing, a strong oncolytic effect of either of the viruses could be documented. As expected, the administration of the prodrug alone had no effect: 5-FC injection in virus-treated mice did not lead to an altered outcome compared to the treatment with virus alone, but importantly it also did not inhibit the virus-mediated effects by early abrogation of virus replication. Additionally, no significant oncolytic differences were observed between the three vectors. In this experimental setting, the direct effect of oncolytic measles vaccine virus seems to be highly effective, so that the additional application of 5-FC does not lead to an enhanced oncolysis or to any survival benefits. Survival of the mice was significantly improved by all treatments compared to the controls. The median survival of control-treated mice was 35 days and that of mice treated with 5-FC only was 32 days (see FIG. 24). All mice from these groups had to be sacrificed before day 50. In contrast, the median survival in the treatment groups ranged between 49 days (MeV P-SCD only) and 82.5 days (MeV Id-SCD only) (see FIG. 24). The mice from both groups treated with MeV P-SCD were sacrificed before day 100, whereas six mice from the other treatment groups survived tumor-free more than 150 days (1 mouse each for MeV Id-SCD only and MeV Id-VP22SCD+5-FC; two mice each for MeV Id-SCD+ 5-FC and for MeV Id-VP22SCD only). Some mice from different treatment groups developed a visible and palpable secondary tumor inside the peritoneal cavity. As this was considered a treatment failure, these mice were not excluded from the statistical analysis.

In all treatment groups, tumors with different growth behaviors were observed. Some tumors grew very quickly and reached the defined endpoint of >2000 $mm^3$ around day 30 after initiation of treatment which was similar to control-treated mice. Several other mice had a retarded tumor growth, with a low tumor volume in the first weeks after treatment initiation, but eventually, their tumors reinitiated growing and reached the endpoint volume. Some other tumors completely disappeared and mice were tumor-free for more than 195 days. This differential behavior is shown exemplarily for both MeV Id-SCD treatment groups. Also, some tumors had an oscillating growth behavior, which was probably due to virus replication reducing tumor volume, followed by growth of remaining tumor cells, offering the virus a new basis for replication, leading again to oncolysis and remission of the tumor. This shrinking and growing of the tumor was accompanied by the loss and regaining of tumor vascularization as detected by the blue color shimmering through the skin of the mice. In the example shown here, the tumor ultimately disappeared at day 91. This oscillating growth was considered as a first hint for a long-term virus replication in tumors.

Similar results were obtained with additional xenograft animal models (HepG2 human hepatocellular carcinoma cells, and PLC/PRF/5 human hepatocellular carcinoma cells): see FIGS. 25 and 26, respectively.

SEQUENCE LISTING

SEQ-ID NO. 1: genetic sequence of measles vaccine strain Schwarz (see FIG. 1)

SEQ-ID NO. 2: genetic sequence of fusion of yeast cytosine deaminase and yeast uracil phosphoribosyltransferase (with linker sequence) (see FIG. 2)

SEQ-ID NO. 3: genetic sequence of basic recombinant measles virus without any trangenes but insertion cassettes (see FIG. 3)

SEQ-ID NO. 4: genetic sequence of vector pc3MerV2 Id-SCD (see FIG. 4)

SEQ-ID No. 5: genetic sequence of helper plasmid required for the expression of the N gene (see FIG. 5)

SEQ-ID No. 6: genetic sequence of helper plasmid required for the expression of the P gene (see FIG. 6)

SEQ-ID No. 7: genetic sequence of helper plasmid required for the expression of the L gene (see FIG. 7)

SEQ-ID No. 8: genetic sequence of vector pMerV2 P-SCD, (see FIG. 28)

SEQ-ID No. 9: genetic sequence of vector pc3MerV2 Id-VP22SCD (see FIG. 29)

The invention claimed is:

1. A pharmaceutical composition comprising a recombinant measles virus comprising the sequence according to SEQ-ID No. 1 and further comprising a suicide gene comprising a fusion of a cytosine deaminase and a uracil phosphoribosyltransferase incorporated therein for use in the treatment of malignant cells.

2. The pharmaceutical composition according to claim 1, wherein said suicide gene comprises a fusion of a yeast cytosine deaminase and a yeast uracil phosphoribosyltransferase.

3. The pharmaceutical composition according to claim 2, wherein said suicide gene comprises a sequence according to SEQ-ID NO. 2.

4. The pharmaceutical composition according to claim 1, wherein said malignant cells have primary or secondary resistances against an oncolytic measles virus without suicide gene activity.

5. The pharmaceutical composition according to claim 4, wherein said malignant cells are identified by performing the following step:

(a) determining the percentage of living cells in a population of cells derived from said malignant cells 72 h, or 96 h, after infecting said population with the oncolytic measles virus at a multiplicity of infection of 1, wherein a percentage of 40% or more of living cells in said population, or 50% or more, or 60% or more, is indicative for said malignant cells being primarily or secondarily resistant to an oncolytic measles virus without suicide gene activity.

6. The pharmaceutical composition according to claim 4, wherein said oncolytic measles virus without suicide gene activity has the sequence according to SEQ-ID No. 1.

7. The pharmaceutical composition according to claim 1, wherein said malignant cells are additionally non-responsive to chemotherapeutics and/or radiation therapy.

8. The pharmaceutical composition according to claim 1, wherein said malignant cells are selected from malignant cells from human sarcoma.

9. The pharmaceutical composition according to claim 1, wherein said malignant cells are selected from the list of: malignant cells from cholangiocarcinoma, hepatocellular carcinoma, head and neck cancer, and sarcoma.

10. The pharmaceutical composition according to claim 1, wherein said treatment is a repeated treatment of every week, or every two weeks, or every three weeks, or every four weeks.

11. A recombinant measles virus comprising the sequence according to SEQ-ID No. 1 and further comprising a suicide gene comprising a fusion of a cytosine deaminase and a uracil phosphoribosyltransferase incorporated therein.

12. The recombinant measles virus according to claim 11, wherein said suicide gene comprises a fusion of a yeast cytosine deaminase and a yeast uracil phosphoribosyltransferase.

13. The recombinant measles virus according to claim 12, wherein said suicide gene comprises a sequence according to SEQ-ID NO. 2.

14. A method for generating the recombinant measles virus, wherein the recombinant measles virus:
comprises a sequence according to SEQ-ID No. 1 and further comprises a suicide gene comprising a fusion of a cytosine deaminase and a uracil phosphoribosyltransferase incorporated therein;
comprises a sequence according to SEQ-ID No. 1, and further comprises a suicide gene comprising a fusion of a yeast cytosine deaminase and a yeast uracil phosphoribosyltransferase incorporated therein; or
comprises a sequence according to SEQ-ID No. 1, and further comprises a suicide gene comprising a sequence according to SEQ ID No. 2
the method comprising the step of
(a) cloning (i) the genome of measles vaccine strain Schwarz, and (ii) a suicide gene comprising a fusion of a cytosine deaminase and a uracil phosphoribosyltransferase into a plasmid under the control of an RNA polymerase II promoter.

15. The method according to claim 14, wherein said suicide gene comprises a sequence according to SEQ-ID NO. 2.

16. The method according to claim 14, further comprising the step of
(b) cloning measles virus helper genes N, P and L, each under the control of an RNA polymerase II promoter, into at least one vector.

17. The method according to claim 16, wherein the viral helper genes N, P and L are each cloned into a separate vector.

18. The method according to claim 17, wherein step (b) comprises the substeps of
(i) cloning measles virus helper genes N under the control of an RNA polymerase II promoter into a first plasmid vector;
(ii) cloning measles virus helper gene P under the control of an RNA polymerase II promoter into a second plasmid vector; and
(iii) cloning measles virus helper gene L under the control of an RNA polymerase II promoter into a third plasmid vector.

19. The method according to claim 18, wherein step (a) and/or (b), or (a), (i), (ii) and/or (iii), further comprise the step of removing putative splicing sequences from said genome and/or any of said helper genes.

20. The method according to claim 18, wherein substeps (i) to (iii) result in plasmids having the sequences according to SEQ-ID No. 5, SEQ-ID No. 6, and SEQ-ID No. 7.

21. The method according to claim 18, further comprising the step of
(c) transfecting host cells with plasmids of steps (a) and (b), or (a) and (i) to (iii).

22. The method according to claim 21, wherein said host cells are from cell lines Vero or MRC 5.

23. The method according to claim 21, further comprising the step of
(d) rescuing recombinant measles virus from the host cell transformed in step (c).

24. A kit comprising
(a) a plasmid comprising (i) the genome of measles vaccine strain Schwarz, and (ii) a suicide gene, which comprises a fusion of a cytosine deaminase, and a uracil phosphoribosyltransferase under the control of an RNA polymerase II promoter, (b) at least one plasmid comprising the measles virus helper genes N, P and L, each in form of a single gene under the control of an RNA polymerase II promoter.

25. The kit according to claim 24, wherein said suicide gene comprises a sequence according to SEQ-ID No. 2.

26. The kit according to claim 24, wherein the viral helper genes N, P and L are each cloned into a separate plasmid, wherein the plasmids have the sequences according to SEQ-ID No. 5, SEQ-ID No. 6, and SEQ-ID No. 7.

27. A method of treating malignant cells comprising administering to a subject in need thereof a pharmaceutical composition according to any one of claims 1-6, 8-9 or 10.

* * * * *

```
                              SEQUENCE LISTING

<160> NUMBER OF SEQ ID NOS: 9

<210> SEQ ID NO 1
<211> LENGTH: 15894
<212> TYPE: DNA
<213> ORGANISM: measles virus

<400> SEQUENCE: 1
accaaacaaa gttgggtaag gatagttcaa tcaatgatca tcttctagtg cacttaggat      60
tcaagatcct attatcaggg acaagagcag gattagggat atccgagatg gccacacttt     120
taaggagctt agcattgttc aaaagaaaca aggacaaacc acccattaca tcaggatccg     180
gtggagccat cagaggaatc aaacacatta ttatagtacc aatccctgga gattcctcaa     240
ttaccactcg atccagactt ctggaccggt tggtgaggtt aattggaaac ccggatgtga     300
gcgggcccaa actaacaggg gcactaatag gtatattatc cttatttgtg gagtctccag     360
gtcaattgat tcagaggatc accgatgacc ctgacgttag cataaggctg ttagaggttg     420
tccagagtga ccagtcacaa tctggcctta ccttcgcatc aagaggtacc aacatggagg     480
atgaggcgga ccaatacttt tcacatgatg atccaattag tagtgatcaa tccaggttcg     540
gatggttcgg gaacaaggaa atctcagata ttgaagtgca agaccctgag ggattcaaca     600
tgattctggg taccatccta gcccaaattt gggtcttgct cgcaaaggcg gttacggccc     660
cagacacggc agctgattcg gagctaagaa ggtggataaa gtacacccaa caaagaaggg     720
tagttggtga atttagattg gagagaaaat ggttggatgt ggtgaggaac aggattgccg     780
aggacctctc cttacgccga ttcatggtcg ctctaatcct ggatatcaag agaacacccg     840
gaaacaaacc caggattgct gaaatgatat gtgacattga tacatatatc gtagaggcag     900
gattagccag tttttatcctg actattaagt ttgggataga aactatgtat cctgctcttg     960
gactgcatga atttgctggt gagttatcca cacttgagtc cttgatgaac ctttaccagc    1020
aaatggggga aactgcaccc tacatggtaa tcctggagaa ctcaattcag aacaagttca    1080
gtgcaggatc ataccctctg ctctggagct atgccatggg agtaggagtg aacttgaaa     1140 actccatggg aggtttgaac tttggccgat cttactttga tccagcatat tttagattag    1200
ggcaagagat ggtaaggagg tcagctggaa aggtcagttc cacattggca tctgaactcg    1260
gtatcactgc cgaggatgca aggcttgttt cagagattgc aatgcatact actgaggaca    1320
agatcagtag agcggttgga cccagacaag cccaagtatc atttctacac ggtgatcaaa    1380
```

```
gtgagaatga gctaccgaga ttgggggca aggaagatag gagggtcaaa cagagtcgag    1440
gagaagccag ggagagctac agagaaaccg ggcccagcag agcaagtgat gcgagagctg    1500
cccatcttcc aaccggcaca cccctagaca ttgacactgc aacggagtcc agccaagatc    1560
cgcaggacag tcgaaggtca gctgacgccc tgcttaggct gcaagccatg caggaatct    1620 cggaagaaca aggctcagac acggacaccc ctatagtgta caatgacaga aatcttctag    1680
actaggtgcg agaggccgag ggccagaaca acatccgcct accatccatc attgttataa    1740
aaaacttagg aaccaggtcc acacagccgc cagcccatca accatccact cccacgattg    1800
gagccaatgg cagaagagca ggcacgccat gtcaaaaacg gactggaatg catccgggct    1860
ctcaaggccg agcccatcgg ctcactggcc atcgaggaag ctatggcagc atggtcagaa    1920
atatcagaca acccaggaca ggagcgagcc acctgcaggg aagagaaggc aggcagttcg    1980
ggtctcagca aaccatgcct ctcagcaatt ggatcaactg aaggcggtgc acctcgcatc    2040
cgcggtcagg gacctggaga gagcgatgac gacgctgaaa cttttgggaat ccccccaaga    2100 aatctccagg catcaagcac tgggttacag tgttattacg tttatgatca cagcggtgaa    2160
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc cccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg acacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt ttgttcctga caccggccct    3180
gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc aacccccatg    3360
ccagtcgacc caactagtac aacctaaatc cattataaaa aacttaggag caaagtgatt    3420
gcctcccaag gtccacaatg acagagacct acgacttcga caagtcggca tgggacatca    3480
aagggtcgat cgctccgata caacccacca cctacagtga tggcaggctg gtgccccagg    3540
tcagagtcat agatcctggt ctaggcgaca ggaaggatga atgctttatg tacatgtttc    3600
tgctgggggt tgttgaggac agcgattccc tagggcctcc aatcgggcga gcatttgggt    3660
tcctgccctt aggtgttggc agatccacag caaagcccga aaaactcctc aaagaggcca    3720
ctgagcttga catagttgtt agacgtacag cagggctcaa tgaaaaactg gtgttctaca    3780
```

```
acaacacccc actaactctc ctcacacctt ggagaaaggt cctaacaaca gggagtgtct    3840
tcaacgcaaa ccaagtgtgc aatgcggtta atctgatacc gctcgatacc ccgcagaggt    3900
tccgtgttgt ttatatgagc atcacccgtc tttcggataa cgggtattac accgttccta    3960
gaagaatgct ggaattcaga tcggtcaatg cagtggcctt caacctgctg gtgaccctta    4020
ggattgacaa ggcgataggc cctgggaaga tcatcgacaa tacagagcaa cttcctgagg    4080
caacatttat ggtccacatc gggaacttca ggagaaagaa gagtgaagtc tactctgccg    4140
attattgcaa aatgaaaatc gaaagatgg gcctggtttt tgcacttggt gggataggg    4200 gcaccagtct tcacattaga agcacaggca aaatgagcaa gactctccat gcacaactcg    4260
ggttcaagaa gaccttatgt tacccgctga tggatatcaa tgaagacctt aatcgattac    4320
tctggaggag cagatgcaag atagtaagaa tccaggcagt tttgcagcca tcagttcctc    4380
aagaattccg catttacgac gacgtgatca taaatgatga ccaaggacta ttcaaagttc    4440
tgtagaccgt agtgcccagc aatgcccgaa aacgaccccc ctcacaatga cagccagaag    4500
gcccggacaa aaaagccccc tccgaaagac tccacggacc aagcgagagg ccagccagca    4560
gccgacggca agcgcgaaca ccaggcggcc ccagcacaga acagccctga cacaaggcca    4620
ccaccagcca ccccaatctg catcctcctc gtgggacccc cgaggaccaa ccccaaggc    4680 tgcccccgat ccaaccacc aaccgcatcc ccaccacccc cgggaaagaa acccccagca    4740
attggaaggc ccctccccct cttcctcaac acaagaactc cacaaccgaa ccgcacaagc    4800
gaccgaggtg acccaaccgc aggcatccga ctccctagac agatcctctc tccccggcaa    4860
actaaacaaa acttagggcc aaggaacata cacacccaac agaacccaga ccccggccca    4920
cggcgccgcg cccccaaccc ccgacaacca gagggagccc ccaaccaatc ccgccggctc    4980
ccccggtgcc cacaggcagg acaccaacc cccgaacaga cccagcaccc aaccatcgac    5040
aatccaagac gggggggccc cccaaaaaaa aggcccccag gggccgacag ccagcaccgc    5100
gaggaagccc acccacccca cacacgacca cggcaaccaa accagaaccc agaccaccct    5160
gggccaccag ctcccagact cggccatcac cccgcagaaa ggaaaggcca caacccgcgc    5220
accccagccc cgatccggcg gggagccacc caacccgaac cagcacccaa gagcgatccc    5280
cgaaggaccc ccgaaccgca aaggacatca gtatcccaca gcctctccaa gtccccggt    5340 ctcctcctct tctcgaaggg accaaaagat caatccacca cacccgacga cactcaactc    5400
cccaccccta aaggagacac cgggaatccc agaatcaaga ctcatccaat gtccatcatg    5460
ggtctcaagg tgaacgtctc tgccatattc atggcagtac tgttaactct ccaaacacc    5520 accggtcaaa tccattgggg caatctctct aagatagggg tggtaggaat aggaagtgca    5580
agctacaaag ttatgactcg ttccagccat caatcattag tcataaaatt aatgcccaat    5640
ataactctcc tcaataactg cacgagggta gagattgcag aatacaggag actactgaga    5700
acagttttgg aaccaattag agatgcactt aatgcaatga cccagaatat aagaccggtt    5760
cagagtgtag cttcaagtag gagacacaag agatttgcgg gagtagtcct ggcaggtgcg    5820
gccctaggcg ttgccacagc tgctcagata acagccggca ttgcacttca ccagtccatg    5880
ctgaactctc aagccatcga caatctgaga gcgagcctgg aaactactaa tcaggcaatt    5940
gagacaatca gacaagcagg gcaggagatg atattggctg ttcagggtgt ccaagactac    6000
atcaataatg agctgatacc gtctatgaac caactatctt gtgatttaat cggccagaag    6060
ctcgggctca aattgctcag atactataca gaaatcctgt cattatttgg ccccagttta    6120
```

```
cgggacccca tatctgcgga gatatctatc caggctttga gctatgcgct tggaggagac    6180
atcaataagg tgttagaaaa gctcggatac agtggaggtg atttactggg catcttagag    6240
agcggaggaa taaaggcccg gataactcac gtcgacacag agtcctactt cattgtcctc    6300
agtatagcct atccgacgct gtccgagatt aaggggtgat tgtccaccg gctagagggg     6360 gtctcgtaca acataggctc tcaagagtgg tataccactg tgcccaagta tgttgcaacc    6420
caagggtacc ttatctcgaa ttttgatgag tcatcgtgta cttcatgcc agaggggact     6480 gtgtgcagcc aaaatgcctt gtacccgatg agtcctctgc tccaagaatg cctccggggg    6540
tacaccaagt cctgtgctcg tacactcgta tccgggtctt ttgggaaccg gttcatttta    6600
tcacaaggga acctaatagc caattgtgca tcaatccttt gcaagtgtta cacaacagga    6660
acgatcatta atcaagaccc tgacaagatc ctaacataca ttgctgccga tcactgcccg    6720
gtagtcgagg tgaacggcgt gaccatccaa gtcgggagca ggaggtatcc agacgctgtg    6780
tacttgcaca gaattgacct cggtcctccc atatcattgg agaggttgga cgtagggaca    6840
aatctgggga atgcaattgc taagttggag gatgccaagg aattgttgga gtcatcggac    6900
cagatattga ggagtatgaa aggtttatcg agcactagca tagtctacat cctgattgca    6960
gtgtgtcttg gagggttgat agggatcccc gctttaatat gttgctgcag ggggcgttgt    7020
aacaaaaagg gagaacaagt tggtatgtca agaccaggcc taaagcctga tcttacggga    7080
acatcaaaat cctatgtaag gtcgctctga tcctctacaa ctcttgaaac acaaatgtcc    7140
cacaagtctc ctcttcgtca tcaagcaacc accgcaccca gcatcaagcc cacctgaaat    7200
tatctccggc ttccctctgg ccgaacaata tcggtagtta atcaaaactt agggtgcaag    7260
atcatccaca atgtcaccac aacgagaccg gataaatgcc ttctacaaag ataaccccca    7320
tcccaaggga agtaggatag tcattaacag agaacatctt atgattgata gaccttatgt    7380
tttgctggct gttctgtttg tcatgtttct gagcttgatc gggttgctag ccattgcagg    7440
cattagactt catcgggcag ccatctacac cgcagagata cataaaagcc tcagcaccaa    7500
tctagatgta actaactcaa tcgagcatca ggtcaaggac gtgctgacac cactcttcaa    7560
aatcatcggt gatgaagtgg gcctgaggac acctcagaga ttcactgacc tagtgaaatt    7620
aatctctgac aagattaaat ccttaatcc ggatagggag tacgacttca gagatctcac    7680
ttggtgtatc aacccgccag agagaatcaa attggattat gatcaatact gtgcagatgt    7740
ggctgctgaa gagctcatga atgcattggt gaactcaact ctactggaga ccagaacaac    7800
caatcagttc ctagctgtct caaagggaaa ctgctcaggg cccactacaa tcagaggtca    7860
attctcaaac atgtcgctgt ccctgttaga cttgtattta ggtcgaggtt acaatgtgtc    7920
atctatagtc actatgacat cccagggaat gtatgggga acttacctag tggaaaagcc    7980
taatctgagc agcaaaaggt cagagttgtc acaactgagc atgtaccgag tgtttgaagt    8040
aggtgttatc agaaatccgg gtttggggc tccggtgttc catatgacaa actatcttga    8100
gcaaccagtc agtaatgatc tcagcaactg tatggtggct ttgggggagc tcaaactcgc    8160
agccctttgt cacggggaag attctatcac aattccctat cagggatcag ggaaaggtgt    8220
cagcttccag ctcgtcaagc taggtgtctg gaaatcccca accgacatgc aatcctgggt    8280
ccccttatca acggatgatc cagtgataga caggctttac ctctcatctc acagaggtgt    8340
tatcgctgac aatcaagcaa aatgggctgt cccgacaaca cgaacagatg acaagttgcg    8400
aatggagaca tgcttccaac aggcgtgtaa gggtaaaatc caagcactct gcgagaatcc    8460
cgagtgggca ccattgaagg ataacaggat tccttcatac ggggtcttgt ctgttgatct    8520
```

```
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
ggttagtccc tacctcttca ctgtcccaat taaggaagca ggcgaagact gccatgcccc   8760
aacataccta cctgcggagg tggatggtga tgtcaaactc agttccaatc tggtgattct   8820
acctggtcaa gatctccaat atgttttggc aacctacgat acttccaggg ttgaacatgc   8880
tgtggtttat tacgtttaca gcccaagccg ctcattttct tactttttatc cttttaggtt   8940 gcctataaag ggggtcccca tcgaattaca agtggaatgc ttcacatggg accaaaaact   9000
ctggtgccgt cacttctgtg tgcttgcgga ctcagaatct ggtggacata tcactcactc   9060
tgggatggtg ggcatgggag tcagctgcac agtcacccgg gaagatggaa ccaatcgcag   9120 ataggggctgc tagtgaacca atcacatgat gtcacccaga catcaggcat acccactagt   9180
gtgaaataga catcagaatt aagaaaaacg tagggtccaa gtggttcccc gttatggact   9240
cgctatctgt caaccagatc ttatacctg aagttcacct agatagcccg atagttacca   9300
ataagatagt agccatcctg gagtatgctc gagtccctca cgcttacagc ctggaggacc   9360
ctacactgtg tcagaacatc aagcaccgcc taaaaaacgg atttttccaac caaatgatta   9420 taaacaatgt ggaagttggg aatgtcatca agtccaagct taggagttat ccggcccact   9480
ctcatattcc atatccaaat tgtaatcagg atttatttaa catagaagac aaagagtcaa   9540
cgaggaagat ccgtgaactc ctcaaaaagg ggaattcgct gtactccaaa gtcagtgata   9600
aggttttcca atgcttaagg gacactaact cacggcttgg cctaggctcc gaattgaggg   9660
aggacatcaa ggagaaagtt attaacttgg gagtttacat gcacagctcc cagtggtttg   9720
agccctttct gttttggttt acagtcaaga ctgagatgag gtcagtgatt aaatcacaaa   9780
cccatacttg ccataggagg agacacacac ctgtattctt cactggtagt tcagttgagt   9840
tgctaatctc tcgtgacctt gttgctataa tcagtaaaga gtctcaacat gtatattacc   9900
tgacatttga actggttttg atgtattgtg atgtcataga ggggaggtta atgacagaga   9960
ccgctatgac tattgatgct aggtatacag agcttctagg aagagtcaga tacatgtgga  10020
aactgataga tggtttcttc cctgcactcg ggaatccaac ttatcaaatt gtagccatgc  10080
tggagcctct ttcacttgct tacctgcagc tgagggatat aacagtagaa ctcagaggtg  10140
ctttccttaa ccactgcttt actgaaatac atgatgttct tgaccaaaac gggttttctg  10200
atgaaggtac ttatcatgag ttaactgaag ctctagatta cattttcata actgatgaca  10260
tacatctgac aggggagatt ttctcatttt tcagaagttt cggccacccc agacttgaag  10320
cagtaacggc tgctgaaaat gttaggaaat acatgaatca gcctaaagtc attgtgtatg  10380
agactctgat gaaaggtcat gccatatttt gtggaatcat aatcaacggc tatcgtgaca  10440
ggcacggagg cagttggcca ccgctgaccc tcccctgca tgctgcagac acaatccgga  10500
atgctcaagc ttcaggtgaa gggttaacac atgagcagtg cgttgataac tggaaatctt  10560
ttgctggagt gaaatttggc tgctttatgc ctcttagcct ggatagtgat ctgacaatgt  10620
acctaaagga caaggcactt gctgctctcc aaagggaatg ggattcagtt tacccgaaag  10680
agttcctgcg ttacgaccct cccaagggaa ccgggtcacg gaggcttgta gatgttttcc  10740
ttaatgattc gagctttgac ccatatgatg tgataatgta tgttgtaagt ggagcttacc  10800
tccatgaccc tgagttcaac ctgtcttaca gcctgaaaga aaaggagatc aaggaaacag  10860
```

```
gtagactttt tgctaaaatg acttacaaaa tgagggcatg ccaagtgatt gctgaaaatc    10920
taatctcaaa cgggattggc aaatatttta aggacaatgg gatggccaag gatgagcacg    10980
atttgactaa ggcactccac actctagctg tctcaggagt ccccaaagat ctcaaagaaa    11040
gtcacagggg ggggccagtc ttaaaaacct actcccgaag cccagtccac acaagtacca    11100
ggaacgtgag agcagcaaaa gggtttatag ggttccctca agtaattcgg caggaccaag    11160
acactgatca tccggagaat atggaagctt acgagacagt cagtgcattt atcacgactg    11220
atctcaagaa gtactgcctt aattggagat atgagaccat cagcttgttt gcacagaggc    11280
taaatgagat ttacggattg ccctcatttt tccagtggct gcataagagg cttgagacct    11340
ctgtcctgta tgtaagtgac cctcattgcc cccccgacct tgacgcccat atcccgttat    11400
ataaagtccc caatgatcaa atcttcatta agtaccctat gggaggtata gaagggtatt    11460
gtcagaagct gtggaccatc agcaccattc cctatctata cctggctgct tatgagagcg    11520
gagtaaggat tgcttcgtta gtgcaagggg acaatcagac catagccgta acaaaaaggg    11580
tacccagcac atggccctac aaccttaaga aacgggaagc tgctagagta actagagatt    11640
actttgtaat tcttaggcaa aggctacatg atattggcca tcacctcaag gcaaatgaga    11700
caattgtttc atcacatttt tttgtctatt caaaaggaat atattatgat gggctacttg    11760
tgtcccaatc actcaagagc atcgcaagat gtgtattctg gtcagagact atagttgatg    11820
aaacaagggc agcatgcagt aatattgcta caacaatggc taaaagcatc gagagaggtt    11880
atgaccgtta ccttgcatat tccctgaacg tcctaaaagt gatacagcaa attctgatct    11940
ctcttggctt cacaatcaat tcaaccatga cccgggatga gtcatacccc tccctcacaa    12000
acaacgacct cttaataagg atggcactgt tgcccgctcc tattgggggg atgaattatc    12060
tgaatatgag caggctgttt gtcagaaaca tcggtgatcc agtaacatca tcaattgctg    12120
atctcaagag aatgattctc gcctcactaa tgcctgaaga gaccctccat caagtaatga    12180
cacaacaacc gggggactct tcattcctag actgggctag cgaccccttac tcagcaaatc    12240 ttgtatgtgt ccagagcatc actagactcc tcaagaacat aactgcaagg tttgtcctga    12300
tccatagtcc aaacccaatg ttaaaaggat tattccatga tgacagtaaa gaagaggacg    12360
agggactggc ggcattcctc atggacaggc atattatagt acctagggca gctcatgaaa    12420
tcctggatca tagtgtcaca ggggcaagag agtctattgc aggcatgctg gataccacaa    12480
aaggcttgat tcgagccagc atgaggaagg gggggttaac ctctcgagtg ataaccagat    12540
tgtccaatta tgactatgaa caattcagag caggatggt gctattgaca ggaagaaaga    12600
gaaatgtcct cattgacaaa gagtcatgtt cagtgcagct ggcgagagct ctaagaagcc    12660
atatgtgggc gaggctagct cgaggacggc ctatttacgg ccttgaggtc cctgatgtac    12720
tagaatctat gcgaggccac cttattcggc gtcatgagac atgtgtcatc tgcgagtgtg    12780
gatcagtcaa ctacggatgg tttttttgtcc cctcggggttg ccaactggat gatattgaca    12840
aggaaacatc atccttgaga gtcccatata ttggttctac cactgatgag agaacagaca    12900
tgaagcttgc cttcgtaaga gccccaagtc gatccttgcg atctgctgtt agaatagcaa    12960
cagtgtactc atgggcttac ggtgatgatg atagctcttg gaacgaagcc tggttgttgg    13020
ctaggcaaag ggccaatgtg agcctggagg agctaagggt gatcactccc atctcaactt    13080
cgactaattt agcgcatagg ttgagggatc gtagcactca agtgaaatac tcaggtacat    13140
cccttgtccg agtggcgagg tataccacaa tctccaacga caatctctca tttgtcatat    13200
cagataagaa ggttgatact aactttatat accaacaagg aatgcttcta gggttgggtg    13260
```

```
tttagaaac attgtttcga ctcgagaaag ataccggatc atctaacacg gtattacatc    13320
ttcacgtcga aacagattgt tgcgtgatcc cgatgatgaa tcatcccagg ataccccagct   13380 cccgcaagct agagctgagg gcagagctat gtaccaaccc attgatatat gataatgcac   13440
ctttaattga cagagatgca acaaggctat acacccagag ccataggagg caccttgtgg    13500
aatttgttac atggtccaca ccccaactat atcacatttt agctaagtcc acagcactat   13560
ctatgattga cctggtaaca aaatttgaga aggaccatat gaatgaaatt tcagctctca    13620
taggggatga cgatatcaat agtttcataa ctgagtttct gctcatagag ccaagattat   13680
tcactatcta cttgggccag tgtgcggcca tcaattgggc atttgatgta cattatcata   13740
gaccatcagg gaaatatcag atgggtgagc tgttgtcatc gttccttct agaatgagca    13800 aaggagtgtt taaggtgctt gtcaatgctc taagccaccc aaagatctac aagaaattct   13860
ggcattgtgg tattatagag cctatccatg gtccttcact tgatgctcaa aacttgcaca   13920
caactgtgtg caacatggtt tacacatgct atatgaccta cctcgacctg ttgttgaatg   13980
aagagttaga agagttcaca tttctcttgt gtgaaagcga cgaggatgta gtaccggaca   14040
gattcgacaa catccaggca aaacacttat gtgttctggc agatttgtac tgtcaaccag   14100
ggacctgccc accaattcga ggtctaagac cggtagagaa atgtgcagtt ctaaccgacc    14160
atatcaaggc agaggctatg ttatctccag caggatcttc gtggaacata aatccaatta    14220
ttgtagacca ttactcatgc tctctgactt atctccggcg aggatcgatc aaacagataa    14280
gattgagagt tgatccagga ttcattttcg acgccctcgc tgaggtaaat gtcagtcagc    14340
caaagatcgg cagcaacaac atctcaaata tgagcatcaa ggctttcaga cccccacacg    14400
atgatgttgc aaaattgctc aaagatatca acacaagcaa gcacaatctt cccatttcag    14460
ggggcaatct cgccaattat gaaatccatg ctttccgcag aatcgggttg aactcatctg    14520
cttgctacaa agctgttgag atatcaacat taattaggag atgccttgag ccaggggagg   14580
acggcttgtt cttgggtgag ggatcgggtt ctatgttgat cacttataaa gagatactta    14640
aactaaacaa gtgcttctat aatagtgggg tttccgccaa ttctagatct ggtcaaaggg   14700
aattagcacc ctatccctcc gaagttggcc ttgtcgaaca cagaatggga gtaggtaata    14760
ttgtcaaagt gctctttaac gggaggcccg aagtcacgtg ggtaggcagt gtagattgct   14820
tcaatttcat agttagtaat atccctacct ctagtgtggg gtttatccat tcagatatag    14880
agaccttgcc tgacaaagat actatagaga agctagagga attggcagcc atcttatcga    14940
tggctctgct cctgggcaaa ataggatcaa tactggtgat taagcttatg cctttcagcg    15000
gggattttgt tcagggattt ataagttatg tagggtctca ttatagagaa gtgaaccttg    15060 tatacctag atacagcaac ttcatctcta ctgaatctta tttggttatg acagatctca    15120
aggctaaccg gctaatgaat cctgaaaaga ttaagcagca gataattgaa tcatctgtga    15180
ggacttcacc tggacttata ggtcacatcc tatccattaa gcaactaagc tgcatacaag    15240
caattgtggg agacgcagtt agtagaggtg atatcaatcc tactctgaaa aaacttacac    15300
ctatagagca ggtgctgatc aattgcgggt tggcaattaa cggacctaag ctgtgcaaag    15360
aattgatcca ccatgatgtt gcctcaggc aagatggatt gcttaattct atactcatcc     15420
tctacaggga gttggcaaga ttcaaagaca accaaagaag tcaacaaggg atgttccacg    15480
cttaccccgt attggtaagt agcaggcaac gagaacttat atctaggatc acccgcaaat    15540
tctgggggca cattcttctt tactccggga acaaaaagtt gataaataag tttatccaga    15600
```

```
atctcaagtc cggctatctg atactagact tacaccagaa tatcttcgtt aagaatctat    15660
ccaagtcaga gaaacagatt attatgacgg ggggtttgaa acgtgagtgg gtttttaagg    15720
taacagtcaa ggagaccaaa gaatggtata agttagtcgg atacagtgcc ctgattaagg    15780
actaattggt tgaactccgg aaccctaatc ctgccctagg tggttaggca ttatttgcaa    15840
tatattaaag aaaactttga aaatacgaag tttctattcc cagctttgtc tggt          15894
```

<210> SEQ ID NO 2
<211> LENGTH: 1122
<212> TYPE: DNA
<213> ORGANISM: Artificial
<220> FEATURE:
<223> OTHER INFORMATION: fusion of yeast cytosine deaminase and yeast
      uracil phosphoribosyltransferase

<400> SEQUENCE: 2

```
atggtgacag ggggaatggc aagcaagtgg gatcagaagg gtatggacat tgcctatgag      60
gaggcggcct taggttacaa agagggtggt gttcctattg gcggatgtct tatcaataac     120
aaagacggaa gtgttctcgg tcgtggtcac aacatgagat ttcaaaaggg atccgccaca     180
ctacatggtg agatctccac ttgaaaac tgtgggagat tagagggcaa agtgtacaaa       240
gataccactt tgtatacgac gctgtctcca tgcgacatgt gtacaggtgc catcatcatg     300
tatggtattc cacgctgtgt tgtcggtgag aacgttaatt tcaaaagtaa gggcgagaaa     360
tatttacaaa ctagaggtca cgaggttgtt gttgttgacg atgagaggtg taaaaagatc     420
atgaaacaat ttatcgatga aagacctcag gattggtttg aagatattgg tgaggcttcg     480
gaaccattta agaacgtcta cttgctacct caaacaaacc aattgctggg tttgtacacc     540
atcatcagaa ataagaatac aactagacct gatttcattt tctactccga tagaatcatc     600
agattgttgg ttgaagaagg tttgaaccat ctacctgtgc aaaagcaaat tgtggaaact     660
gacaccaacg aaaacttcga aggtgtctca ttcatgggta aatctgtggt gtttccatt     720 gtcagagctg gtgaatcgat ggcagcaagga ttaagagact gttgtaggtc tgtgcgtatc    780
ggtaaaattt taattcaaag ggacgaggag actgctttac caaagttatt ctacgaaaaa    840
ttaccagagg atatatctga aaggtatgtc ttcctattag acccaatgct ggccaccggt    900
ggtagtgcta tcatggctac agaagtcttg attaagagag gtgttaagcc agagagaatt    960
tacttcttaa acctaatctg tagtaaggaa gggattgaaa aataccatgc cgccttccca  1020
gaggtcagaa ttgttactgg tgccctcgac agaggtctag atgaaaacaa gtatctagtt   1080
ccagggttgg gtgactttgg tgacagatac tactgtgttt aa                       1122
```

<210> SEQ ID NO 3
<211> LENGTH: 19707
<212> TYPE: DNA
<213> ORGANISM: Artificial
<220> FEATURE:
<223> OTHER INFORMATION: plasmid DNA

<400> SEQUENCE: 3

```
accaaacaaa gttgggtaag gatagttcaa tcaatgatca tcttctagtg cacttaggat       60
tcaagatcct attatcaggg acaagagcag gattagggat atctcgaggc gcgccatcca     120
tcattgttat aaaaaactta ggattcaaga tcctattatc agggacaaga gcaggattag     180
ggatatccga gatggccaca cttttaagga gcttagcatt gttcaaaaga aacaaggaca     240
aaccacccat tacatcagga tccggtggag ccatcagagg aatcaaacac attattatag     300
```

```
taccaatccc tggagattcc tcaattacca ctcgatccag acttctggac cggttggtga      360
ggttaattgg aaacccggat gtgagcgggc ccaaactaac aggggcacta ataggtatat      420
tatccttatt tgtggagtct ccaggtcaat tgattcagag gatcaccgat gaccctgacg      480
ttagcataag gctgttagag gttgtccaga gtgaccagtc acaatctggc cttaccttcg      540
catcaagagg taccaacatg gaggatgagg cggaccaata cttttcacat gatgatccaa      600
ttagtagtga tcaatccagg ttcggatggt tcgggaacaa ggaaatctca gatattgaag      660
tgcaagaccc tgagggattc aacatgattc tgggtaccat cctagcccaa atttgggtct      720
tgctcgcaaa ggcggttacg gccccagaca cggcagctga ttcggagcta agaaggtgga      780
taaagtacac ccaacaaaga agggtagttg gtgaatttag attggagaga aaatggttgg      840
atgtggtgag gaacaggatt gccgaggacc tctccttacg ccgattcatg gtcgctctaa      900
tcctggatat caagagaaca cccggaaaca aacccaggat tgctgaaatg atatgtgaca      960
ttgatacata tatcgtagag gcaggattag ccagttttat cctgactatt aagtttggga     1020
tagaaactat gtatcctgct cttggactgc atgaatttgc tggtgagtta tccacacttg     1080
agtccttgat gaacctttac cagcaaatgg gggaaactgc accctacatg gtaatcctgg     1140
agaactcaat tcagaacaag ttcagtgcag gatcataccc tctgctctgg agctatgcca     1200
tgggagtagg agtggaactt gaaaactcca tgggaggttt gaactttggc cgatcttact     1260
ttgatccagc atattttaga ttagggcaag agatggtaag gaggtcagct ggaaaggtca     1320
gttccacatt ggcatctgaa ctcggtatca ctgccgagga tgcaaggctt gtttcagaga     1380
ttgcaatgca tactactgag gacaagatca gtagagcggt tggacccaga caagcccaag     1440
tatcatttct acacggtgat caaagtgaga atgagctacc gagattgggg ggcaaggaag     1500
ataggagggt caaacagagt cgaggagaag ccagggagag ctacagagaa accgggccca     1560
gcagagcaag tgatgcgaga gctgcccatc ttccaaccgg cacacccta gacattgaca      1620 ctgcaacgga gtccagccaa gatccgcagg acagtcgaag gtcagctgac gccctgctta     1680
ggctgcaagc catggcagga atctcggaag aacaaggctc agacacggac accctatag      1740 tgtacaatga cagaaatctt ctagactagg tgcgagaggc cgagggccag aacaacatcc     1800
gcctaccatc catcattgtt ataaaaaact taggaaccag gtccacacag ccgccagccc     1860
atcaaccatc cactcccacg attggagcca atggcagaag agcaggcacg ccatgtcaaa     1920
aacggactgg aatgcatccg ggctctcaag gccgagccca tcggctcact ggccatcgag     1980
gaagctatgg cagcatggtc agaaatatca gacaacccag gacaggagcg agccacctgc     2040
agggaagaga aggcaggcag ttcgggtctc agcaaaccat gcctctcagc aattggatca     2100
actgaaggcg gtgcacctcg catccgcggt cagggacctg gagagagcga tgacgacgct     2160
gaaactttgg gaatcccccc aagaaatctc caggcatcaa gcactgggtt acagtgttat     2220
tacgtttatg atcacagcgg tgaagcggtt aagggaatcc aagatgctga ctctatcatg     2280
gttcaatcag gccttgatgg tgatagcacc ctctcaggag gagacaatga atctgaaaac     2340
agcgatgtgg atattggcga acctgatacc gagggatatg ctatcactga ccggggatct     2400
gctcccatct ctatggggtt cagggcttct gatgttgaaa ctgcagaagg aggggagatc     2460
cacgagctcc tgagactcca atccagaggc aacaactttc gaagcttgg gaaaactctc      2520 aatgttcctc cgcccccgga ccccggtagg gccagcactt ccgggacacc cattaaaaag     2580
ggcacagacg cgagattagc ctcatttgga acggagatcg cgtctttatt gacaggtggt     2640
gcaacccaat gtgctcgaaa gtcaccctcg gaaccatcag ggccaggtgc acctgcgggg     2700
```

```
aatgtcccccg agtgtgtgag caatgccgca ctgatacagg agtggacacc cgaatctggt   2760
accacaatct ccccgagatc ccagaataat gaagaagggg gagactatta tgatgatgag   2820
ctgttctctg atgtccaaga tattaaaaca gccttggcca aaatacacga ggataatcag   2880
aagataatct ccaagctaga atcactgctg ttattgaagg gagaagttga gtcaattaag   2940
aagcagatca acaggcaaaa tatcagcata tccaccctgg aaggacacct ctcaagcatc   3000
atgatcgcca ttcctggact tgggaaggat cccaacgacc ccactgcaga tgtcgaaatc   3060
aatcccgact tgaaacccat cataggcaga gattcaggcc gagcactggc cgaagttctc   3120
aagaaacccg ttgccagccg acaactccaa ggaatgacaa atggacggac cagttccaga   3180
ggacagctgc tgaaggaatt tcagctaaag ccgatcggga aaagatgag ctcagccgtc    3240 gggtttgttc ctgacaccgg ccctgcatca cgcagtgtaa tccgctccat tataaaatcc   3300
agccggctag aggaggatcg gaagcgttac ctgatgactc tccttgatga tatcaaagga   3360
gccaatgatc ttgccaagtt ccaccagatg ctgatgaaga taataatgaa gtagctacag   3420
ctcaacttac ctgccaaccc catgccagtc gacccaacta gtacaaccta atccattat    3480 aaaaaactta ggagcaaagt gattgcctcc caaggtccac aatgacagag acctacgact   3540
tcgacaagtc ggcatgggac atcaaagggt cgatcgctcc gatacaaccc accacctaca   3600
gtgatggcag gctggtgccc caggtcgag tcatagatcc tggtctaggc gacaggaagg    3660
atgaatgctt tatgtacatg tttctgctgg gggttgttga ggacagcgat tccctagggc   3720
ctccaatcgg gcgagcattt gggttcctgc ccttaggtgt tggcagatcc acagcaaagc   3780
ccgaaaaact cctcaaagag gccactgagc ttgacatagt tgttagacgt acagcagggc   3840
tcaatgaaaa actggtgttc tacaacaaca ccccactaac tctcctcaca ccttggagaa   3900
aggtcctaac aacagggagt gtcttcaacg caaaccaagt gtgcaatgcg gttaatctga   3960
taccgctcga tacccgcag aggttccgtg ttgtttatat gagcatcacc cgtctttcgg    4020
ataacgggta ttacaccgtt cctagaagaa tgctggaatt cagatcggtc aatgcagtgg   4080
ccttcaacct gctggtgacc cttaggattg acaaggcgat aggccctggg aagatcatcg   4140
acaatacaga gcaacttcct gaggcaacat ttatggtcca catcgggaac ttcaggagaa   4200
agaagagtga agtctactct gccgattatt gcaaaatgaa aatcgaaaag atgggcctgg   4260
tttttgcact tggtgggata gggggcacca gtcttcacat tagaagcaca ggcaaaatga   4320
gcaagactct ccatgcacaa ctcgggttca agaagaccct atgttacccg ctgatggata   4380
tcaatgaaga ccttaatcga ttactctgga ggagcagatg caagatagta agaatccagg   4440
cagttttgca gccatcagtt cctcaagaat tccgcattta cgacgacgtg atcataaatg   4500
atgaccaaga actattcaaa gttctgtaga ccgtagtgcc cagcaatgcc cgaaaacgac   4560 cccctcaca atgacagcca gaaggcccgg acaaaaaagc cccctccgaa agactccacg    4620
gaccaagcga gaggccagcc agcagccgac ggcaagcgcg aacaccaggc ggccccagca   4680
cagaacagcc ctgacacaag gccaccacca gccaccccaa tctgcatcct cctcgtggga   4740
cccccgagga ccaacccccca aggctgcccc cgatccaaac caccaaccgc atccccacca   4800
cccccgggaa agaaaccccc agcaattgga aggcccctcc cctcttcct caacacaaga    4860 actccacaac cgaaccgcac aagcgaccga ggtgacccaa ccgcaggcat ccgactccct   4920
agacagatcc tctctcccccg gcaaactaaa caaaacttag ggccaaggaa catacacacc   4980
caacagaacc cagaccccgg cccacggcgc cgcgccccca acccccgaca accagaggga   5040
```

```
gcccccaacc aatcccgccg gctccccgg tgcccacagg cagggacacc aaccccgaa     5100
cagacccagc acccaaccat cgacaatcca agacgggggg gcccccccaa aaaaaggccc    5160
ccaggggccg acagccagca ccgcgaggaa gcccacccac cccacacacg accacggcaa    5220
ccaaaccaga acccagacca ccctgggcca ccagctccca gactcggcca tcaccccgca    5280
gaaaggaaag gccacaaccc gcgcacccca gccccgatcc ggcggggagc cacccaaccc    5340
gaaccagcac ccaagagcga tccccgaagg accccgaac cgcaaaggac atcagtatcc     5400
cacagcctct ccaagtcccc cggtctcctc ctcttctcga agggaccaaa agatcaatcc    5460
accacacccg acgacactca actccccacc cctaaaggag acaccgggaa tcccagaatc    5520
aagactcatc caatgtccat catgggtctc aaggtgaacg tctctgccat attcatggca    5580
gtactgttaa ctctccaaac acccaccggt caaatccatt gggcaatct ctctaagata     5640
ggggtggtag aataggaag tgcaagctac aaagttatga ctcgttccag ccatcaatca     5700
ttagtcataa aattaatgcc caatataact ctcctcaata actgcacgag ggtagagatt    5760
gcagaataca ggagactact gagaacagtt ttggaaccaa ttagagatgc acttaatgca    5820
atgacccaga atataagacc ggttcagagt gtagcttcaa gtaggagaca caagagattt    5880
gcgggagtag tcctggcagg tgcggcccta ggcgttgcca cagctgctca gataacagcc    5940
ggcattgcac ttcaccagtc catgctgaac tctcaagcca tcgacaatct gagagcgagc    6000
ctggaaacta ctaatcaggc aattgagaca atcagacaag cagggcagga gatgatattg    6060
gctgttcagg gtgtccaaga ctacatcaat aatgagctga taccgtctat gaaccaacta    6120
tcttgtgatt taatcggcca gaagctcggg ctcaaattgc tcagtacta tacagaaatc     6180
ctgtcattat ttggccccag tttacgggac cccatatctg cggagatatc tatccaggct    6240
ttgagctatg cgcttggagg agacatcaat aaggtgttag aaaagctcgg atacagtgga    6300
ggtgatttac tgggcatctt agagagcgga ggaataaagg cccggataac tcacgtcgac    6360
acagagtcct acttcattgt cctcagtata gcctatccga cgctgtccga gattaagggg    6420
gtgattgtcc accggctaga gggggtctcg tacaacatag gctctcaaga gtggtatacc    6480
actgtgccca gtatgttgc aacccaaggg taccttatct cgaattttga tgagtcatcg     6540
tgtactttca tgccagaggg gactgtgtgc agccaaaatg ccttgtaccc gatgagtcct    6600
ctgctccaag aatgcctccg ggggtacacc aagtcctgtg ctcgtacact cgtatccggg    6660
tcttttggga accggttcat tttatcacaa gggaacctaa tagccaattg tgcatcaatc    6720
ctttgcaagt gttacacaac aggaacgatc attaatcaag accctgacaa gatcctaaca    6780
tacattgctg ccgatcactg cccggtagtc gaggtgaacg gcgtgaccat ccaagtcggg    6840
agcaggaggt atccagacgc tgtgtacttg cacagaattg acctcggtcc tcccatatca    6900
ttggagaggt tggacgtagg gacaaatctg gggaatgcaa ttgctaagtt ggaggatgcc    6960
aaggaattgt tggagtcatc ggaccagata ttgaggagta tgaaaggttt atcgagcact    7020
agcatagtct acatcctgat tgcagtgtgt cttggagggt tgataggat ccccgctta      7080
atatgttgct gcagggggcg ttgtaacaaa aagggagaac aagttggtat gtcaagacca    7140
ggcctaaagc ctgatcttac gggaacatca aaatcctatg taaggtcgct ctgatcctct    7200
acaactcttg aaacacaaat gtcccacaag tctcctcttc gtcatcaagc aaccaccgca    7260
cccagcatca agcccacctg aaattatctc cggcttccct ctggccgaac aatatcggta    7320
gttaatcaaa acttagggtg caagatcatc cacaatgtca ccacaacgag accggataaa    7380
tgccttctac aaagataacc cccatcccaa gggaagtagg atagtcatta acagagaaca    7440
```

```
tcttatgatt gatagacctt atgttttgct ggctgttctg tttgtcatgt ttctgagctt    7500
gatcgggttg ctagccattg caggcattag acttcatcgg gcagccatct acaccgcaga    7560
gatccataaa agcctcagca ccaatctaga tgtaactaac tcaatcgagc atcaggtcaa    7620
ggacgtgctg acaccactct tcaaaatcat cggtgatgaa gtgggcctga ggacacctca    7680
gagattcact gacctagtga aattaatctc tgacaagatt aaattcctta atccggatag    7740
ggagtacgac ttcagagatc tcacttggtg tatcaacccg ccagagagaa tcaaattgga    7800
ttatgatcaa tactgtgcag atgtggctgc tgaagagctc atgaatgcat tggtgaactc    7860
aactctactg gagaccagaa caaccaatca gttcctagct gtctcaaagg gaaactgctc    7920
agggcccact acaatcagag gtcaattctc aaacatgtcg ctgtccctgt tagacttgta    7980
tttaggtcga ggttacaatg tgtcatctat agtcactatg catcccagg gaatgtatgg     8040
gggaacttac ctagtggaaa agcctaatct gagcagcaaa aggtcagagt tgtcacaact    8100
gagcatgtac cgagtgtttg aagtaggtgt tatcagaaat ccgggtttgg gggctccggt    8160
gttccatatg acaaactatc ttgagcaacc agtcagtaat gatctcagca actgtatggt    8220
ggctttgggg gagctcaaac tcgcagccct ttgtcacggg gaagattcta tcacaattcc    8280
ctatcaggga tcagggaaag gtgtcagctt ccagctcgtc aagctaggtg tctggaaatc    8340
cccaaccgac atgcaatcct gggtccccctt atcaacggat gatccagtga tagacaggct    8400
ttacctctca tctcacagag gtgttatcgc tgacaatcaa gcaaatgggg ctgtcccgac    8460
aacacgaaca gatgacaagt tgcgaatgga gacatgcttc caacaggcgt gtaagggtaa    8520
aatccaagca ctctgcgaga atcccgagtg ggcaccattg aaggataaca ggattccttc    8580
atacgggtc ttgtctgttg atctgagtct gacagttgag cttaaaatca aaattgcttc     8640
gggattcggg ccattgatca cacacggttc agggatggac ctatacaaat ccaaccacaa    8700
caatgtgtat tggctgacta tccgccaat gaagaaccta gccttaggtg taatcaacac    8760
attggagtgg ataccgagat tcaaggttag tccctacctc ttcactgtcc caattaagga    8820
agcaggcgaa gactgccatg ccccaacata cctacctgcg gaggtggatg gtgatgtcaa    8880
actcagttcc aatctggtga ttctacctgg tcaagatctc caatatgttt tggcaaccta    8940
cgatacttcc agggttgaac atgctgtggt ttattacgtt tacagcccaa gccgctcatt    9000
ttcttacttt tatcctttta ggttgcctat aaaggggtc cccatcgaat tacaagtgga     9060
atgcttcaca tgggaccaaa aactctggtg ccgtcacttc tgtgtgcttg cggactcaga    9120
atctggtgga catatcactc actctgggat ggtgggcatg ggagtcagct gcacagtcac    9180
ccgggaagat ggaaccaatc gcagataggg ctgctagtga accaatcaca tgatgtcacc    9240
cagacatcag gcatacccac tagtgtgaaa tagacatcag aattaagaaa acgtagggt     9300
ccaagtggtt ccccgttatg gactcgctat ctgtcaacca gatcttatac cctgaagttc    9360
acctagatag cccgatagtt accaataaga tagtagccat cctggagtat gctcgagtcc    9420
ctcacgctta cagcctggag gaccctacac tgtgtcagaa catcaagcac cgcctaaaaa    9480
acggattttc caaccaaatg attataaaca atgtggaagt tgggaatgtc atcaagtcca    9540
agcttaggag ttatccggcc cactctcata ttccatatcc aaattgtaat caggatttat    9600
ttaacataga agacaaagag tcaacgagga agatccgtga actcctcaaa aaggggaatt    9660
cgctgtactc caaagtcagt gataaggttt tccaatgctt aagggacact aactcacggc    9720
ttggcctagg ctccgaattg agggaggaca tcaaggagaa agttattaac ttgggagttt    9780
```

```
acatgcacag ctcccagtgg tttgagccct ttctgttttg gtttacagtc aagactgaga    9840
tgaggtcagt gattaaatca caaacccata cttgccatag gaggagacac acacctgtat    9900
tcttcactgg tagttcagtt gagttgctaa tctctcgtga ccttgttgct ataatcagta    9960
aagagtctca acatgtatat tacctgacat ttgaactggt tttgatgtat tgtgatgtca   10020
tagaggggag gttaatgaca gagaccgcta tgactattga tgctaggtat acagagcttc   10080
taggaagagt cagatacatg tggaaactga tagatggttt cttccctgca ctcgggaatc   10140
caacttatca aattgtagcc atgctggagc ctctttcact tgcttacctg cagctgaggg   10200
atataacagt agaactcaga ggtgctttcc ttaaccactg ctttactgaa atacatgatg   10260
ttcttgacca aaacgggttt tctgatgaag gtacttatca tgagttaact gaagctctag   10320
attacatttt cataactgat gacatacatc tgacagggga gattttctca tttttcagaa   10380
gtttcggcca ccccagactt gaagcagtaa cggctgctga aaatgttagg aaatacatga   10440
atcagcctaa agtcattgtg tatgagactc tgatgaaagg tcatgccata ttttgtggaa   10500
tcataatcaa cggctatcgt gacaggcacg gaggcagttg gccaccgctg accctccccc   10560
tgcatgctgc agacacaatc cggaatgctc aagcttcagg tgaagggtta acacatgagc   10620
agtgcgttga taactggaaa tcttttgctg gagtgaaatt tggctgcttt atgcctctta   10680
gcctggatag tgatctgaca atgtacctaa aggacaaggc acttgctgct ctccaaaggg   10740
aatgggattc agtttacccg aaagagttcc tgcgttacga ccctcccaag ggaacgggt   10800 cacggaggct tgtagatgtt ttccttaatg attcgagctt tgacccatat gatgtgataa   10860
tgtatgttgt aagtggagct tacctccatg accctgagtt caacctgtct tacagcctga   10920
aagaaaagga gatcaaggaa acaggtagac tttttgctaa aatgacttac aaaatgaggg   10980
catgccaagt gattgctgaa aatctaatct caaacgggat tggcaaatat tttaaggaca   11040
atgggatggc caaggatgag cacgatttga ctaaggcact ccacactcta gctgtctcag   11100
gagtccccaa agatctcaaa gaaagtcaca gggggggccc agtcttaaaa acctactccc   11160
gaagcccagt ccacacaagt accaggaacg tgagagcagc aaaagggttt atagggttcc   11220
ctcaagtaat tcggcaggac caagacactg atcatccgga gaatatggaa gcttacgaga   11280
cagtcagtgc atttatcacg actgatctca agaagtactg ccttaattgg agatatgaga   11340
ccatcagctt gtttgcacag aggctaaatg agatttacgg attgccctca ttttttccagt   11400 ggctgcataa gaggcttgag acctctgtcc tgtatgtaag tgaccctcat tgccccccg   11460 accttgacgc ccatatcccg ttatataaag tccccaatga tcaaatcttc attaagtacc   11520
ctatgggagg tatagaaggg tattgtcaga agctgtggac catcagcacc attccctatc   11580
tatacctggc tgcttatgag agcggagtaa ggattgcttc gttagtgcaa ggggacaatc   11640
agaccatagc cgtaacaaaa agggtaccca gcacatggcc ctacaacctt aagaaacggg   11700
aagctgctag agtaactaga gattactttg taattcttag gcaaaggcta catgatattg   11760
gccatcacct caaggcaaat gagacaattg tttcatcaca ttttttttgtc tattcaaaag   11820 gaatatatta tgatgggcta cttgtgtccc aatcactcaa gagcatcgca agatgtgtat   11880
tctggtcaga gactatagtt gatgaaacaa gggcagcatg cagtaatatt gctacaacaa   11940
tggctaaaag catcgagaga ggttatgacc gttaccttgc atattccctg aacgtcctaa   12000
aagtgataca gcaaattctg atctctcttg gcttcacaat caattcaacc atgacccggg   12060
atgtagtcat accccctcctc acaaacaacg acctcttaat aaggatggca ctgttgcccg   12120
ctcctattgg ggggatgaat tatctgaata tgagcaggct gtttgtcaga aacatcggtg   12180
```

```
atccagtaac atcatcaatt gctgatctca agagaatgat tctcgcctca ctaatgcctg    12240
aagagaccct ccatcaagta atgacacaac aaccggggga ctcttcattc ctagactggg    12300
ctagcgaccc ttactcagca aatcttgtat gtgtccagag catcactaga ctcctcaaga    12360
acataactgc aaggtttgtc ctgatccata gtccaaaccc aatgttaaaa ggattattcc    12420
atgatgacag taaagaagag gacgagggac tggcggcatt cctcatggac aggcatatta    12480
tagtacctag ggcagctcat gaaatcctgg atcatagtgt cacaggggca agagagtcta    12540
ttgcaggcat gctggatacc acaaaaggct tgattcgagc cagcatgagg aaggggggt     12600 taacctctcg agtgataacc agattgtcca attatgacta tgaacaattc agagcaggga    12660
tggtgctatt gacaggaaga aagagaaatg tcctcattga caaagagtca tgttcagtgc    12720
agctggcgag agctctaaga agccatatgt gggcgaggct agctcgagga cggcctattt    12780
acggccttga ggtccctgat gtactagaat ctatgcgagg ccaccttatt cggcgtcatg    12840
agacatgtgt catctgcgag tgtggatcag tcaactacgg atggtttttt gtcccctcgg    12900
gttgccaact ggatgatatt gacaaggaaa catcatcctt gagagtccca tatattggtt    12960
ctaccactga tgagagaaca gacatgaagc ttgccttcgt aagagcccca agtcgatcct    13020
tgcgatctgc tgttagaata gcaacagtgt actcatgggc ttacggtgat gatgatagct    13080
cttggaacga agcctggttg ttggctaggc aaagggccaa tgtgagcctg gaggagctaa    13140
gggtgatcac tcccatctca acttcgacta atttagcgca taggttgagg gatcgtagca    13200
ctcaagtgaa atactcaggt acatcccttg tccgagtggc gaggtatacc acaatctcca    13260
acgacaatct ctcatttgtc atatcagata agaaggttga tactaacttt atataccaac    13320
aaggaatgct tctagggttg ggtgttttag aaacattgtt tcgactcgag aaagataccg    13380
gatcatctaa cacggtatta catcttcacg tcgaaacaga ttgttgcgtg atcccgatga    13440
tagatcatcc caggataccc agctcccgca agctagagct gagggcagag ctatgtacca    13500
acccattgat atatgataat gcaccttaa ttgacagaga tgcaacaagg ctatacaccc     13560
agagccatag gaggcacctt gtggaatttg ttacatggtc cacacccaa ctatatcaca     13620 ttttagctaa gtccacagca ctatctatga ttgacctggt aacaaaattt gagaaggacc    13680
atatgaatga aatttcagct ctcataggg atgacgatat caatagtttc ataactgagt     13740
ttctgctcat agagccaaga ttattcacta tctacttggg ccagtgtgcg gccatcaatt    13800
gggcatttga tgtacattat catagaccat caggggaata tcagatgggt gagctgttgt   13860
catcgttcct ttctagaatg agcaaaggag tgtttaaggt gcttgtcaat gctctaagcc    13920
acccaaagat ctacaagaaa ttctggcatt gtggtattat agagcctatc catggtcctt    13980
cacttgatgc tcaaaacttg cacacaactg tgtgcaacat ggtttacaca tgctatatga    14040
cctacctcga cctgttgttg aatgaagagt tagaagagtt cacatttctc ttgtgtgaaa    14100
gcgacgagga tgtagtaccg gacagattcg acaacatcca ggcaaaacac ttatgtgttc    14160
tggcagattt gtactgtcaa ccagggacct gcccaccaat tcgaggtcta agaccggtag    14220
agaaatgtgc agttctaacc gaccatatca aggcagaggc tatgttatct ccagcaggat    14280
cttcgtggaa cataaatcca attattgtag accattactc atgctctctg acttatctcc    14340
ggcgaggatc gatcaaacag ataagattga gagttgatcc aggattcatt ttcgacgccc    14400
tcgctgaggt aaatgtcagt cagccaaaga tcggcagcaa caacatctca aatatgagca    14460
tcaaggcttt cagacccca cacgatgatg ttgcaaaatt gctcaaagat atcaacacaa      14520
```

```
gcaagcacaa tcttcccatt tcaggggca atctcgccaa ttatgaaatc catgctttcc    14580
gcagaatcgg gttgaactca tctgcttgct acaaagctgt tgagatatca acattaatta    14640
ggagatgcct tgagccaggg gaggacggct tgttcttggg tgagggatcg ggttctatgt    14700
tgatcactta taaagagata cttaaactaa acaagtgctt ctataatagt ggggtttccg    14760
ccaattctag atctggtcaa agggaattag caccctatcc ctccgaagtt ggccttgtcg    14820
aacacagaat gggagtaggt aatattgtca aagtgctctt taacgggagg cccgaagtca    14880
cgtgggtagg cagtgtagat tgcttcaatt tcatagttag taatatccct acctctagtg    14940
tggggtttat ccattcagat atagagacct tgcctgacaa agatactata gagaagctag    15000
aggaattggc agccatctta tcgatggctc tgctcctggg caaaatagga tcaatactgg    15060
tgattaagct tatgccttc agcggggatt ttgttcaggg atttataagt tatgtagggt    15120
ctcattatag agaagtgaac cttgtatacc ctagatacag caacttcatc tctactgaat    15180
cttatttggt tatgacagat ctcaaggcta accggctaat gaatcctgaa aagattaagc    15240
agcagataat tgaatcatct gtgaggactt cacctggact tataggtcac atcctatcca    15300
ttaagcaact aagctgcata caagcaattg tgggagacgc agttagtaga ggtgatatca    15360
atcctactct gaaaaaactt acacctatag agcaggtgct gatcaattgc gggttggcaa    15420
ttaacggacc taagctgtgc aaagaattga tccaccatga tgttgcctca gggcaagatg    15480
gattgcttaa ttctatactc atcctctaca gggagttggc aagattcaaa acaaccaaa    15540 gaagtcaaca agggatgttc cacgcttacc ccgtattggt aagtagcagg caacgagaac    15600
ttatatctag gatcacccgc aaattctggg ggcacattct tctttactcc gggaacaaaa    15660
agttgataaa taagtttatc cagaatctca agtccggcta tctgatacta gacttacacc    15720
agaatatctt cgttaagaat ctatccaagt cagagaaaca gattattatg acgggggggtt    15780 tgaaacgtga gtgggttttt aaggtaacag tcaaggagac caaagaatgg tataagttag    15840
tcggatacag tgcccctgatt aaggactaat tggttgaact ccggaaccct aatcctgccc    15900
taggtggtta ggcattattt gcaatatatt aaagaaaact ttgaaaatac gaagtttcta    15960
ttcccagctt tgtctggtgg ccggcatggt cccagcctcc tcgctggcgc cggctgggca    16020
acattccgag gggaccgtcc cctcggtaat ggcgaatggg acgcggccgg tcgatcgacg    16080
atccggctgc taacaaagcc cgaaaggaag ctgagttggc tgctgccacc gctgagcaat    16140
aactagcata ccccttggg gcctctaaac gggtcttgag gggttttttg ctgaaaggag    16200
gaactatatc cggatcgaga tcaattctgt gagcgtatgg caaacgaagg aaaaatagtt    16260
atagtagccg cactcgatgg gacatttcaa cgtaaaccgt ttaataatat tttgaatctt    16320
attccattat ctgaaatggt ggtaaaacta actgctgtgt gtatgaaatg ctttaaggag    16380
gcttcctttt ctaaacgatt gggtgaggaa accgagatag aaataatagg aggtaatgat    16440
atgtatcaat cggtgtgtag aaagtgttac atcgactcat aatattatat tttttatcta    16500
aaaaactaaa aataaacatt gattaaattt taatataata cttaaaaatg gatgttgtgt    16560
cgttagataa accgtttatg tattttgagg aaattgataa tgagttagat tacgaaccag    16620
aaagtgcaaa tgaggtcgca aaaaaactgc cgtatcaagg acagtaaaaa ctattactag    16680
gagaattatt ttttcttagt aagttacagc gacacggtat attagatggt gccaccgtag    16740
tgtatatagg atctgctccc ggtacacata tacgttattt gagagatcat ttctataatt    16800
taggagtgat cccgaaagga agctgagttg gctgctgcca ccgctgagca ataactagca    16860 taacccctg gggcctctaa acgggtcttg agggggtttt tgctgaaagg aggaacgcgc    16920
```

```
ctgatgcggt attttctcct tacgcatctg tgcggtattt cacaccgcat atatggtgca   16980
ctctcagtac aatctgctct gatgccgcat agttaagcca gccccgacac ccgccaacac   17040
ccgctgacgc gccctgacgg gcttgtctgc tcccggcatc cgcttacaga caagctgtga   17100
ccgtctccgg gagctgcatg tgtcagaggt tttcaccgtc atcaccgaaa cgcgcgagac   17160
gaaagggcct cgtgatacgc ctatttttat aggttaatgt catgataata atggtttctt   17220
agacgtcagg tggcactttt cggggaaatg tgcgcggaac ccctatttgt ttattttttct  17280 aaatacattc aaatatgtat ccgctcatga acaataacc ctgataaatg cttcaataat    17340
attgaaaaag gaagagtatg agtattcaac atttccgtgt cgcccttatt ccttttttg    17400 cggcattttg ccttcctgtt tttgctcacc cagaaacgct ggtgaaagta aagatgctg    17460 aagatcagtt gggtgcacga gtgggttaca tcgaactgga tctcaacagc ggtaagatcc   17520
ttgagagttt tcgccccgaa gaacgttttc caatgatgag cacttttaaa gttctgctat   17580
gtggcgcggt attatcccgt attgacgccg ggcaagagca actcggtcgc cgcatacact   17640
attctcagaa tgacttggtt gagtactcac cagtcacaga aaagcatctt acggatggca   17700
tgacagtaag agaattatgc agtgctgcca taaccatgag tgataacact gcggccaact   17760
tacttctgac aacgatcgga ggaccgaagg agctaaccgc ttttttgcac aacatggggg   17820
atcatgtaac tcgccttgat cgttgggaac cggagctgaa tgaagccata ccaaacgacg   17880
agcgtgacac cacgatgcct gtagcaatgg caacaacgtt gcgcaaacta ttaactggcg   17940
aactacttac tctagcttcc cggcaacaat taatagactg gatggaggcg gataaagttg   18000
caggaccact tctgcgctcg gcccttccgg ctggctggtt tattgctgat aaatctggag   18060
ccggtgagcg tgggtctcgc ggtatcattg cagcactggg gccagatggt aagccctccc   18120
gtatcgtagt tatctacacg acggggagtc aggcaactat ggatgaacga atagacaga    18180 tcgctgagat aggtgcctca ctgattaagc attggtaact gtcagaccaa gtttactcat   18240
atatacttta gattgattta aaacttcatt tttaatttaa aaggatctag gtgaagatcc   18300
tttttgataa tctcatgacc aaaatccctt aacgtgagtt ttcgttccac tgagcgtcag   18360
accccgtaga aaagatcaaa ggatcttctt gagatccttt ttttctgcgc gtaatctgct   18420
gcttgcaaac aaaaaaacca ccgctaccag cggtggtttg tttgccggat caagagctac   18480
caactctttt tccgaaggta actggcttca gcagagcgca gataccaaat actgtccttc   18540
tagtgtagcc gtagttaggc caccacttca agaactctgt agcaccgcct acatacctcg   18600
ctctgctaat cctgttacca gtggctgctg ccagtggcga taagtcgtgt cttaccgggt   18660
tggactcaag acgatagtta ccggataagg cgcagcggtc gggctgaacg ggggggttcgt  18720 gcacacagcc cagcttggag cgaacgacct acaccgaact gagatacccta cagcgtgagc   18780 attgagaaag cgccacgctt cccgaaggga gaaaggcgga caggtatccg gtaagcggca   18840
gggtcggaac aggagagcgc acgagggagc ttccaggggg aaacgcctgg tatctttata   18900
gtcctgtcgg gtttcgccac ctctgacttg agcgtcgatt tttgtgatgc tcgtcagggg   18960
ggcggagcct atggaaaaac gccagcaacg cggccttttt acggttcctg gccttttgct   19020
ggccttttgc tcacatgttc tttcctgcgt tatcccctga ttctgtggat aaccgtatta   19080
ccgcctttga gtgagctgat accgctcgcc gcagccgaac gaccgagcgc agcgagtcag   19140
tgagcgagga agcggaagag cgcccaatac gcaaaccgcc tctccccgcg cgttggccga   19200
ttcattaatg cagctggcac gacaggtttc ccgactggaa agcgggcagt gagcgcaacg   19260
```

```
caattaatgt gagttagctc actcattagg cacccaggc tttacacttt atgcttccgg    19320
ctcgtatgtt gtgtggaatt gtgagcggat aacaatttca cacaggaaac agctatgacc    19380
atgattacgc caagcttacg cgtcctggca ttatgcccag tacatgacct tatgggactt    19440
tcctacttgg cagtacatct acgtattagt catcgctatt accatggtga tgcggttttg    19500
gcagtacatc aatgggcgtg gatagcggtt tgactcacgg ggatttccaa gtctccaccc    19560
cattgacgtc aatgggagtt tgttttggca ccaaaatcaa cgggactttc caaaatgtcg    19620
taacaactcc gccccattga cgcaaatggg cggtaggcgt gtacggtggg aggtctatat    19680
aagcagagct cgtttagtga accgtgg                                        19707
```

<210> SEQ ID NO 4
<211> LENGTH: 20841
<212> TYPE: DNA
<213> ORGANISM: Artificial
<220> FEATURE:
<223> OTHER INFORMATION: plasmid DNA

<400> SEQUENCE: 4

```
accaaacaaa gttgggtaag gatagttcaa tcaatgatca tcttctagtg cacttaggat      60
tcaagatcct attatcaggg acaagagcag gattaggat atctcgaggc gcgtgccacc     120
atggtgacag ggaatggc aagcaagtgg gatcagaagg gtatggacat tgcctatgag      180
gaggcggcct taggttacaa agagggtggt gttcctattg gcggatgtct tatcaataac     240
aaagacggaa gtgttctcgg tcgtggtcac aacatgagat ttcaaaaggg atccgccaca    300
ctacatggtg agatctccac tttgaaaaac tgtgggagat tagagggcaa agtgtacaaa    360
gataccactt tgtatacgac gctgtctcca tgcgacatgt gtacaggtgc catcatcatg    420
tatggtattc cacgctgtgt tgtcggtgag aacgttaatt tcaaaagtaa gggcgagaaa    480
tatttacaaa ctagaggtca cgaggttgtt gttgttgacg atgagaggtg taaaaagatc    540
atgaaacaat ttatcgatga aagacctcag gattggtttg aagatattgg tgaggcttcg    600
gaaccattta agaacgtcta cttgctacct caaacaaacc aattgctggg tttgtacacc    660
atcatcagaa ataagaatac aactagacct gatttcattt tctactccga tagaatcatc    720
agattgttgg ttgaagaagg tttgaaccat ctacctgtgc aaaagcaaat tgtggaaact    780
gacaccaacg aaaacttcga aggtgtctca ttcatgggta aaatctgtgg tgtttccatt    840
gtcagagctg gtgaatcgat ggagcaagga ttaagagact gttgtaggtc tgtgcgtatc    900
ggtaaaattt taattcaaag ggacgaggag actgctttac caaagttatt ctacgaaaaa    960
ttaccagagg atatatctga aggtatgtc ttcctattag accccaatgct ggccaccggt    1020 ggtagtgcta tcatggctac agaagtcttg attaagagag gtgttaagcc agagagaatt    1080
tacttcttaa acctaatctg tagtaaggaa gggattgaaa ataccatgc cgccttccca    1140 gaggtcagaa ttgttactgg tgccctcgac agaggtctag atgaaaacaa gtatctagtt    1200
ccagggttgg gtgactttgg tgacagatac tactgtgttt aaacgcgcca tccatcattg    1260
ttataaaaaa cttaggattc aagatcctat tatcagggac aagagcagga ttagggatat    1320
ccgagatggc cacacttta aggagcttag cattgttcaa aagaaacaag acaaaaccac    1380
ccattacatc aggatccggt ggagccatca gaggaatcaa acacattatt atagtaccaa    1440
tccctggaga ttcctcaatt accactcgat ccagacttct ggaccggttg gtgaggttaa    1500
ttggaaaccc ggatgtgagc gggcccaaac taacaggggc actaataggt atattatcct    1560
tatttgtgga gtctccaggt caattgattc agaggatcac cgatgaccct gacgttagca    1620
```

```
taaggctgtt agaggttgtc cagagtgacc agtcacaatc tggccttacc ttcgcatcaa    1680
gaggtaccaa catggaggat gaggcggacc aatactttc acatgatgat ccaattagta    1740
gtgatcaatc caggttcgga tggttcggga acaaggaaat ctcagatatt gaagtgcaag    1800
accctgaggg attcaacatg attctgggta ccatcctagc ccaaatttgg gtcttgctcg    1860
caaaggcggt tacggcccca gacacggcag ctgattcgga gctaagaagg tggataaagt    1920
acacccaaca aagaagggta gttggtgaat ttagattgga gagaaaatgg ttggatgtgg    1980
tgaggaacag gattgccgag gacctctcct tacgccgatt catggtcgct ctaatcctgg    2040
atatcaagag aacacccgga aacaaaccca ggattgctga atgatatgt gacattgata    2100 catatatcgt agaggcagga ttagccagtt ttatcctgac tattaagttt gggatagaaa    2160
ctatgtatcc tgctcttgga ctgcatgaat ttgctggtga gttatccaca cttgagtcct    2220
tgatgaacct ttaccagcaa atgggggaaa ctgcacccta catggtaatc ctggagaact    2280
caattcagaa caagttcagt gcaggatcat accctctgct ctggagctat gccatgggag    2340
taggagtgga acttgaaaac tccatgggag gtttgaactt tggccgatct tactttgatc    2400
cagcatattt tagattaggg caagagatgg taaggaggtc agctggaaag gtcagttcca    2460
cattggcatc tgaactcggt atcactgccg aggatgcaag gcttgtttca gagattgcaa    2520
tgcatactac tgaggacaag atcagtagag cggttggacc cagacaagcc caagtatcat    2580
ttctacacgg tgatcaaagt gagaatgagc taccgagatt ggggggcaag aagatagga    2640 gggtcaaaca gagtcgagga gaagccaggg agagctacag agaaaccggg cccagcagag    2700
caagtgatgc gagagctgcc catcttccaa ccggcacacc cctagacatt gacactgcaa    2760
cggagtccag ccaagatccg caggacagtc gaaggtcagc tgacgccctg cttaggctgc    2820
aagccatggc aggaatctcg gaagaacaag gctcagacac ggacacccct atagtgtaca    2880
atgacagaaa tcttctagac taggtgcgag aggccgaggg ccagaacaac atccgcctac    2940
catccatcat tgttataaaa aacttaggaa ccaggtccac acagccgcca gcccatcaac    3000
catccactcc cacgattgga gccaatggca gaagagcagg cacgccatgt caaaaacgga    3060
ctggaatgca tccgggctct caaggccgag cccatcggct cactggccat cgaggaagct    3120
atggcagcat ggtcagaaat atcagacaac ccaggacagg agcgagccac ctgcagggaa    3180
gagaaggcag gcagttcggg tctcagcaaa ccatgcctct cagcaattgg atcaactgaa    3240
ggcggtgcac ctcgcatccg cggtcaggga cctggagaga gcgatgacga cgctgaaact    3300
ttgggaatcc ccccaagaaa tctccaggca tcaagcactg ggttacagtg ttattacgtt    3360
tatgatcaca gcggtgaagc ggttaaggga atccaagatg ctgactctat catggttcaa    3420
tcaggccttg atggtgatag caccctctca ggaggagaca atgaatctga aaacagcgat    3480
gtggatattg gcgaacctga taccgaggga tatgctatca ctgaccgggg atctgctccc    3540
atctctatgg ggttcagggc ttctgatgtt gaaactgcag aaggagggga gatccacgag    3600
ctcctgagac tccaatccag aggcaacaac tttccgaagc ttgggaaaac tctcaatgtt    3660
cctccgcccc cggaccccgg tagggccagc acttccggga cacccattaa aaagggcaca    3720
gacgcgagat tagcctcatt tggaacggag atcgcgtctt tattgacagg tggtgcaacc    3780
caatgtgctc gaaagtcacc ctcggaacca tcagggccag gtgcacctgc ggggaatgtc    3840
cccgagtgtg tgagcaatgc cgcactgata caggagtgga cacccgaatc tggtaccaca    3900
atctccccga gatcccagaa taatgaagaa ggggagagact attatgatga tgagctgttc    3960
```

```
tctgatgtcc aagatattaa aacagccttg gccaaaatac acgaggataa tcagaagata    4020
atctccaagc tagaatcact gctgttattg aagggagaag ttgagtcaat taagaagcag    4080
atcaacaggc aaaatatcag catatccacc ctggaaggac acctctcaag catcatgatc    4140
gccattcctg gacttgggaa ggatcccaac gaccccactg cagatgtcga aatcaatccc    4200
gacttgaaac ccatcatagg cagagattca ggccgagcac tggccgaagt tctcaagaaa    4260
cccgttgcca gccgacaact ccaaggaatg acaaatggac ggaccagttc cagaggacag    4320
ctgctgaagg aatttcagct aaagccgatc gggaaaaaga tgagctcagc cgtcgggttt    4380
gttcctgaca ccggccctgc atcacgcagt gtaatccgct ccattataaa atccagccgg    4440
ctagaggagg atcggaagcg ttacctgatg actctccttg atgatatcaa aggagccaat    4500
gatcttgcca agttccacca gatgctgatg aagataataa tgaagtagct acagctcaac    4560
ttacctgcca accccatgcc agtcgaccca actagtacaa cctaaatcca ttataaaaaa    4620
cttaggagca aagtgattgc ctcccaaggt ccacaatgac agagacctac gacttcgaca    4680
agtcggcatg ggacatcaaa gggtcgatcg ctccgataca acccaccacc tacagtgatg    4740
gcaggctggt gccccaggtc agagtcatag atcctggtct aggcgacagg aaggatgaat    4800
gctttatgta catgtttctg ctgggggttg ttgaggacag cgattcccta gggcctccaa    4860
tcgggcgagc atttgggttc ctgcccttag gtgttggcag atccacagca aagcccgaaa    4920
aactcctcaa agaggccact gagcttgaca tagttgttag acgtacagca gggctcaatg    4980
aaaaactggt gttctacaac aacaccccac taactctcct cacaccttgg agaaaggtcc    5040
taacaacagg gagtgtcttc aacgcaaacc aagtgtgcaa tgcggttaat ctgataccgc    5100
tcgatacccc gcagaggttc cgtgttgttt atatgagcat cacccgtctt tcggataacg    5160
ggtattacac cgttcctaga agaatgctgg aattcagatc ggtcaatgca gtggccttca    5220
acctgctggt gacccttagg attgacaagg cgataggccc tgggaagatc atcgacaata    5280
cagagcaact tcctgaggca acatttatgg tccacatcgg gaacttcagg agaaagaaga    5340
gtgaagtcta ctctgccgat tattgcaaaa tgaaaatcga aaagatgggc ctggtttttg    5400
cacttggtgg ataggggggc accagtcttc acattagaag cacaggcaaa atgagcaaga    5460
ctctccatgc acaactcggg ttcaagaaga ccttatgtta cccgctgatg gatatcaatg    5520
aagaccttaa tcgattactc tggaggagca gatgcaagat agtaagaatc caggcagttt    5580
tgcagccatc agttcctcaa gaattccgca tttacgacga cgtgatcata aatgatgacc    5640
aaggactatt caaagttctg tagaccgtag tgcccagcaa tgcccgaaaa cgacccccct    5700
cacaatgaca gccagaaggc ccggacaaaa aagcccctc cgaaagactc cacggaccaa    5760
gcgagaggcc agccagcagc cgacggcaag gcgaacacc aggcggcccc agcacagaac    5820
agccctgaca caaggccacc accagccacc ccaatctgca tcctcctcgt gggacccccg    5880
aggaccaacc cccaaggctg cccccgatcc aaaccaccaa ccgcatcccc accacccccg    5940
ggaaagaaac cccagcaat tggaaggccc ctccccctct tcctcaacac aagaactcca    6000
caaccgaacc gcacaagcga ccgaggtgac ccaaccgcag gcatccgact ccctagacag    6060
atcctctctc cccggcaaac taaacaaaac ttagggccaa ggaacataca cacccaacag    6120
aacccagacc ccggcccacg gcgccgcgcc cccaacccc gacaaccaga gggagcccc    6180
aaccaatccc gccggctccc ccggtgccca caggcaggga caccaacccc gaacagacc    6240
cagcacccaa ccatcgacaa tccaagacgg gggggccccc ccaaaaaaag gcccccaggg    6300
gccgacagcc agcaccgcga ggaagcccac ccaccccaca cacgaccacg gcaaccaaac    6360
```

```
cagaacccag accaccctgg gccaccagct cccagactcg gccatcaccc cgcagaaagg    6420
aaaggccaca cccgcgcac cccagccccg atccggcggg gagccaccca acccgaacca    6480
gcacccaaga gcgatccccg aaggaccccc gaaccgcaaa ggacatcagt atcccacagc    6540
ctctccaagt cccccggtct cctcctcttc tcgaagggac caaaagatca atccaccaca    6600
cccgacgaca ctcaactccc caccccctaaa ggagacaccg ggaatcccag aatcaagact    6660
catccaatgt ccatcatggg tctcaaggtg aacgtctctg ccatattcat ggcagtactg    6720
ttaactctcc aaacacccac cggtcaaatc cattggggca atctctctaa gatagggtg    6780 gtaggaatag gaagtgcaag ctacaaagtt atgactcgtt ccagccatca atcattagtc    6840
ataaaattaa tgcccaatat aactctcctc aataactgca cgagggtaga gattgcagaa    6900
tacaggagac tactgagaac agttttggaa ccaattagag atgcacttaa tgcaatgacc    6960
cagaatataa gaccggttca gagtgtagct tcaagtagga gacacaagag atttgcggga    7020
gtagtcctgg caggtgcggc cctaggcgtt gccacagctg ctcagataac agccggcatt    7080
gcacttcacc agtccatgct gaactctcaa gccatcgaca atctgagagc gagcctggaa    7140
actactaatc aggcaattga gacaatcaga caagcagggc aggagatgat attggctgtt    7200
cagggtgtcc aagactacat caataatgag ctgataccgt ctatgaacca actatcttgt    7260
gatttaatcg gccagaagct cgggctcaaa ttgctcagat actatacaga aatcctgtca    7320
ttatttggcc ccagtttacg ggaccccata tctgcggaga tatctatcca ggctttgagc    7380
tatgcgcttg gaggagacat caataaggtg ttagaaaagc tcggatacag tggaggtgat    7440
ttactgggca tcttagagag cggaggaata aaggcccgga taactcacgt cgacacagag    7500
tcctacttca ttgtcctcag tatagcctat ccgacgctgt ccgagattaa gggggtgatt    7560
gtccaccggc tagagggggt ctcgtacaac ataggctctc aagagtggta taccactgtg    7620
cccaagtatg ttgcaaccca agggtaccTt atctcgaatt ttgatgagtc atcgtgtact    7680
ttcatgccag aggggactgt gtgcagccaa aatgccttgt acccgatgag tcctctgctc    7740
caagaatgcc tccggggggta caccaagtcc tgtgctcgta cactcgtatc cgggtctttt    7800
gggaaccggt tcattttatc acaagggaac ctaatagcca attgtgcatc aatcctttgc    7860
aagtgttaca caacaggaac gatcattaat caagaccctg acaagatcct aacatacatt    7920
gctgccgatc actgcccggt agtcgaggtg aacggcgtga ccatccaagt cgggagcagg    7980
aggtatccag acgctgtgta cttgcacaga attgacctcg gtcctcccat atcattggag    8040
aggttggacg tagggacaaa tctggggaat gcaattgcta agttggagga tgccaaggaa    8100
ttgttggagt catcggacca gatattgagg agtatgaaag gtttatcgag cactagcata    8160
gtctacatcc tgattgcagt gtgtcttgga gggttgatag ggatcccccgc tttaatatgt    8220 tgctgcaggg ggcgttgtaa caaaaaggga gaacaagttg gtatgtcaag accaggccta    8280
aagcctgatc ttacgggaac atcaaaatcc tatgtaaggt cgctctgatc ctctacaact    8340
cttgaaacac aaatgtccca caagtctcct cttcgtcatc aagcaaccac cgcacccagc    8400
atcaagccca cctgaaatta ctccggctt ccctctggcc gaacaatatc ggtagttaat    8460
caaaacttag ggtgcaagat catccacaat gtcaccacaa cgagaccgga taatgccctt    8520
ctacaaagat aaccccatc ccaagggaag taggatagtc attaacagag aacatcttat    8580
gattgataga cctatgttt tgctggctgt tctgtttgtc atgtttctga gcttgatcgg    8640
gttgctagcc attgcaggca ttagacttca tcgggcagcc atctacaccg cagagatcca    8700
```

```
taaaagcctc agcaccaatc tagatgtaac taactcaatc gagcatcagg tcaaggacgt      8760
gctgacacca ctcttcaaaa tcatcggtga tgaagtgggc ctgaggacac ctcagagatt      8820
cactgaccta gtgaaattaa tctctgacaa gattaaattc cttaatccgg atagggagta     8880
cgacttcaga gatctcactt ggtgtatcaa cccgccagag agaatcaaat tggattatga     8940
tcaatactgt gcagatgtgg ctgctgaaga gctcatgaat gcattggtga actcaactct     9000
actggagacc agaacaacca atcagttcct agctgtctca aagggaaact gctcagggcc     9060
cactacaatc agaggtcaat tctcaaacat gtcgctgtcc ctgttagact tgtatttagg     9120
tcgaggttac aatgtgtcat ctatagtcac tatgacatcc cagggaatgt atgggggaac     9180
ttacctagtg gaaaagccta atctgagcag caaaaggtca gagttgtcac aactgagcat     9240
gtaccgagtg tttgaagtag gtgttatcag aaatccgggt ttgggggctc cggtgttcca     9300
tatgacaaac tatcttgagc aaccagtcag taatgatctc agcaactgta tggtggcttt     9360
gggggagctc aaactcgcag cccttttgtca cggggaagat tctatcacaa ttccctatca     9420
gggatcaggg aaaggtgtca gcttccagct cgtcaagcta ggtgtctgga atccccaac     9480
cgacatgcaa tcctgggtcc ccttatcaac ggatgatcca gtgatagaca ggctttacct     9540
ctcatctcac agaggtgtta tcgctgacaa tcaagcaaaa tgggctgtcc cgacaacacg     9600
aacagatgac aagttgcgaa tggagacatg cttccaacag gcgtgtaagg gtaaaatcca     9660
agcactctgc gagaatcccg agtgggcacc attgaaggat aacaggattc cttcatacgg     9720
ggtcttgtct gttgatctga gtctgacagt tgagcttaaa atcaaaattg cttcgggatt     9780
cgggccattg atcacacacg gttcaggggat ggacctatac aaatccaacc acaacaatgt     9840
gtattggctg actatcccgc caatgaagaa cctagcctta ggtgtaatca acacattgga     9900
gtggataccg agattcaagg ttagtcccta cctcttcact gtcccaatta aggaagcagg     9960
cgaagactgc catgccccaa catacctacc tgcggaggtg gatggtgatg tcaaaactcag     10020
ttccaatctg gtgattctac ctggtcaaga tctccaatat gttttggcaa cctacgatac     10080
ttccagggtt gaacatgctg tggtttatta cgtttacagc ccaagccgct catttcctta     10140
cttttatcct tttaggttgc ctataaaggg ggtcccctc gaattacaag tggaatgctt     10200
cacatgggac caaaaactct ggtgccgtca cttctgtgtg cttgcggact cagaatctgg     10260
tggacatatc actcactctg ggatggtggg catgggagtc agctgcacag tcacccggga     10320
agatggaacc aatcgcagat agggctgcta gtgaaccaat cacatgatgt cacccagaca     10380
tcaggcatac ccactagtgt gaaatagaca tcagaattaa gaaaacgta gggtccaagt     10440
ggttccccgt tatggactcg ctatctgtca accagatctt ataccctgaa gttcacctag     10500
atagcccgat agttaccaat aagatagtag ccatcctgga gtatgctcga gtccctcacg     10560
cttacagcct ggaggaccct acactgtgtc agaacatcaa gcaccgccta aaaacggat     10620
tttccaacca aatgattata aacaatgtgg aagttgggaa tgtcatcaag tccaagctta     10680
ggagttatcc ggcccactct catattccat atccaaattg taatcaggat ttatttaaca     10740
tagaagacaa agagtcaacg aggaagatcc gtgaactcct caaaaagggg aattcgctgt     10800
actccaaagt cagtgataag gttttccaat gcttaaggga cactaactca cggcttggcc     10860
taggctccga attgagggag gacatcaagg agaaagttat taacttggga gtttacatgc     10920
acagctccca gtggtttgag ccctttctgt tttggtttac agtcaagact gagatgaggt     10980
cagtgattaa atcacaaacc catacttgcc ataggaggag acacacacct gtattcttca     11040
ctggtagttc agttgagttg ctaatctctc gtgaccttgt tgctataatc agtaaagagt     11100
```

```
ctcaacatgt atattacctg acatttgaac tggttttgat gtattgtgat gtcatagagg   11160
ggaggttaat gacagagacc gctatgacta ttgatgctag gtatacagag cttctaggaa   11220
gagtcagata catgtggaaa ctgatagatg gtttcttccc tgcactcggg aatccaactt   11280
atcaaattgt agccatgctg gagcctcttt cacttgctta cctgcagctg agggatataa   11340
cagtagaact cagaggtgct ttccttaacc actgctttac tgaaatacat gatgttcttg   11400
accaaaacgg gttttctgat gaaggtactt atcatgagtt aactgaagct ctagattaca   11460
ttttcataac tgatgacata catctgacag gggagatttt ctcattttc agaagtttcg    11520
gccacccag acttgaagca gtaacggctg ctgaaaatgt taggaaatac atgaatcagc    11580
ctaaagtcat tgtgtatgag actctgatga aaggtcatgc catattttgt ggaatcataa   11640
tcaacggcta tcgtgacagg cacggaggca gttggccacc gctgaccctc ccctgcatg    11700
ctgcagacac aatccggaat gctcaagctt caggtgaagg gttaacacat gagcagtgcg   11760
ttgataactg gaaatctttt gctggagtga aatttggctg ctttatgcct cttagcctgg   11820
atagtgatct gacaatgtac ctaaaggaca aggcacttgc tgctctccaa agggaatggg   11880
attcagttta cccgaaagag ttcctgcgtt acgaccctcc caagggaacc gggtcacgga   11940
ggcttgtaga tgttttcctt aatgattcga gctttgaccc atatgatgtg ataatgtatg   12000
ttgtaagtgg agcttacctc catgaccctg agttcaacct gtcttacagc ctgaaagaaa   12060
aggagatcaa ggaaacaggt agactttttg ctaaaatgac ttacaaaatg agggcatgcc   12120
aagtgattgc tgaaaatcta atctcaaacg ggattggcaa atattttaag gacaatggga   12180
tggccaagga tgagcacgat ttgactaagg cactccacac tctagctgtc tcaggagtcc   12240
ccaaagatct caaagaaagt cacaggggg ggccagtctt aaaaacctac tcccgaagcc    12300
cagtccacac aagtaccagg aacgtgagag cagcaaaagg gtttataggg ttccctcaag   12360
taattcggca ggaccaagac actgatcatc cggagaatat ggaagcttac gagacagtca   12420
gtgcatttat cacgactgat ctcaagaagt actgccttaa ttggagatat gagaccatca   12480
gcttgtttgc acagaggcta aatgagattt acggattgcc ctcatttttc cagtggctgc   12540
ataagaggct tgagacctct gtcctgtatg taagtgaccc tcattgcccc cccgaccttg   12600
acgcccatat cccgttatat aaagtcccca atgatcaaat cttcattaag taccctatgg   12660
gaggtataga agggtattgt cagaagctgt ggaccatcag caccattccc tatctatacc   12720
tggctgctta tgagagcgga gtaaggattg cttcgttagt gcaagggac aatcagacca    12780
tagccgtaac aaaaagggta cccagcacat ggccctacaa ccttaagaaa cgggaagctg   12840
ctagagtaac tagagattac tttgtaattc ttaggcaaag gctacatgat attggccatc   12900
acctcaaggc aaatgagaca attgtttcat cacattttt tgtctattca aaaggaatat    12960
attatgatgg gctacttgtg tcccaatcac tcaagagcat cgcaagatgt gtattctggt   13020
cagagactat agttgatgaa acaagggcag catgcagtaa tattgctaca acaatggcta   13080
aaagcatcga gagaggttat gaccgttacc ttgcatattc cctgaacgtc ctaaaagtga   13140
tacagcaaat tctgatctct cttggcttca caatcaattc aaccatgacc cgggatgtag   13200
tcataccct cctcacaaac aacgacctct taataaggat ggcactgttg cccgctccta    13260
ttggggggat gaattatctg aatatgagca ggctgtttgt cagaaacatc ggtgatccag   13320
taacatcatc aattgctgat ctcaagagaa tgattctcgc ctcactaatg cctgaagaga   13380
ccctccatca agtaatgaca caacaaccgg gggactcttc attcctagac tgggctagcg   13440
```

```
accccttactc agcaaatctt gtatgtgtcc agagcatcac tagactcctc aagaacataa    13500
ctgcaaggtt tgtcctgatc catagtccaa acccaatgtt aaaaggatta ttccatgatg    13560
acagtaaaga agaggacgag ggactggcgg cattcctcat ggacaggcat attatagtac    13620
ctagggcagc tcatgaaatc ctggatcata gtgtcacagg gcaagagag tctattgcag     13680 gcatgctgga taccacaaaa ggcttgattc gagccagcat gaggaagggg gggttaacct    13740
ctcgagtgat aaccagattg tccaattatg actatgaaca attcagagca gggatggtgc    13800
tattgacagg aagaaagaga aatgtcctca ttgacaaaga gtcatgttca gtgcagctgg    13860
cgagagctct aagaagccat atgtgggcga ggctagctcg aggacggcct atttacggcc    13920
ttgaggtccc tgatgtacta gaatctatgc gaggccacct tattcggcgt catgagacat    13980
gtgtcatctg cgagtgtgga tcagtcaact acgatggtt ttttgtcccc tcgggttgcc     14040
aactggatga tattgacaag gaaacatcat ccttgagagt cccatatatt ggttctacca    14100
ctgatgagag aacagacatg aagcttgcct tcgtaagagc cccaagtcga tccttgcgat    14160
ctgctgttag aatagcaaca gtgtactcat gggcttacgg tgatgatgat agctcttgga    14220
acgaagcctg gttgttggct aggcaaaggg ccaatgtgag cctggaggag ctaagggtga    14280
tcactcccat ctcaacttcg actaatttag cgcataggtt gagggatcgt agcactcaag    14340
tgaaatactc aggtacatcc cttgtccgag tggcgaggta taccacaatc tccaacgaca    14400
atctctcatt tgtcatatca gataagaagg ttgatactaa cttatatac caacaaggaa     14460 tgcttctagg gttgggtgtt ttagaaacat tgtttcgact cgagaaagat accggatcat    14520
ctaacacggt attacatctt cacgtcgaaa cagattgttg cgtgatcccg atgatagatc    14580
atcccaggat acccagctcc cgcaagctag agctgagggc agagctatgt accaacccat    14640
tgatatatga taatgcacct ttaattgaca gagatgcaac aaggctatac acccagagcc    14700
ataggaggca ccttgtggaa tttgttacat ggtccacacc ccaactatat cacatttag     14760 ctaagtccac agcactatct atgattgacc tggtaacaaa atttgagaag gaccatatga    14820
atgaaatttc agctctcata ggggatgacg atatcaatag tttcataact gagtttctgc    14880
tcatagagcc aagattattc actatctact tgggccagtg tgcggccatc aattgggcat    14940
ttgatgtaca ttatcataga ccatcaggga aatatcagat gggtgagctg ttgtcatcgt    15000
tccttcctag aatgagcaaa ggagtgttta aggtgcttgt caatgctcta agccacccaa    15060
agatctacaa gaaattctgg cattgtggta ttatagagcc tatccatggt ccttcacttg    15120
atgctcaaaa cttgcacaca actgtgtgca acatggttta cacatgctat atgacctacc    15180
tcgacctgtt gttgaatgaa gagttagaag agttcacatt tctcttgtgt gaaagcgacg    15240
aggatgtagt accggacaga ttcgacaaca tccaggcaaa acacttatgt gttctggcag    15300
atttgtactg tcaaccaggg acctgcccac caattcgagg tctaagaccg gtagagaaat    15360
gtgcagttct aaccgaccat atcaaggcag aggctatgtt atctccagca ggatcttcgt    15420
ggaacataaa tccaattatt gtagaccatt actcatgctc tctgacttat ctccggcgag    15480
gatcgatcaa acagataaga ttgagagttg atccaggatt cattttcgac gccctcgctg    15540
aggtaaatgt cagtcagcca aagatcggca gcaacaacat ctcaaatatg agcatcaagg    15600 cttttcagacc cccacacgat gatgttgcaa aattgctcaa agatatcaac acaagcaagc    15660
acaatcttcc catttcaggg ggcaatctcg ccaattatga atccatgct ttccgcagaa      15720 tcgggttgaa ctcatctgct tgctacaaag ctgttgagat atcaacatta attaggagat    15780
gccttgagcc aggggaggac ggcttgttct tgggtgaggg atcgggttct atgttgatca    15840
```

```
cttataaaga gatacttaaa ctaaacaagt gcttctataa tagtggggtt tccgccaatt   15900
ctagatctgg tcaaagggaa ttagcaccct atccctccga agttggcctt gtcgaacaca   15960
gaatgggagt aggtaatatt gtcaaagtgc tctttaacgg gaggcccgaa gtcacgtggg   16020
taggcagtgt agattgcttc aatttcatag ttagtaatat ccctacctct agtgtggggt   16080
ttatccattc agatatagag accttgcctg acaaagatac tatagagaag ctagaggaat   16140
tggcagccat cttatcgatg gctctgctcc tgggcaaaat aggatcaata ctggtgatta   16200
agcttatgcc tttcagcggg gattttgttc agggatttat aagttatgta gggtctcatt   16260
atagagaagt gaaccttgta taccctagat acagcaactt catctctact gaatcttatt   16320
tggttatgac agatctcaag gctaaccggc taatgaatcc tgaaaagatt aagcagcaga   16380
taattgaatc atctgtgagg acttcacctg gacttatagg tcacatccta tccattaagc   16440
aactaagctg catacaagca attgtgggag acgcagttag tagaggtgat atcaatccta   16500
ctctgaaaaa acttacacct atagagcagg tgctgatcaa ttgcgggttg gcaattaacg   16560
gacctaagct gtgcaaagaa ttgatccacc atgatgttgc ctcagggcaa gatggattgc   16620
ttaattctat actcatcctc tacagggagt tggcaagatt caaagacaac caaagaagtc   16680
aacagggat gttccacgct taccccgtat tggtaagtag caggcaacga gaacttatat    16740
ctaggatcac ccgcaaattc tgggggcaca ttcttcttta ctccgggaac aaaaagttga   16800
taaataagtt tatccagaat ctcaagtccg gctatctgat actagactta caccagaata   16860
tcttcgttaa gaatctatcc aagtcagaga aacagattat tatgacgggg ggtttgaaac   16920
gtgagtgggt tttaaggta acagtcaagg agaccaaaga atggtataag ttagtcggat    16980
acagtgccct gattaaggac taattggttg aactccggaa ccctaatcct gccctaggtg   17040
gttaggcatt atttgcaata tattaaagaa actttgaaa atacgaagtt ctattccca    17100
gctttgtctg gtggccggca tggtcccagc ctcctcgctg gcgccggctg ggcaacattc   17160
cgagggacc gtcccctcgg taatggcgaa tgggacgcgg ccggtcgatc gacgatccgg    17220
ctgctaacaa gcccgaaaag gaagctgagt tggctgctgc caccgctgag caataactag   17280
cataacccct tggggcctct aaacgggtct tgaggggttt tttgctgaaa ggaggaacta   17340
tatccggatc gagatcaatt ctgtgagcgt atggcaaacg aaggaaaaat agttatagta   17400
gccgcactcg atgggacatt tcaacgtaaa ccgtttaata atattttgaa tcttattcca   17460
ttatctgaaa tggtggtaaa actaactgct gtgtgtatga aatgctttaa ggaggcttcc   17520
ttttctaaac gattgggtga ggaaccgag atagaaataa taggaggtaa tgatatgtat     17580
caatcggtgt gtagaaagtg ttacatcgac tcataatatt atatttttta tctaaaaaac   17640
taaaaataaa cattgattaa attttaatat aatacttaaa aatggatgtt gtgtcgttag   17700
ataaaccgtt tatgtatttt gaggaaattg ataatgagtt agattacgaa ccagaaagtg   17760
caaatgaggt cgcaaaaaaa ctgccgtatc aaggacagtt aaaactatta ctaggagaat   17820
tattttttct tagtaagtta cagcgacacg gtatattaga tggtgccacc gtagtgtata   17880
taggatctgc tcccggtaca catatacgtt atttgagaga tcatttctat aatttaggag   17940
tgatcccgaa aggaagctga gttggctgct gccaccgctg agcaataact agcataaccc   18000
cttggggcct ctaaacgggt cttgaggggt ttttgctga aaggaggaac gcgcctgatg    18060
cggtattttc tccttacgca tctgtgcggt atttcacacc gcatatatgg tgcactctca   18120
gtacaatctg ctctgatgcc gcatagttaa gccagccccg acacccgcca acacccgctg   18180
```

```
acgcgccctg acgggcttgt ctgctcccgg catccgctta cagacaagct gtgaccgtct   18240
ccgggagctg catgtgtcag aggttttcac cgtcatcacc gaaacgcgcg agacgaaagg   18300
gcctcgtgat acgcctattt ttataggtta atgtcatgat aataatggtt tcttagacgt   18360
caggtggcac ttttcgggga aatgtgcgcg aaccccctat ttgtttattt ttctaaatac   18420
attcaaatat gtatccgctc atgagacaat aaccctgata aatgcttcaa taatattgaa   18480
aaaggaagag tatgagtatt caacatttcc gtgtcgccct tattccctt tttgcggcat    18540 tttgccttcc tgtttttgct cacccagaaa cgctggtgaa agtaaaagat gctgaagatc   18600
agttgggtgc acgagtgggt tacatcgaac tggatctcaa cagcggtaag atccttgaga   18660
gttttcgccc cgaagaacgt tttccaatga tgagcacttt taaagttctg ctatgtggcg   18720
cggtattatc ccgtattgac gccgggcaag agcaactcgg tcgccgcata cactattctc   18780
agaatgactt ggttgagtac tcaccagtca cagaaaagca tcttacggat ggcatgacag   18840
taagagaatt atgcagtgct gccataacca tgagtgataa cactgcgcc aacttacttc    18900 tgacaacgat cggaggaccg aaggagctaa ccgcttttt gcacaacatg ggggatcatg    18960
taactcgcct tgatcgttgg gaaccggagc tgaatgaagc cataccaaac gacgagcgtg   19020
acaccacgat gcctgtagca atggcaacaa cgttgcgcaa actattaact ggcgaactac   19080
ttactctagc ttcccggcaa caattaatag actggatgga ggcggataaa gttgcaggac   19140
cacttctgcg ctcggccctt ccggctggct ggtttattgc tgataaatct ggagccggtg   19200
agcgtgggtc tcgcggtatc attgcagcac tggggccaga tggtaagccc tcccgtatcg   19260
tagttatcta cacgacgggg agtcaggcaa ctatggatga acgaaataga cagatcgctg   19320
agataggtgc ctcactgatt aagcattggt aactgtcaga ccaagtttac tcatatatac   19380
tttagattga tttaaaactt cattttaat ttaaaaggat ctaggtgaag atccttttg     19440 ataatctcat gaccaaaatc ccttaacgtg agttttcgtt ccactgagcg tcagaccccg   19500
tagaaaagat caaaggatct tcttgagatc ctttttttct gcgcgtaatc tgctgcttgc   19560
aaacaaaaaa accaccgcta ccagcggtgg tttgtttgcc ggatcaagag ctaccaactc   19620 ttttccgaa ggtaactggc ttcagcagag cgcagatacc aaatactgtc cttctagtgt    19680
agccgtagtt aggccaccac ttcaagaact ctgtagcacc gcctacatac ctcgctctgc   19740
taatcctgtt accagtggct gctgccagtg gcgataagtc gtgtcttacc gggttggact   19800
caagacgata gttaccggat aaggcgcagc ggtcgggctg aacggggggt tcgtgcacac   19860
agcccagctt ggagcgaacg acctacaccg aactgagata cctacagcgt gagcattgag   19920
aaagcgccac gcttcccgaa gggagaaagg cggacaggta tccggtaagc ggcagggtcg   19980
gaacaggaga gcgcacgagg gagcttccag ggggaaacgc ctggtatctt tatagtcctg   20040
tcgggtttcg ccacctctga cttgagcgtc gatttttgtg atgctcgtca gggggcgga    20100 gcctatggaa aaacgccagc aacgcggcct ttttacggtt cctggccttt tgctggcctt   20160
ttgctcacat gttctttcct gcgttatccc ctgattctgt ggataaccgt attaccgcct   20220
ttgagtgagc tgataccgct cgccgcagcc gaacgaccga gcgcagcgag tcagtgagcg   20280
aggaagcgga gagcgccca atacgcaaac cgcctctccc cgcgcgttgg ccgattcatt    20340
aatgcagctg gcacgacagg tttcccgact ggaaagcggg cagtgagcgc aacgcaatta   20400
atgtgagtta gctcactcat taggcacccc aggctttaca ctttatgctt ccggctcgta   20460
tgttgtgtgg aattgtgagc ggataacaat ttcacacagg aaacagctat gaccatgatt   20520
acgccaagct tacgcgtcct ggcattatgc ccagtacatg accttatggg actttcctac   20580
```

| | | | | |
|---|---|---|---|---|
| ttggcagtac | atctacgtat | tagtcatcgc | tattaccatg gtgatgcggt | tttggcagta | 20640 |
| catcaatggg | cgtggatagc | ggtttgactc | acggggattt ccaagtctcc | accccattga | 20700 |
| cgtcaatggg | agtttgtttt | ggcaccaaaa | tcaacggac tttccaaaat | gtcgtaacaa | 20760 |
| ctccgcccca | ttgacgcaaa | tgggcggtag | gcgtgtacgg tgggaggtct | atataagcag | 20820 |
| agctcgttta | gtgaaccgtg | g | | 20841 |

<210> SEQ ID NO 5
<211> LENGTH: 7765
<212> TYPE: DNA
<213> ORGANISM: Artificial
<220> FEATURE:
<223> OTHER INFORMATION: plasmid DNA

<400> SEQUENCE: 5

| | | | | |
|---|---|---|---|---|
| agcttgcatg | cctgcaggtc | aattccctgg | cattatgccc agtacatgac | cttatgggac | 60 |
| tttcctactt | ggcagtacat | ctacgtatta | gtcatcgcta ttaccatggt | gatgcggttt | 120 |
| tggcagtaca | tcaatgcgcg | tggataccgg | tttgactcac ggggatttcc | aagtctccac | 180 |
| cccattcacg | tcaatgggag | tttgttttgg | caccaaaatc aacggacttt | ccaaaatgt | 240 |
| cgtaacaact | ccgccccatt | gacgcaaatg | gcggtaggc gtgtacggtg | gaggtctat | 300 |
| ataagcagag | ctcgtttagt | gaaccgtcag | atcgcctgga cgccatcc | acgctgtttt | 360 |
| gacctccata | agagacaccg | ggaccgatcc | agcctgggga tctagcctcc | gcggccggga | 420 |
| acggtgcatt | ggaacgcgga | ttccccgtgc | aagagtgac gtaagtaccg | cctatagagt | 480 |
| ctataggccc | accccttggc | ttcttatgc | atgctatact gttttggct | tggggtctat | 540 |
| acaccccgc | ttcctcatgt | tataggtgat | ggtatagctt agcctatagg | tgtgggttat | 600 |
| tgaccattat | tgaccactcc | cctattggtg | acgatacttt ccattactaa | tccataacat | 660 |
| ggctctttgc | cacaactctc | tttattggct | atatgccaat acactgtcct | tcagagactg | 720 |
| acacggactc | tgtattttta | caggatgggg | tctcatttat tatttacaaa | ttcacatata | 780 |
| caacaccacc | gtccccagtg | cccgcagttt | ttattaaaca taacgtggga | tctccacgcg | 840 |
| aatctcgggt | acgtgttccg | gacatgggct | cttctccggt agcggcggag | ctcctacatc | 900 |
| cgagccctgc | tcccatgcct | ccagcgactc | atggtcgctc ggcagctcct | tgctcctaac | 960 |
| agtggaggcc | agacttaggc | acagcacgat | gcccaccacc accagtgtgc | cgcacaaggc | 1020 |
| cgtggcggta | gggtatgtgt | ctgaaaatga | gctcggggag cgggcttgca | ccgctgacgc | 1080 |
| atttggaaga | cttaaggcag | cggcagaaga | agatgcaggc agctgagttg | ttgtgttctg | 1140 |
| ataagagtca | gaggtaactc | ccgttgcggt | gctgttaacg gtggaggca | gtgtagtctg | 1200 |
| agcagtactc | gttgctgccg | cgcgcgccac | cagacataat agctgacaga | ctaacagact | 1260 |
| gttcctttcc | atgggtcttt | tctgcagtca | ccgtccttga cacgatcgga | tcccgggtac | 1320 |
| ctctagaaga | tctgatatcg | tcgacctcga | ggccaccatg ccacacttt | taaggagctt | 1380 |
| agcattgttc | aaaagaaaca | aggacaaacc | acccattaca tcaggatccg | gtggagccat | 1440 |
| cagaggaatc | aaaacacatta | ttatagtacc | aatccctgga gattcctcaa | ttaccactcg | 1500 |
| atccagactt | ctggaccggt | tggtgaggtt | aattggaaac ccggatgtga | gcgggcccaa | 1560 |
| actaacaggg | gcactaatag | gtatattatc | cttatttgtg gagtctccag | gtcaattgat | 1620 |
| tcagaggatc | accgatgacc | ctgacgttag | cataaggctg ttagaggttg | tccagagtga | 1680 |
| ccagtcacaa | tctggcctta | ccttcgcatc | aagaggtacc aacatggagg | atgaggcgga | 1740 |

```
ccaatacttt tcacatgatg atccaattag tagtgatcaa tccaggttcg gatggttcgg      1800
gaacaaggaa atctcagata ttgaagtgca agaccctgag ggattcaaca tgattctggg      1860
taccatccta gcccaaattt gggtcttgct cgcaaaggcg gttacggccc cagacacggc      1920
agctgattcg gagctaagaa ggtggataaa gtacacccaa caaagaaggg tagttggtga      1980
atttagattg gagagaaaat ggttggatgt ggtgaggaac aggattgccg aggacctctc      2040
cttacgccga ttcatggtcg ctctaatcct ggatatcaag agaacacccg gaaacaaacc      2100
caggattgct gaaatgatat gtgacattga tacatatatc gtagaggcag gattagccag      2160
ttttatcctg actattaagt ttgggataga aactatgtat cctgctcttg gactgcatga      2220
atttgctggt gagttatcca cacttgagtc cttgatgaac ctttaccagc aaatggggga      2280
aactgcaccc tacatggtaa tcctggagaa ctcaattcag aacaagttca gtgcaggatc      2340
ataccctctg ctctggagct atgccatggg agtaggagtg gaacttgaaa actccatggg      2400 aggttttgaac tttggccgat cttactttga tccagcatat tttagattag ggcaagagat      2460
ggtaaggagg tcagctggaa aggtcagttc acattggca tctgaactcg gtatcactgc       2520
cgaggatgca aggcttgttt cagagattgc aatgcatact actgaggaca agatcagtag      2580
agcggttgga cccagacaag cccaagtatc atttctacac ggtgatcaaa gtgagaatga      2640
gctaccgaga ttgggggggca aggaagatag gagggtcaaa cagagtcgag gagaagccag      2700
ggagagctac agagaaaccg ggcccagcag agcaagtgat gcgagagctg cccatcttcc      2760
aaccggcaca cccctagaca ttgacactgc aacggagtcc agccaagatc cgcaggacag      2820
tcgaaggtca gctgacgccc tgcttaggct gcaagccatg gcaggaatct cggaagaaca      2880
aggctcagac acggacaccc ctatagtgta caatgacaga aatcttctag actaggtgcg      2940
agaggccgag ggccagaaca acatccgcct accatccatc attctcgagg aattctagat      3000
cccacgtcac tattgtatac tctatattat actctatgtt atactctgta atcctactca      3060
ataaacgtgt cacgcctgtg aaaccgtact aagtctcccg tgtcttctta tcaccatcag      3120
gtgacatcct cgcccaggct gtcaatcatg ccggtatcga ttccagtagc accggcccca      3180
cgctgacaac ccactcttgc agcgttagca gcgcccctct taacaagccg acccccacca      3240
gcgtcgcggt tactaacact cctctccccg acctgcagcc caagctctag agggccctat      3300
tctatagtgt cacctaaatg ctagagctcg ctgatcagcc tcgactgtgc cttctagttg      3360
ccagccatct gttgtttgcc cctcccccgt gccttccttg accctggaag gtgccactcc      3420
cactgtcctt tcctaataaa atgaggaaat tgcatcgcat tgtctgagta ggtgtcattc      3480
tattctgggg ggtggggtgg ggcaggacag caagggggag gattgggaag acaatagcag      3540
gcatgctggg gatgcggtgg gctctatggc ttctgaggcg gaaagaacca gctgggctc       3600 taggggtat ccccacgcgc cctgtagcgg cgcattaagc gcggcgggtg tggtggttac       3660
gcgcagcgtg accgctacac ttgccagcgc cctagcgccc gctcctttcg ctttcttccc      3720
ttcctttctc gccacgttcg ccggctttcc ccgtcaagct ctaaatcggg gcatcccttt      3780
agggttccga tttagtgctt tacggcacct cgaccccaaa aaacttgatt agggtgatgg      3840
ttcacgtagt gggccatcgc cctgatagac ggtttttcgc cctttgacgt tggagtccac      3900
gttctttaat agtggactct tgttccaaac tggaacaaca ctcaaccta tctcggtcta       3960 ttcttttgat ttataaggga ttttggggat ttcggcctat tggttaaaaa atgagctgat      4020
ttaacaaaaa tttaacgcga attaattctg tggaatgtgt gtcagttagg gtgtggaaag      4080
tccccaggct ccccaggcag gcagaagtat gcaaagcatg catctcaatt agtcagcaac      4140
```

```
caggtgtgga aagtccccag gctccccagc aggcagaagt atgcaaagca tgcatctcaa    4200
ttagtcagca accatagtcc cgcccctaac tccgcccatc ccgcccctaa ctccgcccag    4260
ttccgcccat tctccgcccc atggctgact aatttttttt atttatgcag aggccgaggc    4320
cgcctctgcc tctgagctat tccagaagta gtgaggaggc ttttttggag cctaggcttt    4380
ttgcaaaaag ctcccgggag cttgtatatc cattttcgga tctgatcaag agacaggatg    4440
aggatcgttt cgcatgattg aacaagatgg attgcacgca ggttctccgg ccgcttgggt    4500
ggagaggcta ttcggctatg actgggcaca acagacaatc ggctgctctg atgccgccgt    4560
gttccggctg tcagcgcagg ggcgcccggt tctttttgtc aagaccgacc tgtccggtgc    4620
cctgaatgaa ctgcaggacg aggcagcgcg gctatcgtgg ctggccacga cgggcgttcc    4680
ttgcgcagct gtgctcgacg ttgtcactga agcgggaagg gactggctgc tattgggcga    4740
agtgccgggg caggatctcc tgtcatctca ccttgctcct gccgagaaag tatccatcat    4800
ggctgatgca atgcggcggc tgcatacgct tgatccggct acctgcccat tcgaccacca    4860
agcgaaacat cgcatcgagc gagcacgtac tcggatggaa gccggtcttg tcgatcagga    4920
tgatctggac gaagagcatc aggggctcgc gccagccgaa ctgttcgcca ggctcaaggc    4980
gcgcatgccc gacggcgagg atctcgtcgt gacccatggc gatgcctgct tgccgaatat    5040
catggtggaa aatggccgct tttctggatt catcgactgt ggccggctgg gtgtggcgga    5100
ccgctatcag gacatagcgt tggctacccg tgatattgct gaagagcttg gcggcgaatg    5160
ggctgaccgc ttcctcgtgc tttacggtat cgccgctccc gattcgcagc gcatcgcctt    5220
ctatcgcctt cttgacgagt tcttctgagc gggactctgg ggttcgaaat gaccgaccaa    5280
gcgacgccca acctgccatc acgagatttc gattccaccg ccgccttcta tgaaaggttg    5340
ggcttcggaa tcgttttccg ggacgccggc tggatgatcc tccagcgcgg ggatctcatg    5400
ctggagttct tcgcccaccc caacttgttt attgcagctt ataatggtta caaataaagc    5460
aatagcatca caaatttcac aaataaagca tttttttcac tgcattctag ttgtggtttg    5520
tccaaactca tcaatgtatc ttatcatgtc tgtataccgt cgacctctag ctagagcttg    5580
gcgtaatcat ggtcatagct gtttcctgtg tgaaattgtt atccgctcac aattccacac    5640
aacatacgag ccggaagcat aaagtgtaaa gcctggggtg cctaatgagt gagctaactc    5700
acattaattg cgttgcgctc actgcccgct ttccagtcgg gaaacctgtc gtgccagctg    5760
cattaatgaa tcggccaacg cgcggggaga ggcggtttgc gtattgggcg ctcttccgct    5820
tcctcgctca ctgactcgct gcgctcggtc gttcggctgc ggcgagcggt atcagctcac    5880
tcaaaggcgg taatacggtt atccacagaa tcaggggata acgcaggaaa gaacatgtga    5940
gcaaaaggcc agcaaaaggc caggaaccgt aaaaaggccg cgttgctggc gttttttcat    6000
aggctccgcc cccctgacga gcatcacaaa aatcgacgct caagtcagag gtggcgaaac    6060
ccgacaggac tataaagata ccaggcgttt cccectggaa gctccctcgt gcgctctcct    6120
gttccgaccc tgccgcttac cggatacctg tccgcctttc tcccttcggg aagcgtggcg    6180
ctttctcaat gctcacgctg taggtatctc agttcggtgt aggtcgttcg ctccaagctg    6240
ggctgtgtgc acgaacccc cgttcagccc gaccgctgcg ccttatccgg taactatcgt    6300
cttgagtcca acccggtaag acacgactta tcgccactgg cagcagccac tggtaacagg    6360
attagcagag cgaggtatgt aggcggtgct acagagttct tgaagtggtg gcctaactac    6420
ggctacacta gaaggacagt atttggtatc tgcgctctgc tgaagccagt taccttcgga    6480
```

```
aaaagagttg gtagctcttg atccggcaaa caaaccaccg ctggtagcgg tggttttttt    6540
gtttgcaagc agcagattac gcgcagaaaa aaggatctc aagaagatcc tttgatcttt    6600
tctacggggt ctgacgctca gtggaacgaa aactcacgtt aagggatttt ggtcatgaga    6660
ttatcaaaaa ggatcttcac ctagatcctt taaattaaa aatgaagttt taaatcaatc    6720
taaagtatat atgagtaaac ttggtctgac agttaccaat gcttaatcag tgaggcacct    6780
atctcagcga tctgtctatt tcgttcatcc atagttgcct gactccccgt cgtgtagata    6840
actacgatac gggagggctt accatctggc cccagtgctg caatgatacc gcgagaccca    6900
cgctcaccgg ctccagattt atcagcaata accagccag ccggaagggc cgagcgcaga    6960
agtggtcctg caactttatc cgcctccatc cagtctatta attgttgccg ggaagctaga    7020
gtaagtagtt cgccagttaa tagttttcgc aacgttgttg ccattgctac aggcatcgtg    7080
gtgtcacgct cgtcgtttgg tatggcttca ttcagctccg gttcccaacg atcaaggcga    7140
gttacatgat cccccatgtt gtgcaaaaaa gcggttagct ccttcggtcc tccgatcgtt    7200
gtcagaagta agttggccgc agtgttatca ctcatggtta tggcagcact gcataattct    7260
cttactgtca tgccatccgt aagatgcttt tctgtgactg gtgagtactc aaccaagtca    7320
ttctgagaat agtgtatgcg cgaccgagt tgctcttgcc cggcgtcaat acgggataat    7380
accgcgccac atagcagaac tttaaaagtg ctcatcattg gaaaacgttc ttcggggcga    7440
aaactctcaa ggatcttacc gctgttgaga tccagttcga tgtaacccac tcgtgcaccc    7500
aactgatctt cagcatcttt tactttcacc agcgtttctg ggtgagcaaa aacaggaagg    7560
caaaatgccg caaaaaaggg aataagggcg acacggaaat gttgaatact catactcttc    7620 cttttttcaat attattgaag catttatcag ggttattgtc tcatgagcgg atacatattt    7680
gaatgtattt agaaaaataa acaaataggg gttccgcgca catttccccg aaaagtgcca    7740
cctgacgtcg acggatcggg agatc                                        7765

<210> SEQ ID NO 6
<211> LENGTH: 7723
<212> TYPE: DNA
<213> ORGANISM: Artificial
<220> FEATURE:
<223> OTHER INFORMATION: plasmid DNA

<400> SEQUENCE: 6
agcttgcatg cctgcaggtc aattccctgg cattatgccc agtacatgac cttatgggac      60
tttcctactt ggcagtacat ctacgtatta gtcatcgcta ttaccatggt gatgcggttt     120
tggcagtaca tcaatgcgcg tggataccgg tttgactcac ggggatttcc aagtctccac     180
cccattcacg tcaatgggag tttgttttgg caccaaaatc aacgggactt tccaaaatgt     240
cgtaacaact ccgccccatt gacgcaaatg ggcggtaggc gtgtacggtg ggaggtctat     300
ataagcagag ctcgtttagt gaaccgtcag atcgcctgga cacgccatcc acgctgtttt     360
gacctccata gaagacaccg ggaccgatcc agcctgggga tctagcctcc gcggccggga     420
acggtgcatt ggaacgcgga ttccccgtgc caagagtgac gtaagtaccg cctatagagt     480
ctataggccc acccccttgg cttcttatgc atgctatact gtttttggct ggggtctat     540 acacccccgc ttcctcatgt tataggtgat ggtatagctt agcctatagg tgtgggttat     600
tgaccattat tgaccactcc ctattggtg acgatacttt ccattactaa tccataacat     660
ggctctttgc cacaactctc tttattggct atatgccaat acactgtcct tcagagactg     720
acacggactc tgtatttta caggatgggg tctcatttat tatttacaaa ttcacatata     780
```

```
caacaccacc gtccccagtg cccgcagttt ttattaaaca taacgtggga tctccacgcg      840
aatctcgggt acgtgttccg gacatgggct cttctccggt agcggcggag ctcctacatc      900
cgagccctgc tcccatgcct ccagcgactc atggtcgctc ggcagctcct tgctcctaac      960
agtggaggcc agacttaggc acagcacgat gcccaccacc accagtgtgc cgcacaaggc     1020
cgtggcggta gggtatgtgt ctgaaaatga gctcggggag cgggcttgca ccgctgacgc     1080
atttggaaga cttaaggcag cggcagaaga agatgcaggc agctgagttg ttgtgttctg     1140
ataagagtca gaggtaactc ccgttgcggt gctgttaacg gtggagggca gtgtagtctg     1200
agcagtactc gttgctgccg cgcgcgccac cagacataat agctgacaga ctaacagact     1260
gttcctttcc atgggtcttt tctgcagtca ccgtccttga cacgatcgga tcccgggtac     1320
ctctagaaga tctgatatcg tcgacctcga ggccaccatg gcagaagagc aggcacgcca     1380
tgtcaaaaac ggactggaat gcatccgggc tctcaaggcc gagcccatcg gctcactggc     1440
catcgaggaa gctatggcag catggtcaga aatatcagac aacccaggac aggagcgagc     1500
cacctgcagg gaagagaagg caggcagttc gggtctcagc aaaccatgcc tctcagcaat     1560
tggatcaact gaaggcggtg cacctcgcat ccgcggtcag ggacctggag agagcgatga     1620
cgacgctgaa actttgggaa tccccccaag aaatctccag gcatcaagca ctgggttaca     1680
gtgttattac gttatgatc acagcggtga agcggttaag ggaatccaag atgctgactc     1740
tatcatggtt caatcaggcc ttgatggtga tagcaccctc tcaggaggag acaatgaatc     1800
tgaaaacagc gatgtggata ttggcgaacc tgataccgag ggatatgcta tcactgaccg     1860
gggatctgct cccatctcta tggggttcag ggcttctgat gttgaaactg cagaaggagg     1920
ggagatccac gagctcctga gactccaatc cagaggcaac aactttccga agcttgggaa     1980
aactctcaat gttcctccgc ccccggaccc cggtagggcc agcacttccg ggacacccat     2040
taaaaagggc acagacgcga gattagcctc atttggaacg gagatcgcgt ctttattgac     2100
aggtggtgca acccaatgtg ctcgaaagtc accctcggaa ccatcagggc caggtgcacc     2160 tgcgggaat gtccccgagt gtgtgagcaa tgccgcactg atacaggagt ggacacccga     2220
atctggtacc acaatctccc cgagatccca gaataatgaa gaaggggag actattatga     2280 tgatgagctg ttctctgatg tccaagatat taaaacagcc ttggccaaaa tacacgagga     2340
taatcagaag ataatctcca agctagaatc actgctgtta ttgaagggag aagttgagtc     2400
aattaagaag cagatcaaca ggcaaaatat cagcatatcc accctggaag gacacctctc     2460
aagcatcatg atcgccattc ctggacttgg gaaggatccc aacgacccca ctgcagatgt     2520
cgaaatcaat cccgacttga aacccatcat aggcagagat tcaggccgag cactggccga     2580
agttctcaag aaacccgttg ccagccgaca actccaagga atgacaaatg gacggaccag     2640
ttccagagga cagctgctga aggaatttca gctaaagccg atcgggaaaa agatgagctc     2700
agccgtcggg tttgttcctg acaccggccc tgcatcacgc agtgtaatcc gctccattat     2760
aaaatccagc cggctagagg aggatcggaa gcgttacctg atgactctcc ttgatgatat     2820
caaaggagcc aatgatcttg ccaagttcca ccagatgctg atgaagataa taatgaagta     2880
gctacagctc aacttacctg ccaaccccat gccagtcgac ccaactagta caacctaaat     2940
cctcgaggaa ttctagatcc cacgtcacta ttgtatactc tatattatac tctatgttat     3000
actctgtaat cctactcaat aaacgtgtca cgcctgtgaa accgtactaa gtctcccgtg     3060
tcttcttatc accatcaggt gacatcctcg cccaggctgt caatcatgcc ggtatcgatt     3120
```

```
ccagtagcac cggccccacg ctgacaaccc actcttgcag cgttagcagc gcccctctta    3180
acaagccgac ccccaccagc gtcgcggtta ctaacactcc tctccccgac ctgcagccca    3240
agctctagag ggccctattc tatagtgtca cctaaatgct agagctcgct gatcagcctc    3300
gactgtgcct tctagttgcc agccatctgt tgtttgcccc tccccgtgc cttccttgac     3360 cctggaaggt gccactccca ctgtcctttc ctaataaaat gaggaaattg catcgcattg    3420
tctgagtagg tgtcattcta ttctgggggg tggggtgggg caggacagca agggggagga    3480
ttgggaagac aatagcaggc atgctgggga tgcggtgggc tctatggctt ctgaggcgga    3540
aagaaccagc tggggctcta gggggtatcc ccacgcgccc tgtagcggcg cattaagcgc    3600
ggcgggtgtg gtggttacgc gcagcgtgac cgctacactt gccagcgccc tagcgcccgc    3660
tcctttcgct ttcttccctt cctttctcgc cacgttcgcc ggctttcccc gtcaagctct    3720
aaatcggggc atccctttag ggttccgatt tagtgcttta cggcacctcg accccaaaaa    3780
acttgattag ggtgatggtt cacgtagtgg gccatcgccc tgatagacgg ttttcgccc     3840 tttgacgttg gagtccacgt tctttaatag tggactcttg ttccaaactg gaacaacact    3900
caaccctatc tcggtctatt cttttgattt ataagggatt ttggggattt cggcctattg    3960
gttaaaaaat gagctgattt aacaaaaatt taacgcgaat taattctgtg gaatgtgtgt    4020
cagttagggt gtggaaagtc cccaggctcc ccaggcaggc agaagtatgc aaagcatgca    4080
tctcaattag tcagcaacca ggtgtggaaa gtccccaggc tccccagcag gcagaagtat    4140
gcaaagcatg catctcaatt agtcagcaac catagtcccg cccctaactc cgcccatccc    4200
gcccctaact ccgcccagtt ccgcccattc tccgccccat ggctgactaa ttttttttat    4260
ttatgcagag gccgaggccg cctctgcctc tgagctattc cagaagtagt gaggaggctt    4320
ttttggagcc ctaggctttt gcaaaaagct cccgggagct gtatatcca ttttcggatc     4380 tgatcaagag acaggatgag gatcgtttcg catgattgaa caagatggat tgcacgcagg    4440
ttctccggcc gcttgggtgg agaggctatt cggctatgac tgggcacaac agacaatcgg    4500
ctgctctgat gccgccgtgt tccggctgtc agcgcagggg cgcccggttc ttttgtcaa     4560 gaccgacctg tccggtgccc tgaatgaact gcaggacgag gcagcgcggc tatcgtggct    4620
ggccacgacg ggcgttcctt gcgcagctgt gctcgacgtt gtcactgaag cgggaaggga    4680
ctggctgcta ttgggcgaag tgccggggca ggatctcctg tcatctcacc ttgctcctgc    4740
cgagaaagta tccatcatgg ctgatgcaat gcggcggctg catacgcttg atccggctac    4800
ctgcccattc gaccaccaag cgaaacatcg catcgagcga gcacgtactc ggatggaagc    4860
cggtcttgtc gatcaggatg atctggacga agagcatcag gggctcgcgc cagccgaact    4920
gttcgccagg ctcaaggcgc gcatgcccga cggcgaggat ctcgtcgtga cccatggcga    4980
tgcctgcttg ccgaatatca tggtggaaaa tggccgcttt tctggattca tcgactgtgg    5040
ccggctgggt gtggcggacc gctatcagga catagcgttg ctacccgtg atattgctga    5100 agagcttggc ggcgaatggg ctgaccgctt cctcgtgctt tacggtatcg ccgctcccga    5160
ttcgcagcgc atcgccttct atcgccttct tgacgagttc ttctgagcgg gactctgggg    5220
ttcgaaatga ccgaccaagc gacgcccaac ctgccatcac gagatttcga ttccaccgcc    5280
gccttctatg aaaggttggg cttcggaatc gttttccggg acgccggctg atgatcctc     5340 cagcgcgggg atctcatgct ggagttcttc gcccacccca acttgtttat tgcagcttat    5400
aatggttaca aataaagcaa tagcatcaca aatttcacaa ataaagcatt ttttcactg     5460 cattctagtt gtggtttgtc caaactcatc aatgtatctt atcatgtctg tataccgtcg    5520
```

```
acctctagct agagcttggc gtaatcatgg tcatagctgt ttcctgtgtg aaattgttat   5580
ccgctcacaa ttccacacaa catacgagcc ggaagcataa agtgtaaagc ctggggtgcc   5640
taatgagtga gctaactcac attaattgcg ttgcgctcac tgcccgcttt ccagtcggga   5700
aacctgtcgt gccagctgca ttaatgaatc ggccaacgcg cggggagagg cggtttgcgt   5760
attgggcgct cttccgcttc ctcgctcact gactcgctgc gctcggtcgt tcggctgcgg   5820
cgagcggtat cagctcactc aaaggcggta atacggttat ccacagaatc aggggataac   5880
gcaggaaaga acatgtgagc aaaaggccag caaaaggcca ggaaccgtaa aaaggccgcg   5940
ttgctggcgt ttttccatag gctccgcccc cctgacgagc atcacaaaaa tcgacgctca   6000
agtcagaggt ggcgaaaccc gacaggacta taaagatacc aggcgtttcc ccctggaagc   6060
tccctcgtgc gctctcctgt tccgaccctg ccgcttaccg gatacctgtc cgcctttctc   6120
ccttcgggaa gcgtggcgct ttctcaatgc tcacgctgta ggtatctcag ttcggtgtag   6180
gtcgttcgct ccaagctggg ctgtgtgcac gaaccccccg ttcagcccga ccgctgcgcc   6240
ttatccggta actatcgtct tgagtccaac ccggtaagac acgacttatc gccactggca   6300
gcagccactg gtaacaggat tagcagagcg aggtatgtag cggtgctac agagttcttg    6360
aagtggtggc ctaactacgg ctacactaga aggacagtat ttggtatctg cgctctgctg   6420
aagccagtta ccttcggaaa aagagttggt agctcttgat ccggcaaaca aaccaccgct   6480
ggtagcggtg gtttttttgt ttgcaagcag cagattacgc gcagaaaaaa aggatctcaa   6540
gaagatcctt tgatcttttc tacggggtct gacgctcagt ggaacgaaaa ctcacgttaa   6600
gggattttgg tcatgagatt atcaaaaagg atcttcacct agatcctttt aaattaaaaa   6660
tgaagtttta aatcaatcta agtatatat gagtaaactt ggtctgacag ttaccaatgc    6720
ttaatcagtg aggcacctat ctcagcgatc tgtctatttc gttcatccat agttgcctga   6780
ctccccgtcg tgtagataac tacgatacgg gagggcttac catctggccc cagtgctgca   6840
atgataccgc gagacccacg ctcaccggct ccagatttat cagcaataaa ccagccagcc   6900
ggaagggccg agcgcagaag tggtcctgca actttatccg cctccatcca gtctattaat   6960
tgttgccggg aagctagagt aagtagttcg ccagttaata gtttgcgcaa cgttgttgcc   7020
attgctacag gcatcgtggt gtcacgctcg tcgtttggta tggcttcatt cagctccggt   7080
tcccaacgat caaggcgagt tacatgatcc cccatgttgt gcaaaaaagc ggttagctcc   7140
ttcggtcctc cgatcgttgt cagaagtaag ttggccgcag tgttatcact catggttatg   7200
gcagcactgc ataattctct tactgtcatg ccatccgtaa gatgcttttc tgtgactggt   7260
gagtactcaa ccaagtcatt ctgagaatag tgtatgcggc gaccgagttg ctcttgcccg   7320
gcgtcaatac gggataatac cgcgccacat agcagaactt taaaagtgct catcattgga   7380
aaacgttctt cggggcgaaa actctcaagg atcttaccgc tgttgagatc cagttcgatg   7440
taacccactc gtgcacccaa ctgatcttca gcatctttta ctttcaccag cgtttctggg   7500
tgagcaaaaa caggaaggca aaatgccgca aaaagggaa taagggcgac acggaaatgt    7560
tgaatactca tactcttcct ttttcaatat tattgaagca tttatcaggg ttattgtctc   7620
atgagcggat acatatttga atgtatttag aaaaataaac aaatagggt tccgcgcaca    7680
tttccccgaa aagtgccacc tgacgtcgac ggatcgggag atc                     7723
```

<210> SEQ ID NO 7
<211> LENGTH: 12739
<212> TYPE: DNA

<213> ORGANISM: Artificial
<220> FEATURE:
<223> OTHER INFORMATION: plasmid DNA

<400> SEQUENCE: 7

```
agcttgcatg cctgcaggtc aattccctgg cattatgccc agtacatgac cttatgggac      60
tttcctactt ggcagtacat ctacgtatta gtcatcgcta ttaccatggt gatgcggttt     120
tggcagtaca tcaatgcgcg tggataccgg tttgactcac ggggatttcc aagtctccac     180
cccattcacg tcaatgggag tttgttttgg caccaaaatc aacgggactt tccaaaatgt     240
cgtaacaact ccgccccatt gacgcaaatg ggcggtaggc gtgtacggtg ggaggtctat     300
ataagcagag ctcgtttagt gaaccgtcag atcgcctgga gacgccatcc acgctgtttt     360
gacctccata gaagacaccg ggaccgatcc agcctgggga tctagcctcc gcggccggga     420
acggtgcatt ggaacgcgga ttccccgtgc caagagtgac gtaagtaccg cctatagagt     480
ctataggccc accccttgg cttcttatgc atgctatact gtttttggct tggggtctat     540
acaccccgc ttcctcatgt tataggtgat ggtatagctt agcctatagg tgtgggttat     600
tgaccattat tgaccactcc cctattggtg acgatacttt ccattactaa tccataacat     660
ggctctttgc cacaactctc tttattggct atatgccaat acactgtcct tcagagactg     720
acacggactc tgtatttta caggatgggg tctcatttat tatttacaaa ttcacatata     780
caacaccacc gtccccagtg cccgcagttt ttattaaaca taacgtggga tctccacgcg     840
aatctcgggt acgtgttccg gacatgggct cttctccggt agcggcggag ctcctacatc     900
cgagccctgc tccatgcct ccagcgactc atggtcgctc ggcagctcct tgctcctaac     960
agtggaggcc agacttaggc acagcacgat gcccaccacc accagtgtgc cgcacaaggc    1020
cgtggcggta gggtatgtgt ctgaaaatga gctcggggag cgggcttgca ccgctgacgc    1080
atttggaaga cttaaggcag cggcagaaga agatgcaggc agctgagttg ttgtgttctg    1140
ataagagtca gaggtaactc ccgttgcggt gctgttaacg gtggagggca gtgtagtctg    1200
agcagtactc gttgctgccg cgcgcgccac cagacataat agctgacaga ctaacagact    1260
gttcctttcc atgggtcttt tctgcagtca ccgtccttga cacgatcgga tcccgggtac    1320
ctctagaaga tctgatatcg tcgacctcga cgccaccatg gactcgctat ctgtcaacca    1380
gatcttatac cctgaagttc acctagatag cccgatagtt accaataaga tagtagccat    1440
cctggagtat gctcgagtcc ctcacgctta cagcctggag gaccctacac tgtgtcagaa    1500
catcaagcac cgcctaaaaa acggattttc caaccaaatg attataaaca atgtggaagt    1560
tgggaatgtc atcaagtcca agcttaggag ttatccggcc cactctcata ttccatatcc    1620
aaattgtaat caggatttat ttaacataga agacaaagag tcaacgagga agatccgtga    1680
actcctcaaa aagggggaatt cgctgtactc caaagtcagt gataaggttt tccaatgctt    1740
aagggacact aactcacggc ttggcctagg ctccgaattg agggaggaca tcaaggagaa    1800
agttattaac ttgggagttt acatgcacag ctcccagtgg tttgagccct ttctgttttg    1860
gtttacagtc aagactgaga tgaggtcagt gattaaatca caaacccata cttgccatag    1920
gaggagacac acacctgtat tcttcactgg tagttcagtt gagttgctaa tctctcgtga    1980
ccttgttgct ataatcagta aagagtctca acatgtatat tacctgacat ttgaactggt    2040
tttgatgtat tgtgatgtca tagaggggag gttaatgaca gagaccgcta tgactattga    2100
tgctaggtat acagagcttc taggaagagt cagatacatg tggaaactga tagatggttt    2160
cttccctgca ctcgggaatc caacttatca aattgtagcc atgctggagc ctctttcact    2220
```

```
tgcttacctg cagctgaggg atataacagt agaactcaga ggtgctttcc ttaaccactg    2280
ctttactgaa atacatgatg ttcttgacca aaacgggttt tctgatgaag gtacttatca    2340
tgagttaact gaagctctag attacatttt cataactgat gacatacatc tgacagggga    2400
gattttctca tttttcagaa gtttcggcca ccccagactt gaagcagtaa cggctgctga    2460
aaatgttagg aaatacatga atcagcctaa agtcattgtg tatgagactc tgatgaaagg    2520
tcatgccata ttttgtggaa tcataatcaa cggctatcgt gacaggcacg gaggcagttg    2580
gccaccgctg accctccccc tgcatgctgc agacacaatc cggaatgctc aagcttcagg    2640
tgaagggtta acacatgagc agtgcgttga taactggaaa tcttttgctg gagtgaaatt    2700
tggctgcttt atgcctctta gcctggatag tgatctgaca atgtacctaa aggacaaggc    2760
acttgctgct ctccaaaggg aatgggattc agtttacccg aaagagttcc tgcgttacga    2820
ccctcccaag ggaaccgggt cacggaggct tgtagatgtt ttccttaatg attcgagctt    2880
tgacccatat gatgtgataa tgtatgttgt aagtggagct tacctccatg accctgagtt    2940
caacctgtct tacagcctga agaaaaagga gatcaaggaa acaggtagac tttttgctaa    3000
aatgacttac aaaatgaggg catgccaagt gattgctgaa atctaatct caaacgggat     3060 tggcaaatat tttaaggaca atgggatggc caaggatgag cacgatttga ctaaggcact    3120
ccacactcta gctgtctcag gagtccccaa agatctcaaa gaaagtcaca gggggggcc     3180 agtcttaaaa acctactccc gaagcccagt ccacacaagt accaggaacg tgagagcagc    3240
aaaagggttt atagggttcc ctcaagtaat tcggcaggac caagacactg atcatccgga    3300
gaatatggaa gcttacgaga cagtcagtgc atttatcacg actgatctca agaagtactg    3360
ccttaattgg agatatgaga ccatcagctt gtttgcacag aggctaaatg agatttacgg    3420
attgccctca ttttccagt ggctgcataa gaggcttgag acctctgtcc tgtatgtaag     3480
tgaccctcat tgcccccccg accttgacgc ccatatcccg ttatataaag tccccaatga    3540
tcaaatcttc attaagtacc ctatgggagg tatagaaggg tattgtcaga agctgtggac    3600
catcagcacc attccctatc tatacctggc tgcttatgag agcggagtaa ggattgcttc    3660
gttagtgcaa ggggacaatc agaccatagc cgtaacaaaa agggtaccca gcacatggcc    3720
ctacaacctt aagaaacggg aagctgctag agtaactaga gattactttg taattcttag    3780
gcaaaggcta catgatattg ccatcaccct caaggcaaat gagacaattg tttcatcaca    3840 ttttttttgtc tattcaaaag gaatatatta tgatgggcta cttgtgtccc aatcactcaa    3900
gagcatcgca agatgtgtat tctggtcaga gactatagtt gatgaaacaa gggcagcatg    3960
cagtaatatt gctacaacaa tggctaaaag catcgagaga ggttatgacc gttaccttgc    4020
atattccctg aacgtcctaa aagtgataca gcaaattctg atctctcttg gcttcacaat    4080
caattcaacc atgacccggg atgtagtcat accctcctc acaaacaacg acctcttaat     4140
aaggatggca ctgttgcccg ctcctattgg ggggatgaat tatctgaata tgagcaggct    4200
gtttgtcaga aacatcggtg atccagtaac atcatcaatt gctgatctca agagaatgat    4260
tctcgcctca ctaatgcctg aagagaccct ccatcaagta atgacacaac aaccggggga    4320
ctcttcattc ctagactggg ctagcgaccc ttactcagca aatcttgtat gtgtccagag    4380
catcactaga ctcctcaaga acataactgc aaggtttgtc ctgatccata gtccaaaccc    4440
aatgttaaaa ggattattcc atgatgacag taaagaagag gacagagggac tggcggcatt    4500 cctcatggac aggcatatta tagtacctag ggcagctcat gaaatcctgg atcatagtgt    4560
```

```
cacaggggca agagagtcta ttgcaggcat gctggatacc acaaaaggct tgattcgagc    4620
cagcatgagg aagggggggt taacctctcg agtgataacc agattgtcca attatgacta    4680
tgaacaattc agagcaggga tggtgctatt gacaggaaga aagagaaatg tcctcattga    4740
caaagagtca tgttcagtgc agctggcgag agctctaaga agccatatgt gggcgaggct    4800
agctcgagga cggcctattt acggccttga ggtccctgat gtactagaat ctatgcgagg    4860
ccaccttatt cggcgtcatg agacatgtgt catctgcgag tgtggatcag tcaactacgg    4920
atggtttttt gtcccctcgg gttgccaact ggatgatatt gacaaggaaa catcatcctt    4980
gagagtccca tatattggtt ctaccactga tgagagaaca gacatgaagc ttgccttcgt    5040
aagagcccca agtcgatcct tgcgatctgc tgttagaata gcaacagtgt actcatgggc    5100
ttacggtgat gatgatagct cttggaacga agcctggttg ttggctaggc aaagggccaa    5160
tgtgagcctg gaggagctaa gggtgatcac tcccatctca acttcgacta atttagcgca    5220
taggttgagg gatcgtagca ctcaagtgaa atactcaggt acatcccttg tccgagtggc    5280
gaggtatacc acaatctcca acgacaatct ctcatttgtc atatcagata gaaggttga    5340
tactaacttt atataccaac aaggaatgct tctaggggttg ggtgttttag aaacattgtt    5400
tcgactcgag aaagataccg gatcatctaa cacggtatta catcttcacg tcgaaacaga    5460
ttgttgcgtg atcccgatga tagatcatcc caggataccc agctcccgca agctagagct    5520
gagggcagag ctatgtacca acccattgat atatgataat gcacctttaa ttgacagaga    5580
tgcaacaagg ctatacaccc agagccatag gaggcacctt gtggaatttg ttacatggtc    5640
cacacccaa ctatatcaca ttttagctaa gtccacagca ctatctatga ttgacctggt    5700
aacaaaattt gagaaggacc atatgaatga aatttcagct ctcatagggg atgacgatat    5760
caatagtttc ataactgagt ttctgctcat agagccaaga ttattcacta tctacttggg    5820
ccagtgtgcg gccatcaatt gggcatttga tgtacattat catagaccat cagggaaata    5880
tcagatgggt gagctgttgt catcgttcct ttctagaatg agcaaaggag tgtttaaggt    5940
gcttgtcaat gctctaagcc acccaaagat ctacaagaaa ttctggcatt gtggtattat    6000
agagcctatc catggtcctt cacttgatgc tcaaaacttg cacacaactg tgtgcaacat    6060
ggtttacaca tgctatatga cctacctcga cctgttgttg aatgaagagt tagaagagtt    6120
cacatttctc ttgtgtgaaa gcgacgagga tgtagtaccg gacagattcg acaacatcca    6180
ggcaaaacac ttatgtgttc tggcagattt gtactgtcaa ccagggacct gcccaccaat    6240
tcgaggtcta agaccggtag agaaatgtgc agttctaacc gaccatatca aggcagaggc    6300
tatgttatct ccagcaggat cttcgtggaa cataaatcca attattgtag accattactc    6360
atgctctctg acttatctcc ggcgaggatc gatcaaacag ataagattga gagttgatcc    6420
aggattcatt ttcgacgccc tcgctgaggt aaatgtcagt cagccaaaga tcggcagcaa    6480
caacatctca aatatgagca tcaaggcttt cagacccca cacgatgatg ttgcaaaatt    6540
gctcaaagat atcaacacaa gcaagcacaa tcttcccatt tcagggggca atctcgccaa    6600
ttatgaaatc catgctttcc gcagaatcgg gttgaactca tctgcttgct acaaagctgt    6660
tgagatatca acattaatta ggagatgcct tgagccaggg gaggacggct tgttcttggg    6720
tgagggatcg ggttctatgt tgatcactta taaagagata cttaaactaa acaagtgctt    6780
ctataatagt gggggtttccg ccaattctag atctggtcaa agggaattag caccctatcc    6840
ctccgaagtt ggccttgtcg aacacagaat gggagtaggg aatattgtca aagtgctctt    6900
taacgggagg cccgaagtca cgtgggtagg cagtgtagat tgcttcaatt tcatagttag    6960
```

```
taatatccct acctctagtg tggggtttat ccattcagat atagagacct tgcctgacaa    7020
agatactata gagaagctag aggaattggc agccatctta tcgatggctc tgctcctggg    7080
caaaatagga tcaatactgg tgattaagct tatgcctttc agcggggatt ttgttcaggg    7140
atttataagt tatgtagggt ctcattatag agaagtgaac cttgtatacc ctagatacag    7200
caacttcatc tctactgaat cttatttggt tatgacagat ctcaaggcta accggctaat    7260
gaatcctgaa aagattaagc agcagataat tgaatcatct gtgaggactt cacctggact    7320
tataggtcac atcctatcca ttaagcaact aagctgcata caagcaattg tgggagacgc    7380
agttagtaga ggtgatatca atcctactct gaaaaaactt acacctatag agcaggtgct    7440
gatcaattgc gggttggcaa ttaacggacc taagctgtgc aaagaattga tccaccatga    7500
tgttgcctca gggcaagatg gattgcttaa ttctatactc atcctctaca gggagttggc    7560
aagattcaaa gacaaccaaa gaagtcaaca agggatgttc cacgcttacc ccgtattggt    7620
aagtagcagg caacgagaac ttatatctag gatcacccgc aaattctggg ggcacattct    7680
tctttactcc gggaacaaaa agttgataaa taagtttatc cagaatctca agtccggcta    7740
tctgatacta gacttacacc agaatatctt cgttaagaat ctatccaagt cagagaaaca    7800
gattattatg acgggggggtt tgaaacgtga gtgggttttt aaggtaacag tcaaggagac    7860
caaagaatgg tataagttag tcggatacag tgccctgatt aaggactaat tggttgaact    7920
ccggaacccct aatcctgccc taggtggtta ggcattattt gcagaattct agatcccacg    7980
tcactattgt atactctata ttatactcta tgttatactc tgtaatccta ctcaataaac    8040
gtgtcacgcc tgtgaaaccg tactaagtct cccgtgtctt cttatcacca tcaggtgaca    8100
tcctcgccca ggctgtcaat catgccggta tcgattccag tagcaccggc cccacgctga    8160
caacccactc ttgcagcgtt agcagcgccc ctcttaacaa gccgaccccc accagcgtcg    8220
cggttactaa cactcctctc cccgacctgc agcccaagct ctagagggcc ctattctata    8280
gtgtcaccta aatgctagag ctcgctgatc agcctcgact gtgccttcta gttgccagcc    8340
atctgttgtt tgcccctccc ccgtgccttc cttgaccctg gaaggtgcca ctcccactgt    8400
cctttcctaa taaaatgagg aaattgcatc gcattgtctg agtaggtgtc attctattct    8460
ggggggtggg gtggggcagg acagcaaggg ggaggattgg gaagacaata gcaggcatgc    8520
tggggatgcg gtgggctcta tggcttctga ggcggaaaga accagctggg gctctagggg    8580
gtatccccac gcgccctgta gcggcgcatt aagcgcggcg ggtgtggtgg ttacgcgcag    8640
cgtgaccgct acacttgcca gcgccctagc gcccgctcct ttcgctttct tcccttcctt    8700
tctcgccacg ttcgccggct ttccccgtca gctctaaat cggggcatcc ctttagggtt    8760
ccgatttagt gctttacggc acctcgaccc caaaaaactt gattagggtg atggttcacg    8820
tagtgggcca tcgccctgat agacggtttt tcgcccttttg acgttggagt ccacgttctt    8880
taatagtgga ctcttgttcc aaactggaac aacactcaac cctatctcgg tctattcttt    8940
tgatttataa gggattttgg ggatttcggc ctattggtta aaaaatgagc tgatttaaca    9000
aaaatttaac gcgaattaat tctgtggaat gtgtgtcagt tagggtgtgg aaagtcccca    9060
ggctcccag gcaggcagaa gtatgcaaag catgcatctc aattagtcag caaccaggtg    9120
tggaaagtcc ccaggctccc cagcaggcag aagtatgcaa agcatgcatc tcaattagtc    9180
agcaaccata gtcccgcccc taactccgcc catcccgccc ctaactccgc ccagttccgc    9240
ccattctccg ccccatggct gactaatttt ttttatttat gcagaggccg aggccgcctc    9300
```

```
tgcctctgag ctattccaga agtagtgagg aggcttttt ggaggcctag gcttttgcaa    9360
aaagctcccg ggagcttgta tatccatttt cggatctgat caagagacag gatgaggatc    9420
gtttcgcatg attgaacaag atggattgca cgcaggttct ccggccgctt gggtggagag    9480
gctattcggc tatgactggg cacaacagac aatcggctgc tctgatgccg ccgtgttccg    9540
gctgtcagcg caggggcgcc cggttctttt tgtcaagacc gacctgtccg gtgccctgaa    9600
tgaactgcag gacgaggcag cgcggctatc gtggctggcc acgacgggcg ttccttgcgc    9660
agctgtgctc gacgttgtca ctgaagcggg aagggactgg ctgctattgg gcgaagtgcc    9720
ggggcaggat ctcctgtcat ctcaccttgc tcctgccgag aaagtatcca tcatggctga    9780
tgcaatgcgg cggctgcata cgcttgatcc ggctacctgc ccattcgacc accaagcgaa    9840
acatcgcatc gagcgagcac gtactcggat ggaagccggt cttgtcgatc aggatgatct    9900
ggacgaagag catcaggggc tcgcgccagc cgaactgttc gccaggctca aggcgcgcat    9960
gcccgacggc gaggatctcg tcgtgaccca tggcgatgcc tgcttgccga atatcatggt   10020
ggaaaatggc cgcttttctg gattcatcga ctgtggccgg ctgggtgtgg cggaccgcta   10080
tcaggacata gcgttggcta cccgtgatat tgctgaagag cttggcggcg aatgggctga   10140
ccgcttcctc gtgctttacg gtatcgccgc tcccgattcg cagcgcatcg ccttctatcg   10200
ccttcttgac gagttcttct gagcgggact ctggggttcg aaatgaccga ccaagcgacg   10260
cccaacctgc catcacgaga tttcgattcc accgccgcct tctatgaaag gttgggcttc   10320
ggaatcgttt tccgggacgc cggctggatg atcctccagc gcggggatct catgctggag   10380
ttcttcgccc accccaactt gtttattgca gcttataatg gttacaaata agcaatagc   10440
atcacaaatt tcacaaataa agcatttttt tcactgcatt ctagttgtgg tttgtccaaa   10500
ctcatcaatg tatcttatca tgtctgtata ccgtcgacct ctagctagag cttggcgtaa   10560
tcatggtcat agctgtttcc tgtgtgaaat tgttatccgc tcacaattcc acacaacata   10620
cgagccggaa gcataaagtg taaagcctgg ggtgcctaat gagtgagcta actcacatta   10680
attgcgttgc gctcactgcc cgctttccag tcgggaaacc tgtcgtgcca gctgcattaa   10740
tgaatcggcc aacgcgcggg gagaggcggt ttgcgtattg ggcgctcttc cgcttcctcg   10800
ctcactgact cgctgcgctc ggtcgttcgg ctgcggcgag cggtatcagc tcactcaaag   10860
gcggtaatac ggttatccac agaatcaggg gataacgcag gaaagaacat gtgagcaaaa   10920
ggccagcaaa aggccaggaa ccgtaaaaag gccgcgttgc tggcgttttt ccataggctc   10980
cgcccccctg acgagcatca caaaaatcga cgctcaagtc agaggtggcg aaacccgaca   11040
ggactataaa gataccaggc gtttccccct ggaagctccc tcgtgcgctc tcctgttccg   11100
accctgccgc ttaccggata cctgtccgcc tttctccctt cgggaagcgt ggcgctttct   11160
caatgctcac gctgtaggta tctcagttcg gtgtaggtcg ttcgctccaa gctgggctgt   11220
gtgcacgaac cccccgttca gcccgaccgc tgcgccttat ccggtaacta tcgtcttgag   11280
tccaacccgg taagacacga cttatcgcca ctggcagcag ccactggtaa caggattagc   11340
agagcgaggt atgtaggcgg tgctacagag ttcttgaagt ggtggcctaa ctacggctac   11400
actagaagga cagtatttgg tatctgcgct ctgctgaagc cagttacctt cggaaaaaga   11460
gttggtagct cttgatccgg caaacaaacc accgctggta gcggtggttt ttttgtttgc   11520
aagcagcaga ttacgcgcag aaaaaaagga tctcaagaag atcctttgat cttttctacg   11580
gggtctgacg ctcagtggaa cgaaaactca cgttaaggga ttttggtcat gagattatca   11640
aaaaggatct tcacctagat ccttttaaat taaaaatgaa gttttaaatc aatctaaagt   11700
```

```
atatatgagt aaacttggtc tgacagttac caatgcttaa tcagtgaggc acctatctca    11760
gcgatctgtc tatttcgttc atccatagtt gcctgactcc ccgtcgtgta gataactacg    11820
atacgggagg gcttaccatc tggccccagt gctgcaatga taccgcgaga cccacgctca    11880
ccggctccag atttatcagc aataaaccag ccagccggaa gggccgagcg cagaagtggt    11940
cctgcaactt tatccgcctc catccagtct attaattgtt gccgggaagc tagagtaagt    12000
agttcgccag ttaatagttt gcgcaacgtt gttgccattg ctacaggcat cgtggtgtca    12060
cgctcgtcgt ttggtatggc ttcattcagc tccggttccc aacgatcaag gcgagttaca    12120
tgatccccca tgttgtgcaa aaaagcggtt agctccttcg tcctccgat cgttgtcaga    12180 agtaagttgg ccgcagtgtt atcactcatg gttatggcag cactgcataa ttctcttact    12240
gtcatgccat ccgtaagatg cttttctgtg actggtgagt actcaaccaa gtcattctga    12300
gaatagtgta tgcggcgacc gagttgctct tgcccggcgt caatacggga taataccgcg    12360
ccacatagca gaactttaaa agtgctcatc attggaaaac gttcttcggg gcgaaaactc    12420
tcaaggatct taccgctgtt gagatccagt tcgatgtaac ccactcgtgc acccaactga    12480
tcttcagcat cttttacttt caccagcgtt tctgggtgag caaaaacagg aaggcaaaat    12540
gccgcaaaaa agggaataag ggcgacacgg aaatgttgaa tactcatact cttccttttt    12600
caatattatt gaagcattta tcagggttat tgtctcatga gcggatacat atttgaatgt    12660
atttagaaaa ataaacaaat aggggttccg cgcacatttc cccgaaaagt gccacctgac    12720
gtcgacggat cgggagatc                                                 12739

<210> SEQ ID NO 8
<211> LENGTH: 20546
<212> TYPE: DNA
<213> ORGANISM: Artificial
<220> FEATURE:
<223> OTHER INFORMATION: plasmid DNA

<400> SEQUENCE: 8
accaaacaaa gttgggtaag gatagttcaa tcaatgatca tcttctagtg cacttaggat      60
tcaagatcct attatcaggg acaagagcag gattagggat atccgagatg gccacacttt     120
taaggagctt agcattgttc aaaagaaaca aggacaaacc acccattaca tcaggatccg     180
gtggagccat cagaggaatc aaaacacatt ttatagtacc aatccctgga gattcctcaa     240
ttaccactcg atccagactt ctggaccggt tggtgaggtt aattggaaac ccggatgtga     300
gcgggcccaa actaacaggg gcactaatag gtatattatc cttatttgtg gagtctccag     360
gtcaattgat tcagaggatc accgatgacc ctgacgttag cataaggctg ttagaggttg     420
tccagagtga ccagtcacaa tctggcctta ccttcgcatc aagaggtacc aacatggagg     480
atgaggcgga ccaatacttt tcacatgatg atccaattag tagtgatcaa tccaggttcg     540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
```

```
gactgcatga atttgctggt gagttatcca cacttgagtc cttgatgaac ctttaccagc    1020
aaatggggga aactgcaccc tacatggtaa tcctggagaa ctcaattcag aacaagttca    1080
gtgcaggatc ataccctctg ctctggagct atgccatggg agtaggagtg aacttgaaa    1140 actccatggg aggtttgaac tttggccgat cttactttga tccagcatat tttagattag    1200
ggcaagagat ggtaaggagg tcagctggaa aggtcagttc cacattggca tctgaactcg    1260
gtatcactgc cgaggatgca aggcttgttt cagagattgc aatgcatact actgaggaca    1320
agatcagtag agcggttgga cccagacaag cccaagtatc atttctacac ggtgatcaaa    1380
gtgagaatga gctaccgaga ttgggggca aggaagatag gagggtcaaa cagagtcgag    1440
gagaagccag ggagagctac agagaaaccg ggcccagcag agcaagtgat gcgagagctg    1500
cccatcttcc aaccggcaca cccctagaca ttgacactgc aacggagtcc agccaagatc    1560
cgcaggacag tcgaaggtca gctgacgccc tgcttaggct gcaagccatg gcaggaatct    1620
cggaagaaca aggctcagac acggacaccc ctatagtgta caatgacaga aatcttctag    1680
actaggtgcg agaggccgag ggccagaaca acatccgcct accatccatc attgttataa    1740
aaaacttagg aaccaggtcc acacagccgc cagcccatca accatccact cccacgattg    1800
gagccaatgg cagaagagca ggcacgccat gtcaaaaacg gactgaatg catccgggct    1860 ctcaaggccg agcccatcgg ctcactggcc atcgaggaag ctatggcagc atggtcagaa    1920
atatcagaca cccaggaca ggagcgagcc acctgcaggg aagagaaggc aggcagttcg    1980
ggtctcagca aaccatgcct ctcagcaatt ggatcaactg aaggcggtgc acctcgcatc    2040
cgcggtcagg gacctggaga gagcgatgac gacgctgaaa ctttgggaat cccccccaaga   2100 aatctccagg catcaagcac tgggttacag tgttattacg tttatgatca cagcggtgaa    2160
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc cccggacccc    2460
ggtagggcca gcacttccgg gacacccatt aaaaagggca cagacgcgag attagcctca    2520 tttgaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctgaagg cacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt tgttcctga caccggccct    3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
```

```
ccagtcgacc caactagtcc tccatcattg ttataaaaaa cttaggaacc aggtccatac   3420
accgtacgct cgaggcgcgt gccaccatgg tgacaggggg aatggcaagc aagtgggatc   3480
agaagggtat ggacattgcc tatgaggagg cggccttagg ttacaaagag ggtggtgttc   3540
ctattggcgg atgtcttatc aataacaaag acggaagtgt tctcggtcgt ggtcacaaca   3600
tgagatttca aaagggatcc gccacactac atggtgagat ctccactttg gaaaactgtg   3660
ggagattaga gggcaaagtg tacaaagata ccactttgta tacgacgctg tctccatgcg   3720
acatgtgtac aggtgccatc atcatgtatg gtattccacg ctgtgttgtc ggtgagaacg   3780
ttaatttcaa aagtaagggc gagaaatatt tacaaactag aggtcacgag gttgttgttg   3840
ttgacgatga gaggtgtaaa aagatcatga acaatttat cgatgaaaga cctcaggatt   3900
ggtttgaaga tattggtgag gcttcggaac catttaagaa cgtctacttg ctacctcaaa   3960
caaaccaatt gctgggtttg tacaccatca tcagaaataa gaatacaact agacctgatt   4020
tcattttcta ctccgataga atcatcagat tgttggttga agaaggtttg aaccatctac   4080
ctgtgcaaaa gcaaattgtg gaaactgaca ccaacgaaaa cttcgaaggt gtctcattca   4140
tgggtaaaat ctgtggtgtt tccattgtca gagctggtga atcgatggag caaggattaa   4200
gagactgttg taggtctgtg cgtatcggta aaatttttaat tcaaagggac gaggagactg   4260
ctttaccaaa gttattctac gaaaaattac cagaggatat atctgaaagg tatgtcttcc   4320
tattagaccc aatgctggcc accggtggta gtgctatcat ggctacagaa gtcttgatta   4380
agagaggtgt taagccagag agaatttact tcttaaaacct aatctgtagt aaggaaggga   4440
ttgaaaaata ccatgccgcc ttcccagagg tcagaattgt tactggtgcc ctcgacagag   4500
gtctagatga aaacaagtat ctagttccag ggttgggtga cttggtgac agatactact   4560 gtgtttaaac gcgcgacgtc tagtacaacc taaatccatt ataaaaaact taggagcaaa   4620
gtgattgcct cccaaggtcc acaatgcag agacctacga cttcgacaag tcggcatggg   4680
acatcaaagg gtcgatcgct ccgatacaac ccaccaccta cagtgatggc aggctggtgc   4740
cccaggtcag agtcatagat cctggtctag gcgacaggaa ggatgaatgc tttatgtaca   4800
tgtttctgct gggggttgtt gaggacagcg attccctagg gcctccaatc gggcgagcat   4860
ttgggttcct gcccttaggt gttggcagat ccacagcaaa gcccgaaaaa ctcctcaaag   4920
aggccactga gcttgacata gttgttagac gtacagcagg gctcaatgaa aaactggtgt   4980
tctacaacaa caccccacta actctcctca caccttggag aaaggtccta acaacaggga   5040
gtgtcttcaa cgcaaaccaa gtgtgcaatg cggttaatct gataccgctc gatacccgc   5100 agaggttccg tgttgtttat atgagcatca cccgtctttc ggataacggg tattacaccg   5160
ttcctagaag aatgctggaa ttcagatcgg tcaatgcagt ggccttcaac ctgctggtga   5220
cccttaggat tgacaaggcg ataggccctg ggaagatcat cgacaataca gagcaacttc   5280
ctgaggcaac atttatggtc cacatcggga acttcaggag aaagaagagt gaagtctact   5340
ctgccgatta ttgcaaaatg aaaatcgaaa agatgggcct ggttttgca cttggtggga   5400 taggggcac cagtcttcac attagaagca caggcaaaat gagcaagact ctccatgcac   5460
aactcgggtt caagaagacc ttatgttacc cgctgatgga tatcaatgaa gaccttaatc   5520
gattactctg gaggagcaga tgcaagatag taagaatcca ggcagttttg cagccatcag   5580
ttcctcaaga attccgcatt tacgacgacg tgatcataaa tgatgaccaa ggactattca   5640
aagttctgta gaccgtagtg cccagcaatg cccgaaaacg accccccctca caatgacagc   5700
```

```
cagaaggccc ggacaaaaaa gcccctccg aaagactcca cggaccaagc gagaggccag    5760
ccagcagccg acggcaagcg cgaacaccag gcggcccag cacagaacag ccctgacaca     5820
aggccaccac cagccacccc aatctgcatc ctcctcgtgg accccgag gaccaacccc     5880 caaggctgcc cccgatccaa accaccaacc gcatcccca caccccggg aaagaaaccc     5940 ccagcaattg aaggcccct ccccctcttc ctcaacacaa gaactccaca accgaaccgc    6000
acaagcgacc gaggtgaccc aaccgcaggc atccgactcc ctagacagat cctctctccc    6060
cggcaaacta acaaaactt agggccaagg aacatacaca cccaacagaa cccagacccc     6120
ggcccacggc gccgcgcccc caaccccga caaccagagg gagcccccaa ccaatcccgc     6180
cggctccccc ggtgcccaca ggcagggaca ccaaccccg aacagaccca gcacccaacc    6240
atcgacaatc caagacgggg gggcccccc aaaaaaggc cccaggggc cgacagccag      6300 caccgcgagg aagcccaccc accccacaca cgaccacggc aaccaaacca gaacccagac    6360
caccctgggc caccagctcc cagactcggc catcaccccg cagaaaggaa aggccacaac    6420
ccgcgcaccc cagcccgat ccggcgggga gccacccaac ccgaaccagc acccaagagc     6480
gatccccgaa ggaccccga accgcaaagg acatcagtat cccacagcct ctccaagtcc    6540
cccggtctcc tcctcttctc gaagggacca aaagatcaat ccaccacacc cgacgacact    6600
caactcccca cccctaaagg agacaccggg aatcccagaa tcaagactca tccaatgtcc    6660
atcatgggtc tcaaggtgaa cgtctctgcc atattcatgg cagtactgtt aactctccaa    6720
acacccaccg gtcaaatcca ttgggcaat ctctctaaga taggggtggt aggaatagga    6780
agtgcaagct acaaagttat gactcgttcc agccatcaat cattagtcat aaaattaatg    6840
cccaatataa ctctcctcaa taactgcacg agggtagaga ttgcagaata caggagacta    6900
ctgagaacag ttttggaacc aattagagat gcacttaatg caatgaccca gaatataaga    6960
ccggttcaga gtgtagcttc aagtaggaga cacaagagat ttgcgggagt agtcctggca    7020
ggtgcggccc taggcgttgc cacagctgct cagataacag ccggcattgc acttcaccag    7080
tccatgctga actctcaagc catcgacaat ctgagagcga gcctggaaac tactaatcag    7140
gcaattgaga caatcagaca agcagggcag gagatgatat tggctgttca gggtgtccaa    7200
gactacatca ataatgagct gataccgtct atgaaccaac tatcttgtga tttaatcggc    7260
cagaagctcg ggctcaaatt gctcagatac tatacagaaa tcctgtcatt atttggcccc    7320
agtttacggg accccatatc tgcggagata tctatccagg ctttgagcta tgcgcttgga    7380
ggagacatca ataaggtgtt agaaaagctc ggatacagtg gaggtgattt actgggcatc    7440
ttagagagcg gaggaataaa ggcccggata actcacgtcg acacagagtc ctacttcatt    7500
gtcctcagta tagcctatcc gacgctgtcc gagattaagg gggtgattgt ccaccggcta    7560 gaggggtct cgtacaacat aggctctcaa gagtggtata ccactgtgcc caagtatgtt    7620
gcaacccaag gtaccttat ctcgaatttt gatgagtcat cgtgtacttt catgccagag    7680
gggactgtgt gcagccaaaa tgccttgtac ccgatgagtc ctctgctcca agaatgcctc    7740
cgggggtaca ccaagtcctg tgctcgtaca ctcgtatccg ggtcttttgg gaaccggttc    7800
attttatcac aagggaacct aatagccaat tgtgcatcaa tcctttgcaa gtgttacaca    7860
acaggaacga tcattaatca agaccctgac aagatcctaa catacattgc tgccgatcac    7920
tgcccggtag tcgaggtgaa cggcgtgacc atccaagtcg ggagcaggag gtatccagac    7980
gctgtgtact gcacagaat tgacctcggt cctcccatat cattggagag gttggacgta    8040
gggacaaatc tggggaatgc aattgctaag ttggaggatg ccaaggaatt gttggagtca    8100
```

```
tcggaccaga tattgaggag tatgaaaggt ttatcgagca ctagcatagt ctacatcctg    8160
attgcagtgt gtcttggagg gttgataggg atccccgctt taatatgttg ctgcaggggg    8220
cgttgtaaca aaaagggaga acaagttggt atgtcaagac caggcctaaa gcctgatctt    8280
acgggaacat caaaatccta tgtaaggtcg ctctgatcct ctacaactct tgaaacacaa    8340
atgtcccaca agtctcctct tcgtcatcaa gcaaccaccg cacccagcat caagcccacc    8400
tgaaattatc tccggcttcc ctctggccga acaatatcgg tagttaatca aaacttaggg    8460
tgcaagatca tccacaatgt caccacaacg agaccggata aatgccttct acaaagataa    8520
cccccatccc aagggaagta ggatagtcat taacagagaa catcttatga ttgatagacc    8580
ttatgttttg ctggctgttc tgtttgtcat gtttctgagc ttgatcgggt tgctagccat    8640
tgcaggcatt agacttcatc gggcagccat ctacaccgca gagatccata aaagcctcag    8700
caccaatcta gatgtaacta actcaatcga gcatcaggtc aaggacgtgc tgacaccact    8760
cttcaaaatc atcggtgatg aagtgggcct gaggacacct cagagattca ctgacctagt    8820
gaaattaatc tctgacaaga ttaaattcct taatccggat agggagtacg acttcagaga    8880
tctcacttgg tgtatcaacc cgccagagag aatcaaattg gattatgatc aatactgtgc    8940
agatgtggct gctgaagagc tcatgaatgc attggtgaac tcaactctac tggagaccag    9000
aacaaccaat cagttcctag ctgtctcaaa gggaaactgc tcagggccca ctacaatcag    9060
aggtcaattc tcaaacatgt cgctgtccct gttagacttg tatttaggtc gaggttacaa    9120
tgtgtcatct atagtcacta tgacatccca gggaatgtat gggggaactt acctagtgga    9180
aaagcctaat ctgagcagca aaaggtcaga gttgtcacaa ctgagcatgt accgagtgtt    9240
tgaagtaggt gttatcagaa atccgggttt gggggctccg gtgttccata tgacaaacta    9300
tcttgagcaa ccagtcagta atgatctcag caactgtatg gtggctttgg gggagctcaa    9360
actcgcagcc ctttgtcacg gggaagattc tatcacaatt ccctatcagg gatcagggaa    9420
aggtgtcagc ttccagctcg tcaagctagg tgtctggaaa tccccaaccg acatgcaatc    9480
ctgggtcccc ttatcaacgg atgatccagt gatagacagg ctttacctct catctcacag    9540
aggtgttatc gctgacaatc aagcaaaatg ggctgtcccg acaacacgaa cagatgacaa    9600
gttgcgaatg gagacatgct tccaacaggc gtgtaagggt aaaatccaag cactctgcga    9660
gaatcccgag tgggcaccat tgaaggataa caggattcct tcatacgggg tcttgtctgt    9720
tgatctgagt ctgacagttg agcttaaaat caaaattgct tcgggattcg ggccattgat    9780
cacacacggt tcagggatgg acctatacaa atccaaccac aacaatgtgt attggctgac    9840
tatcccgcca atgaagaacc tagccttagg tgtaatcaac acattggagt ggataccgag    9900
attcaaggtt agtccctacc tcttcactgt cccaattaag gaagcaggcg aagactgcca    9960
tgccccaaca tacctacctg cggaggtgga tggtgatgtc aaactcagtt ccaatctggt   10020
gattctacct ggtcaagatc tccaatatgt tttggcaacc tacgatactt ccaggggtga   10080
acatgctgtg gtttattacg tttacagccc aagccgctca ttttcttact tttatccttt   10140
taggttgcct ataaaggggg tccccatcga attacaagtg gaatgcttca catgggacca   10200
aaaactctgg tgccgtcact tctgtgtgct tgcggactca gaatctggtg acatatcac    10260 tcactctggg atggtgggca tgggagtcag ctgcacagtc acccgggaag atggaaccaa   10320
tcgcagatag ggctgctagt gaaccaatca catgatgtca cccagacatc aggcataccc   10380
actagtgtga aatagacatc agaattaaga aaaacgtagg gtccaagtgg ttccccgtta   10440
```

```
tggactcgct atctgtcaac cagatcttat accctgaagt tcacctagat agcccgatag   10500
ttaccaataa gatagtagcc atcctggagt atgctcgagt ccctcacgct tacagcctgg   10560
aggaccctac actgtgtcag aacatcaagc accgcctaaa aaacggattt tccaaccaaa   10620
tgattataaa caatgtggaa gttgggaatg tcatcaagtc caagcttagg agttatccgg   10680
cccactctca tattccatat ccaaattgta atcaggattt atttaacata gaagacaaag   10740
agtcaacgag gaagatccgt gaactcctca aaaaggggaa ttcgctgtac tccaaagtca   10800
gtgataaggt tttccaatgc ttaagggaca ctaactcacg gcttggccta ggctccgaat   10860
tgagggagga catcaaggag aaagttatta acttgggagt ttacatgcac agctcccagt   10920
ggtttgagcc ctttctgttt tggtttacag tcaagactga gatgaggtca gtgattaaat   10980
cacaaaccca tacttgccat aggaggagac acacacctgt attcttcact ggtagttcag   11040
ttgagttgct aatctctcgt gaccttgttg ctataatcag taaagagtct caacatgtat   11100
attacctgac atttgaactg gtttttgatgt attgtgatgt catagagggg aggttaatga   11160
cagagaccgc tatgactatt gatgctaggt atacagagct tctaggaaga gtcagataca   11220
tgtggaaact gatagatggt ttcttccctg cactcgggaa tccaacttat caaattgtag   11280
ccatgctgga gcctctttca cttgcttacc tgcagctgag ggatataaca gtagaactca   11340
gaggtgcttt ccttaaccac tgctttactg aaatacatga tgttcttgac caaaacgggt   11400
tttctgatga aggtacttat catgagttaa ctgaagctct agattacatt ttcataactg   11460
atgacataca tctgacaggg gagatttttct cattttttcag aagtttcggc cacccccagac   11520 ttgaagcagt aacggctgct gaaaatgtta ggaaatacat gaatcagcct aaagtcattg   11580
tgtatgagac tctgatgaaa ggtcatgcca tattttgtgg aatcataatc aacggctatc   11640
gtgacaggca cggaggcagt tggccaccgc tgaccctccc cctgcatgct gcagacacaa   11700
tccggaatgc tcaagcttca ggtgaagggt taacacatga gcagtgcgtt gataactgga   11760
aatcttttgc tggagtgaaa tttggctgct ttatgcctct tagcctggat agtgatctga   11820
caatgtacct aaaggacaag gcacttgctg ctctccaaag ggaatgggat tcagtttacc   11880
cgaaagagtt cctgcgttac gaccctccca agggaaccgg gtcacggagg cttgtagatg   11940 tttttccttaa tgattcgagc tttgacccat atgatgtgat aatgtatgtt gtaagtggag   12000
cttacctcca tgaccctgag ttcaacctgt cttacagcct gaaagaaaag gagatcaagg   12060
aaacaggtag acttttttgct aaaatgactt acaaaatgag ggcatgccaa gtgattgctg   12120
aaaatctaat ctcaaacggg attggcaaat attttaagga caatgggatg ccaaggatg   12180 agcacgattt gactaaggca ctccacactc tagctgtctc aggagtcccc aaagatctca   12240
aagaaagtca cagggggggg ccagtcttaa aaacctactc ccgaagccca gtccacacaa   12300
gtaccaggaa cgtgagagca gcaaaagggt ttatagggtt ccctcaagta attcggcagg   12360
accaagacac tgatcatccg gagaatatgg aagcttacga gacagtcagt gcatttatca   12420
cgactgatct caagaagtac tgccttaatt ggagatatga gaccatcagc ttgtttgcac   12480
agaggctaaa tgagatttac ggattgccct catttttcca gtggctgcat aagaggcttg   12540
agacctctgt cctgtatgta agtgaccctc attgccccc cgaccttgac gcccatatcc   12600
cgttatataa agtccccaat gatcaaatct tcattaagta ccctatggga ggtatagaag   12660
ggtattgtca gaagctgtgg accatcagca ccattcccta tctatacctg gctgcttatg   12720
agagcggagt aaggattgct tcgttagtgc aaggggacaa tcagaccata gccgtaacaa   12780
aaagggtacc cagcacatgg ccctacaacc ttaagaaacg ggaagctgct agagtaacta   12840
```

```
gagattactt tgtaattctt aggcaaaggc tacatgatat tggccatcac ctcaaggcaa   12900
atgagacaat tgtttcatca cattttttg tctattcaaa aggaatatat tatgatgggc   12960
tacttgtgtc ccaatcactc aagagcatcg caagatgtgt attctggtca gagactatag   13020
ttgatgaaac aagggcagca tgcagtaata ttgctacaac aatggctaaa agcatcgaga   13080
gaggttatga ccgttacctt gcatattccc tgaacgtcct aaaagtgata cagcaaattc   13140
tgatctctct tggcttcaca atcaattcaa ccatgacccg ggatgtagtc ataccoctcc   13200 tcacaaacaa cgacctctta ataaggatgg cactgttgcc cgctcctatt gggggatga   13260 attatctgaa tatgagcagg ctgtttgtca gaaacatcgg tgatccagta acatcatcaa   13320
ttgctgatct caagagaatg attctcgcct cactaatgcc tgaagagacc ctccatcaag   13380
taatgacaca acaaccgggg gactcttcat tcctagactg gctagcgac ccttactcag   13440 caaatcttgt atgtgtccag agcatcacta gactcctcaa gaacataact gcaaggttg   13500 tcctgatcca tagtccaaac ccaatgttaa aaggattatt ccatgatgac agtaaagaag   13560
aggacgaggg actggcggca ttcctcatgg acaggcatat tatagtacct agggcagctc   13620
atgaaatcct ggatcatagt gtcacagggg caagagagtc tattgcaggc atgctggata   13680
ccacaaaagg cttgattcga gccagcatga ggaaggggg gttaacctct cgagtgataa   13740
ccagattgtc caattatgac tatgaacaat tcagagcagg gatggtgcta ttgacaggaa   13800
gaaagagaaa tgtcctcatt gacaaagagt catgttcagt gcagctggcg agagctctaa   13860
gaagccatat gtgggcgagg ctagctcgag gacggcctat ttacggcctt gaggtccctg   13920
atgtactaga atctatgcga ggccaccta ttcggcgtca tgagacatgt gtcatctgcg   13980
agtgtggatc agtcaactac ggatggtttt ttgtcccctc gggttgccaa ctggatgata   14040
ttgacaagga aacatcatcc ttgagagtcc catatattgg ttctaccact gatgagagaa   14100
cagacatgaa gcttgccttc gtaagagccc caagtcgatc cttgcgatct gctgttagaa   14160
tagcaacagt gtactcatgg gcttacggtg atgatgatag ctcttggaac gaagcctggt   14220
tgttggctag gcaaagggcc aatgtgagcc tggaggagct aagggtgatc actcccatct   14280
caacttcgac taatttagcg cataggttga gggatcgtag cactcaagtg aaatactcag   14340
gtacatccct tgtccgagtg gcgaggtata ccacaatctc caacgacaat ctctcatttg   14400
tcatatcaga taagaaggtt gatactaact ttatatacca acaaggaatg cttctagggt   14460
tgggtgtttt agaaacattg tttcgactcg agaaagatac cggatcatct aacacggtat   14520
tacatcttca cgtcgaaaca gattgttgcg tgatcccgat gatagatcat cccaggatac   14580
ccagctcccg caagctagag ctgagggcag agctatgtac caacccattg atatatgata   14640
atgcaccttt aattgacaga gatgcaacaa ggctatacac ccagagccat aggaggcacc   14700
ttgtggaatt tgttacatgg tccacacccc aactatatca cattttagct aagtccacag   14760
cactatctat gattgacctg gtaacaaaat ttgagaagga ccatatgaat gaaatttcag   14820
ctctcatagg ggatgacgat atcaatagtt tcataactga gtttctgctc atagagccaa   14880
gattattcac tatctacttg ggccagtgtg cggccatcaa ttgggcattt gatgtacatt   14940
atcatagacc atcagggaaa tatcagatgg gtgagctgtt gtcatcgttc ctttctagaa   15000
tgagcaaagg agtgtttaag gtgcttgtca atgctctaag ccacccaaag atctacaaga   15060
aattctggca ttgtggtatt atagagccta tccatggtcc ttcacttgat gctcaaaact   15120
tgcacacaac tgtgtgcaac atggtttaca catgctatat gacctacctc gacctgttgt   15180
```

```
tgaatgaaga gttagaagag ttcacatttc tcttgtgtga aagcgacgag gatgtagtac   15240
cggacagatt cgacaacatc caggcaaaac acttatgtgt tctggcagat ttgtactgtc   15300
aaccagggac ctgcccacca attcgaggtc taagaccggt agagaaatgt gcagttctaa   15360
ccgaccatat caaggcagag gctatgttat ctccagcagg atcttcgtgg aacataaatc   15420
caattattgt agaccattac tcatgctctc tgacttatct ccggcgagga tcgatcaaac   15480
agataagatt gagagttgat ccaggattca ttttcgacgc cctcgctgag gtaaatgtca   15540
gtcagccaaa gatcggcagc aacaacatct caaatatgag catcaaggct ttcagacccc   15600
cacacgatga tgttgcaaaa ttgctcaaag atatcaacac aagcaagcac aatcttccca   15660
tttcaggggg caatctcgcc aattatgaaa tccatgcttt ccgcagaatc gggttgaact   15720
catctgcttg ctacaaagct gttgagatat caacattaat taggagatgc cttgagccag   15780
gggaggacgg cttgttcttg ggtgagggat cgggttctat gttgatcact tataaagaga   15840
tacttaaact aaacaagtgc ttctataata gtggggtttc cgccaattct agatctggtc   15900
aaagggaatt agcaccctat ccctccgaag ttggccttgt cgaacacaga atgggagtag   15960
gtaatattgt caaagtgctc tttaacggga ggcccgaagt cacgtgggta ggcagtgtag   16020
attgcttcaa tttcatagtt agtaatatcc ctacctctag tgtggggttt atccattcag   16080
atatagagac cttgcctgac aaagatacta tagagaagct agaggaattg gcagccatct   16140
tatcgatggc tctgctcctg ggcaaaatag gatcaatact ggtgattaag cttatgcctt   16200
tcagcgggga ttttgttcag ggatttataa gttatgtagg gtctcattat agagaagtga   16260
accttgtata ccctagatac agcaacttca tctctactga atcttatttg gttatgacag   16320
atctcaaggc taaccggcta atgaatcctg aaaagattaa gcagcagata attgaatcat   16380
ctgtgaggac ttcacctgga cttataggtc acatcctatc cattaagcaa ctaagctgca   16440
tacaagcaat tgtgggagac gcagttagta gaggtgatat caatcctact ctgaaaaaac   16500
ttacacctat agagcaggtg ctgatcaatt gcgggttggc aattaacgga cctaagctgt   16560
gcaaagaatt gatccaccat gatgttgcct cagggcaaga tggattgctt aattctatac   16620
tcatcctcta cagggagttg gcaagattca aagacaacca aagaagtcaa caagggatgt   16680
tccacgctta ccccgtattg gtaagtagca ggcaacgaga acttatatct aggatcaccc   16740
gcaaattctg ggggcacatt cttctttact ccgggaacaa aaagttgata aataagttta   16800
tccagaatct caagtccggc tatctgatac tagacttaca ccagaatatc ttcgttaaga   16860
atctatccaa gtcagagaaa cagattatta tgacgggggg tttgaaacgt gagtgggttt   16920
ttaaggtaac agtcaaggag accaaagaat ggtataagtt agtcggatac agtgccctga   16980
ttaaggacta attggttgaa ctccggaacc ctaatcctgc cctaggtggt taggcattat   17040
ttgcaatata ttaaagaaaa ctttgaaaat acgaagtttc tattcccagc tttgtctggt   17100
ggccggcatg gtcccagcct cctcgctggc gccggctggg caacattccg aggggaccgt   17160
cccctcggta atggcgaatg ggacgcggcc ggtcgatcga cgatccggct gctaacaaag   17220
cccgaaagga agctgagttg gctgctgcca ccgctgagca ataactagca taaccccttg   17280
gggcctctaa acgggtcttg agggggtttt tgctgaaagg aggaactata tccgatcga   17340 gatcaattct gtgagcgtat ggcaaacgaa ggaaaaatag ttatagtagc cgcactcgat   17400
gggacatttc aacgtaaacc gtttaataat attttgaatc ttattccatt atctgaaatg   17460
gtggtaaaac taactgctgt gtgtatgaaa tgctttaagg aggcttcctt ttctaaacga   17520
ttgggtgagg aaaccgagat agaaataata ggaggtaatg atatgtatca atcggtgtgt   17580
```

```
agaaagtgtt acatcgactc ataatattat attttttatc taaaaaacta aaaataaaca  17640
ttgattaaat tttaatataa tacttaaaaa tggatgttgt gtcgttagat aaaccgttta  17700
tgtattttga ggaaattgat aatgagttag attacgaacc agaaagtgca aatgaggtcg  17760
caaaaaaact gccgtatcaa ggacagttaa aactattact aggagaatta ttttttctta  17820
gtaagttaca gcgacacggt atattagatg gtgccaccgt agtgtatata ggatctgctc  17880
ccggtacaca tatacgttat ttgagagatc atttctataa tttaggagtg atcccgaaag  17940
gaagctgagt tggctgctgc caccgctgag caataactag cataacccct tggggcctct  18000
aaacgggtct tgagggggttt tttgctgaaa ggaggaacgc gcctgatgcg gtattttctc  18060
cttacgcatc tgtgcggtat ttcacaccgc atatatggtg cactctcagt acaatctgct  18120
ctgatgccgc atagttaagc cagccccgac acccgccaac acccgctgac gcgcctgac  18180 gggcttgtct gctcccggca tccgcttaca gacaagctgt gaccgtctcc gggagctgca  18240
tgtgtcagag gttttcaccg tcatcaccga acgcgcgag acgaaagggc ctcgtgatac  18300 gcctatttt ataggttaat gtcatgataa taatggtttc ttagacgtca ggtggcactt  18360
ttcggggaaa tgtgcgcgga acccctattt gtttattttt ctaaatacat tcaaatatgt  18420
atccgctcat gagacaataa ccctgataaa tgcttcaata atattgaaaa aggaagagta  18480
tgagtattca acatttccgt gtcgccctta ttcccttttt tgcggcattt tgccttcctg  18540 ttttgctca cccagaaacg ctggtgaaag taaaagatgc tgaagatcag ttgggtgcac  18600
gagtgggtta catcgaactg gatctcaaca gcggtaagat ccttgagagt tttcgccccg  18660
aagaacgttt tccaatgatg agcacttta aagttctgct atgtggcgcg gtattatccc  18720
gtattgacgc cgggcaagag caactcggtc gccgcataca ctattctcag aatgacttgg  18780
ttgagtactc accagtcaca gaaaagcatc ttacggatgg catgacagta agagaattat  18840
gcagtgctgc cataaccatg agtgataaca ctgcggccaa cttacttctg acaacgatcg  18900
gaggaccgaa ggagctaacc gcttttttgc acaacatggg ggatcatgta actcgccttg  18960
atcgttggga accggagctg aatgaagcca taccaaacga cgagcgtgac accacgatgc  19020
ctgtagcaat ggcaacaacg ttgcgcaaac tattaactgg cgaactactt actctagctt  19080
cccggcaaca attaatagac tggatggagg cggataaagt tgcaggacca cttctgcgct  19140
cggcccttcc ggctggctgg tttattgctg ataaatctgg agccggtgag cgtgggtctc  19200
gcggtatcat tgcagcactg gggccagatg gtaagccctc ccgtatcgta gttatctaca  19260
cgacggggag tcaggcaact atggatgaac gaaatagaca gatcgctgag ataggtgcct  19320
cactgattaa gcattggtaa ctgtcagacc aagtttactc atatatactt tagattgatt  19380
taaaacttca tttttaattt aaaaggatct aggtgaagat cctttttgat aatctcatga  19440
ccaaaatccc ttaacgtgag ttttcgttcc actgagcgtc agaccccgta gaaaagatca  19500
aaggatcttc ttgagatcct ttttttctgc gcgtaatctg ctgcttgcaa acaaaaaaac  19560
caccgctacc agcggtggtt tgtttgccgg atcaagagct accaactctt tttccgaagg  19620
taactggctt cagcagagcg cagataccaa atactgtcct tctagtgtag ccgtagttag  19680
gccaccactt caagaactct gtagcaccgc ctacatacct cgctctgcta atcctgttac  19740
cagtggctgc tgccagtggc gataagtcgt gtcttaccgg gttggactca agacgatagt  19800
taccggataa ggcgcagcgg tcgggctgaa cggggggttc gtgcacacag cccagcttgg  19860
agcgaacgac ctacaccgaa ctgagatacc tacagcgtga gcattgagaa agcgccacgc  19920
```

| | | | | | |
|---|---|---|---|---|---|
| ttcccgaagg | gagaaaggcg | gacaggtatc | cggtaagcgg | cagggtcgga | acaggagagc | 19980
| gcacgaggga | gcttccaggg | ggaaacgcct | ggtatcttta | tagtcctgtc | gggtttcgcc | 20040
| acctctgact | tgagcgtcga | tttttgtgat | gctcgtcagg | ggggcggagc | ctatggaaaa | 20100
| acgccagcaa | cgcggccttt | ttacggttcc | tggccttttg | ctggcctttt | gctcacatgt | 20160
| tctttcctgc | gttatcccct | gattctgtgg | ataaccgtat | taccgccttt | gagtgagctg | 20220
| ataccgctcg | ccgcagccga | acgaccgagc | gcagcgagtc | agtgagcgag | gaagcggaag | 20280
| agcgcccaat | acgcaaaccg | cctctccccg | cgcgttggcc | gattcattaa | tgcagctggc | 20340
| acgacaggtt | tcccgactgg | aaagcgggca | gtgagcgcaa | cgcaattaat | gtgagttagc | 20400
| tcactcatta | ggcaccccag | gctttacact | ttatgcttcc | ggctcgtatg | ttgtgtggaa | 20460
| ttgtgagcgg | ataacaattt | cacacaggaa | acagctatga | ccatgattac | gccaagctta | 20520
| cgcgtgtaat | acgactcact | ataggg | | | | 20546

<210> SEQ ID NO 9
<211> LENGTH: 21759
<212> TYPE: DNA
<213> ORGANISM: Artificial
<220> FEATURE:
<223> OTHER INFORMATION: plasmid DNA

<400> SEQUENCE: 9

| | | | | | |
|---|---|---|---|---|---|
| accaaacaaa | gttgggtaag | gatagttcaa | tcaatgatca | tcttctagtg | cacttaggat | 60
| tcaagatcct | attatcaggg | acaagagcag | gattagggat | atctcgaggc | gcgtgccacc | 120
| atgacctctc | gccgctccgt | gaagtcgggt | ccgcgggagg | ttccgcgcga | tgagtacgag | 180
| gatctgtact | acaccccgtc | ttcaggtatg | gcgagtcccg | atagtccgcc | tgacacctcc | 240
| cgccgtggcg | ccctacagac | acgctcgcgc | cagaggggcg | aggtccgttt | cgtccagtac | 300
| gacgagtcgg | attatgccct | ctacggggc | tcgtcatccg | aagacgacga | acaccccggag | 360
| gtccccccgga | cgcggcgtcc | cgtttccggg | gcggttttgt | ccggcccggg | gcctgcgcgg | 420
| gcgcctccgc | cacccgctgg | gtccggaggg | gccggacgca | cacccaccac | cgccccccgg | 480
| gccccccgaa | cccagcgggt | ggcgactaag | gccccgcgg | cccggcggc | ggagaccacc | 540
| cgcggcagga | aatcggccca | gccagaatcc | gccgcactcc | cagacgcccc | cgcctcgacg | 600
| gcgccaaccc | gatccaagac | acccgcgcag | gggctggcca | gaaagctgca | ctttagcacc | 660
| gccccccaa | acccgacgc | gccatggacc | ccccgggtgg | ccggctttaa | caagcgcgtc | 720
| ttctgcgccg | cggtcgggcg | cctggcgcc | atgcatgccc | ggatggcggc | ggtccagctc | 780
| tgggacatgt | cgcgtccgcg | cacagacgaa | gacctcaacg | aactccttgg | catcaccacc | 840
| atccgcgtga | cggtctgcga | gggcaaaaac | ctgcttcagc | gcgccaacga | gttggtgaat | 900
| ccagacgtgg | tgcaggacgt | tgacgcggcc | acggcgactc | gagggcgttc | tgcggcgtcg | 960
| cgccccaccg | agcgacctcg | agcccagcc | cgctccgctt | ctcgcccag | acggccgtc | 1020
| gaggatatcg | ccaccatggt | gacaggggga | atggcaagca | agtgggatca | gaagggtatg | 1080
| gacattgcct | atgaggaggc | ggccttaggt | tacaaagagg | gtggtgttcc | tattggcgga | 1140
| tgtcttatca | ataacaaaga | cggaagtgtt | ctcggtcgtg | gtcacaacat | gagatttcaa | 1200
| aagggatccg | ccacactaca | tggtgagatc | tccactttgg | aaaactgtgg | gagattagag | 1260
| ggcaaagtgt | acaaagatac | cactttgtat | acgacgctgt | ctccatgcga | catgtgtaca | 1320
| ggtgccatca | tcatgtatgg | tattccacgc | tgtgttgtcg | gtgagaacgt | taatttcaaa | 1380
| agtaagggcg | agaaatattt | acaaactaga | ggtcacgagg | ttgttgttgt | tgacgatgag | 1440

```
aggtgtaaaa agatcatgaa acaatttatc gatgaaagac ctcaggattg gtttgaagat   1500
attggtgagg cttcggaacc atttaagaac gtctacttgc tacctcaaac aaaccaattg   1560
ctgggtttgt acaccatcat cagaaataag aatacaacta gacctgattt cattttctac   1620
tccgatagaa tcatcagatt gttggttgaa gaaggtttga accatctacc tgtgcaaaag   1680
caaattgtgg aaactgacac caacgaaaac ttcgaaggtg tctcattcat gggtaaaatc   1740
tgtggtgttt ccattgtcag agctggtgaa tcgatggagc aaggattaag agactgttgt   1800
aggtctgtgc gtatcggtaa aattttaatt caaagggacg aggagactgc tttaccaaag   1860
ttattctacg aaaaattacc agaggatata tctgaaaggt atgtcttcct attagaccca   1920
atgctggcca ccgtggtag tgctatcatg gctacagaag tcttgattaa gagaggtgtt   1980
aagccagaga gaatttactt cttaaaccta atctgtagta aggaagggat tgaaaaatac   2040
catgccgcct tcccagaggt cagaattgtt actggtgccc tcgacagagg tctagatgaa   2100
aacaagtatc tagttccagg gttgggtgac tttggtgaca gatactactg tgtttaataa   2160
acgcgccatc catcattgtt ataaaaaact taggattcaa gatcctatta tcagggacaa   2220
gagcaggatt agggatatcc gagatggcca cacttttaag gagcttagca ttgttcaaaa   2280
gaaacaagga caaaccaccc attacatcag gatccggtgg agccatcaga ggaatcaaac   2340
acattattat agtaccaatc cctggagatt cctcaattac cactcgatcc agacttctgg   2400
accggttggt gaggttaatt ggaaacccgg atgtgagcgg gcccaaacta acaggggcac   2460
taataggtat attatcctta tttgtggagt ctccaggtca attgattcag aggatcaccg   2520
atgaccctga cgttagcata aggctgttag aggttgtcca gagtgaccag tcacaatctg   2580
gccttacctt cgcatcaaga ggtaccaaca tggaggatga ggcggaccaa tacttttcac   2640
atgatgatcc aattagtagt gatcaatcca ggttcggatg gttcgggaac aaggaaatct   2700
cagatattga agtgcaagac cctgagggat tcaacatgat tctgggtacc atcctagccc   2760
aaatttgggt cttgctcgca aaggcggtta cggccccaga cacggcagct gattcggagc   2820
taagaaggtg gataaagtac acccaacaaa gaagggtagt tggtgaattt agattggaga   2880
gaaaatggtt ggatgtggtg aggaacagga ttgccgagga cctctcctta cgccgattca   2940
tggtcgctct aatcctggat atcaagagaa cacccggaaa caaacccagg attgctgaaa   3000
tgatatgtga cattgataca tatatcgtag aggcaggatt agccagtttt atcctgacta   3060
ttaagtttgg gatagaaact atgtatcctg ctcttggact gcatgaattt gctggtgagt   3120
tatccacact tgagtccttg atgaacctt accagcaaat gggggaaact gcaccctaca   3180
tggtaatcct ggagaactca attcagaaca gttcagtgc aggatcatac cctctgctct   3240
ggagctatgc catgggagta ggagtggaac ttgaaaactc catgggaggt ttgaactttg   3300
gccgatctta ctttgatcca gcatatttta gattagggca agagatggta aggaggtcag   3360
ctggaaaggt cagttccaca ttggcatctg aactcggtat cactgccgag gatgcaaggc   3420
ttgtttcaga gattgcaatg catactactg aggacaagat cagtagagcg gttggaccca   3480
gacaagccca agtatcattt ctacacggtg atcaaagtga gaatgagcta ccgagattgg   3540
ggggcaagga agataggagg gtcaaacaga gtcgaggaga agccagggag agctacagag   3600
aaaccgggcc cagcagagca agtgatgcga gagctgccca tcttccaacc ggcacacccc   3660
tagacattga cactgcaacg gagtccagcc aagatccgca ggacagtcga aggtcagctg   3720
acgccctgct taggctgcaa gccatggcag gaatctcgga agaacaaggc tcagacacgg   3780
```

```
acacccctat agtgtacaat gacagaaatc ttctagacta ggtgcgagag gccgagggcc    3840
agaacaacat ccgcctacca tccatcattg ttataaaaaa cttaggaacc aggtccacac    3900
agccgccagc ccatcaacca tccactccca cgattggagc caatggcaga agagcaggca    3960
cgccatgtca aaaacggact ggaatgcatc cgggctctca aggccgagcc catcggctca    4020
ctggccatcg aggaagctat ggcagcatgg tcagaaatat cagacaaccc aggacaggag    4080
cgagccacct gcagggaaga gaaggcaggc agttcgggtc tcagcaaacc atgcctctca    4140
gcaattggat caactgaagg cggtgcacct cgcatccgcg gtcagggacc tggagagagc    4200
gatgacgacg ctgaaacttt gggaatcccc ccaagaaatc tccaggcatc aagcactggg    4260
ttacagtgtt attacgttta tgatcacagc ggtgaagcgg ttaagggaat ccaagatgct    4320
gactctatca tggttcaatc aggccttgat ggtgatagca ccctctcagg aggagacaat    4380
gaatctgaaa acagcgatgt ggatattggc gaacctgata ccgagggata tgctatcact    4440
gaccggggat ctgctcccat ctctatgggg ttcagggctt ctgatgttga aactgcagaa    4500
ggaggggaga tccacgagct cctgagactc caatccagag caacaacttt ccgaagcttt    4560
gggaaaactc tcaatgttcc tccgcccccg accccggta gggccagcac ttccgggaca    4620
cccattaaaa agggcacaga cgcgagatta gcctcatttg gaacggagat cgcgtcttta    4680
ttgacaggtg gtgcaaccca atgtgctcga aagtcaccct cggaaccatc agggccaggt    4740
gcacctgcgg ggaatgtccc cgagtgtgtg agcaatgccg cactgataca ggagtggaca    4800
cccgaatctg gtaccacaat ctccccgaga tcccagaata tgaagaagg gggagactat    4860 tatgatgatg agctgttctc tgatgtccaa gatattaaaa cagccttggc caaaatacac    4920
gaggataatc agaagataat ctccaagcta gaatcactgc tgttattgaa gggagaagtt    4980
gagtcaatta agaagcagat caacaggcaa aatatcagca tatccaccct ggaaggacac    5040
ctctcaagca tcatgatcgc cattcctgga cttgggaagg atcccaacga ccccactgca    5100
gatgtcgaaa tcaatcccga cttgaaaccc atcataggca gagattcagg ccgagcactg    5160
gccgaagttc tcaagaaacc cgttgccagc cgacaactcc aaggaatgac aaatggacgg    5220
accagttcca gaggacagct gctgaaggaa tttcagctaa agccgatcgg gaaaaagatg    5280
agctcagccg tcgggtttgt tcctgacacc ggccctgcat cacgcagtgt aatccgctcc    5340 attataaaaat ccagccggct agaggaggat cggaagcgtt acctgatgac tctccttgat    5400
gatatcaaag gagccaatga tcttgccaag ttccaccaga tgctgatgaa gataataatg    5460
aagtagctac agctcaactt acctgccaac cccatgccag tcgacccaac tagtacaacc    5520
taaatccatt ataaaaaact taggagcaaa gtgattgcct cccaaggtcc acaatgacag    5580
agacctacga cttcgacaag tcggcatggg acatcaaagg gtcgatcgct ccgatacaac    5640
ccaccaccta cagtgatggc aggctggtgc cccaggtcag agtcatagat cctggtctag    5700
gcgacaggaa ggatgaatgc tttatgtaca tgtttctgct gggggttgtt gaggacagcg    5760
attccctagg gcctccaatc gggcgagcat ttgggttcct gcccttaggt gttggcagat    5820
ccacagcaaa gcccgaaaaa ctcctcaaag aggccactga gcttgacata gttgttagac    5880
gtacagcagg gctcaatgaa aaactggtgt tctacaacaa caccccacta actctcctca    5940
caccttggag aaaggtccta acaacaggga gtgtcttcaa cgcaaaccaa gtgtgcaatg    6000
cggttaatct gataccgctc gataccccgc agaggttccg tgttgtttat atgagcatca    6060
cccgtctttc ggataacggg tattacaccg ttcctagaag aatgctggaa ttcagatcgg    6120
tcaatgcagt ggccttcaac ctgctggtga cccttaggat tgacaaggcg ataggccctg    6180
```

```
ggaagatcat cgacaataca gagcaacttc ctgaggcaac atttatggtc cacatcggga    6240
acttcaggag aaagaagagt gaagtctact ctgccgatta ttgcaaaatg aaaatcgaaa    6300
agatgggcct ggtttttgca cttggtggga taggggcac  cagtcttcac attagaagca    6360
caggcaaaat gagcaagact ctccatgcac aactcgggtt caagaagacc ttatgttacc    6420
cgctgatgga tatcaatgaa gaccttaatc gattactctg gaggagcaga tgcaagatag    6480
taagaatcca ggcagttttg cagccatcag ttcctcaaga attccgcatt tacgacgacg    6540
tgatcataaa tgatgaccaa ggactattca aagttctgta gaccgtagtg cccagcaatg    6600
cccgaaaacg acccccctca caatgacagc cagaaggccc ggacaaaaaa gcccctccg     6660 aaagactcca cggaccaagc gagaggccag ccagcagccg acggcaagcg cgaacaccag    6720
gcggccccag cacagaacag ccctgacaca aggccaccac cagccacccc aatctgcatc    6780
ctcctcgtgg gaccccgag  gaccaacccc caaggctgcc cccgatccaa accaccaacc    6840
gcatccccac caccccggg  aaagaaaccc ccagcaattg gaaggcccct cccctcttc     6900 ctcaacacaa gaactccaca accgaaccgc acaagcgacc gaggtgaccc aaccgcaggc    6960
atccgactcc ctagacagat cctctctccc cggcaaacta acaaaacttt agggccaagg    7020
aacatacaca cccaacagaa cccagacccc ggcccacggc gccgcgcccc caaccccga    7080 caaccagagg gagcccccaa ccaatcccgc cggctccccc ggtgcccaca ggcagggaca    7140 ccaaccccg  aacagaccca gcaccaacc  atcgacaatc caagacgggg gggcccccc    7200 aaaaaaggc  cccagggc   cgacagccag caccgcgagg aagcccaccc accccacaca    7260
cgaccacggc aaccaaacca gaacccagac caccctgggc caccagctcc cagactcggc    7320
catcaccccg cagaaaggaa aggccacaac ccgcgcaccc cagcccccgat ccggcgggga    7380 gccacccaac ccgaaccagc acccaagagc gatccccgaa ggaccccga  accgcaaagg    7440 acatcagtat cccacagcct ctccaagtcc cccggtctcc tcctcttctc gaagggacca    7500
aaagatcaat ccaccacacc cgacgacact caactcccca cccctaaagg agacaccggg    7560
aatcccagaa tcaagactca tccaatgtcc atcatgggtc tcaaggtgaa cgtctctgcc    7620
atattcatgg cagtactgtt aactctccaa acacccaccg gtcaaatcca ttggggcaat    7680
ctctctaaga taggggtggt aggaatagga agtgcaagct acaaagttat gactcgttcc    7740
agccatcaat cattagtcat aaaattaatg cccaatataa ctctcctcaa taactgcacg    7800
agggtagaga ttgcagaata caggagacta ctgagaacag ttttggaacc aattagagat    7860
gcacttaatg caatgaccca gaatataaga ccggttcaga gtgtagcttc aagtaggaga    7920
cacaagagat ttgcgggagt agtcctggca ggtgcggccc taggcgttgc cacagctgct    7980
cagataacag ccggcattgc acttcaccag tccatgctga actctcaagc catcgacaat    8040
ctgagagcga gcctggaaac tactaatcag gcaattgaga caatcagaca agcagggcag    8100
gagatgatat tggctgttca gggtgtccaa gactacatca ataatgagct gataccgtct    8160
atgaaccaac tatcttgtga tttaatcggc cagaagctcg gctcaaatt  gctcagatac    8220 tatacagaaa tcctgtcatt atttggcccc agtttacggg accccatatc tgcggagata    8280
tctatccagg ctttgagcta tgcgcttgga ggagacatca ataaggtgtt agaaaagctc    8340
ggatacagtg gaggtgattt actgggcatc ttagagagcg gaggaataaa ggcccggata    8400
actcacgtcg acacagagtc ctacttcatt gtcctcagta tagcctatcc gacgctgtcc    8460
gagattaagg gggtgattgt ccaccggcta gagggggtct cgtacaacat aggctctcaa    8520
```

```
gagtggtata ccactgtgcc caagtatgtt gcaacccaag ggtaccttat ctcgaatttt    8580
gatgagtcat cgtgtacttt catgccagag gggactgtgt gcagccaaaa tgccttgtac    8640
ccgatgagtc ctctgctcca agaatgcctc cgggggtaca ccaagtcctg tgctcgtaca    8700
ctcgtatccg ggtcttttgg gaaccggttc attttatcac aagggaacct aatagccaat    8760
tgtgcatcaa tcctttgcaa gtgttacaca acaggaacga tcattaatca agaccctgac    8820
aagatcctaa catacattgc tgccgatcac tgcccggtag tcgaggtgaa cggcgtgacc    8880
atccaagtcg ggagcaggag gtatccagac gctgtgtact tgcacagaat tgacctcggt    8940
cctcccatat cattggagag gttggacgta gggacaaatc tggggaatgc aattgctaag    9000
ttggaggatg ccaaggaatt gttggagtca tcggaccaga tattgaggag tatgaaaggt    9060
ttatcgagca ctagcatagt ctacatcctg attgcagtgt gtcttggagg gttgataggg    9120
atccccgctt taatatgttg ctgcagggggg cgttgtaaca aaaagggaga acaagttggt    9180
atgtcaagac caggcctaaa gcctgatctt acgggaacat caaaatccta tgtaaggtcg    9240
ctctgatcct ctacaactct tgaaacacaa atgtcccaca agtctcctct tcgtcatcaa    9300
gcaaccaccg cacccagcat caagcccacc tgaaattatc tccggcttcc ctctggccga    9360
acaatatcgg tagttaatca aaacttaggg tgcaagatca tccacaatgt caccacaacg    9420
agaccggata aatgccttct acaaagataa ccccccatccc aagggaagta ggatagtcat    9480
taacagagaa catcttatga ttgatagacc ttatgttttg ctggctgttc tgtttgtcat    9540
gtttctgagc ttgatcgggt tgctagccat tgcaggcatt agacttcatc gggcagccat    9600
ctacaccgca gagatccata aaagcctcag caccaatcta gatgtaacta actcaatcga    9660
gcatcaggtc aaggacgtgc tgacaccact cttcaaaatc atcggtgatg aagtgggcct    9720
gaggacacct cagagattca ctgacctagt gaaattaatc tctgacaaga ttaaattcct    9780
taatccggat agggagtacg acttcagaga tctcacttgg tgtatcaacc cgccagagag    9840
aatcaaattg gattatgatc aatactgtgc agatgtggct gctgaagagc tcatgaatgc    9900
attggtgaac tcaactctac tggagaccag aacaaccaat cagttcctag ctgtctcaaa    9960
gggaaactgc tcagggccca ctacaatcag aggtcaattc tcaaacatgt cgctgtccct   10020
gttagacttg tatttaggtc gaggttacaa tgtgtcatct atagtcacta tgacatccca   10080
gggaatgtat gggggaactt acctagtgga aaagcctaat ctgagcagca aaaggtcaga   10140
gttgtcacaa ctgagcatgt accgagtgtt tgaagtaggt gttatcagaa atccgggttt   10200
gggggctccg gtgttccata tgacaaacta tcttgagcaa ccagtcagta atgatctcag   10260
caactgtatg gtggctttgg gggagctcaa actcgcagcc ctttgtcacg gggaagattc   10320
tatcacaatt ccctatcagg gatcaggaa aggtgtcagc ttccagctcg tcaagctagg   10380
tgtctggaaa tccccaaccg acatgcaatc ctgggtcccc ttatcaacgg atgatccagt   10440
gatagacagg ctttacctct catctcacag aggtgttatc gctgacaatc aagcaaaatg   10500
ggctgtcccg acaacacgaa cagatgacaa gttgcgaatg gagacatgct ccaacaggc    10560
gtgtaagggt aaaatccaag cactctgcga gaatcccgag tgggcaccat tgaaggataa   10620
caggattcct tcatacgggg tcttgtctgt tgatctgagt ctgacagttg agcttaaaat   10680
caaaattgct tcgggattcg gccattgat cacacacggt tcagggatgg acctatacaa   10740
atccaaccac aacaatgtgt attggctgac tatcccgcca atgaagaacc tagccttagg   10800
tgtaatcaac acattggagt ggataccgag attcaaggtt agtccctacc tcttcactgt   10860
cccaattaag gaagcaggcg aagactgcca tgccccaaca tacctacctg cggaggtgga   10920
```

```
tggtgatgtc aaactcagtt ccaatctggt gattctacct ggtcaagatc tccaatatgt   10980
tttggcaacc tacgatactt ccagggttga acatgctgtg gtttattacg tttacagccc   11040
aagccgctca ttttcttact tttatccttt taggttgcct ataaagggg tccccatcga    11100
attacaagtg gaatgcttca catgggacca aaaactctgg tgccgtcact tctgtgtgct   11160
tgcggactca gaatctggtg gacatatcac tcactctggg atggtgggca tgggagtcag   11220
ctgcacagtc acccgggaag atggaaccaa tcgcagatag ggctgctagt gaaccaatca   11280
catgatgtca cccagacatc aggcataccc actagtgtga aatagacatc agaattaaga   11340
aaaacgtagg gtccaagtgg ttccccgtta tggactcgct atctgtcaac cagatcttat   11400
accctgaagt tcacctagat agcccgatag ttaccaataa gatagtagcc atcctggagt   11460
atgctcgagt ccctcacgct tacagcctgg aggaccctac actgtgtcag aacatcaagc   11520
accgcctaaa aaacggattt tccaaccaaa tgattataaa caatgtggaa gttgggaatg   11580
tcatcaagtc caagcttagg agttatccgg cccactctca tattccatat ccaaattgta   11640
atcaggattt atttaacata gaagacaaag agtcaacgag gaagatccgt gaactcctca   11700
aaaggggaa ttcgctgtac tccaaagtca gtgataaggt tttccaatgc ttaagggaca    11760
ctaactcacg gcttggccta ggctccgaat tgagggagga catcaaggag aaagttatta   11820
acttgggagt ttacatgcac agctcccagt ggtttgagcc cttttctgttt tggtttacag  11880
tcaagactga gatgaggtca gtgattaaat cacaaaccca tacttgccat aggaggagac   11940
acacacctgt attcttcact ggtagttcag ttgagttgct aatctctcgt gaccttgttg   12000
ctataatcag taaagagtct caacatgtat attacctgac atttgaactg gttttgatgt   12060
attgtgatgt catagagggg aggttaatga cagagaccgc tatgactatt gatgctaggt   12120
atacagagct tctaggaaga gtcagataca tgtggaaact gatagatggt ttcttccctg   12180
cactcgggaa tccaacttat caaattgtag ccatgctgga gcctctttca cttgcttacc   12240
tgcagctgag ggatataaca gtagaactca gaggtgcttt ccttaaccac tgctttactg   12300
aaatacatga tgttcttgac caaaacgggt tttctgatga aggtacttat catgagttaa   12360
ctgaagctct agattacatt ttcataactg atgcatacaa tctgacaggg gagattttct   12420
cattttcag aagtttcggc cacccccagac ttgaagcagt aacggctgct gaaaatgtta   12480
ggaaatacat gaatcagcct aaagtcattg tgtatgagac tctgatgaaa ggtcatgcca   12540
tattttgtgg aatcataatc aacggctatc gtgacaggca cggaggcagt tggccaccgc   12600
tgacccctccc cctgcatgct gcagacacaa tccggaatgc tcaagcttca ggtgaagggt   12660
taacacatga gcagtgcgtt gataactgga aatcttttgc tggagtgaaa tttggctgct   12720
ttatgcctct tagcctggat agtgatctga caatgtacct aaaggacaag gcacttgctg   12780
ctctccaaag ggaatgggat tcagtttacc cgaaagagtt cctgcgttac gaccctccca   12840
agggaaccgg gtcacggagg cttgtagatg ttttccttaa tgattcgagc tttgacccat   12900
atgatgtgat aatgtatgtt gtaagtggag cttacctcca tgaccctgag ttcaacctgt   12960
cttacagcct gaaagaaaag gagatcaagg aaacaggtag acttttttgct aaaatgactt   13020
acaaaatgag ggcatgccaa gtgattgctg aaaatctaat ctcaaacggg attggcaaat   13080
attttaagga caatgggatg gccaaggatg agcacgattt gactaaggca ctccacactc   13140
tagctgtctc aggagtcccc aaagatctca aagaaagtca cagggggggg ccagtcttaa   13200
aaacctactc ccgaagccca gtccacacaa gtaccaggaa cgtgagagca gcaaaagggt   13260
```

```
ttatagggtt ccctcaagta attcggcagg accaagacac tgatcatccg gagaatatgg    13320
aagcttacga gacagtcagt gcatttatca cgactgatct caagaagtac tgccttaatt    13380
ggagatatga gaccatcagc ttgtttgcac agaggctaaa tgagatttac ggattgccct    13440
cattttccca gtggctgcat aagaggcttg agacctctgt cctgtatgta agtgaccctc    13500 attgccccc cgaccttgac gcccatatcc cgttatataa agtccccaat gatcaaatct    13560
tcattaagta ccctatggga ggtatagaag ggtattgtca gaagctgtgg accatcagca    13620
ccattcccta tctatacctg gctgcttatg agagcggagt aaggattgct tcgttagtgc    13680
aaggggacaa tcagaccata gccgtaacaa aaagggtacc cagcacatgg ccctacaacc    13740
ttaagaaacg ggaagctgct agagtaacta gagattactt tgtaattctt aggcaaaggc    13800
tacatgatat tggccatcac ctcaaggcaa atgagacaat tgtttcatca cattttttg    13860 tctattcaaa aggaatatat tatgatgggc tacttgtgtc ccaatcactc aagagcatcg    13920
caagatgtgt attctggtca gagactatag ttgatgaaac aagggcagca tgcagtaata    13980
ttgctacaac aatggctaaa agcatcgaga gaggttatga ccgttacctt gcatattccc    14040
tgaacgtcct aaaagtgata cagcaaattc tgatctctct tggcttcaca atcaattcaa    14100
ccatgacccg ggatgtagtc ataccctcc tcacaaacaa cgacctctta ataaggatgg    14160
cactgttgcc cgctcctatt gggggatga attatctgaa tatgagcagg ctgtttgtca    14220
gaaacatcgg tgatccagta acatcatcaa ttgctgatct caagagaatg attctcgcct    14280
cactaatgcc tgaagagacc ctccatcaag taatgacaca acaaccgggg gactcttcat    14340
tcctagactg ggctagcgac ccttactcag caaatcttgt atgtgtccag agcatcacta    14400
gactcctcaa gaacataact gcaaggtttg tcctgatcca tagtccaaac ccaatgttaa    14460
aaggattatt ccatgatgac agtaaagaag aggacgaggg actggcggca ttcctcatgg    14520
acaggcatat tatagtacct agggcagctc atgaaatcct ggatcatagt gtcacagggg    14580
caagagagtc tattgcaggc atgctggata ccacaaaagg cttgattcga gccagcatga    14640 ggaaggggg gttaacctct cgagtgataa ccagattgtc caattatgac tatgaacaat    14700
tcagagcagg gatggtgcta ttgacaggaa gaaagagaaa tgtcctcatt gacaaagagt    14760
catgttcagt gcagctggcg agagctctaa gaagccatat gtgggcgagg ctagctcgag    14820
gacggcctat ttacggcctt gaggtccctg atgtactaga atctatgcga ggccaccta    14880 ttcggcgtca tgagacatgt gtcatctgcg agtgtggatc agtcaactac ggatggtttt    14940
ttgtcccctc gggttgccaa ctggatgata ttgacaagga acatcatcc ttgagagtcc    15000 catatattgg ttctaccact gatgagagaa cagacatgaa gcttgccttc gtaagagccc    15060
caagtcgatc cttgcgatct gctgttagaa tagcaacagt gtactcatgg gcttacggtg    15120
atgatgatag ctcttggaac gaagcctggt tgttggctag gcaaagggcc aatgtgagcc    15180
tggaggagct aagggtgatc actcccatct caacttcgac taatttagcg cataggttga    15240
gggatcgtag cactcaagtg aaatactcag gtacatccct tgtccgagtg gcgaggtata    15300
ccacaatctc caacgacaat ctctcatttg tcatatcaga taagaaggtt gatactaact    15360
ttatatacca acaaggaatg cttctagggt tgggtgtttt agaaacattg tttcgactcg    15420
agaaagatac cggatcatct aacacggtat tacatcttca cgtcgaaaca gattgttgcg    15480
tgatcccgat gatagatcat cccaggatac ccagctcccg caagctagag ctgagggcag    15540
agctatgtac caacccattg atatatgata atgcaccttt aattgacaga gatgcaacaa    15600
ggctatacac ccagagccat aggaggcacc ttgtggaatt tgttacatgg tccacacccc    15660
```

```
aactatatca cattttagct aagtccacag cactatctat gattgacctg gtaacaaaat    15720
ttgagaagga ccatatgaat gaaatttcag ctctcatagg ggatgacgat atcaatagtt    15780
tcataactga gtttctgctc atagagccaa gattattcac tatctacttg ggccagtgtg    15840
cggccatcaa ttgggcattt gatgtacatt atcatagacc atcagggaaa tatcagatgg    15900
gtgagctgtt gtcatcgttc ctttctagaa tgagcaaagg agtgtttaag gtgcttgtca    15960
atgctctaag ccacccaaag atctacaaga aattctggca ttgtggtatt atagagccta    16020
tccatggtcc ttcacttgat gctcaaaact tgcacacaac tgtgtgcaac atggtttaca    16080
catgctatat gacctacctc gacctgttgt tgaatgaaga gttagaagag ttcacatttc    16140
tcttgtgtga aagcgacgag gatgtagtac cggacagatt cgacaacatc caggcaaaac    16200
acttatgtgt tctggcagat ttgtactgtc aaccagggac ctgcccacca attcgaggtc    16260
taagaccggt agagaaatgt gcagttctaa ccgaccatat caaggcagag gctatgttat    16320
ctccagcagg atcttcgtgg aacataaatc caattattgt agaccattac tcatgctctc    16380
tgacttatct ccggcgagga tcgatcaaac agataagatt gagagttgat ccaggattca    16440
ttttcgacgc cctcgctgag gtaaatgtca gtcagccaaa gatcggcagc aacaacatct    16500
caaatatgag catcaaggct ttcagacccc cacacgatga tgttgcaaaa ttgctcaaag    16560
atatcaacac aagcaagcac aatcttccca tttcaggggg caatctcgcc aattatgaaa    16620
tccatgcttt ccgcagaatc gggttgaact catctgcttg ctacaaagct gttgagatat    16680
caacattaat taggagatgc cttgagccag gggaggacgg cttgttcttg ggtgagggat    16740
cgggttctat gttgatcact tataaagaga tacttaaact aaacaagtgc ttctataata    16800
gtggggtttc cgccaattct agatctggtc aaagggaatt agcacccctat ccctccgaag    16860
ttggccttgt cgaacacaga atgggagtag gtaatattgt caaagtgctc tttaacggga    16920
ggcccgaagt cacgtgggta ggcagtgtag attgcttcaa tttcatagtt agtaatatcc    16980
ctacctctag tgtggggttt atccattcag atatagagac cttgcctgac aaagatacta    17040
tagagaagct agaggaattg gcagccatct tatcgatggc tctgctcctg ggcaaaatag    17100
gatcaatact ggtgattaag cttatgcctt tcagcgggga ttttgttcag ggatttataa    17160
gttatgtagg gtctcattat agagaagtga accttgtata ccctagatac agcaacttca    17220
tctctactga atcttatttg gttatgacag atctcaaggc taaccggcta atgaatcctg    17280
aaaagattaa gcagcagata attgaatcat ctgtgaggac ttcacctgga cttataggtc    17340
acatcctatc cattaagcaa ctaagctgca tacaagcaat tgtgggagac gcagttagta    17400
gaggtgatat caatcctact ctgaaaaaac ttacacctat agagcaggtg ctgatcaatt    17460
gcgggttggc aattaacgga cctaagctgt gcaaagaatt gatccaccat gatgttgcct    17520
cagggcaaga tggattgctt aattctatac tcatcctcta cagggagttg gcaagattca    17580
aagacaacca aagaagtcaa caagggatgt tccacgctta ccccgtattg gtaagtagca    17640
ggcaacgaga acttatatct aggatcaccc gcaaattctg ggggcacatt cttctttact    17700
ccgggaacaa aaagttgata aataagttta tccagaatct caagtccggc tatctgatac    17760
tagacttaca ccagaatatc ttcgttaaga atctatccaa gtcagagaaa cagattatta    17820
tgacgggggg tttgaaacgt gagtgggttt ttaaggtaac agtcaaggag accaaagaat    17880
ggtataagtt agtcggatac agtgccctga ttaaggacta attggttgaa ctccggaacc    17940
ctaatcctgc cctaggtggt taggcattat ttgcaatata ttaaagaaaa ctttgaaaat    18000
```

```
acgaagtttc tattcccagc tttgtctggt ggccggcatg gtcccagcct cctcgctggc   18060
gccggctggg caacattccg aggggaccgt cccctcggta atggcgaatg ggacgcggcc   18120
ggtcgatcga cgatccggct gctaacaaag cccgaaagga agctgagttg gctgctgcca   18180
ccgctgagca ataactagca taacccttg gggcctctaa acgggtcttg aggggttttt   18240
tgctgaaagg aggaactata tccggatcga gatcaattct gtgagcgtat ggcaaacgaa   18300
ggaaaaatag ttatagtagc cgcactcgat gggacatttc aacgtaaacc gtttaataat   18360
attttgaatc ttattccatt atctgaaatg gtggtaaaac taactgctgt gtgtatgaaa   18420
tgctttaagg aggcttcctt ttctaaacga ttgggtgagg aaaccgagat agaaataata   18480
ggaggtaatg atatgtatca atcggtgtgt agaaagtgtt acatcgactc ataatattat   18540
attttttatc taaaaaacta aaataaaca ttgattaaat tttaatataa acttaaaaa   18600
tggatgttgt gtcgttagat aaaccgttta tgtattttga ggaaattgat aatgagttag   18660
attacgaacc agaaagtgca aatgaggtcg caaaaaact gccgtatcaa ggacagttaa   18720
aactattact aggagaatta ttttttctta gtaagttaca gcgacacggt atattagatg   18780
gtgccaccgt agtgtatata ggatctgctc ccggtacaca tatacgttat ttgagagatc   18840
atttctataa tttaggagtg atcccgaaag gaagctgagt tggctgctgc caccgctgag   18900
caataactag cataacccct tggggcctct aaacgggtct tgaggggttt tttgctgaaa   18960
ggaggaacgc gcctgatgcg gtattttctc cttacgcatc tgtgcggtat ttcacaccgc   19020
atatatggtg cactctcagt acaatctgct ctgatgccgc atagttaagc cagccccgac   19080
acccgccaac acccgctgac gcgccctgac gggcttgtct gctcccggca tccgcttaca   19140
gacaagctgt gaccgtctcc gggagctgca tgtgtcagag gttttcaccg tcatcaccga   19200
aacgcgcgag acgaaagggc ctcgtgatac gcctattttt ataggttaat gtcatgataa   19260
taatggtttc ttagacgtca ggtggcactt tcggggaaa tgtgcgcgga ccccctattt   19320
gtttattttt ctaaatacat tcaaatatgt atccgctcat gagacaataa ccctgataaa   19380
tgcttcaata atattgaaaa aggaagagta tgagtattca acatttccgt gtcgccctta   19440
ttccctttt tgcggcattt tgccttcctg ttttgctca cccagaaacg ctggtgaaag   19500
taaagatgc tgaagatcag ttgggtgcac gagtgggtta catcgaactg gatctcaaca   19560
gcggtaagat ccttgagagt tttcgccccg aagaacgttt tccaatgatg agcacttta   19620
aagttctgct atgtggcgcg gtattatccc gtattgacgc cgggcaagag caactcggtc   19680
gccgcataca ctattctcag aatgacttgg ttgagtactc accagtcaca gaaaagcatc   19740
ttacggatgg catgacagta agagaattat gcagtgctgc cataaccatg agtgataaca   19800
ctgcggccaa cttacttctg acaacgatcg gaggaccgaa ggagctaacc gcttttttgc   19860
acaacatggg ggatcatgta actcgccttg atcgttggga accggagctg aatgaagcca   19920
taccaaacga cgagcgtgac accacgatgc ctgtagcaat ggcaacaacg ttgcgcaaac   19980
tattaactgg cgaactactt actctagctt cccggcaaca attaatagac tggatggagg   20040
cggataaagt tgcaggacca cttctgcgct cggcccttcc ggctggctgg tttattgctg   20100
ataaatctgg agccggtgag cgtgggtctc gcggtatcat tgcagcactg gggccagatg   20160
gtaagccctc ccgtatcgta gttatctaca cgacggggag tcaggcaact atggatgaac   20220
gaaatagaca gatcgctgag ataggtgcct cactgattaa gcattggtaa ctgtcagacc   20280
aagtttactc atatatactt tagattgatt taaaacttca ttttttaattt aaaaggatct   20340
aggtgaagat ccttttttgat aatctcatga ccaaaatccc ttaacgtgag ttttcgttcc   20400
```

```
actgagcgtc agacccegta gaaaagatca aagqatcttc ttgagatcct tttttctgc  20460
gcgtaatctg ctgcttgcaa acaaaaaaac caccgctacc agcggtggtt tgtttgccgg  20520
atcaagagct accaactctt tttccgaagg taactggctt cagcagagcg cagataccaa  20580
atactgtcct tctagtgtag ccgtagttag gccaccactt caagaactct gtagcaccgc  20640
ctacatacct cgctctgcta atcctgttac cagtggctgc tgccagtggc gataagtcgt  20700
gtcttaccgg gttggactca agacgatagt taccggataa ggcgcagcgg tcgggctgaa  20760
cgggggggttc gtgcacacag cccagcttgg agcgaacgac ctacaccgaa ctgagatacc  20820
tacagcgtga gcattgagaa agcgccacgc ttcccgaagg gagaaaggcg gacaggtatc  20880
cggtaagcgg cagggtcgga acaggagagc gcacgaggga gcttccaggg ggaaacgcct  20940
ggtatcttta tagtcctgtc gggtttcgcc acctctgact tgagcgtcga ttttgtgat  21000
gctcgtcagg ggggcggagc ctatggaaaa acgccagcaa cgcggccttt ttacggttcc  21060
tggcctttg ctggcctttt gctcacatgt tctttcctgc gttatcccct gattctgtgg  21120
ataaccgtat taccgccttt gagtgagctg ataccgctcg ccgcagccga acgaccgagc  21180
gcagcgagtc agtgagcgag gaagcggaag agcgcccaat acgcaaaccg cctctccccg  21240
cgcgttggcc gattcattaa tgcagctggc acgacaggtt tcccgactgg aaagcgggca  21300
gtgagcgcaa cgcaattaat gtgagttagc tcactcatta ggcacccag gctttacact  21360
ttatgcttcc ggctcgtatg ttgtgtggaa ttgtgagcgg ataacaattt cacacaggaa  21420
acagctatga ccatgattac gccaagctta cgcgtcctgg cattatgccc agtacatgac  21480
cttatgggac tttcctactt ggcagtacat ctacgtatta gtcatcgcta ttaccatggt  21540
gatgcggttt tggcagtaca tcaatgggcg tggatagcgg tttgactcac ggggatttcc  21600
aagtctccac cccattgacg tcaatgggag tttgttttgg caccaaaatc aacgggactt  21660
tccaaaatgt cgtaacaact ccgccccatt gacgcaaatg ggcggtaggc gtgtacggtg  21720
ggaggtctat ataagcagag ctcgtttagt gaaccgtgg                         21759
```